United States Patent
Yen et al.

(10) Patent No.: US 11,276,828 B2
(45) Date of Patent: Mar. 15, 2022

(54) ORGANIC COMPOUND AND ORGANIC ELECTROLUMINESCENCE DEVICE USING THE SAME

(71) Applicants: Feng-Wen Yen, Taipei (TW); Li-Chieh Chuang, Nantou (TW)

(72) Inventors: Feng-Wen Yen, Taipei (TW); Li-Chieh Chuang, Nantou (TW)

(73) Assignee: LUMINESCENCE TECHNOLOGY CORP., Hsin-Chu (TW)

( * ) Notice: Subject to any disclaimer, the term of this patent is extended or adjusted under 35 U.S.C. 154(b) by 334 days.

(21) Appl. No.: 16/252,711

(22) Filed: Jan. 21, 2019

(65) Prior Publication Data
US 2020/0235315 A1    Jul. 23, 2020

(51) Int. Cl.
*H01L 51/00* (2006.01)
*C07D 333/50* (2006.01)
(Continued)

(52) U.S. Cl.
CPC ........ *H01L 51/0074* (2013.01); *C07D 307/77* (2013.01); *C07D 333/50* (2013.01); *C07D 405/04* (2013.01); *C07D 405/10* (2013.01); *C07D 405/14* (2013.01); *C07D 409/04* (2013.01); *C07D 409/14* (2013.01); *C07D 471/04* (2013.01); *C09K 11/06* (2013.01); *H01L 51/0052* (2013.01); *H01L 51/0056* (2013.01);
(Continued)

(58) Field of Classification Search
None
See application file for complete search history.

(56) References Cited

U.S. PATENT DOCUMENTS

2015/0144898 A1* 5/2015 Dai et al. ............ H01L 51/0058
2016/0240784 A1  8/2016 Yen
2018/0244659 A1* 8/2018 Kim ........................ H01L 51/50

FOREIGN PATENT DOCUMENTS

WO    WO-2016/137068 A1 *  9/2016
WO    WO-2020/013657 A1 *  1/2020

OTHER PUBLICATIONS

Machine English translation of Kim et al. (WO 2020/013657 A1). Feb. 3, 2021.*

* cited by examiner

*Primary Examiner* — Jay Yang

(57) ABSTRACT

The present invention discloses an organic compound and an organic electroluminescence device using the organic compound as a host material, a fluorescent guest material, an electron transporting or a hole blocking material in the light emitting layer of the organic electroluminescence device. The organic compound may be for lowering a driving voltage, power consumption or increasing a current efficiency or half-life of the organic electroluminescence device.

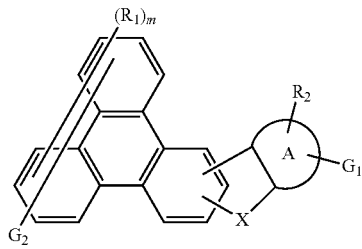

formula (A)

The same definition as described in the present invention.

10 Claims, 1 Drawing Sheet

(51) Int. Cl.
*C09K 11/06* (2006.01)
*C07D 405/14* (2006.01)
*C07D 405/04* (2006.01)
*C07D 409/04* (2006.01)
*C07D 471/04* (2006.01)
*C07D 409/14* (2006.01)
*C07D 307/77* (2006.01)
*C07D 405/10* (2006.01)
*H01L 51/50* (2006.01)

(52) U.S. Cl.
CPC ...... *H01L 51/0061* (2013.01); *H01L 51/0067* (2013.01); *H01L 51/0072* (2013.01); *H01L 51/0073* (2013.01); *C09K 2211/1018* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 2251/558* (2013.01)

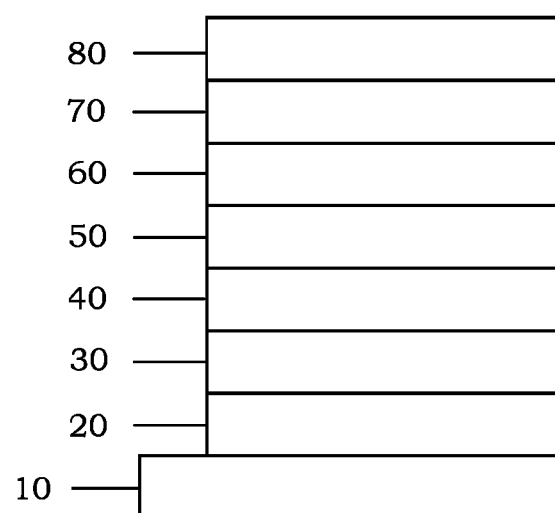

ORGANIC COMPOUND AND ORGANIC ELECTROLUMINESCENCE DEVICE USING THE SAME

FIELD OF INVENTION

The present invention relates to an organic compound and, more particularly, to an organic electroluminescence device using the organic compound.

BACKGROUND OF THE INVENTION

An organic electroluminescence (organic EL) device is an organic light-emitting diode (OLED) in which the light emitting layer is a film made from organic compounds, which emits light in response to the electric current. The light emitting layer containing the organic compound is sandwiched between two electrodes. The organic EL device is applied to flat panel displays due to its high illumination, low weight, ultra-thin profile, self-illumination without back light, low power consumption, wide viewing angle, high contrast, simple fabrication methods and rapid response time.

Typically, the organic EL device is composed of organic material layers sandwiched between two electrodes. The organic material layers include, e.g., hole injection layer (HIL), hole transporting layer (HTL), emitting layer (EML), electron transporting layer (ETL), and electron injection layer (EIL). The basic mechanism of organic EL involves the injection, transport, and recombination of carriers as well as exciton formation for emitting light. When an external voltage is applied across the organic EL device, electrons and holes are injected from the cathode and the anode, respectively. Electrons will be injected from the cathode into a LUMO (lowest unoccupied molecular orbital) and holes will be injected from the anode into a HOMO (highest occupied molecular orbital). Subsequently, the electrons recombine with holes in the light emitting layer to form excitons, which then deactivate to emit light. When luminescent molecules absorb energy to achieve an excited state, the exciton may either be in a singlet state or a triplet state, depending on how the spins of the electrons and holes have been combined. It is well known that the excitons formed under electrical excitation typically include 25% singlet excitons and 75% triplet excitons. In the fluorescence materials, however, the electrically generated energy in the 75% triplet excitons will be dissipated as heat for decay from the triplet state is spin forbidden. Therefore, a fluorescent electroluminescence device has only 25% internal quantum efficiency, which leads to the theoretically highest external quantum efficiency (EQE) of only 5% due to only ~20% of the light out-coupling efficiency of the device. In contrast to fluorescent electroluminescence devices, phosphorescent organic EL devices make use of spin-orbit interactions to facilitate intersystem crossing between singlet and triplet states, thus obtaining emission from both singlet and triplet states and the internal quantum efficiency of electroluminescence devices from 25% to 100%.

However, there is still a need for improvement in the case of use of those organic materials in an organic EL device of some prior art displays, for example, in relation to the driving voltage, current efficiency or half-life time of the organic EL device.

SUMMARY OF THE INVENTION

Accordingly, an object of the present invention is to provide an organic compound, which can be used as a host material, an electron transfer, or a hole blocking material in the organic EL device to improve the power consumption, current efficiency, or half-life of the device.

Another object of the invention is to provide an organic compound and an organic EL device using the same, which may lower a driving voltage, or increasing a current efficiency or longer half-life time to the organic EL device.

According to the present invention, an organic compound which may be used in organic EL devices is disclosed. The organic compound may be represented by the following formula (A):

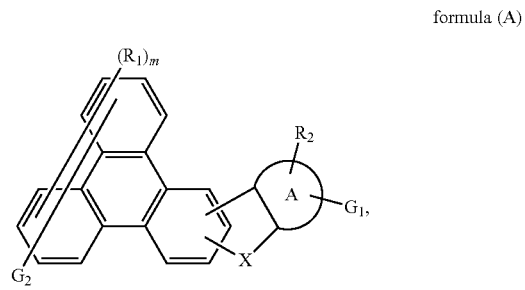

formula (A)

wherein X may be a divalent bridge selected from the group consisting of O, S, SO, $SO_2$, Se, $NR_3$, and $SiR_4R_5$. The symbol m may represent an integer of 0, 1, 2, 3, 4, 5, 6, 7 or 8. A may represent a substituted or unsubstituted fused ring hydrocarbons unit with three rings, if X is, for example, but not limited to $NR_3$. A may represent a substituted or unsubstituted fused ring hydrocarbons unit with two to three rings, if X is, for example, but not limited to O, S, SO, $SO_2$, Se, $NR_3$ or $SiR_4R$. The fused ring hydrocarbons unit may be, for example, a polycyclic aromatic hydrocarbons (PAHs) unit. $G_1$ and $G_2$ may be independently selected from the group consisting of a hydrogen, a methyl group, a halogen (e.g., fluoride), a phenylphosphine oxide group, a substituted or unsubstituted aryl group having 6 to 30 (e.g., 10, 12, 14, 16, 18, 20, 24, 26 or 30) ring carbon atoms, a substituted or unsubstituted heteroaryl group having 3 to 30 (e.g., 12, 15, 16, 17, 18, 21, 22, 23, 24 or 30) ring carbon atoms, a substituted or unsubstituted arylamine group having 6 to 30 (e.g., 12, 17, 18, 20, 24, 27 or 28) ring carbon atoms, and a substituted or unsubstituted heteroarylamine group having 3 to 30 (e.g., 21 or 27) ring carbon atoms. $R_1$ to $R_5$ may be independently selected from the group consisting of a hydrogen atom, a methyl group, a halogen (e.g., fluoride), a substituted or unsubstituted alkyl group having 1 to 30 (e.g., 8 or 10) carbon atoms, a substituted or unsubstituted aralkyl group having 7 to 30 (e.g., 8, 12 or 24,) ring carbon atoms, a substituted or unsubstituted aryl group having 6 to 30 (e.g., 6 or 12) ring carbon atoms, and a substituted or unsubstituted heteroaryl group having 3 to 30 (e.g., 5 or 10) ring carbon atom. The heteroaryl group may comprise, for example, a heteroaromatic PAHs unit having two, three, four, five or six rings. The heteroaromatic PAHs may contain an oxygen atom, a sulfur atom or one, two or three N atoms.

The substituted aryl group may be an aryl group substituted by an alkoxy group or by a methyl or ethyl substituted heteroaromatic PAHs unit having two rings. The two-rings heteroaromatic PAHs may contain one, two or three N atoms.

$R_1$ to $R_5$ may also represent a phenyl group, a naphthyl group, a dibenzofuranyl group, a benzo[b]naphtho[2,3-d]furanyl group, an isopropyl-benzo[b]naphtho[2,1-d]furanyl group, a carbazole group, a N-phenylcarbazole group, a trifluoromethyl group, a cumene (isopropylbenzene) group, a phenyl-phenylpyrimidine group, a biphenyl-phenylpyrimidine group, a diphenyl-triazine group or a 4,6-diphenyl-1,3,5-triazine group.

A may represent a polycyclic aromatic hydrocarbons (PAHs) unit having two or three rings. A may comprise, for example, a naphthyl group, an anthracenyl group, or a phenanthrenyl group. Each of the groups may be substituted by, for example, an isopropyl group, an isobutyl group or a hexyl group.

The present invention further discloses an organic electroluminescence device. The organic electroluminescence (EL) device comprises a pair of electrodes composed of a cathode and an anode. The organic EL device may comprise a light emitting layer and one or more layers of organic thin film layers between the pair of electrodes. The light emitting layer and/or the one or more organic thin film layers comprise the organic compound of formula (A). The light emitting layer may be an emitting layer comprising an emitting host material and an emitting guest (dopant) material. The emitting host material may be doped with about 15% emitting guest material. The emitting layer may have a thickness of about 30 nm between the pair of electrodes. The light emitting layer comprises the organic compound represented by formula (A).

The organic EL device of the present invention may comprise the organic compound of formula (A) as a host material of the light emitting layer. The organic EL device having the light emitting layer may have a driving voltage of about but not limited to 3.3-4.2 V, a current efficiency of about but not limited to 4.7-6.2 cd/A, or a half-life time of about but not limited to 260-470 hours.

An organic EL device of the present invention comprises an organic compound of formula (A) as a dopant material to collocate with, for example, a host material H2 to emit a blue light, thereby lowering a driving voltage to about but not limited to 3.4-3.6 V, increasing a current efficiency to about but not limited to 5.4-6.0 cd/A, or increasing a half-life time to about but not limited to 380-450 hours.

The organic EL device of may comprise an organic compound of formula (A) as a host material to collocate with a dopant material D1, thereby lowering a driving voltage to about but not limited to 3.5-3.7 V, increasing a current efficiency to about but not limited to 41-44 cd/A, or increasing a half-life time to about but not limited to 740-770 hours.

The organic EL device of the present invention may comprise the organic compound of formula (A) as a dopant material of the light emitting layer. The organic EL device having the light emitting layer may have a driving voltage of about but not limited to 3.3-4.2 V, a current efficiency of about but not limited to 4.7-6.2 cd/A, or a half-life time of about but not limited to 270-460 hours.

The organic EL device of may comprise an organic compound of formula (A) as an electron transporting material (for ETL), thereby lowering a driving voltage to about but not limited to 3.5-4.8 V, increasing a current efficiency to about but not limited to 21-38 cd/A, or increasing a half-life time to about but not limited to 410-620 hours.

The organic EL device of may comprise an organic compound of formula (A) as an electron transporting material (for ETL) to collocate with a hole blocking material (e.g., HB1 for HBL), thereby lowering a driving voltage to about but not limited to 3.6-3.8 V, increasing a current efficiency to about but not limited to 34-37 cd/A, or increasing a half-life time to about but not limited to 550-600 hours.

Alternatively, an organic EL device of may comprise an organic compound of formula (A) as a hole blocking material (for HBL), thereby lowering a driving voltage to about but not limited to 4.0-4.3 V, increasing a current efficiency to about but not limited to 21-35 cd/A, or increasing a half-life time to about but not limited to 400-550 hours.

Alternatively, an organic EL device of may comprise an organic compound of formula (A) as a hole blocking material (for HBL) to collocate with an electron transporting material (e.g., ET1 for ETL), thereby lowering a driving voltage to about but not limited to 4.1-4.3 V, increasing a current efficiency to about but not limited to 31-33 cd/A, or increasing a half-life time to about but not limited to 480-530 hours.

BRIEF DESCRIPTION OF THE DRAWINGS

The FIGURE is a schematic view showing an organic EL device according to an embodiment of the present invention.

DESCRIPTION OF THE PREFERRED EMBODIMENTS

What probed into the invention is the organic compound and organic EL device using the organic compound. Detailed descriptions of the production, structure and elements will be provided as follows such that the invention can be fully understood. Obviously, the application of the invention is not confined to specific details familiar to those skilled in the art. On the other hand, the common elements and procedures that are known to everyone are not described in details to avoid unnecessary limits of the invention. Some preferred embodiments of the present invention will now be described in greater detail as follows. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In one embodiment of the present invention, an organic compound which can be used as the host and dopant material of the light emitting layer in the organic EL device is disclosed. The organic compound may be represented by the following formula (A):

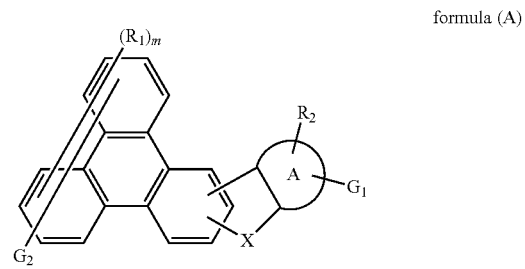

formula (A)

Wherein X may be a divalent bridge selected from the group consisting of O, S, SO, $SO_2$, Se, $NR_3$, and $SiR_4R_5$. The symbol m may represent an integer of 0, 1, 2, 3, 4, 5, 6, 7 or 8. A may represent a substituted or unsubstituted fused ring hydrocarbons unit with three rings, if X is, for example, but not limited to $NR_3$. A may represent a substituted or unsubstituted fused ring hydrocarbons unit with two to three rings, if X is, for example, but not limited to O, S, SO, SO$_2$, Se, NR$_3$ or SiR$_4$R. G$_1$ and G$_2$ are independently selected from the group consisting of a hydrogen, a methyl group, a halogen (e.g., fluoride), a phenylphosphine oxide group, a substituted or unsubstituted aryl group having 6 to 30 (e.g., 10, 12, 14, 16, 18, 20, 24, 26 or 30) ring carbon atoms, a substituted or unsubstituted heteroaryl group having 3 to 30 (e.g., 12, 15, 16, 17, 18, 21, 22, 23, 24 or 30) ring carbon atoms, a substituted or unsubstituted arylamine group having 6 to 30 (e.g., 12, 17, 18, 20, 24, 27 or 28) ring carbon atoms, and a substituted or unsubstituted heteroarylamine group having 3 to 30 (e.g., 21 or 27) ring carbon atoms. R$_1$ to R$_5$ may be independently selected from the group consisting of a hydrogen atom, a methyl group, a halogen (e.g., fluoride), a substituted or unsubstituted alkyl group having 1 to 30 (e.g., 8 or 10) carbon atoms, a substituted or unsubstituted aralkyl group having 7 to 30 (e.g., 8, 12 or 24,) ring carbon atoms, a substituted or unsubstituted aryl group having 6 to 30 (e.g., 6 or 12) ring carbon atoms, and a substituted or unsubstituted heteroaryl group having 3 to 30 (e.g., 5 or 10) ring carbon atom. The heteroaryl group may comprise, for example, a heteroaromatic PAHs unit having two, three, four, five or six rings. The heteroaromatic PAHs may contain an oxygen atom, a sulfur atom or one, two or three N atoms.

In some embodiments, the organic compound can be represented by one of the following formula (1) to formula (18):

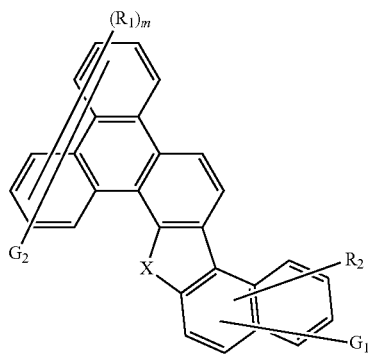

formula (1)

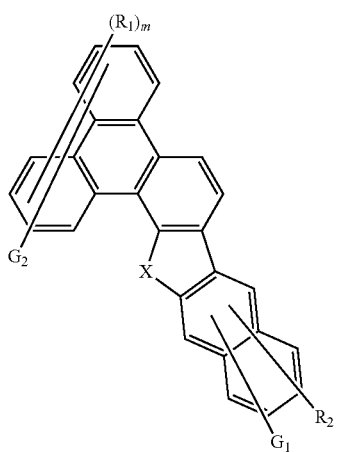

formula (2)

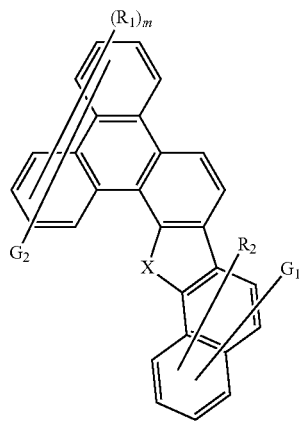

formula (3)

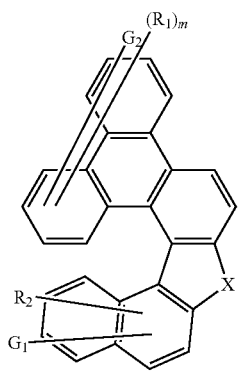

formula (4)

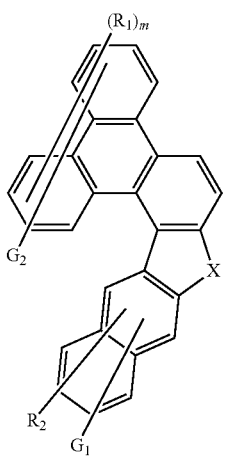

formula (5)

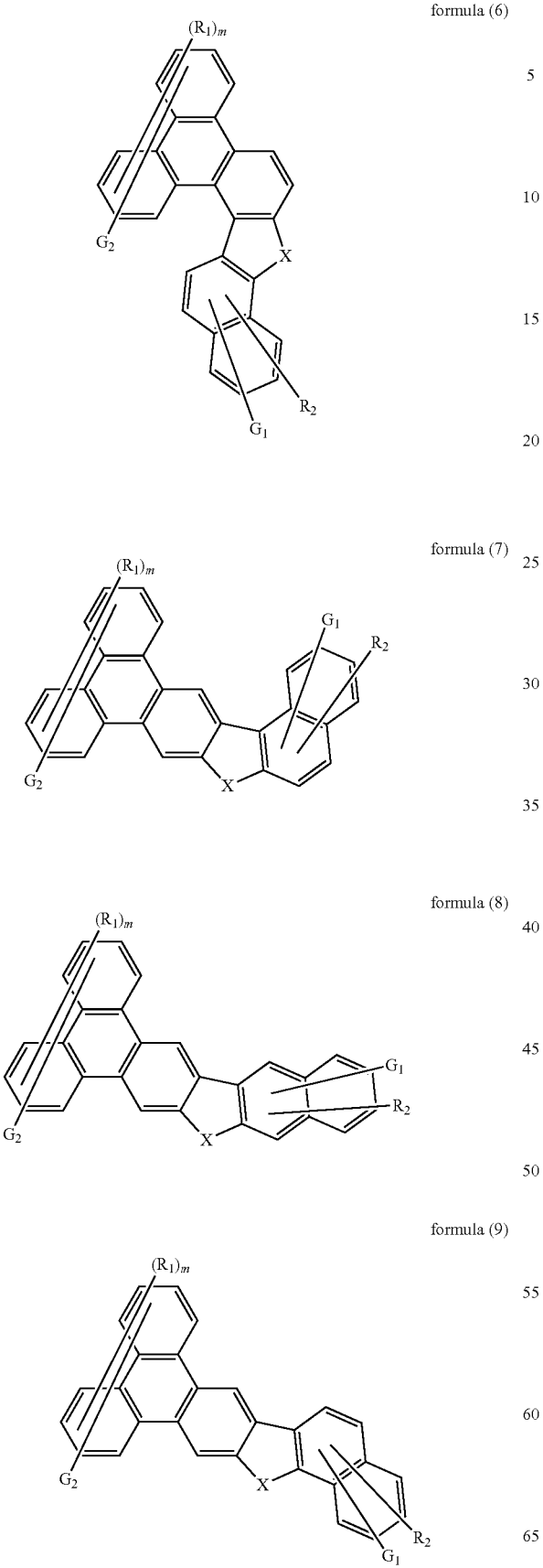
formula (6)
formula (7)
formula (8)
formula (9)
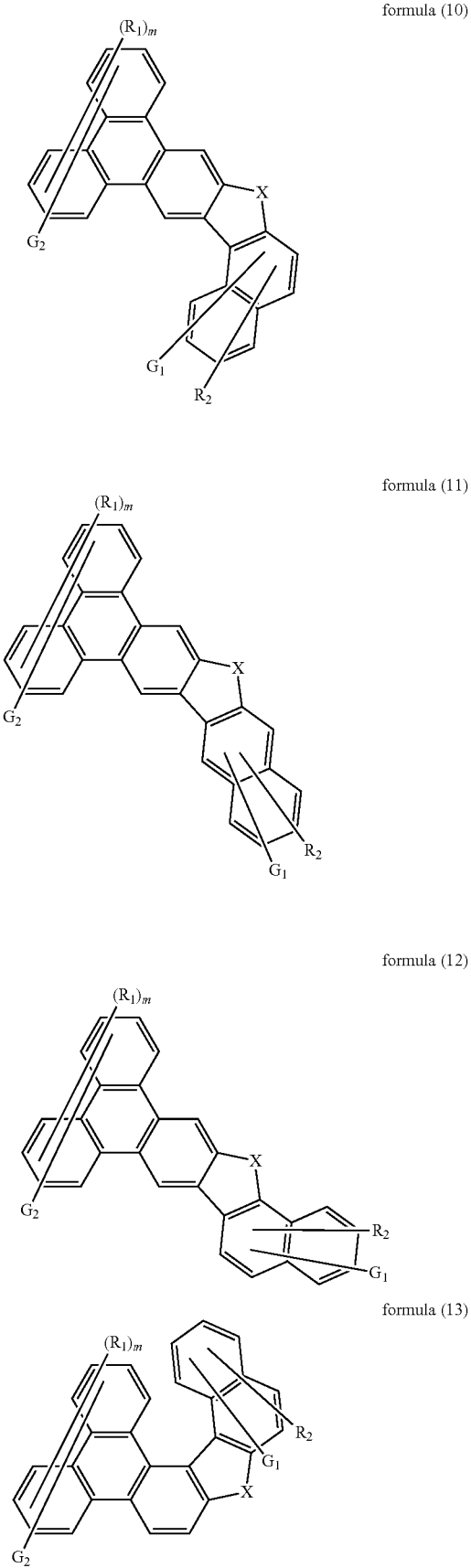
formula (10)
formula (11)
formula (12)
formula (13)

formula (14)
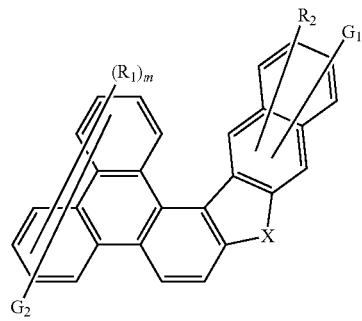

formula (15)
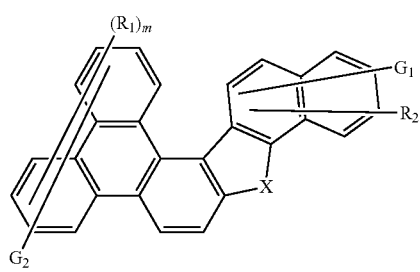

formula (16)
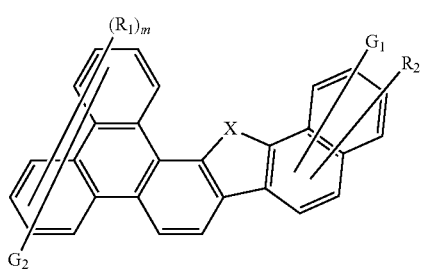

formula (17)
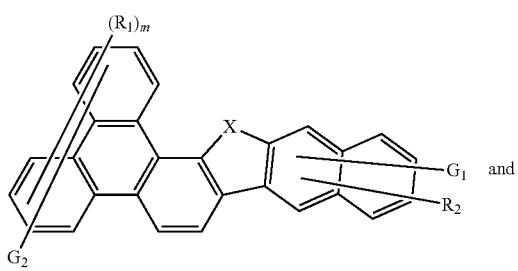 and formula (18)
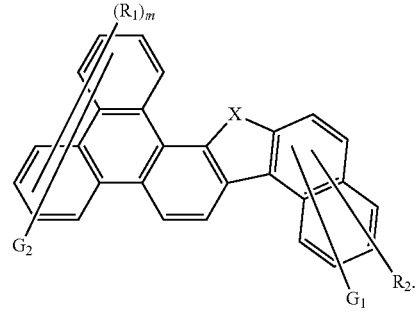

In some embodiments, the alkyl group, aralkyl group, aryl group, or heteroaryl group may be substituted by a halogen, an alkyl group, an aryl group, or a heteroaryl group.

In some embodiments, $G_1$ and $G_2$ independently represent a substituted or unsubstituted phenyl group, a substituted or unsubstituted biphenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted triphenylenyl group, a substituted or unsubstituted benzimidazole group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted diphenylphosphine oxide group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group, a substituted or unsubstituted dihydrophenazine group, a substituted or unsubstituted diphenylamine group, a substituted or unsubstituted triphenylamine group, a substituted or unsubstituted phenyldibenzofuranylamine group, or a substituted or unsubstituted phenyldibenzothiophenylamine group.

In some embodiments, $G_1$ and $G_2$ independently represent one of the following substituents:

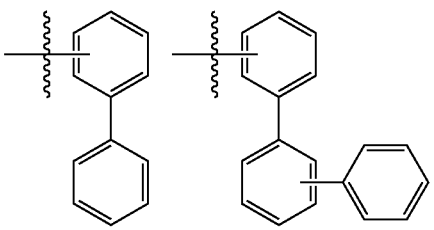

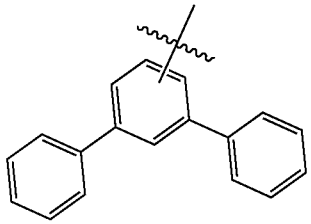

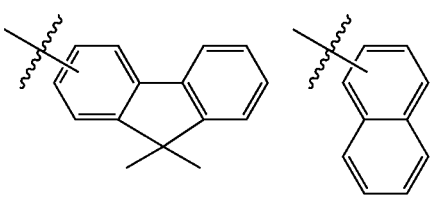

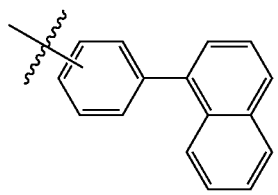

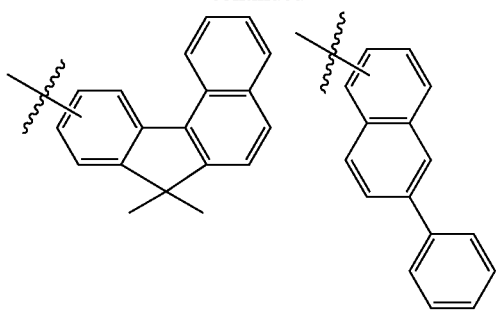
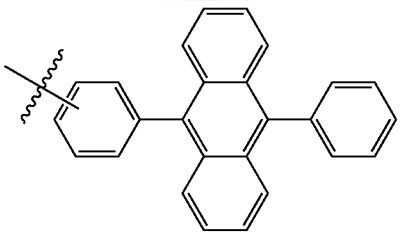
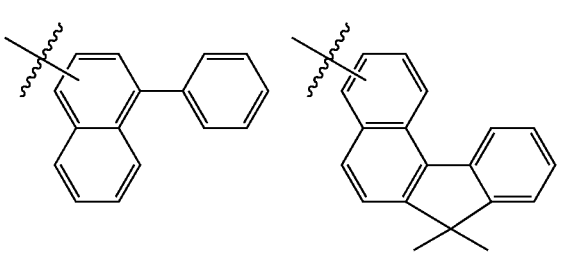
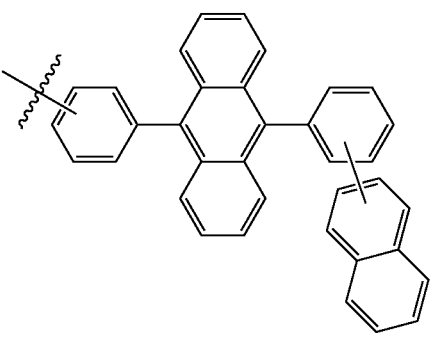
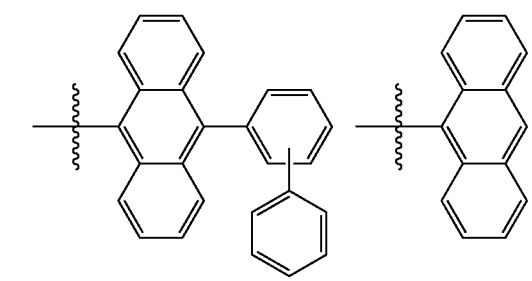
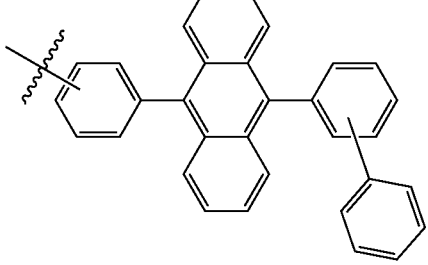
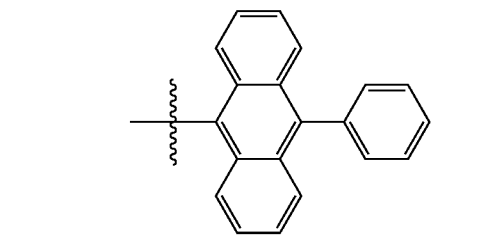
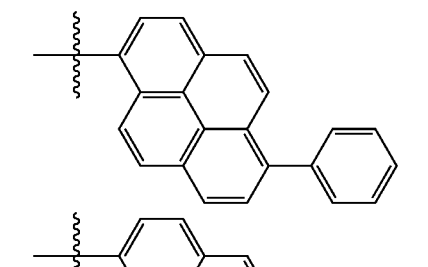
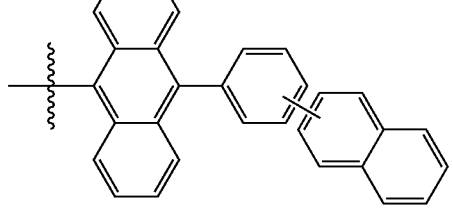
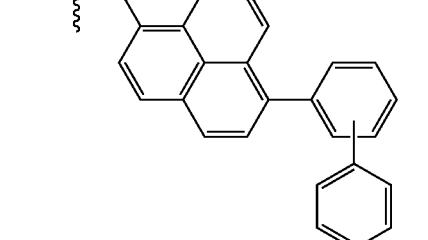
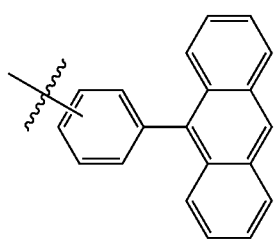
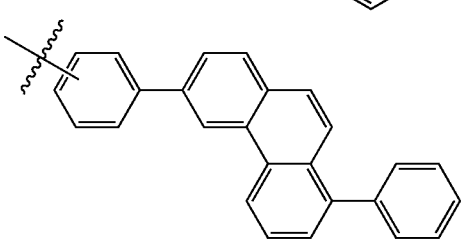

-continued
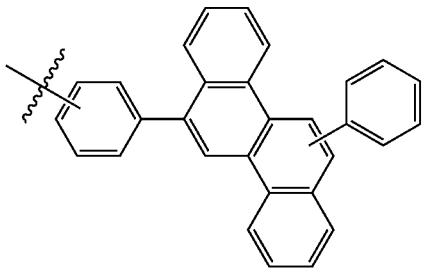
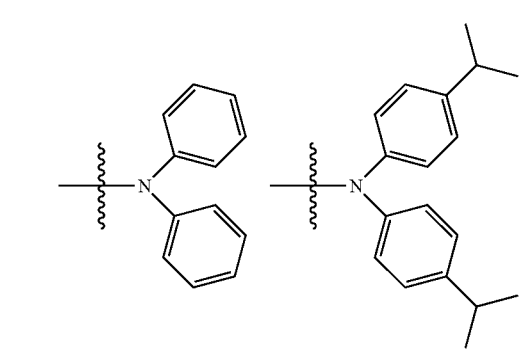
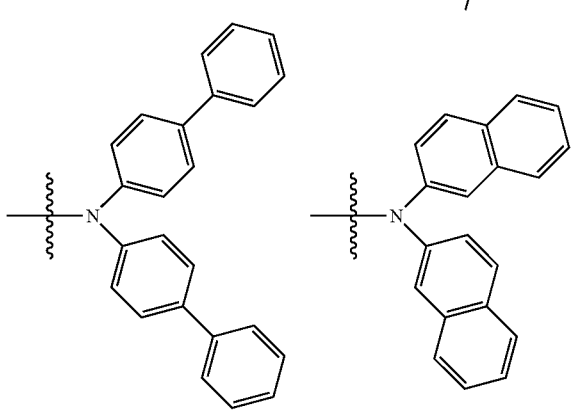
-continued
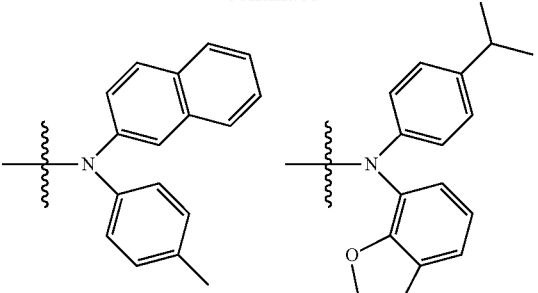
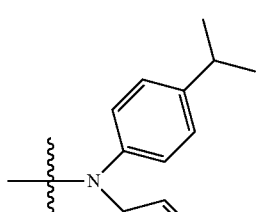
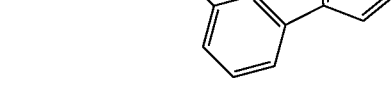
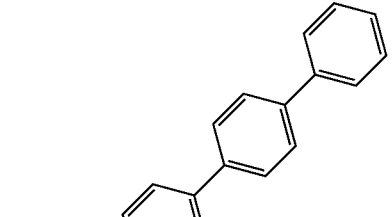
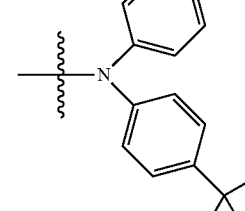
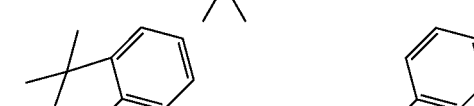
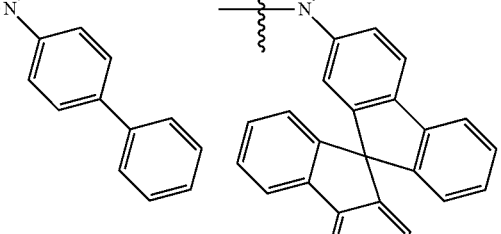

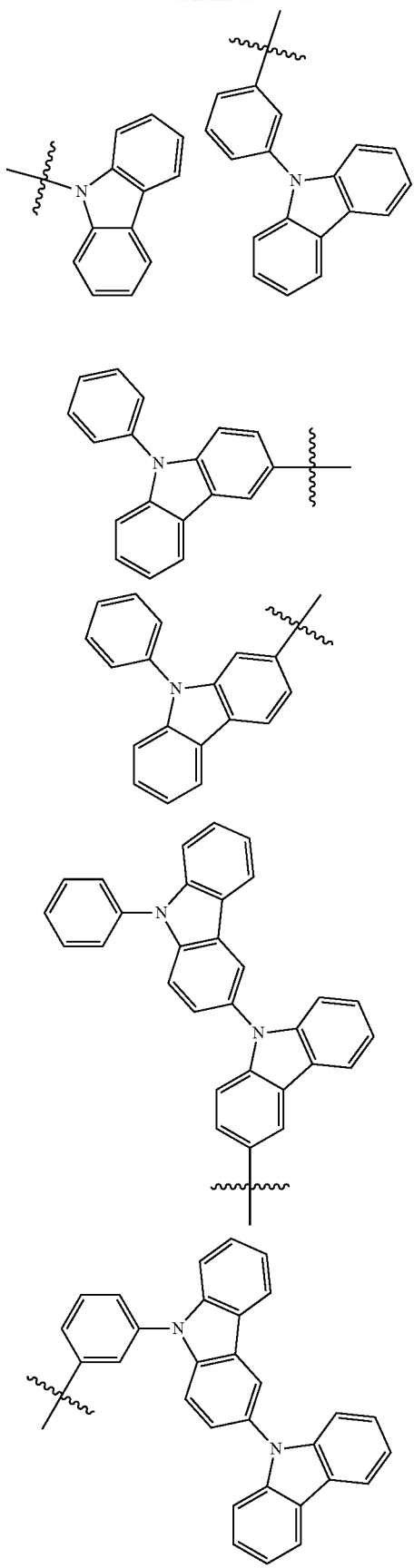
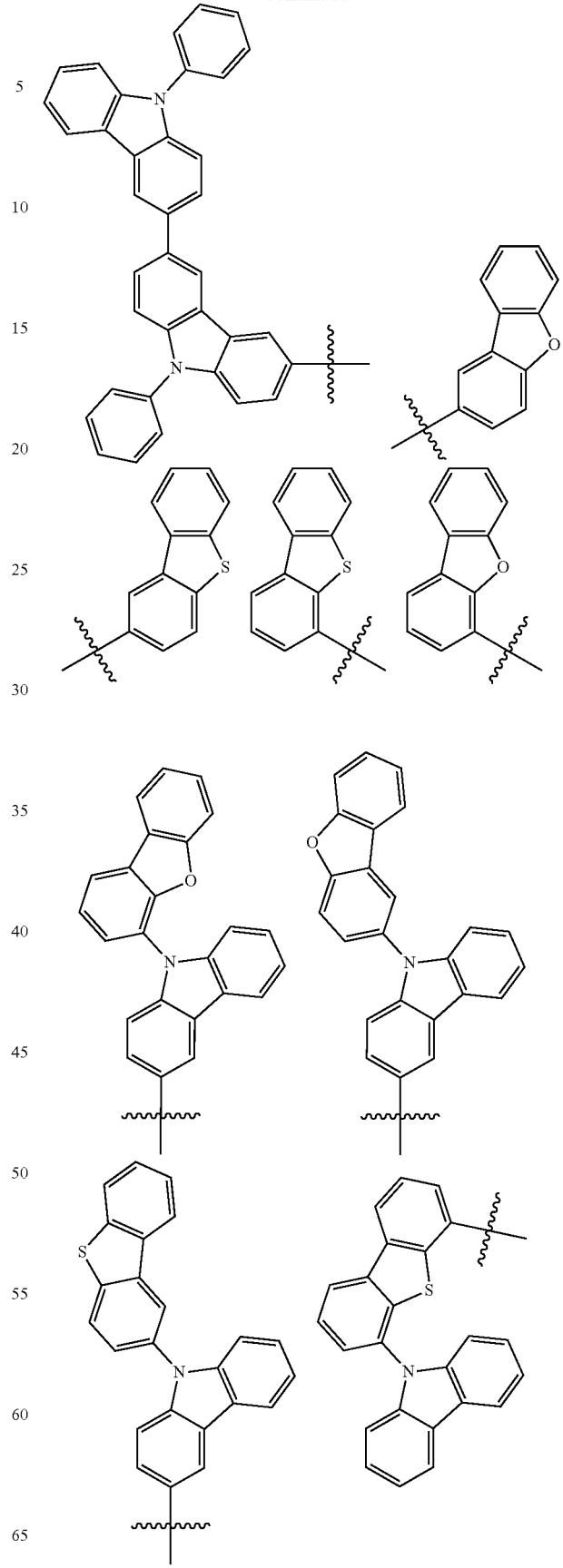

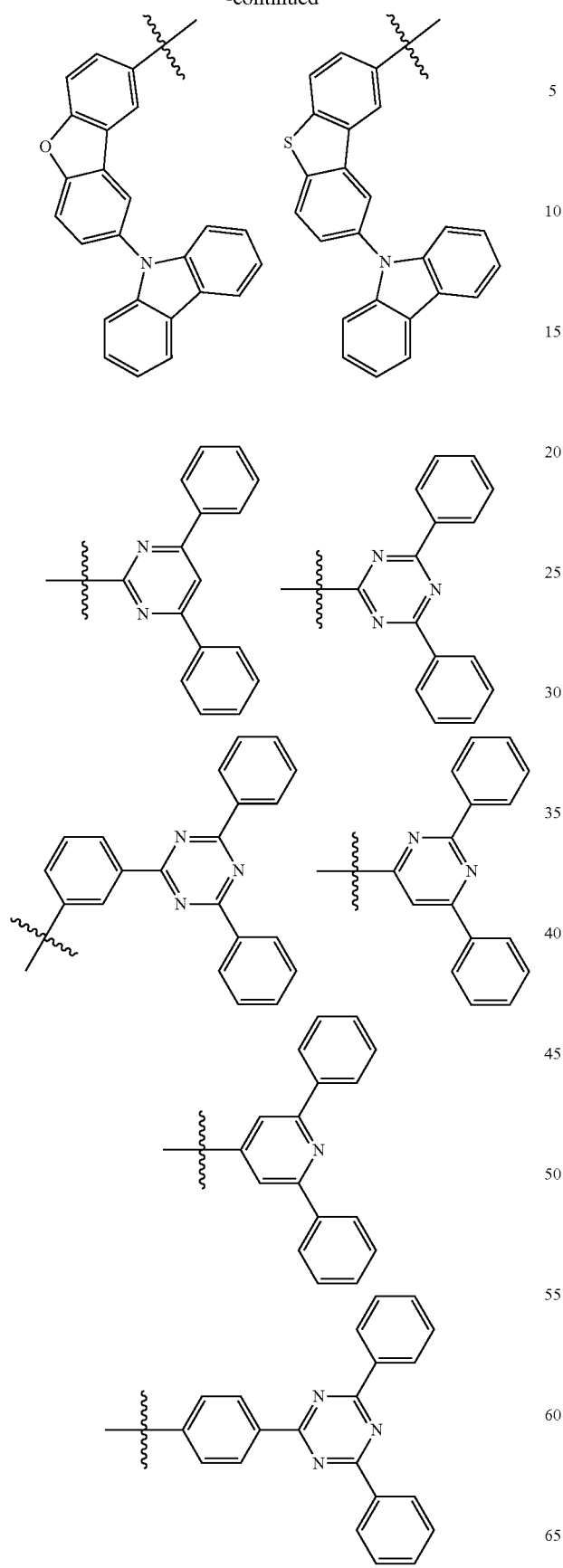
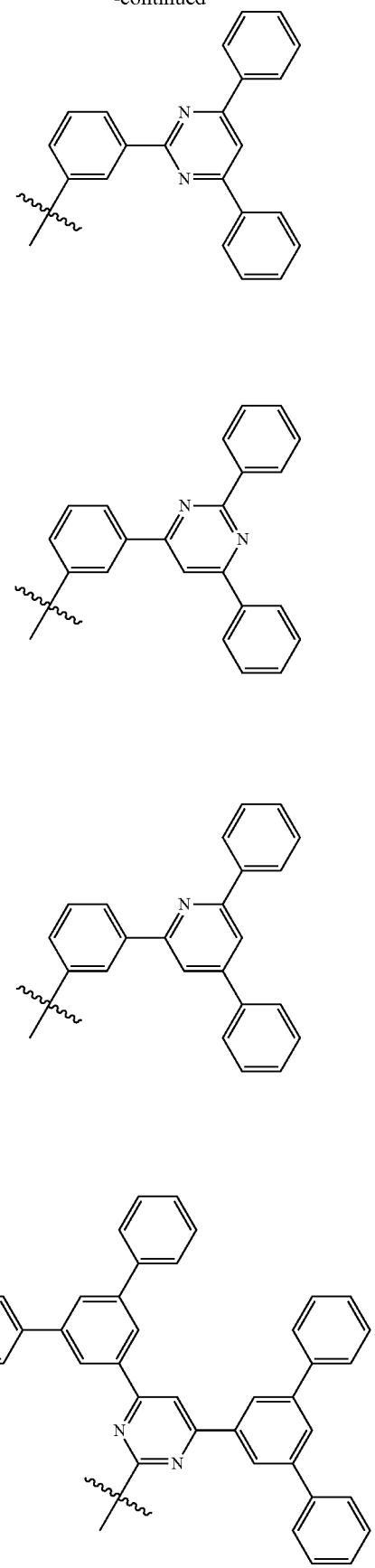

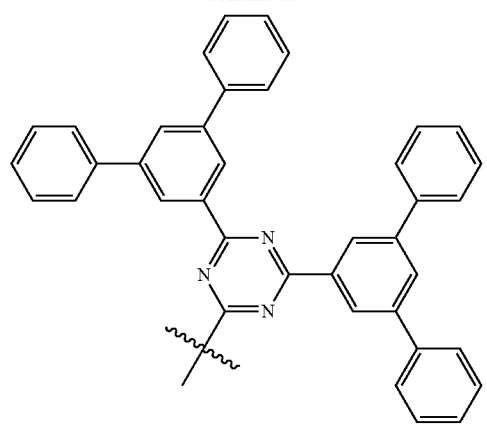
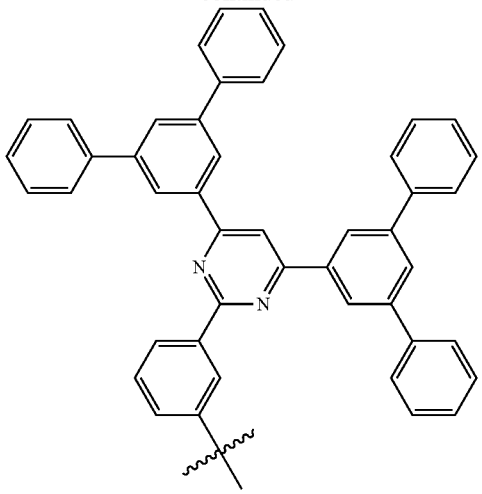
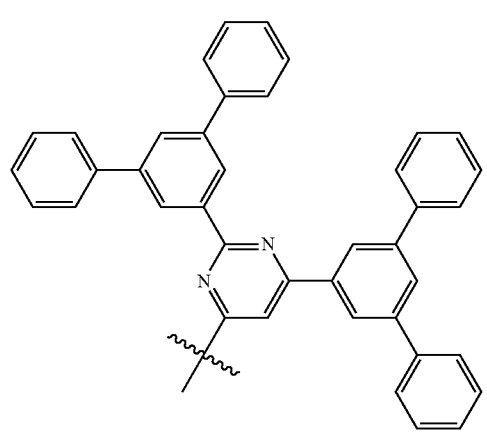
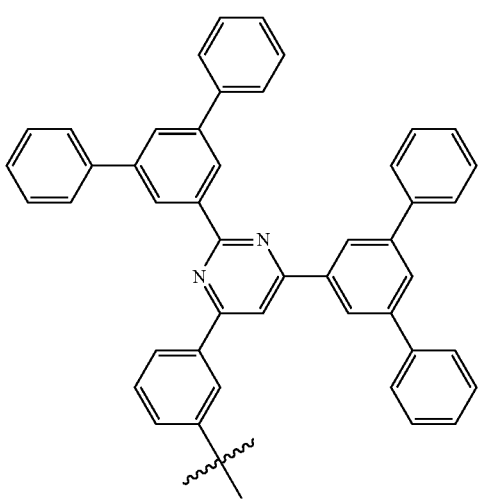
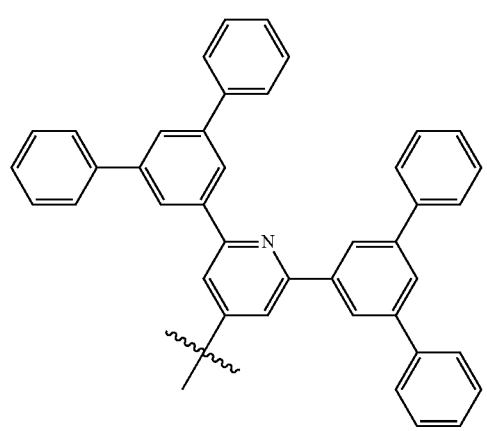
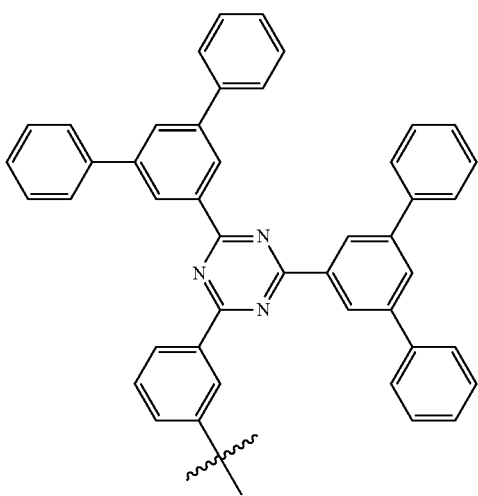

-continued
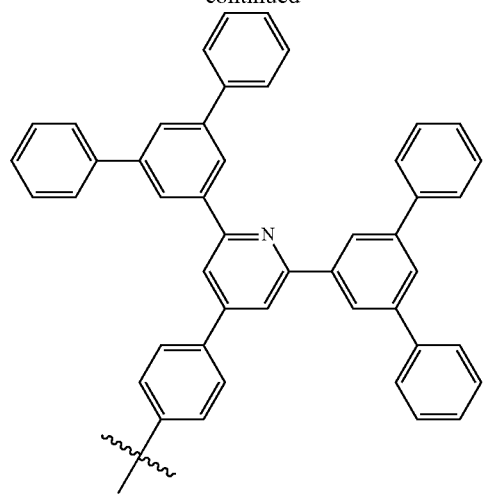
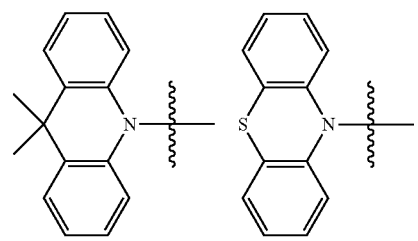
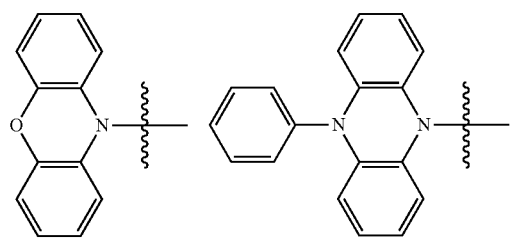
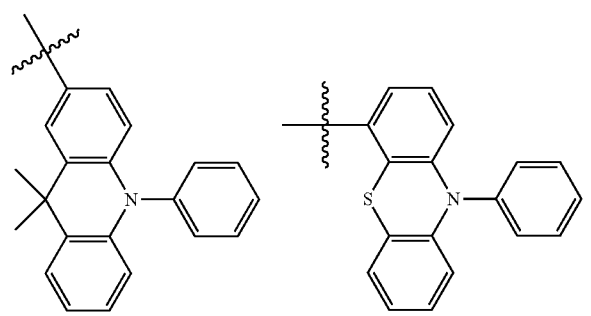
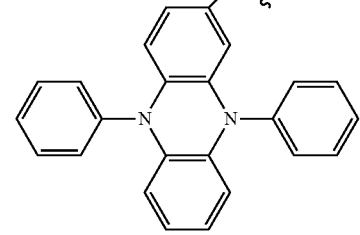
-continued
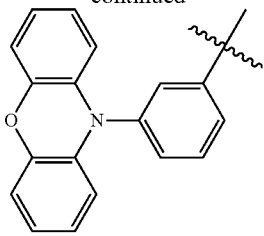
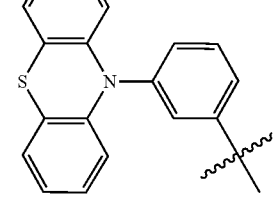 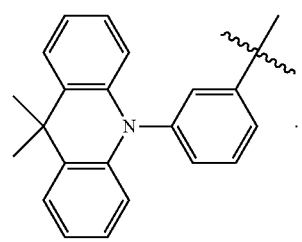
The organic compound may be one of the following compounds
Compound 1
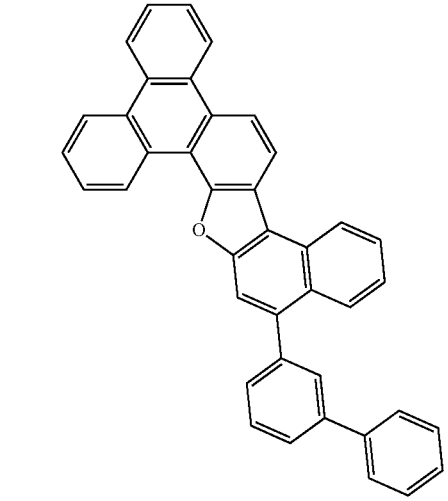
Compound 2
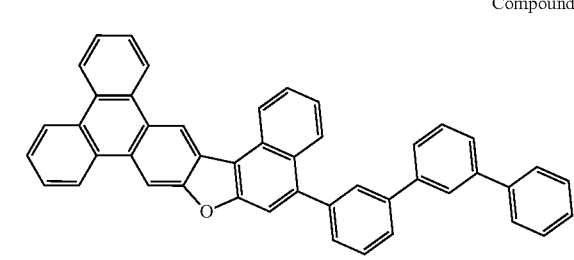

Compound 3
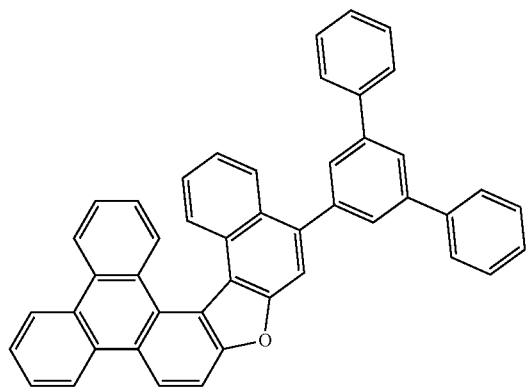
Compound 4
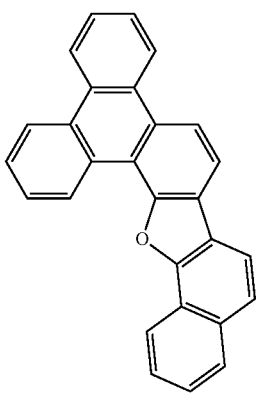
Compound 5
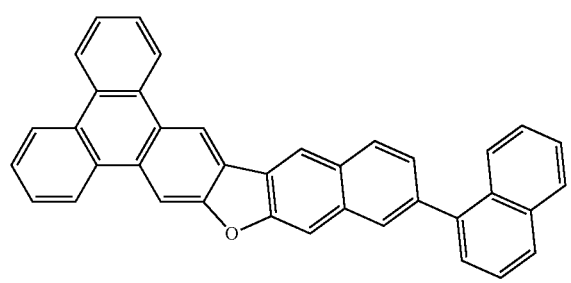
Compound 6
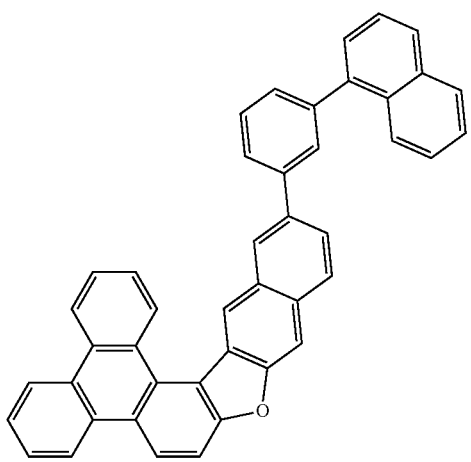
Compound 7
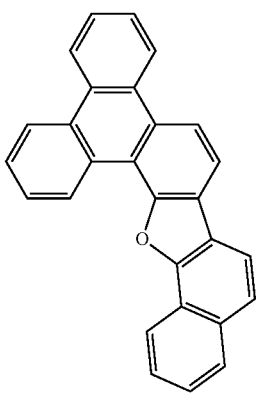
Compound 8
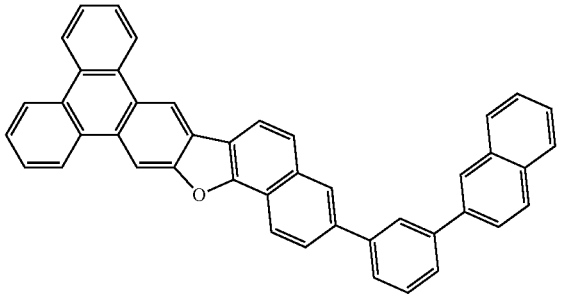
Compound 9
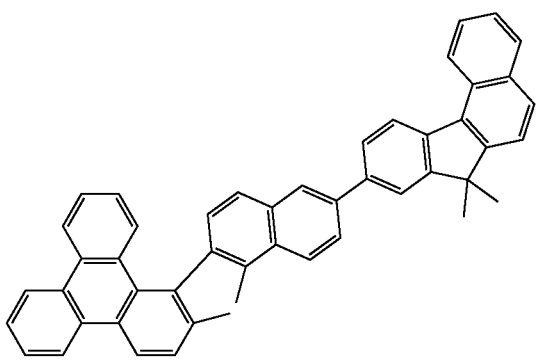

-continued
Compound 10
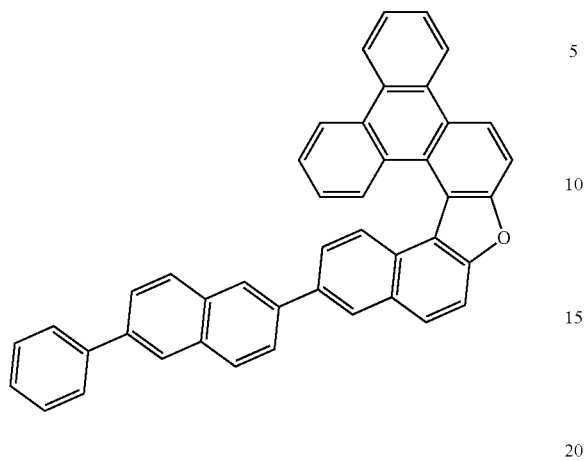
Compound 11
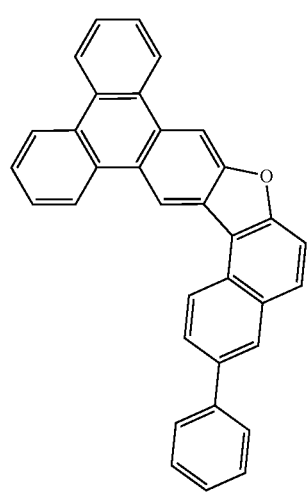
Compound 12
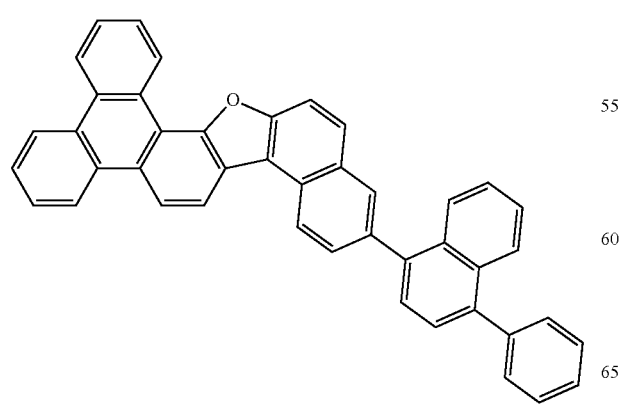
Compound 13
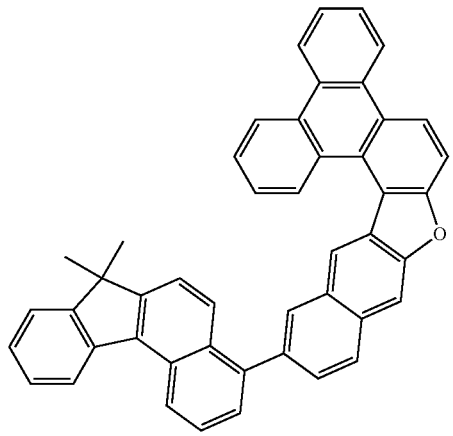
Compound 14
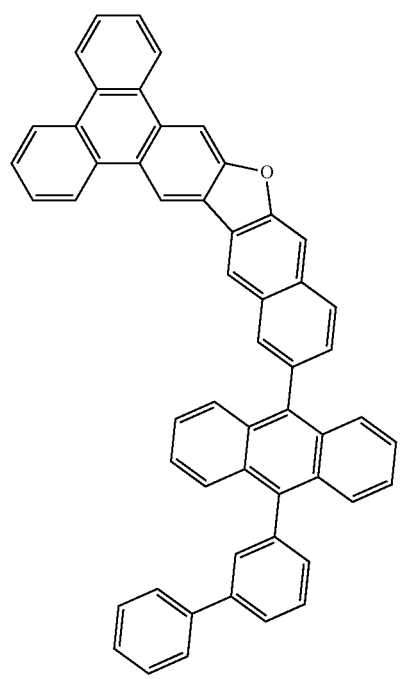
Compound 15
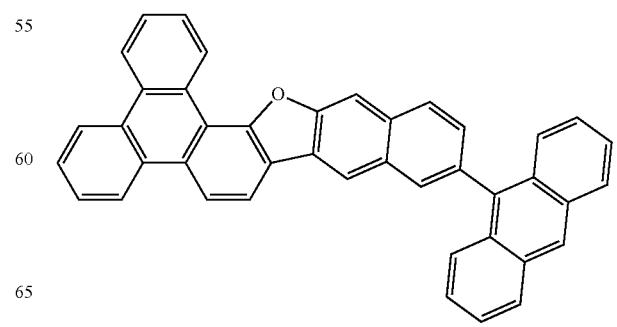

Compound 16
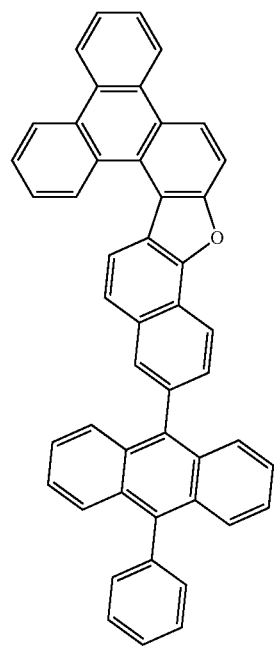
Compound 17
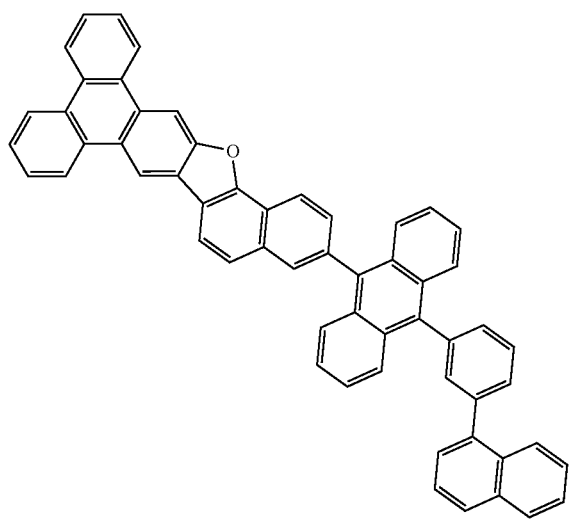
Compound 18
Compound 19
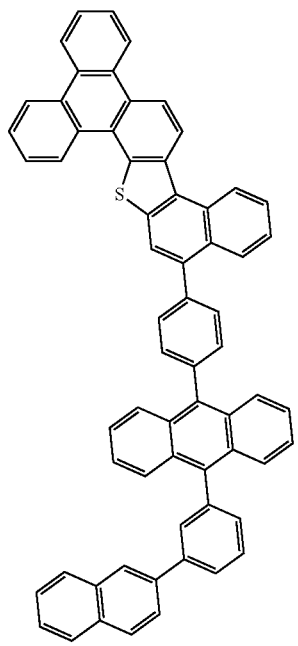
Compound 20
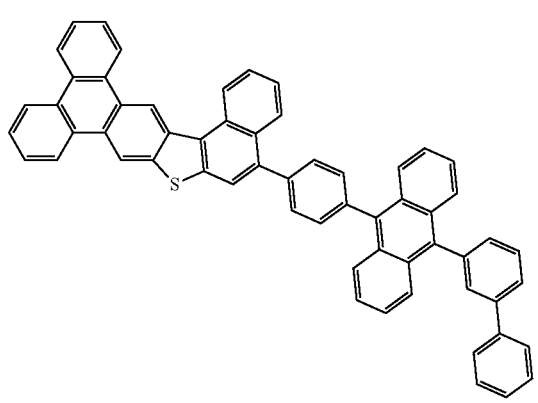
Compound 21
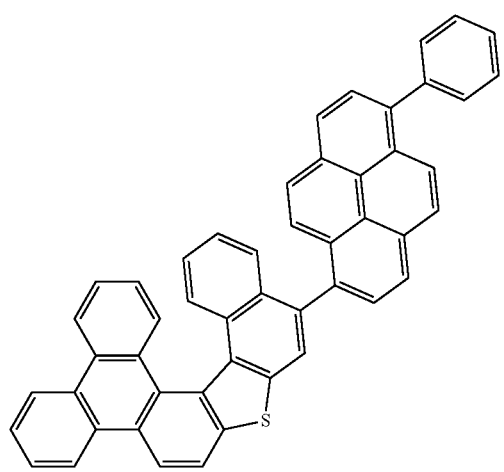

-continued
Compound 22
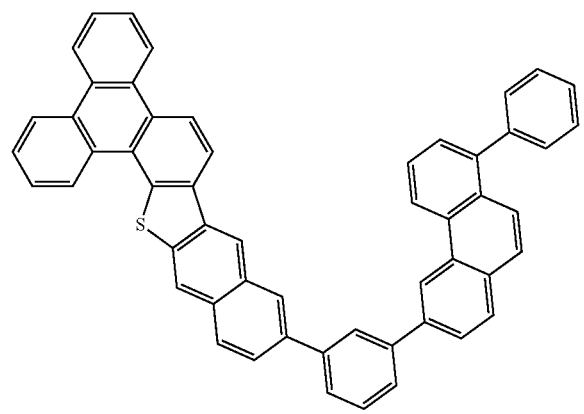
Compound 23
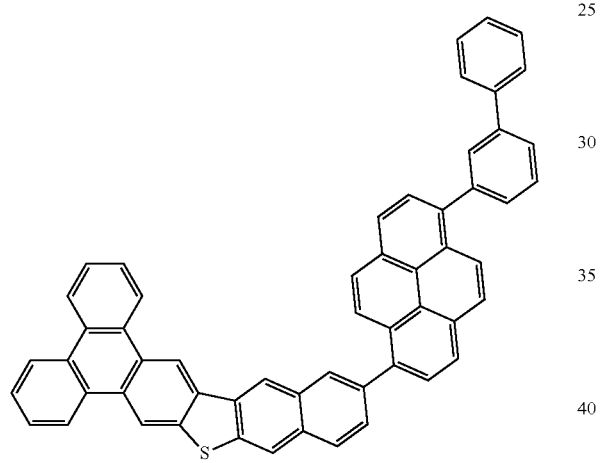
Compound 24
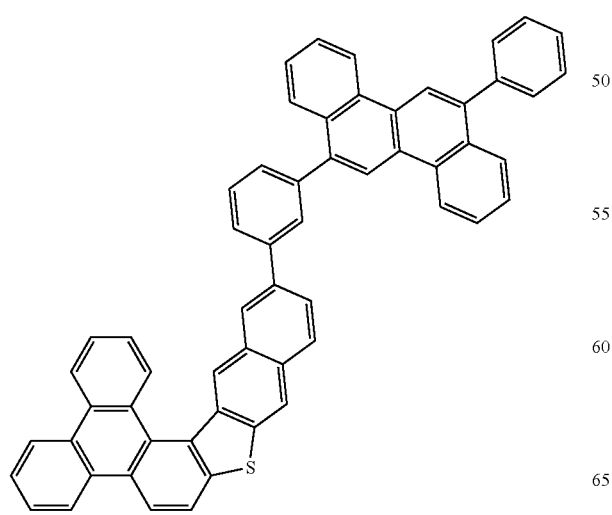
Compound 25
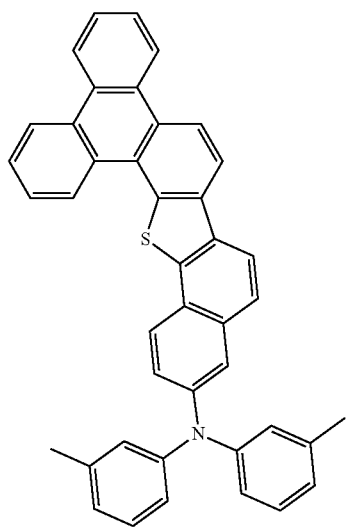
Compound 26
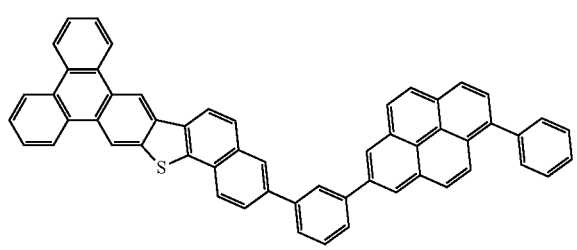
Compound 27
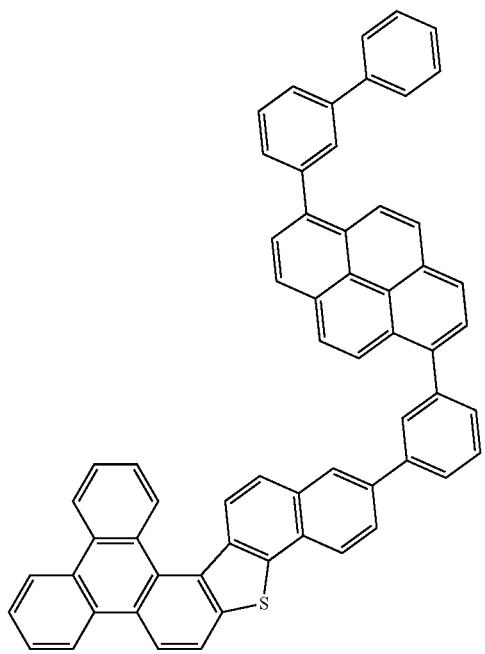

Compound 28
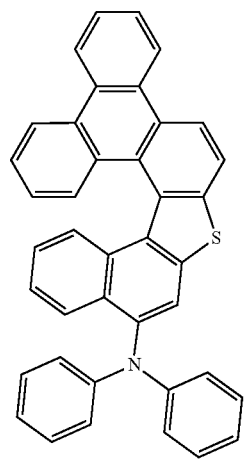
Compound 31
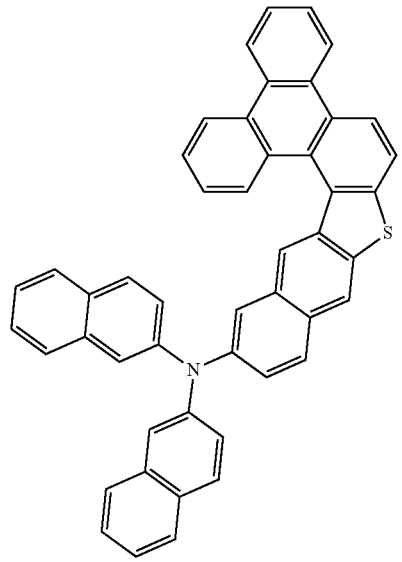
Comound 29
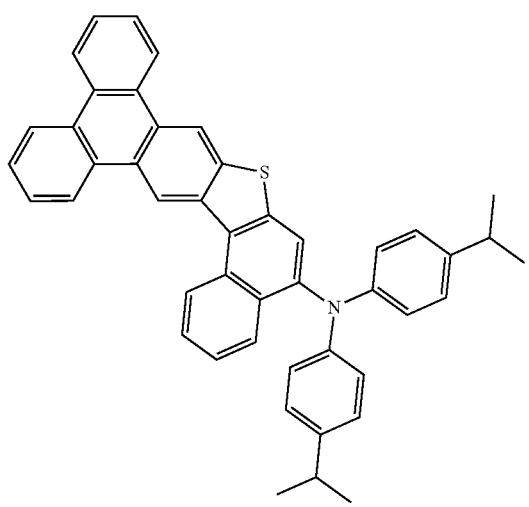
Compound 32
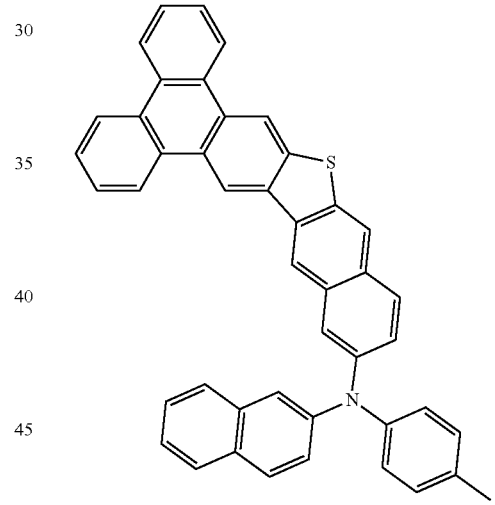
Compound 30
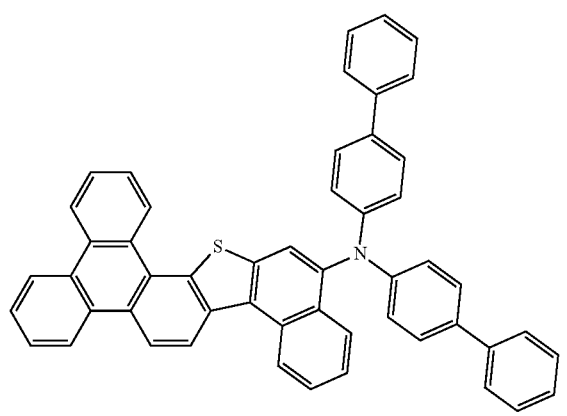
Compound 33
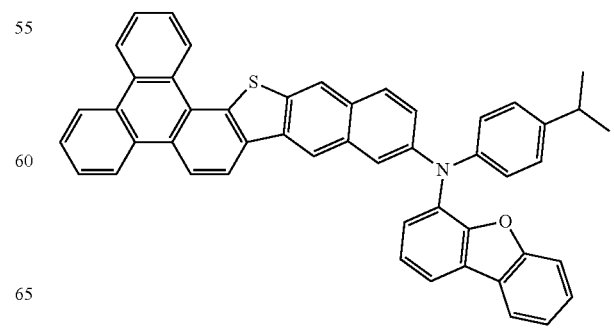

Compound 34
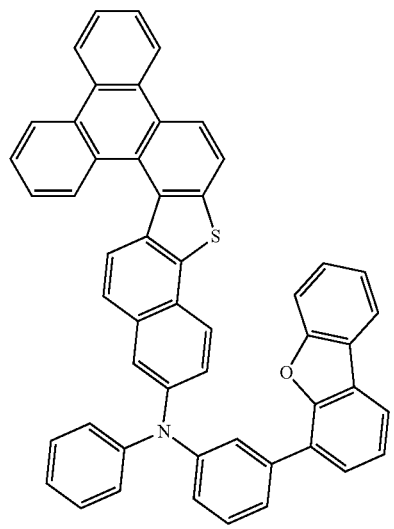
Compound 35
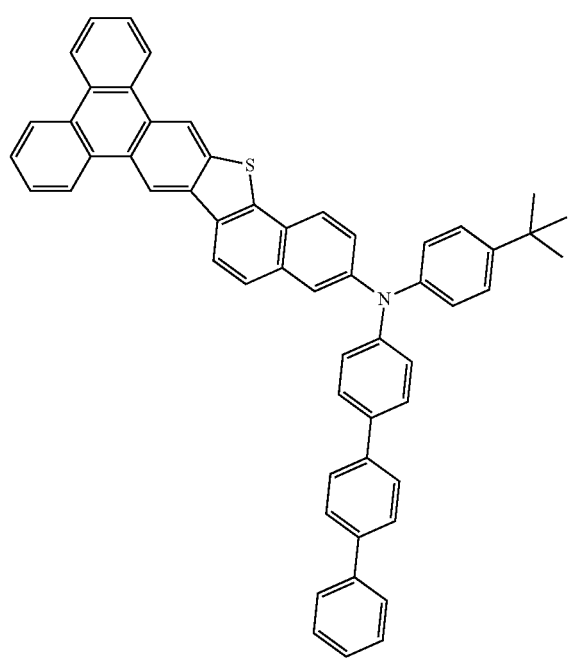
Compound 36
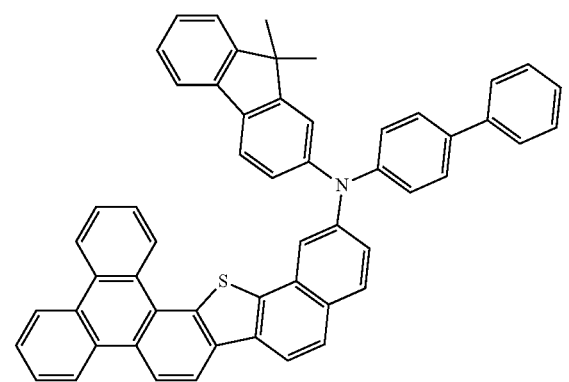
Compound 37
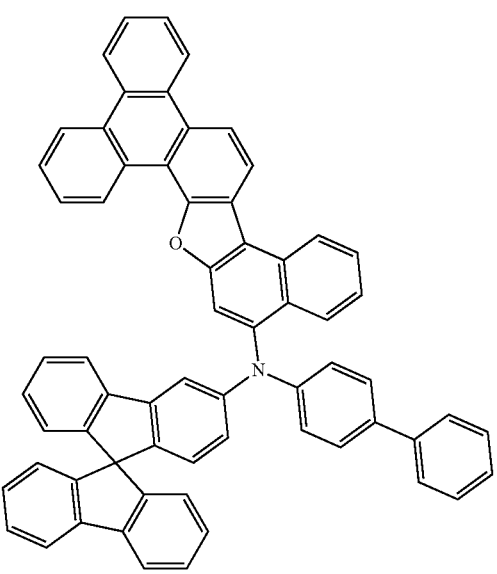
Compound 38
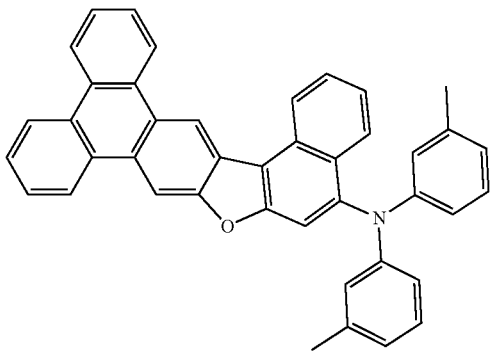
Compound 39
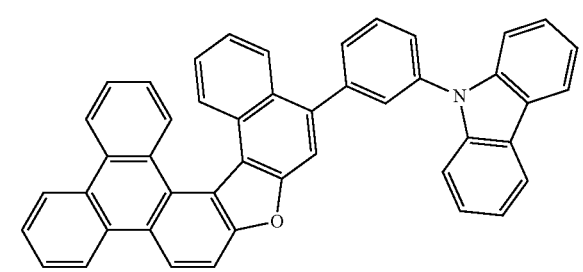

Compound 40
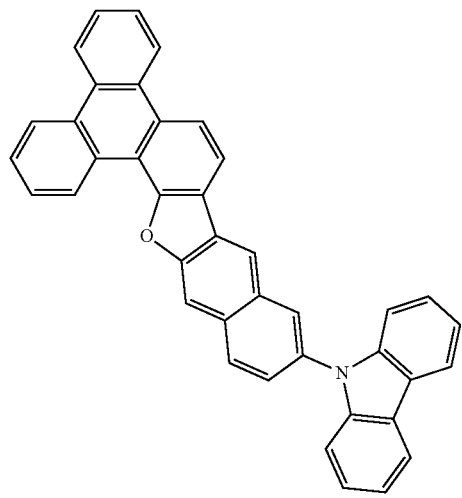
Compound 41
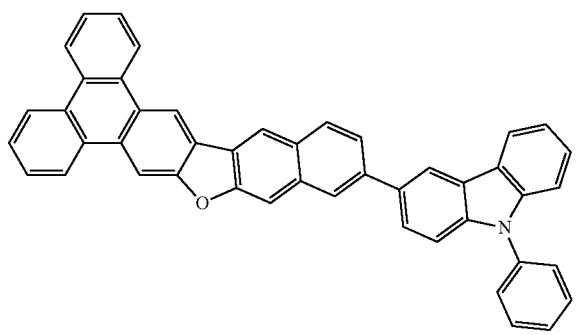
Compound 42
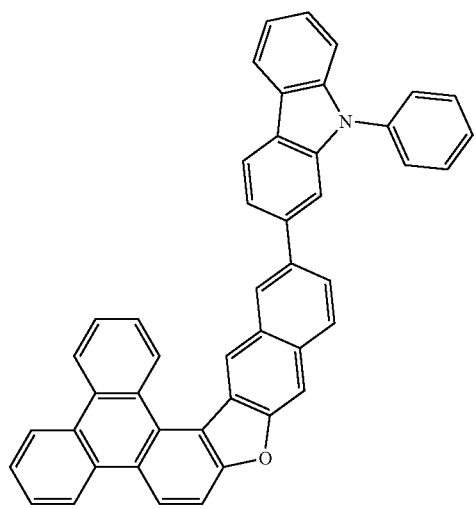
Compound 43
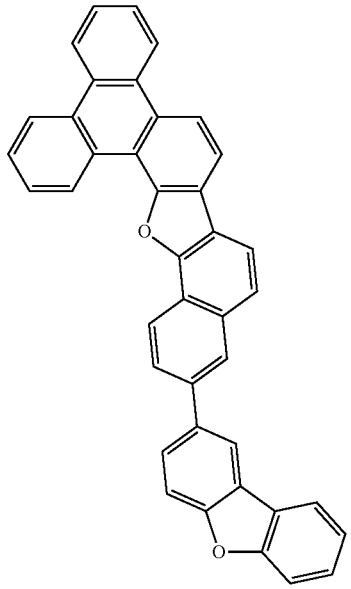
Compound 44
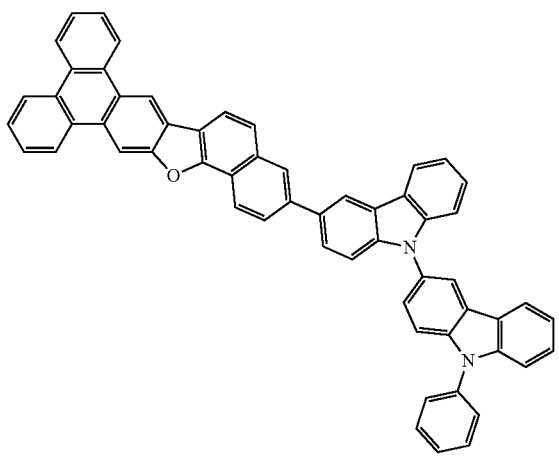
Compound 45
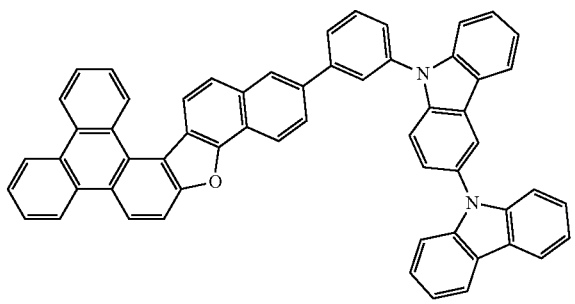

Compound 46
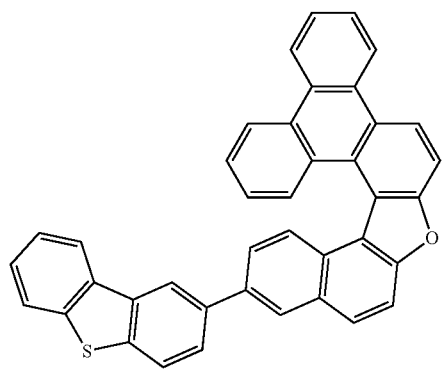
Compound 47
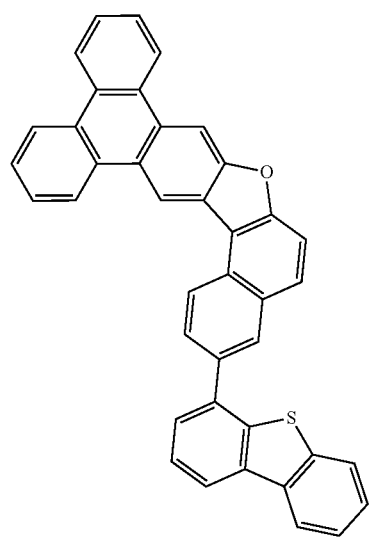
Compound 48
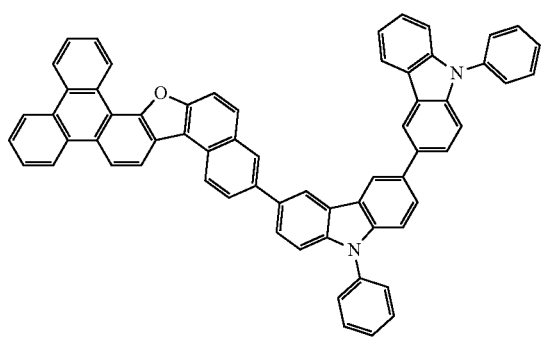
Compound 49
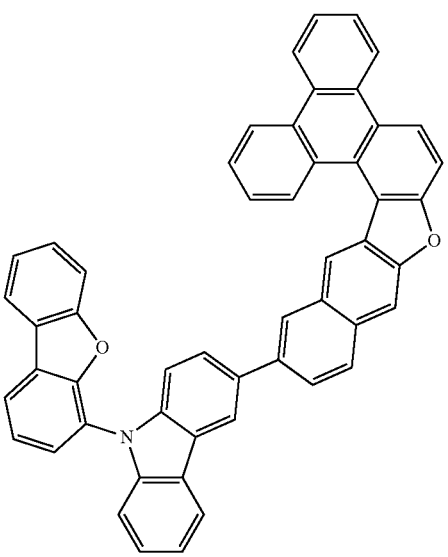
Compound 50
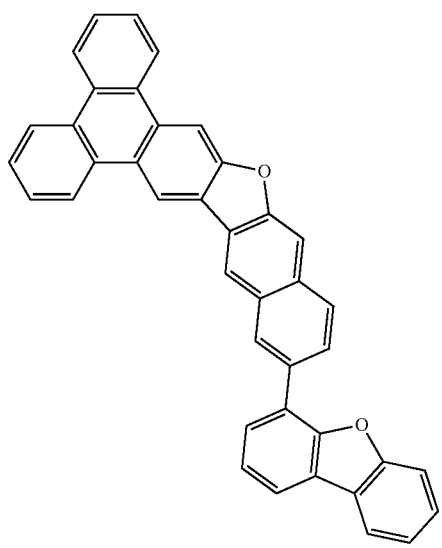
Compound 51
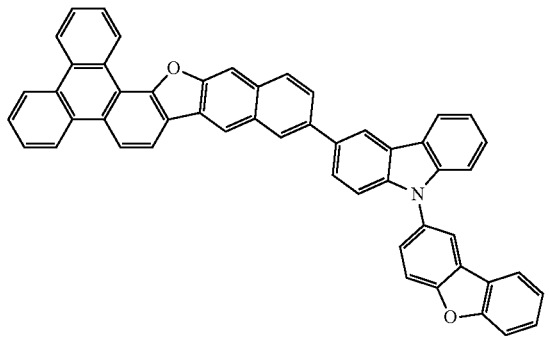

Compound 52
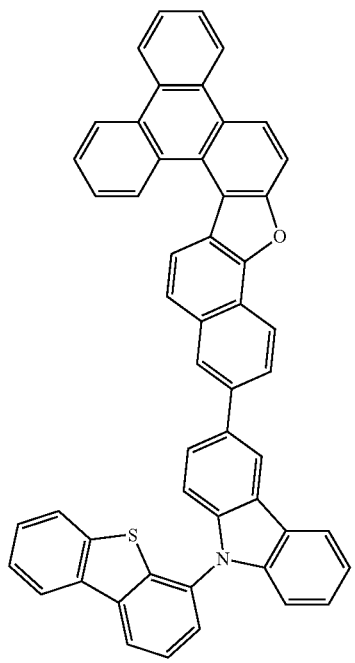
Compound 55
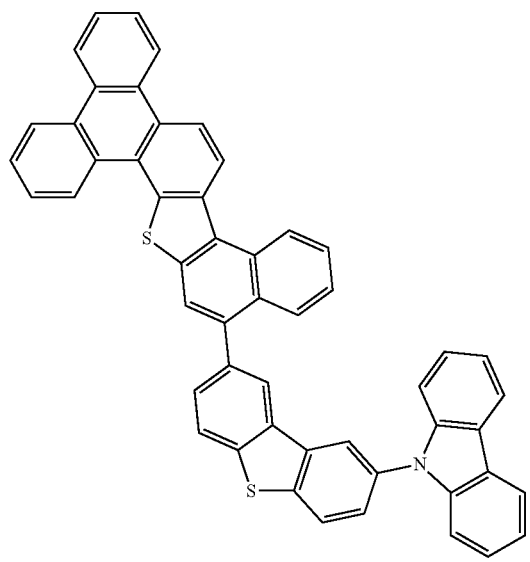
Compound 53
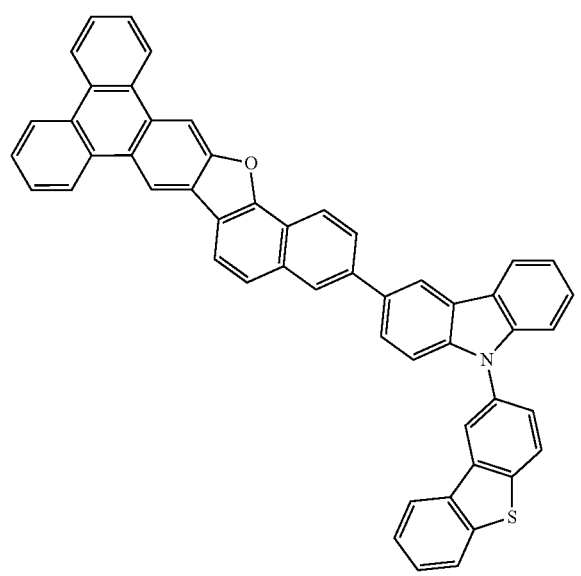
Compound 56
Compound 54
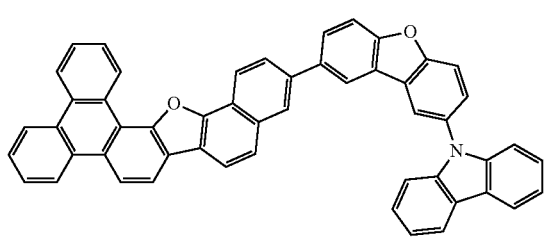
Compound 57
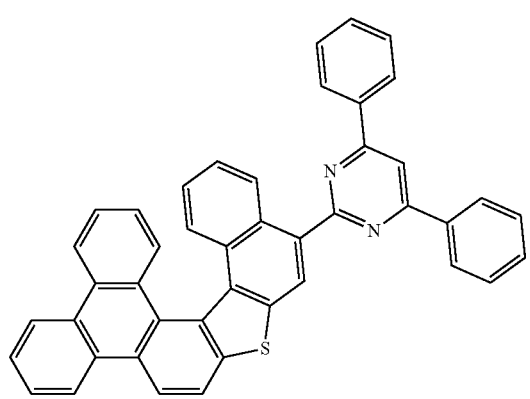

Compound 58
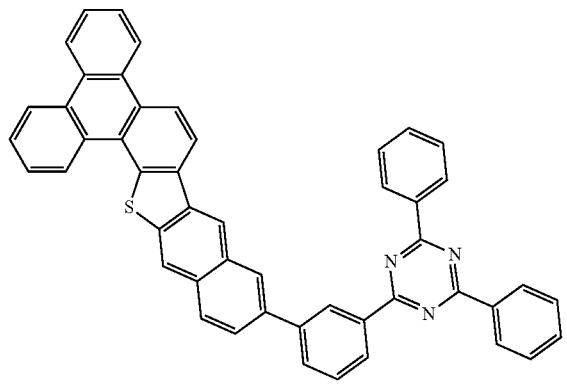
Compound 59
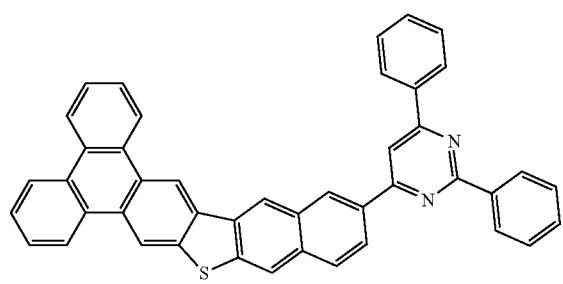
Compound 60
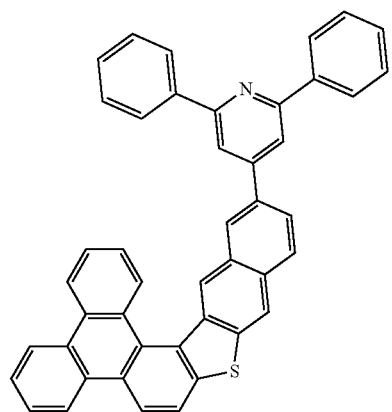
Compound 61
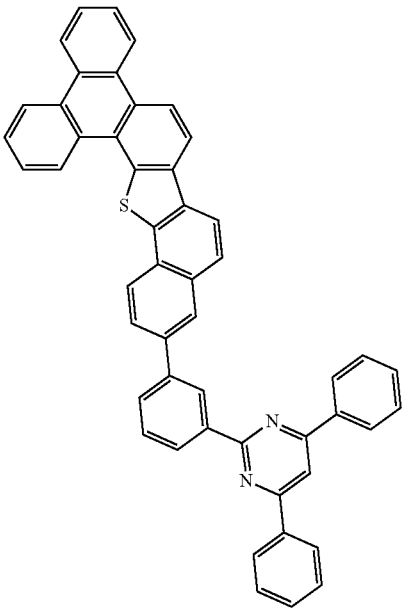
Compound 62
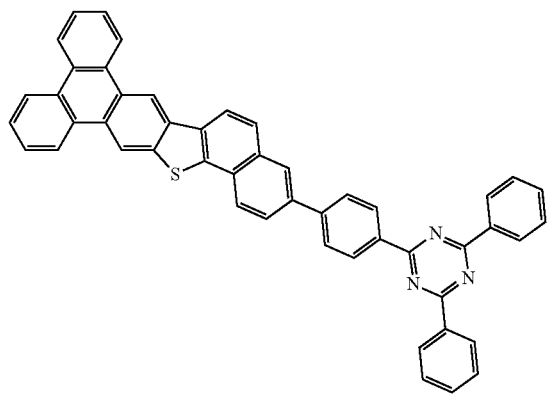
Compound 63
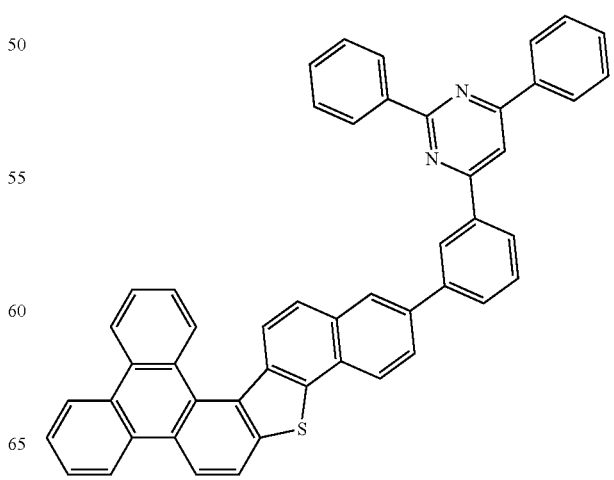

Compound 64
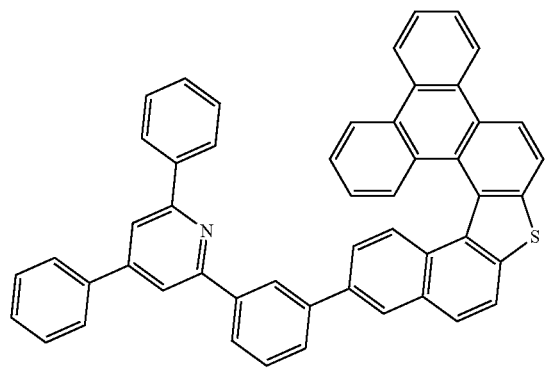
Compound 65
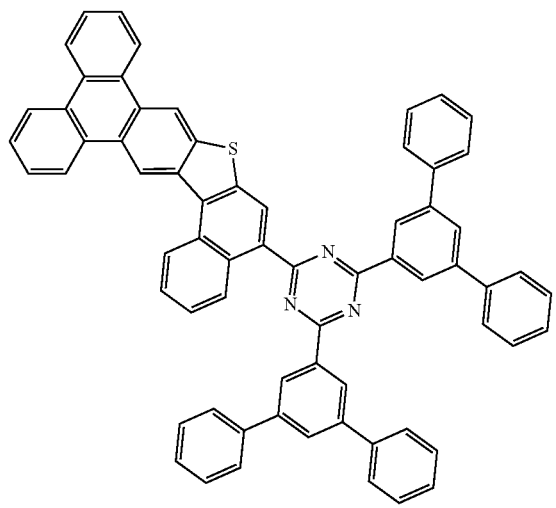
Compound 66
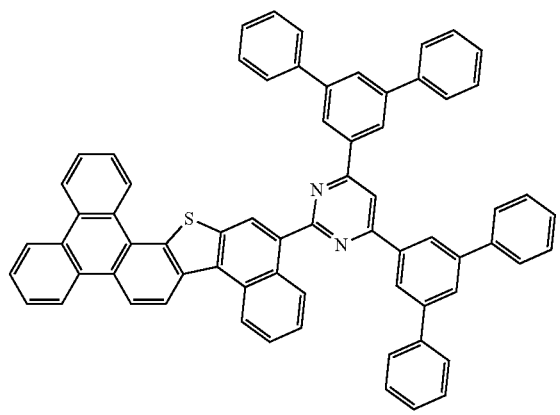
Compound 67
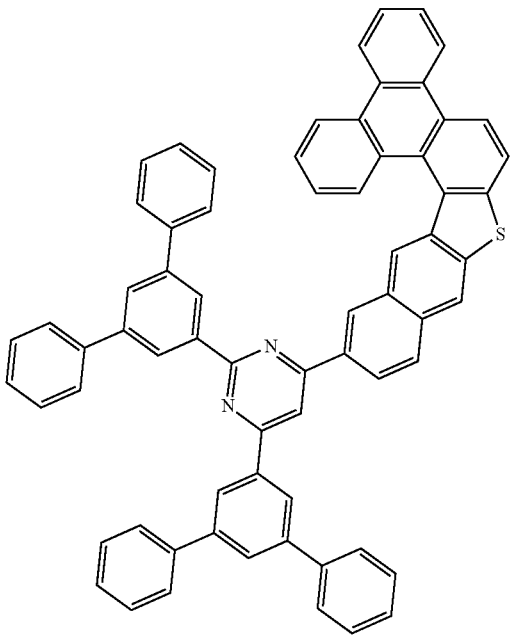
Compound 68
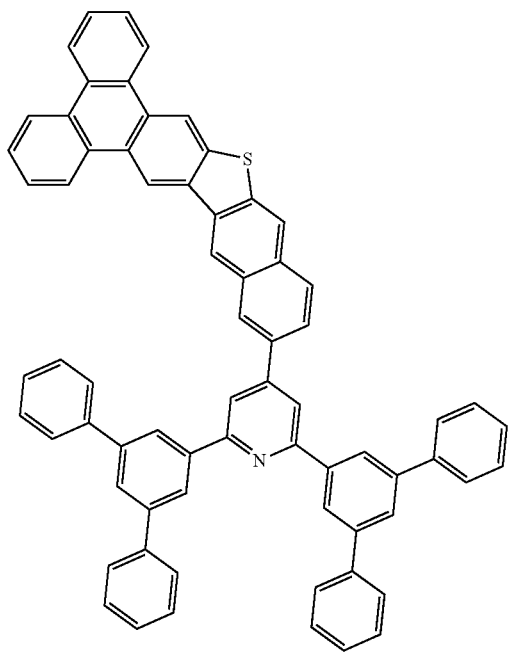
Compound 69
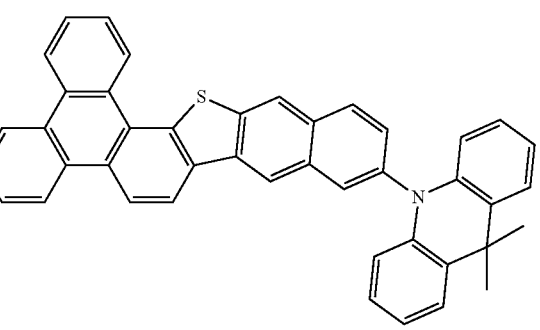

Compound 70
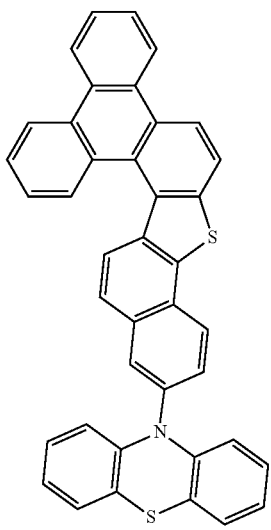
Compound 73
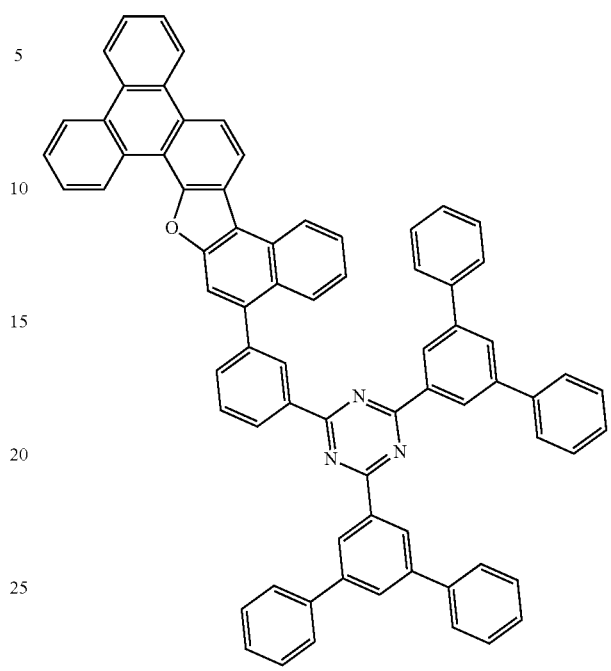
Compound 71
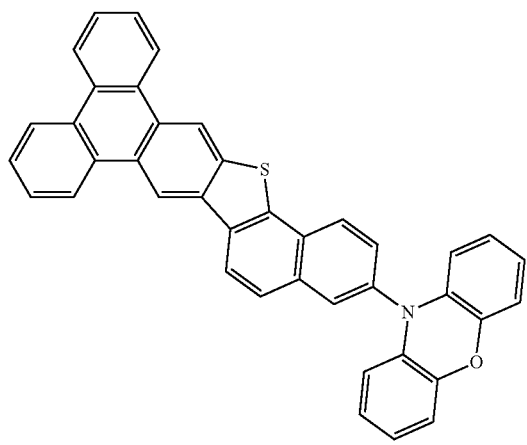
Compound 74
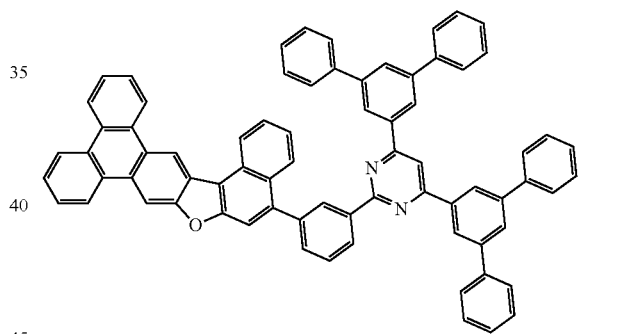
Compound 72
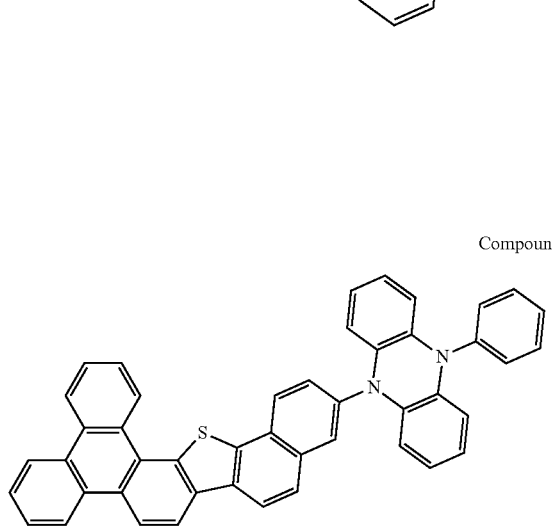
Compound 75
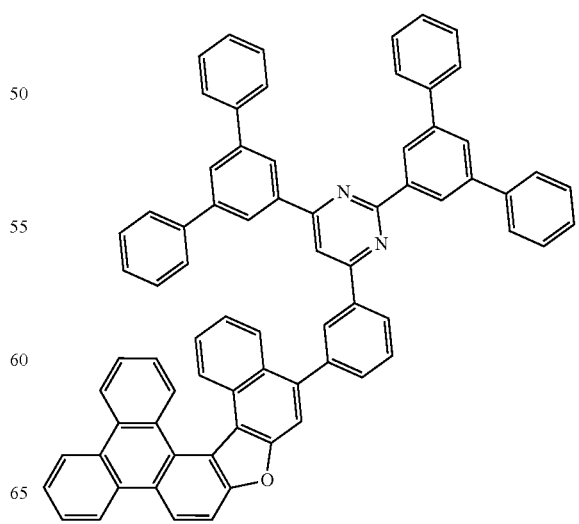

Compound 76
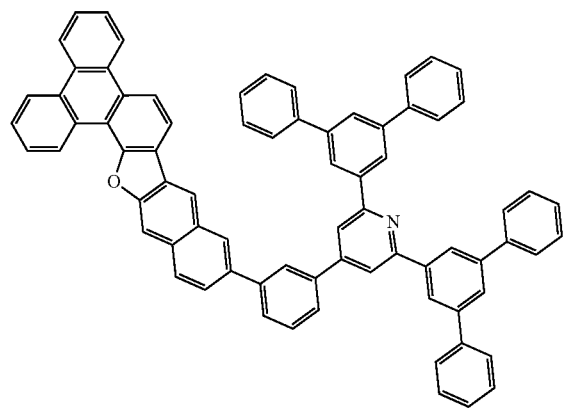
Compound 77
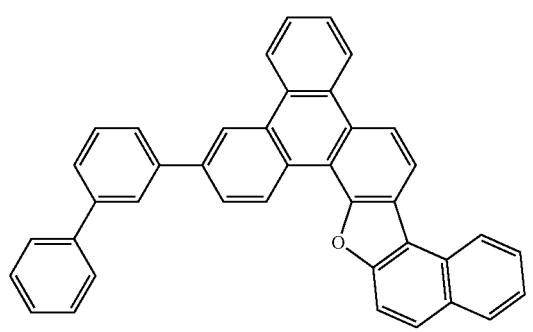
Compound 78
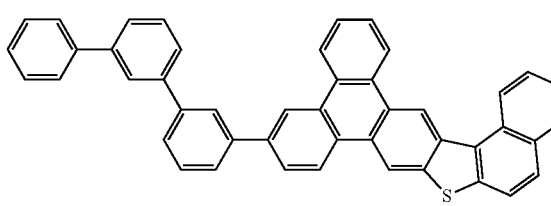
Compound 79
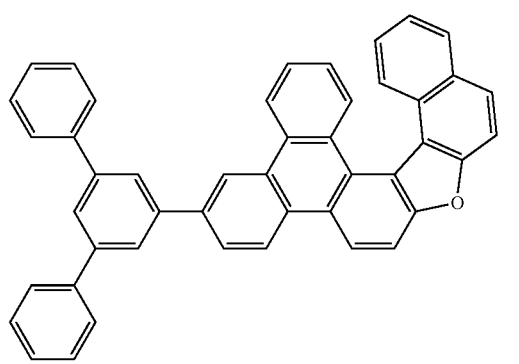
Compound 80
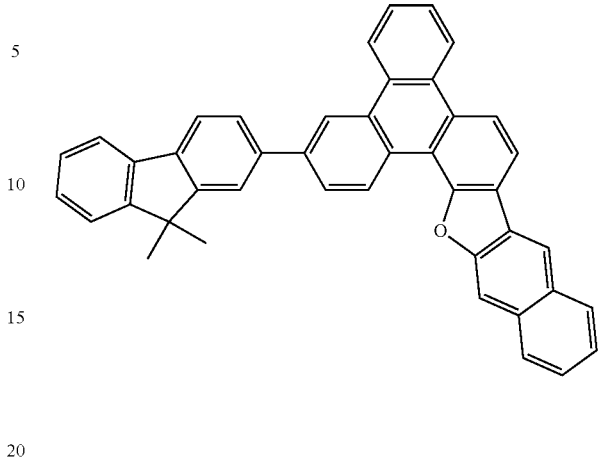
Compound 81
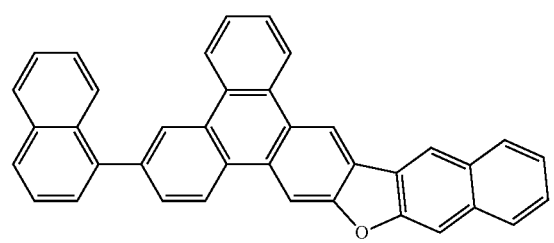
Compound 82
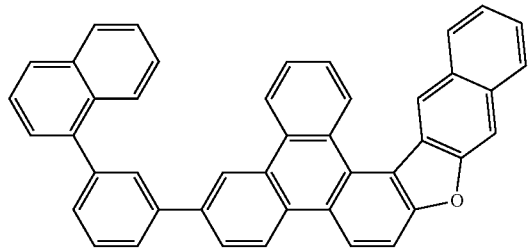
Compound 83
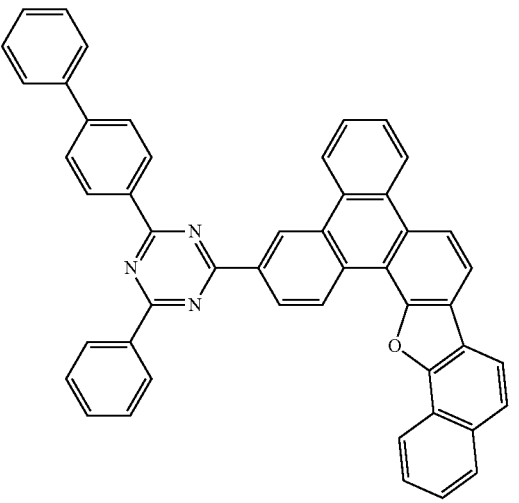

Compound 84
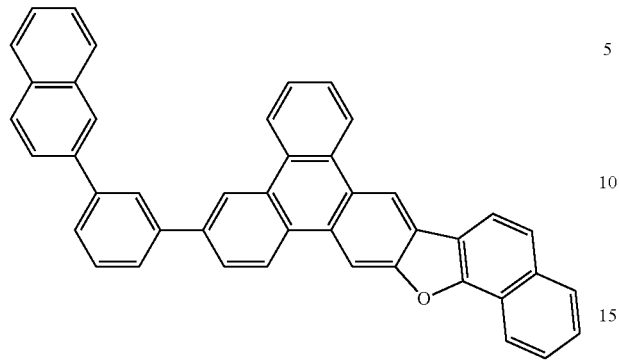
Compound 85
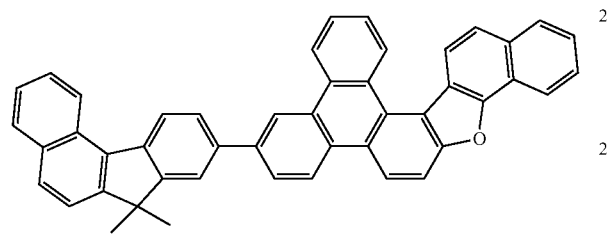
Compound 86
Compound 87
Compound 88
Compound 89
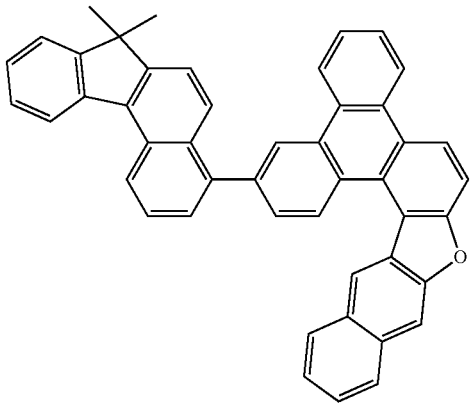
Compound 90
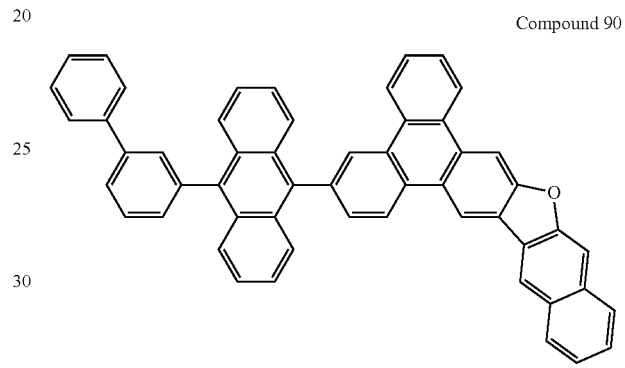
Compound 91
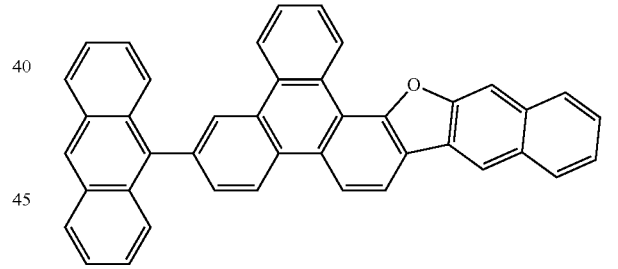
Compound 92
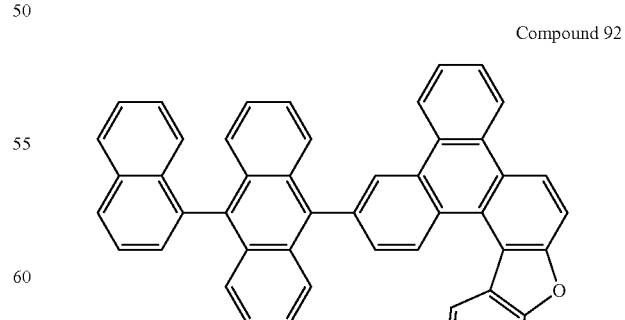

Compound 93
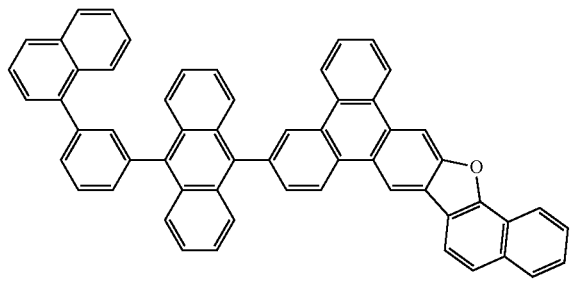
Compound 94
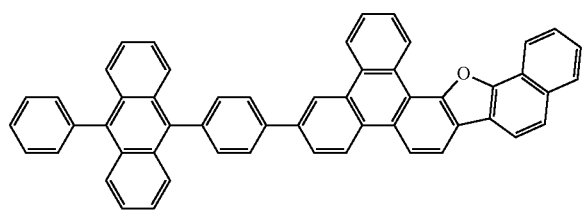
Compound 95
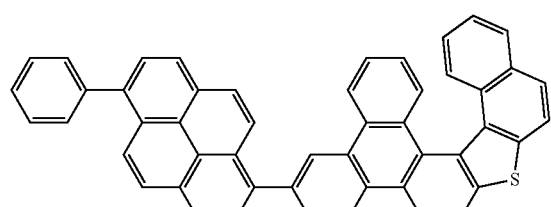
Compound 96
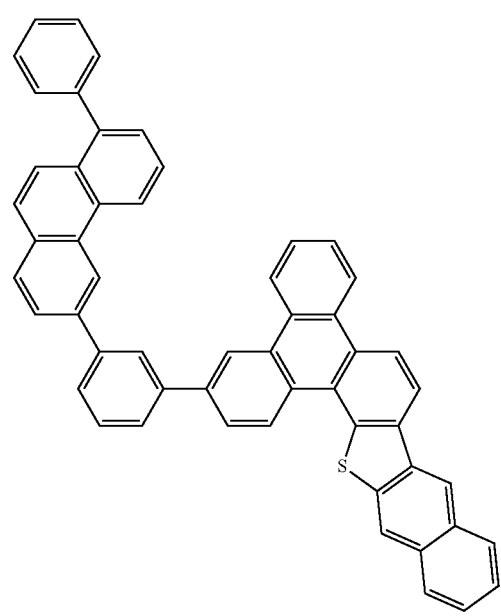
Compound 97
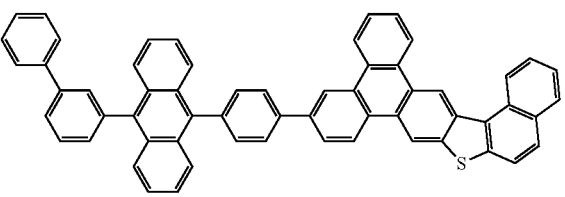
Compound 98
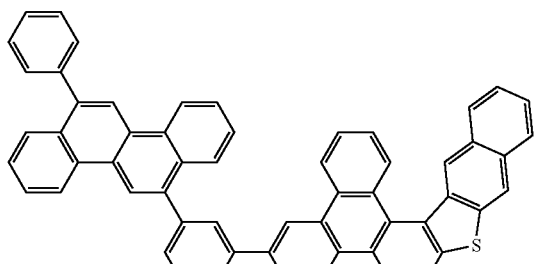
Compound 99
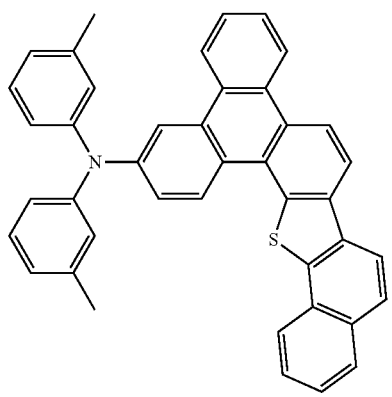
Compound 100
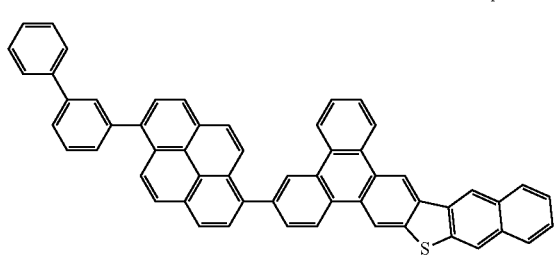
Compound 101

Compound 102
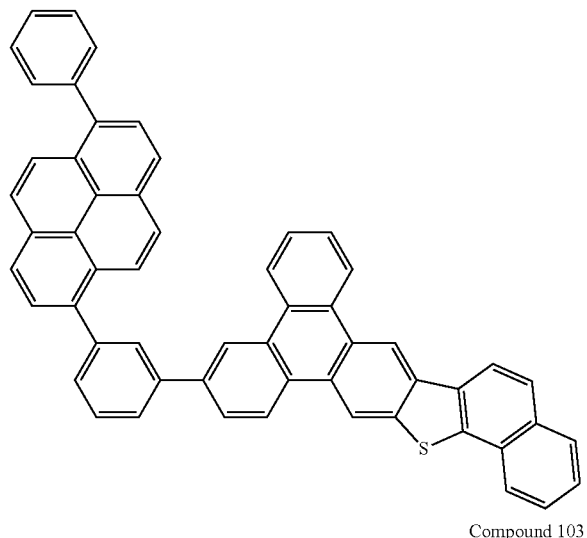
Compound 103
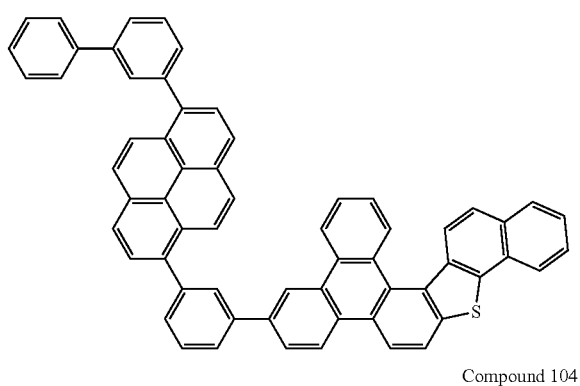
Compound 104
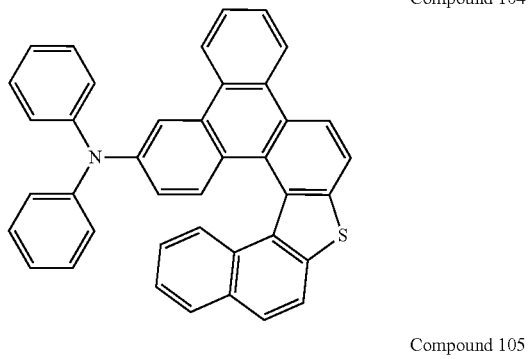
Compound 106
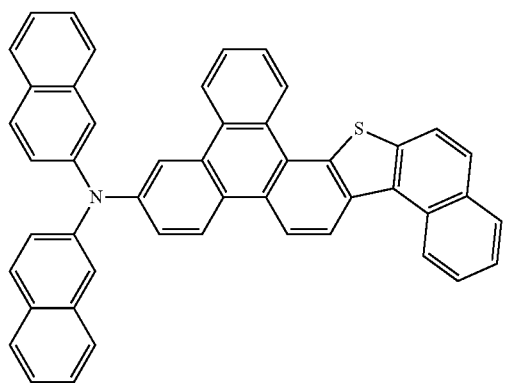
Compound 107
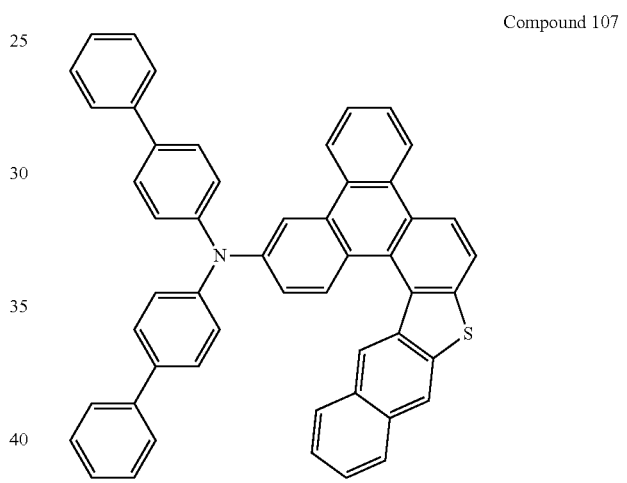
Compound 108
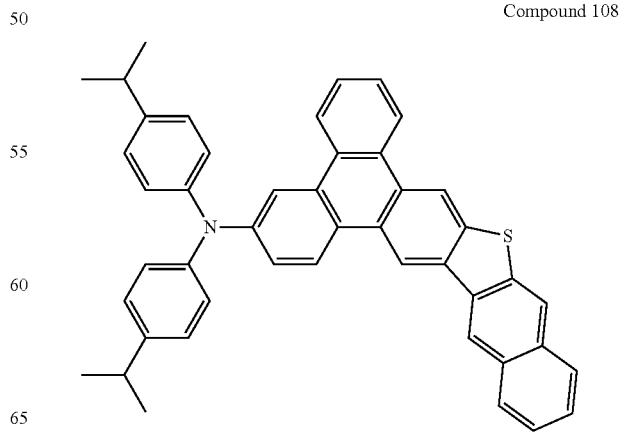

Compound 109
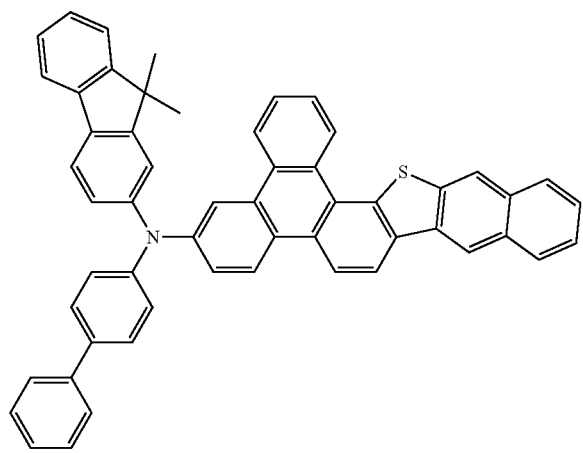
Compound 112
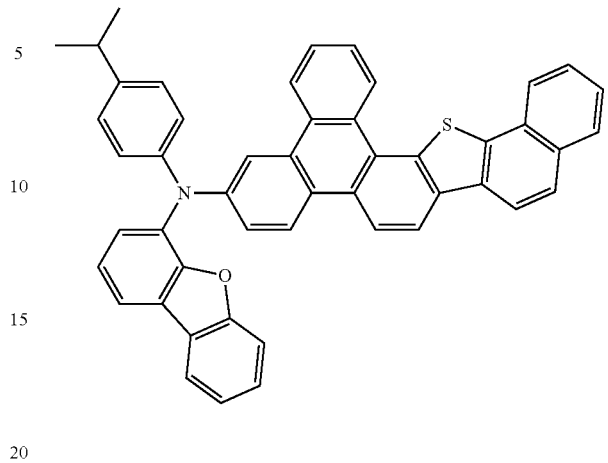
Compound 110
Compound 113
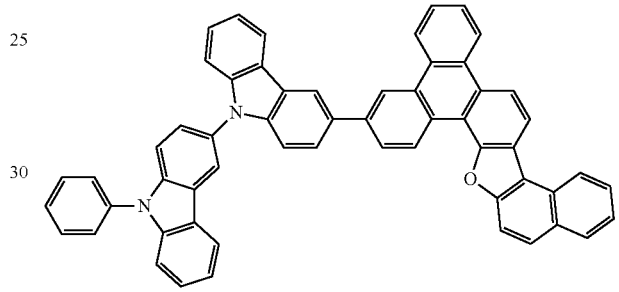
Compound 114
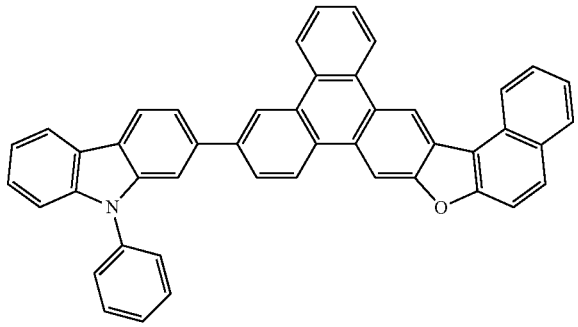
Compound 111
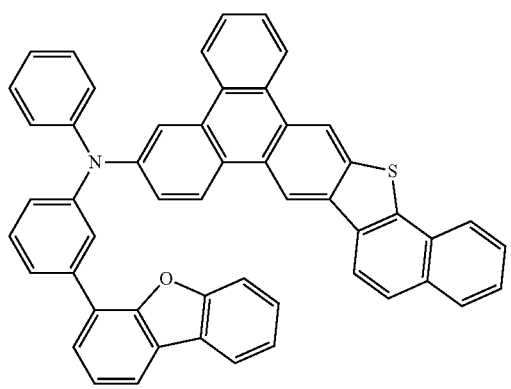
Compound 115

Compound 116
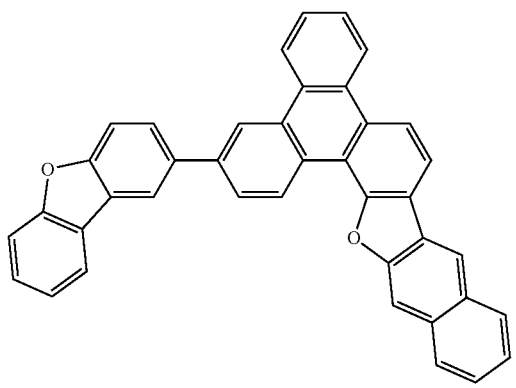
Compound 117
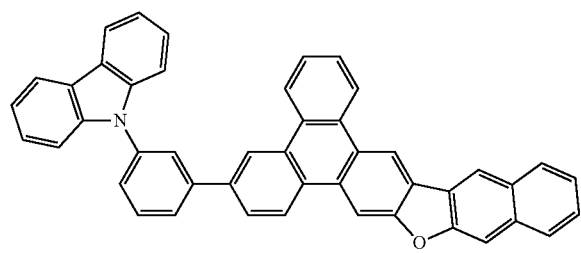
Compound 118
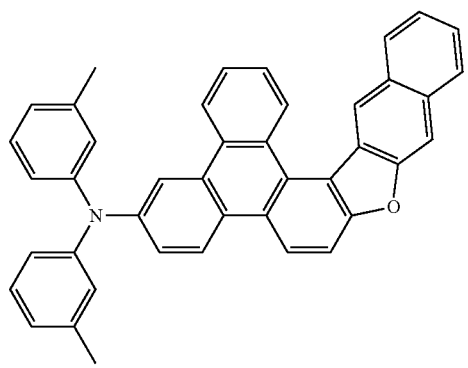
Compound 119
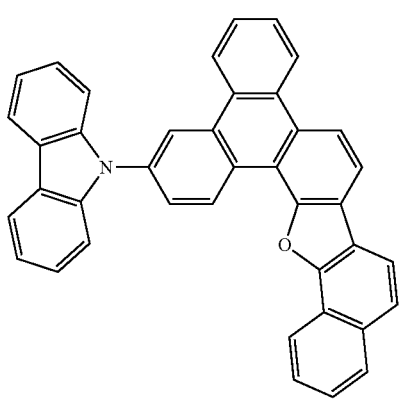
Compound 120
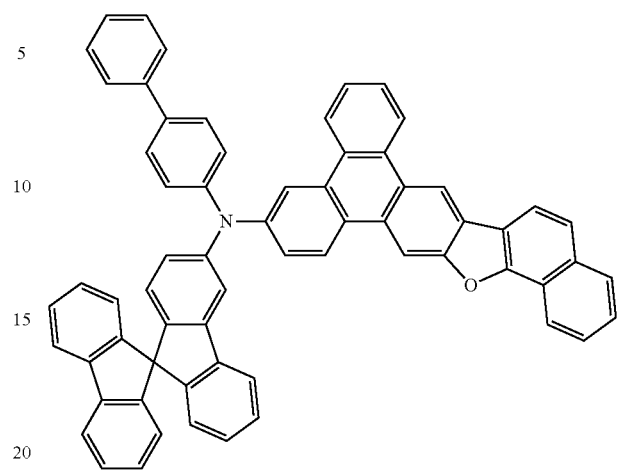
Compound 121
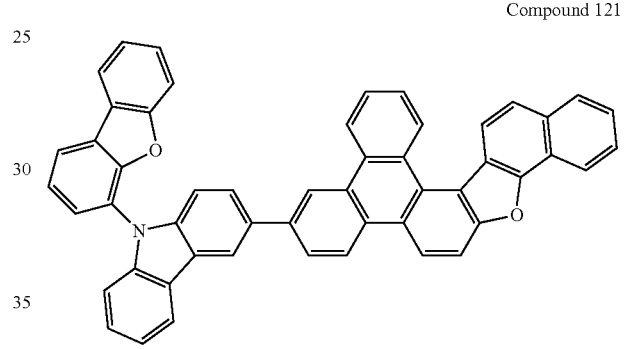
Compound 122
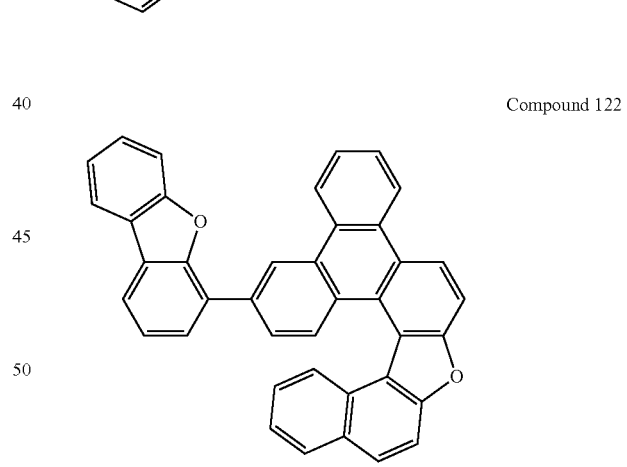
Compound 123
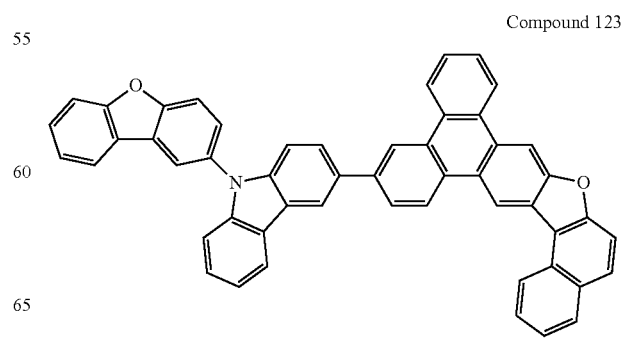

Compound 124
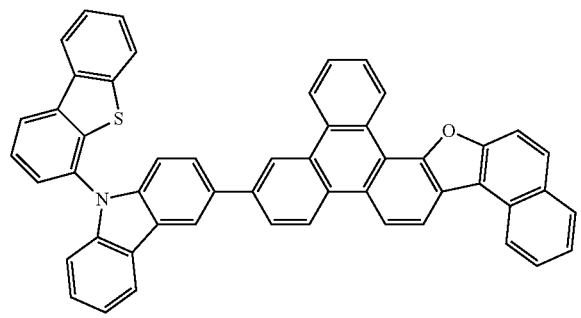
Compound 125
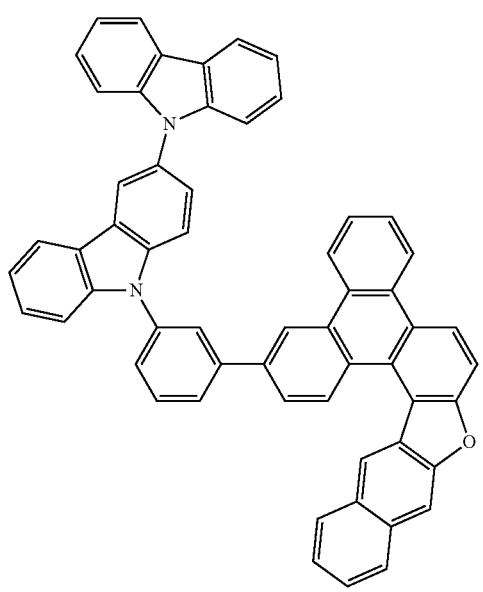
Compound 126
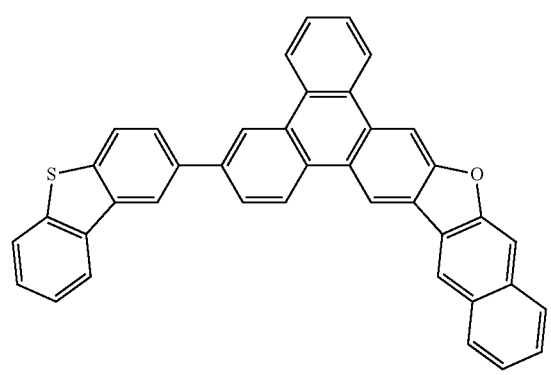
Compound 127
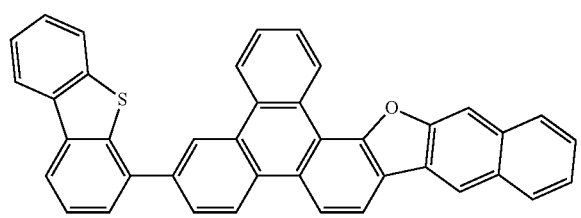
Compound 128
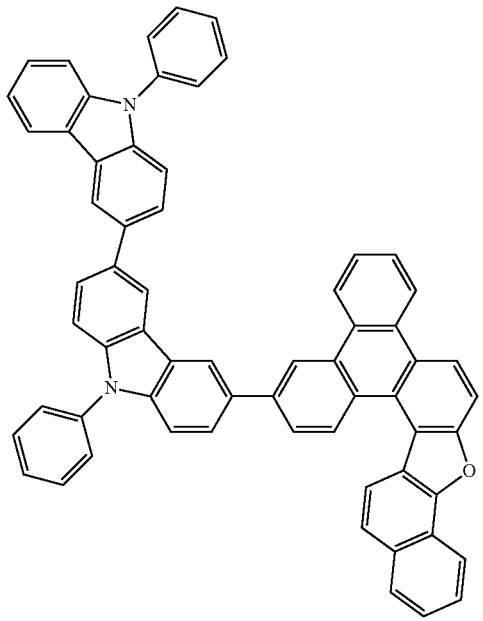
Compound 129
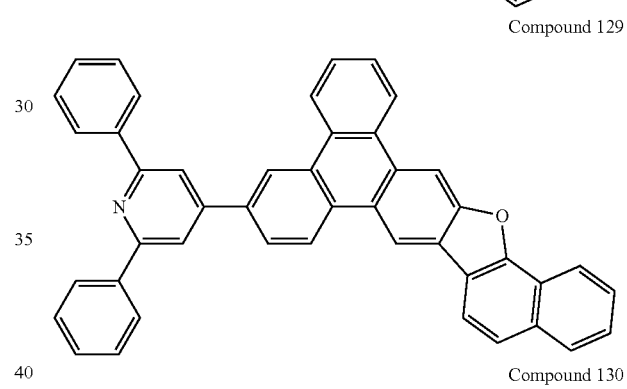
Compound 130
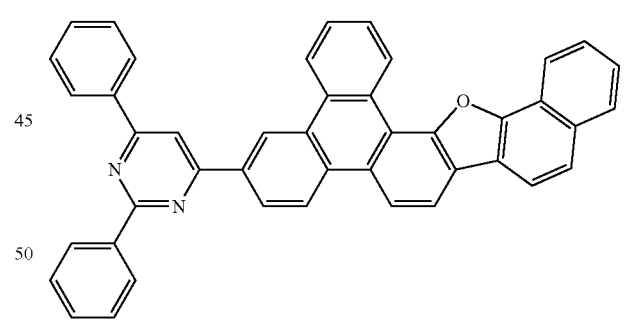
Compound 131
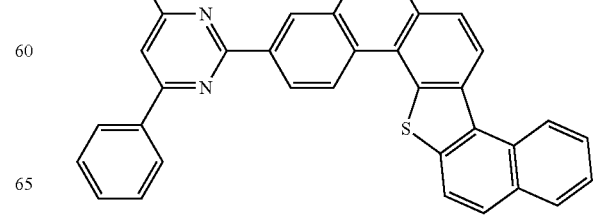

Compound 132
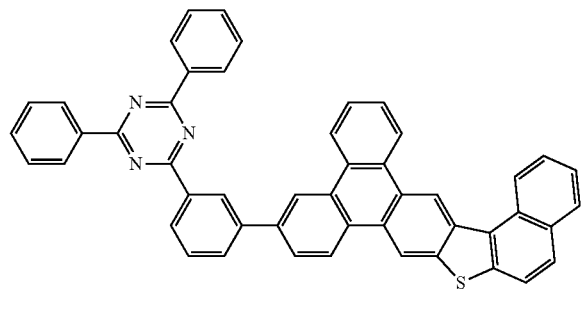
Compound 133
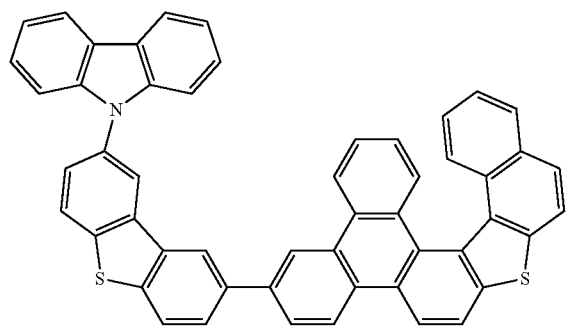
Compound 134
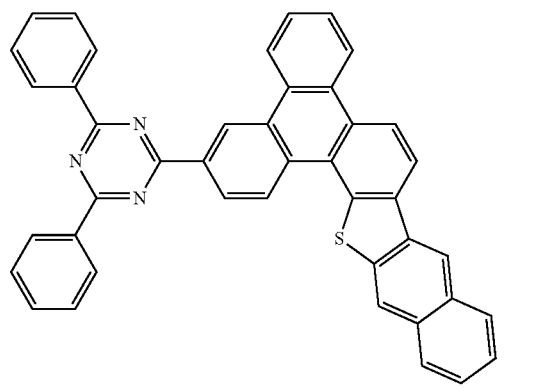
Compound 135
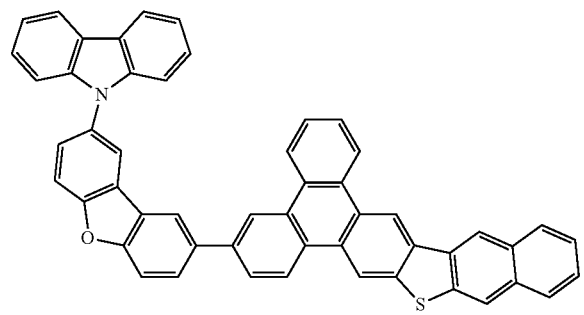
Compound 136
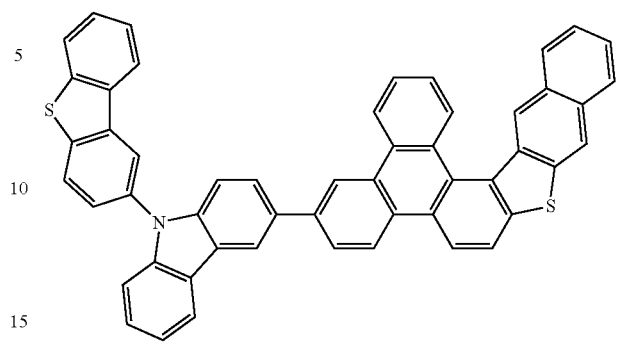
Compound 137
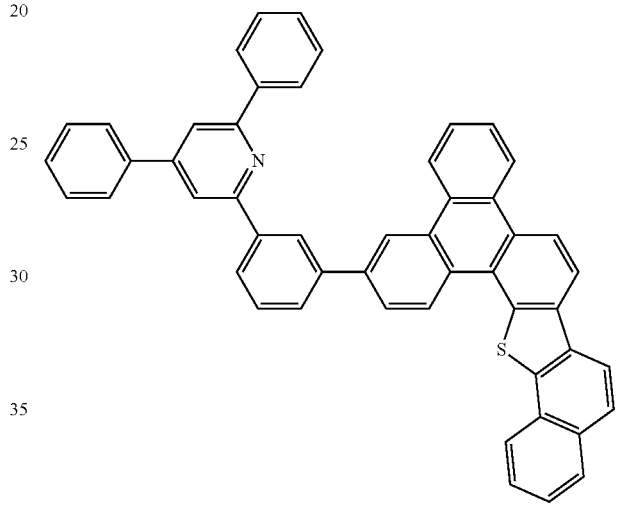
Compound 138
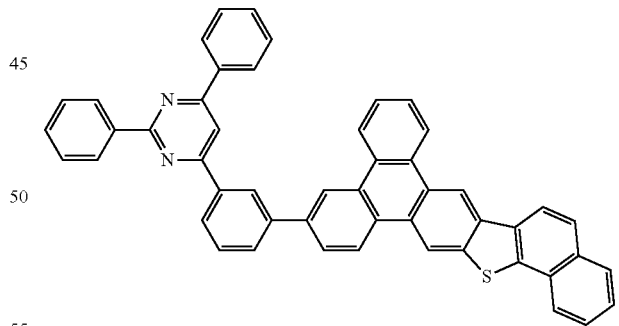
Compound 139
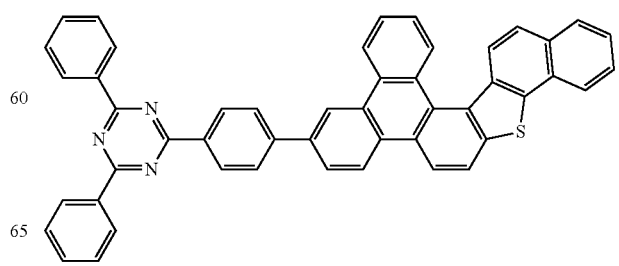

-continued
Compound 140
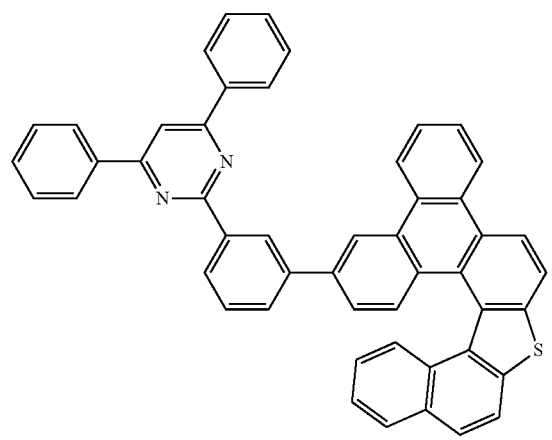
Compound 141
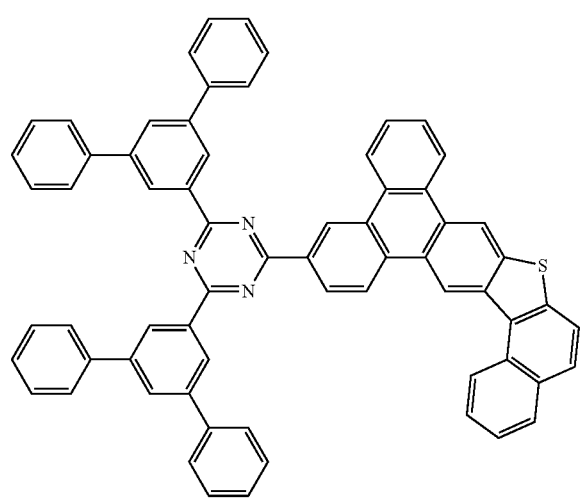
Compound 142
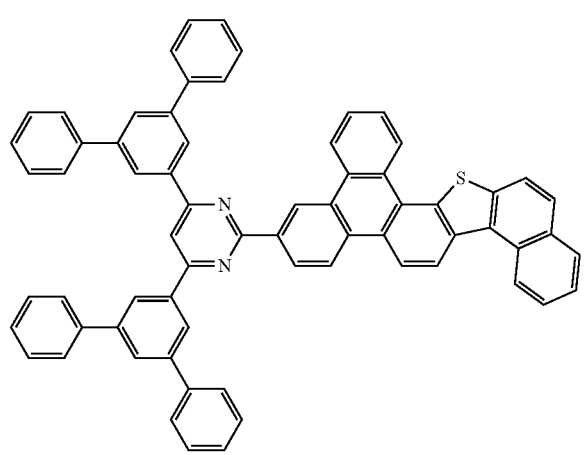
-continued
Compound 143
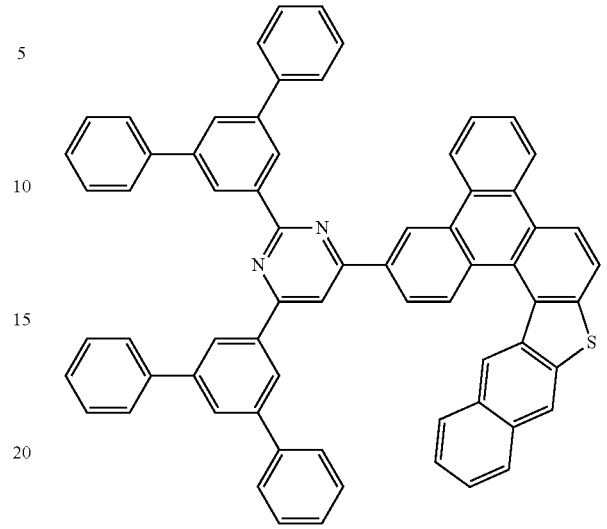
Compound 144
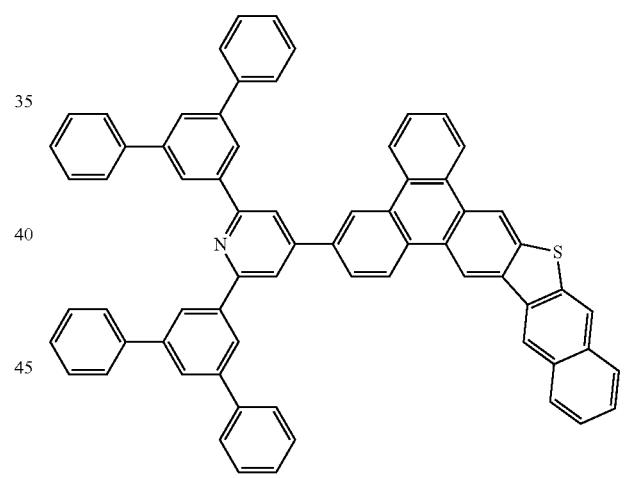
Compound 145
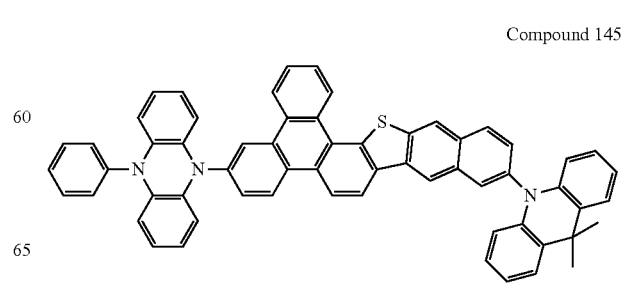

Compound 146
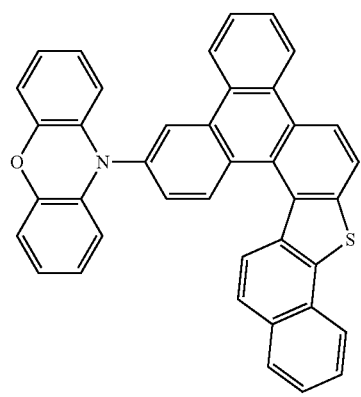
Compound 147
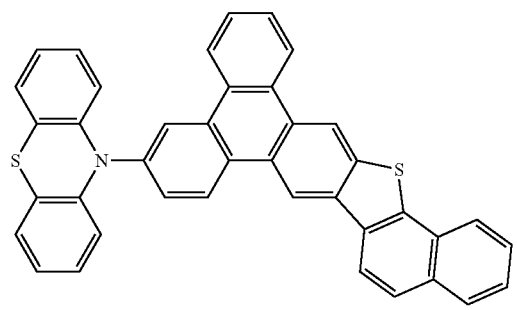
Compound 148
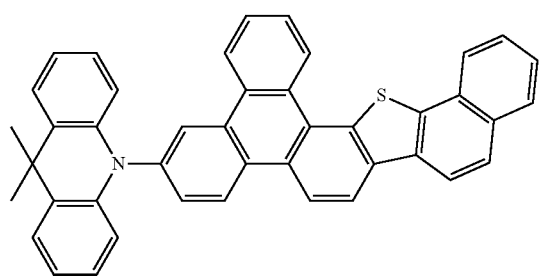
Compound 149
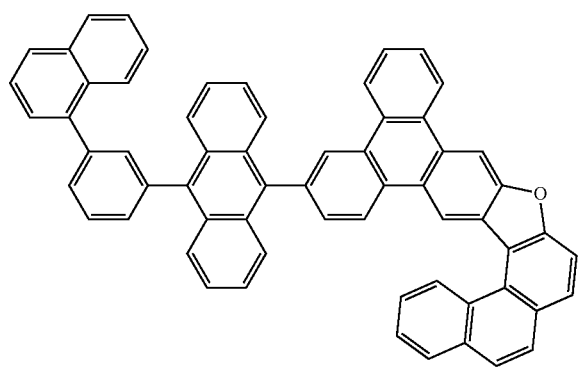
Compound 150
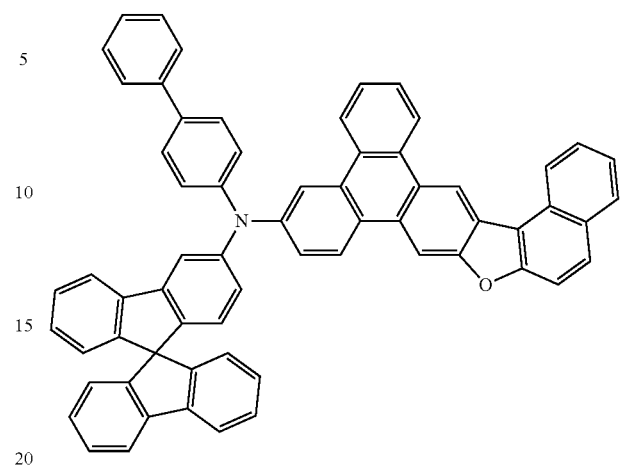
Compound 151
Compound 152
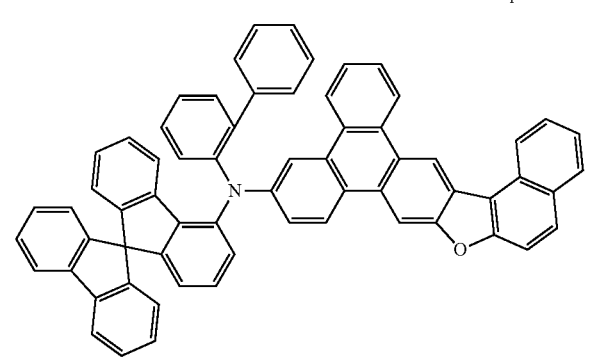

Compound 153
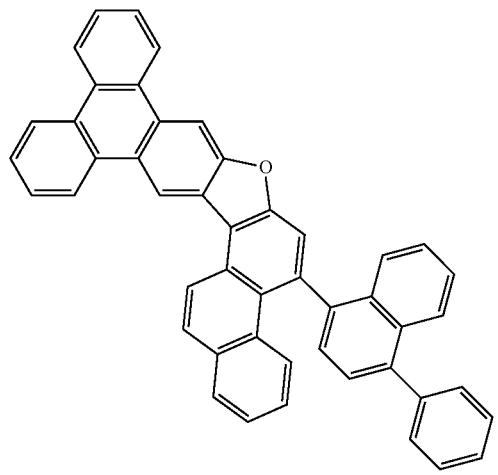
Compound 154
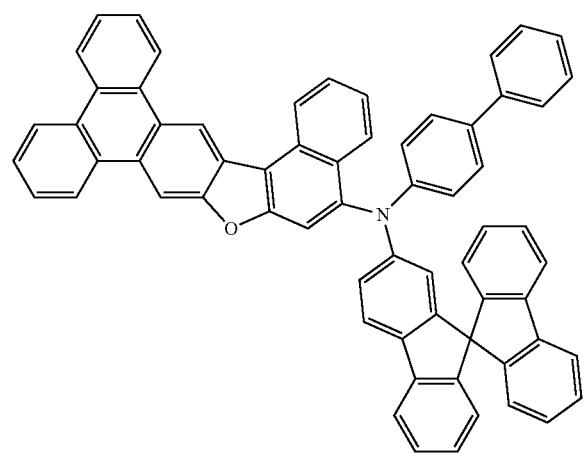
Compound 155
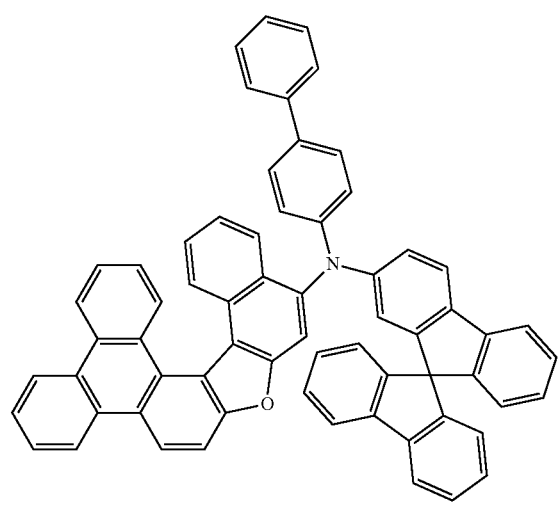
Compound 156
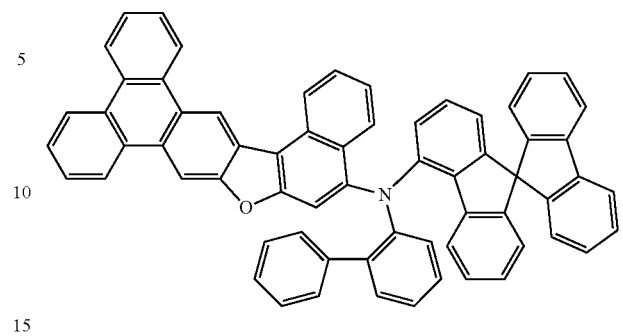
Compound 157
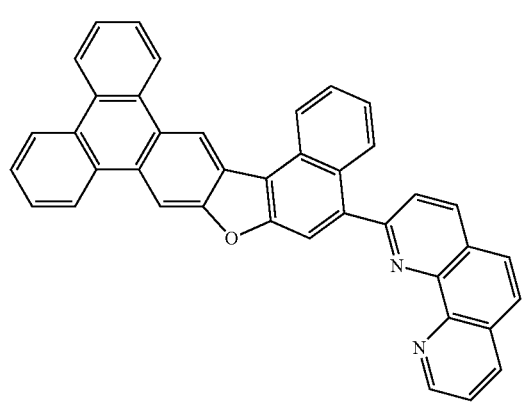
Compound 158
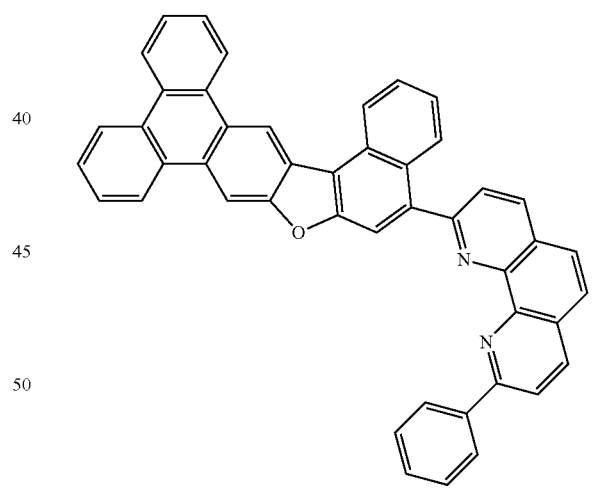
Compound 159
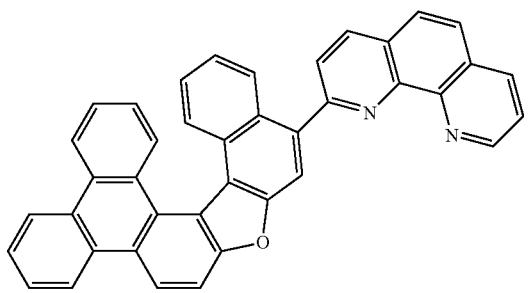

Compound 160
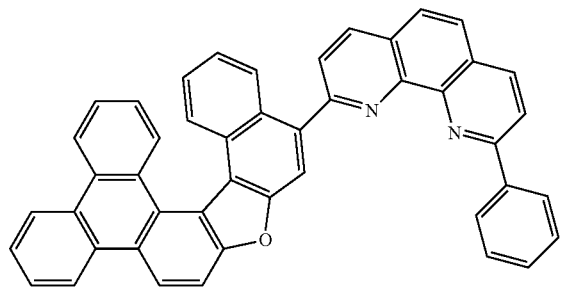
Compound 161
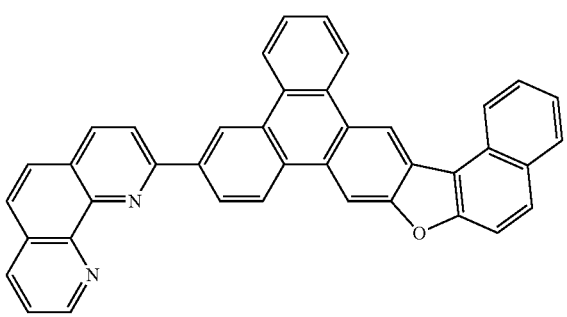
Compound 162
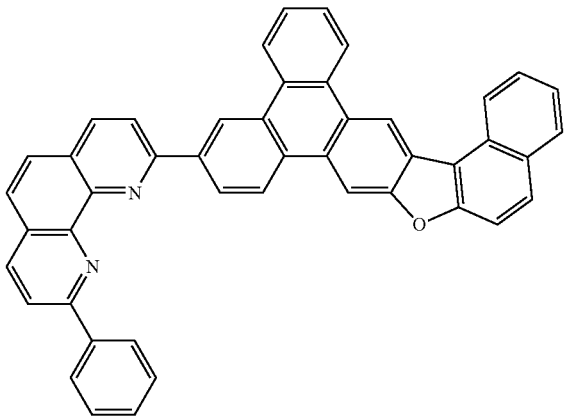
Compound 163
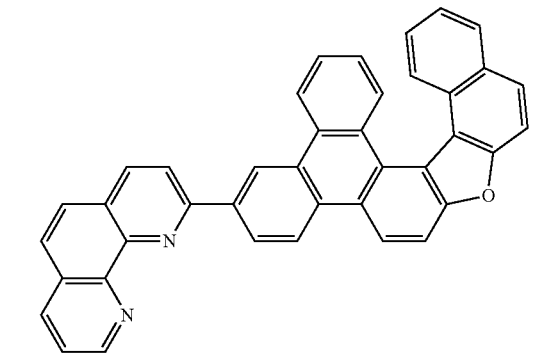
Compound 164
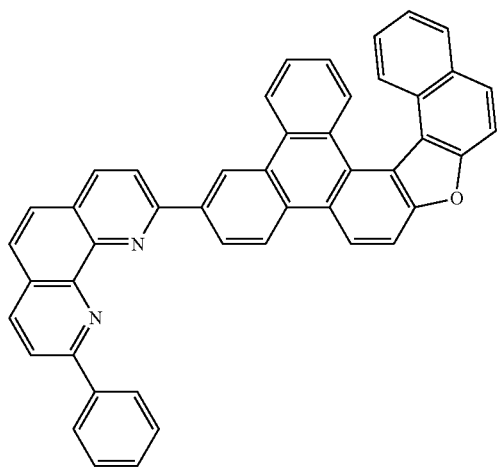
Compound 165
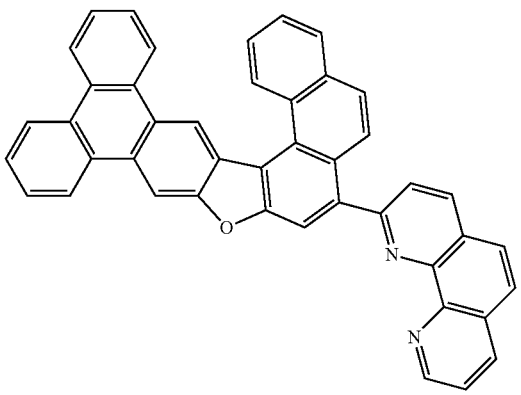
Compound 166
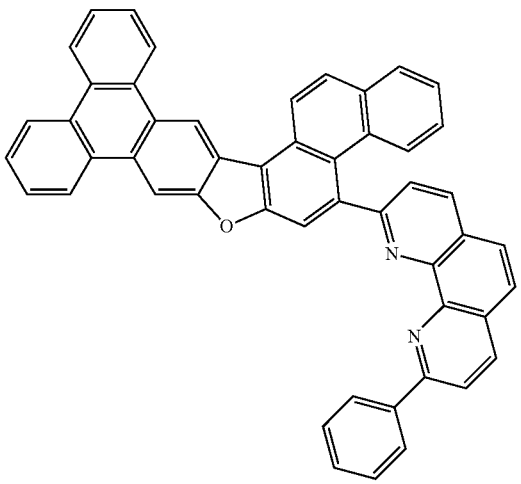

Compound 167
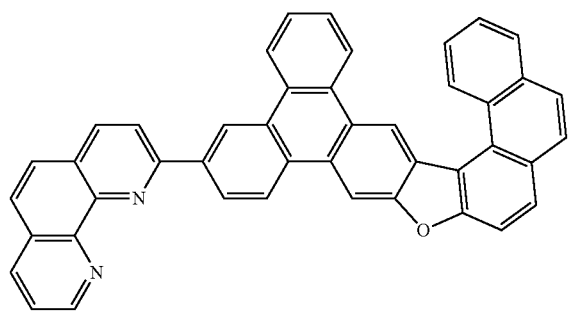
Compound 168
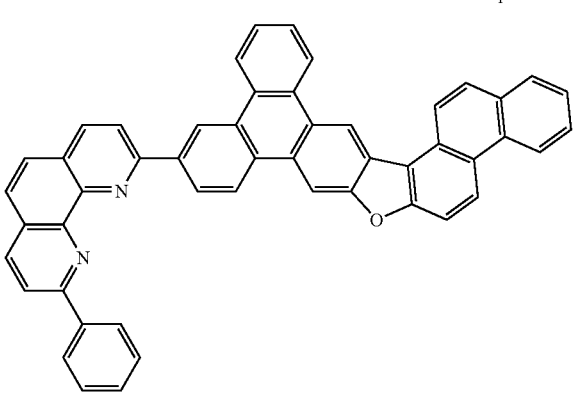
Compound 169
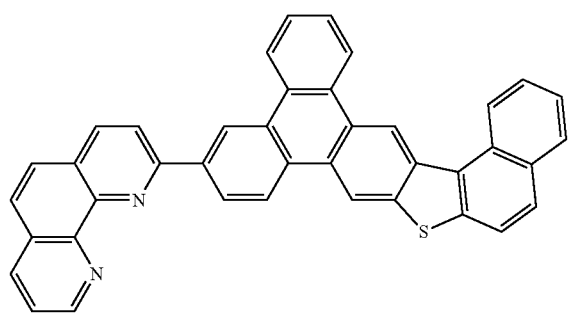
Compound 170
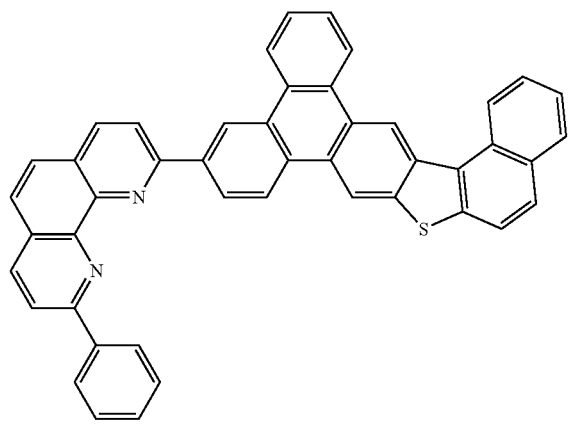
Compound 171
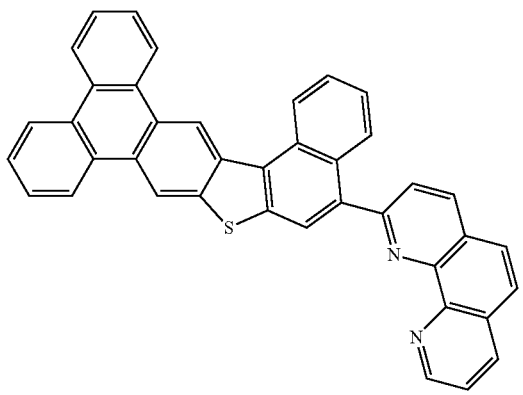
Compound 172
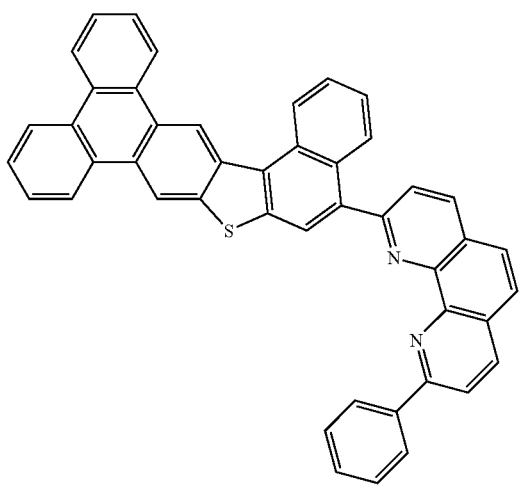
Compound 173
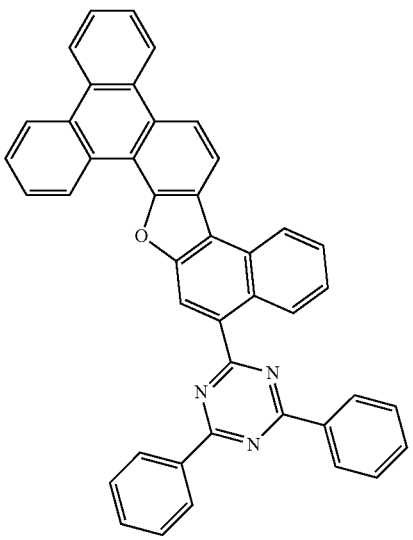

Compound 174
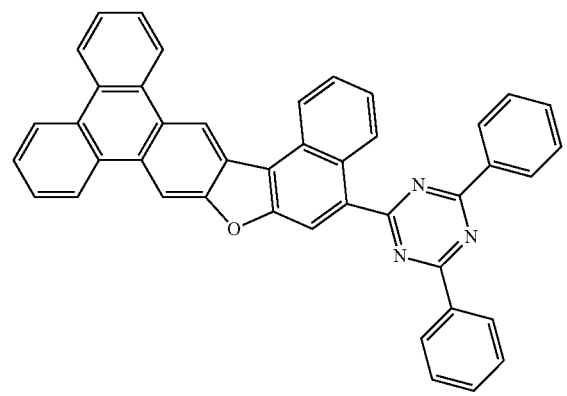
Compound 177
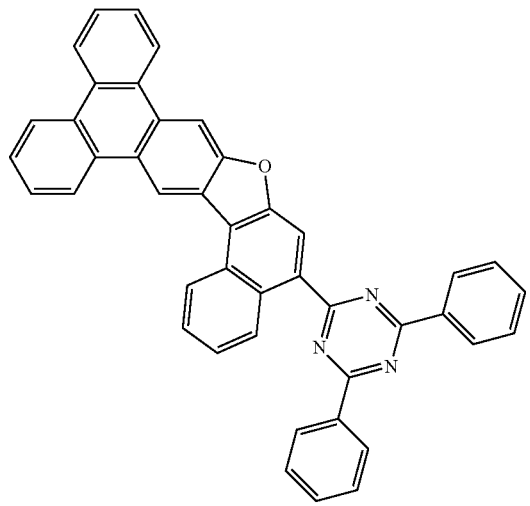
Compound 175
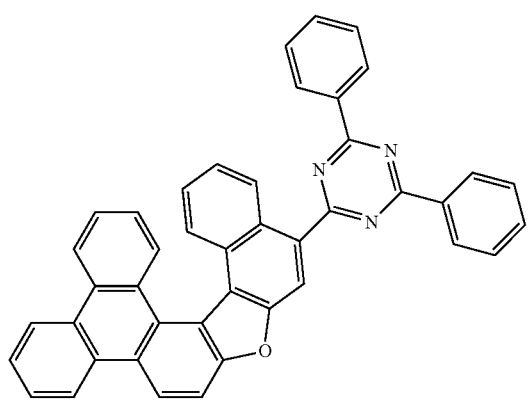
Compound 178
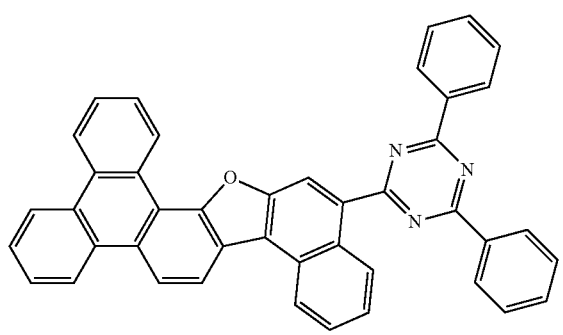
Compound 179
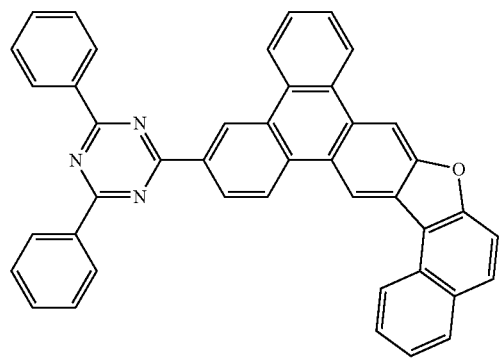
Compound 176
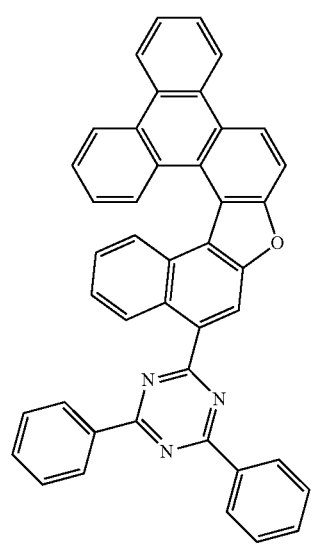
Compound 180
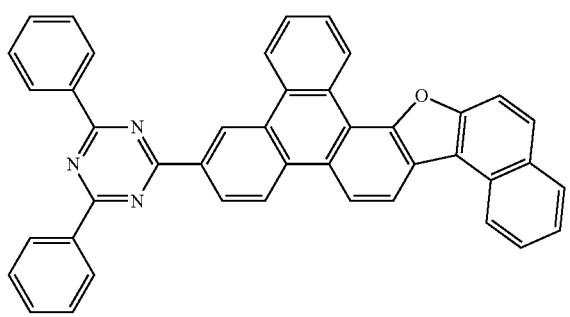

Compound 181
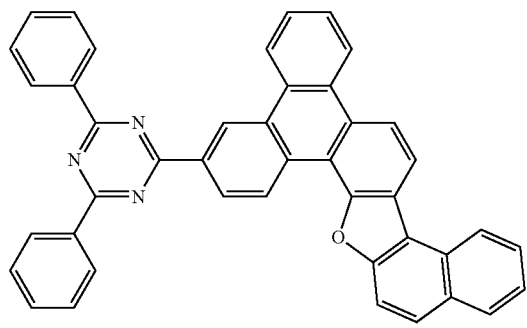
Compound 182
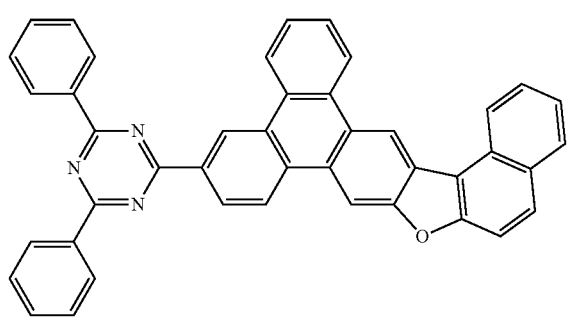
Compound 183
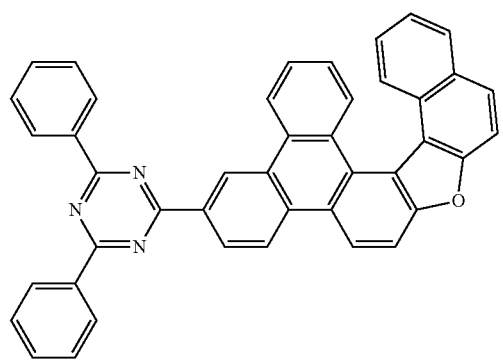
Compound 184
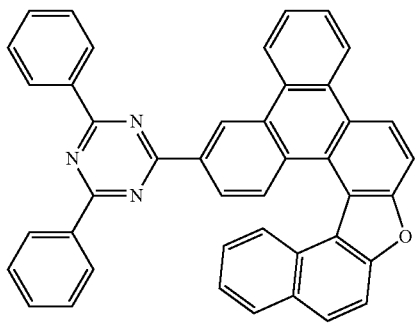
Compound 185
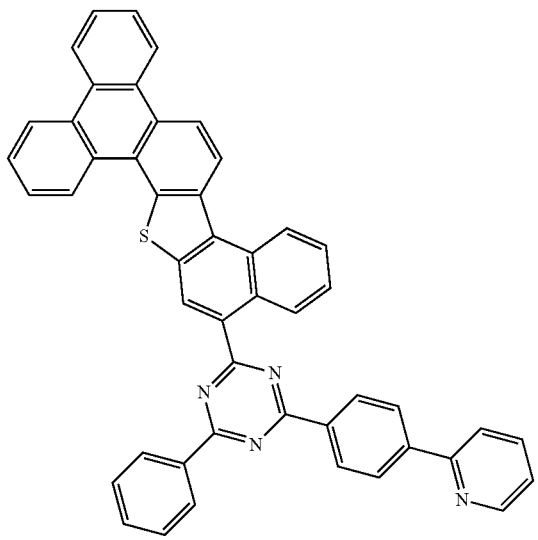
Compound 186
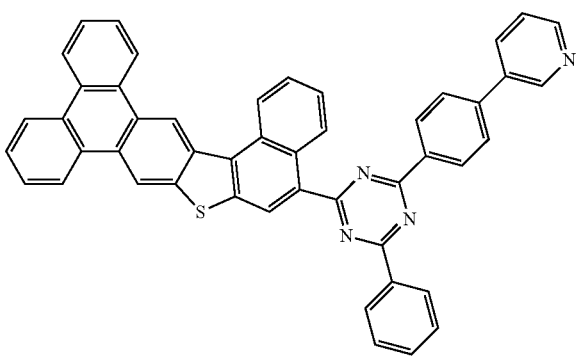
Compound 187
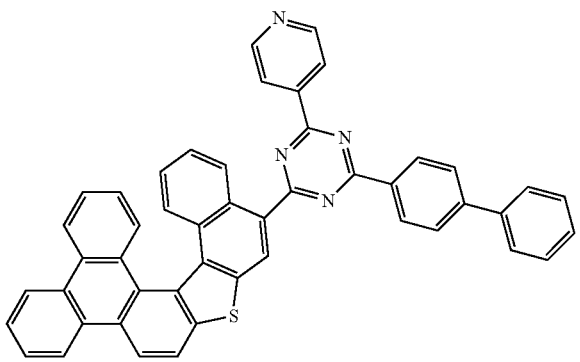

Compound 188
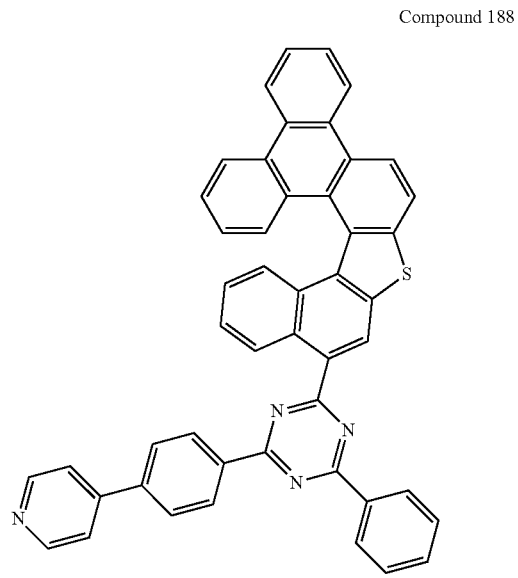
Compound 191
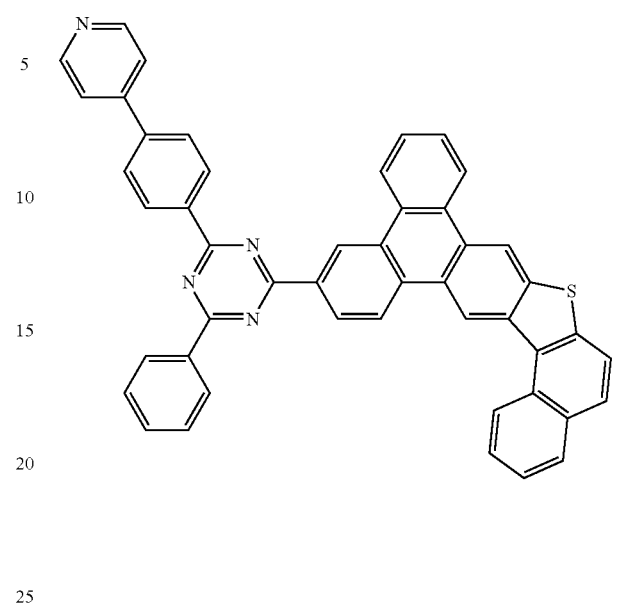
Compound 189
Compound 192
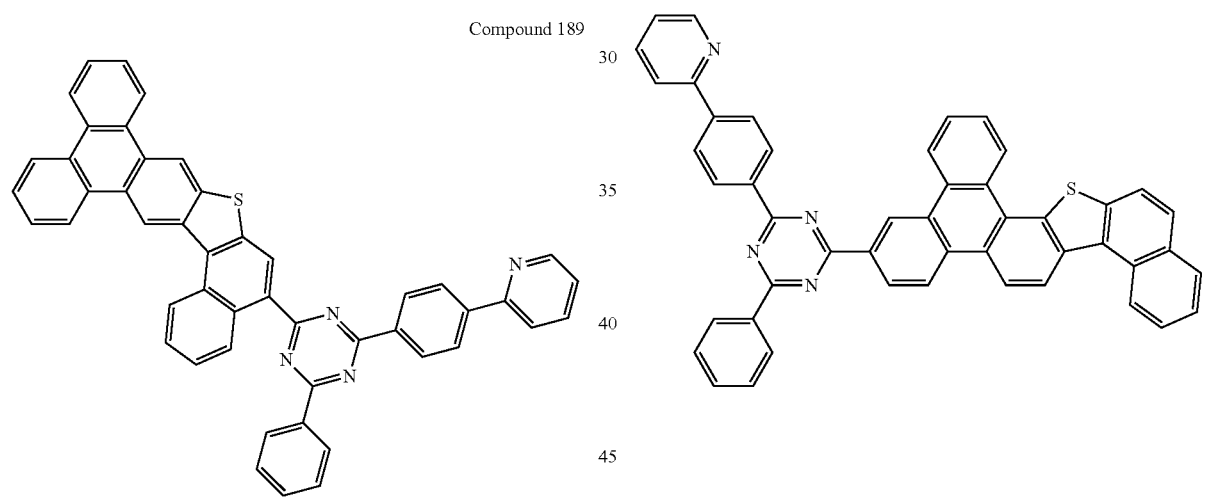
Compound 190
Compound 193
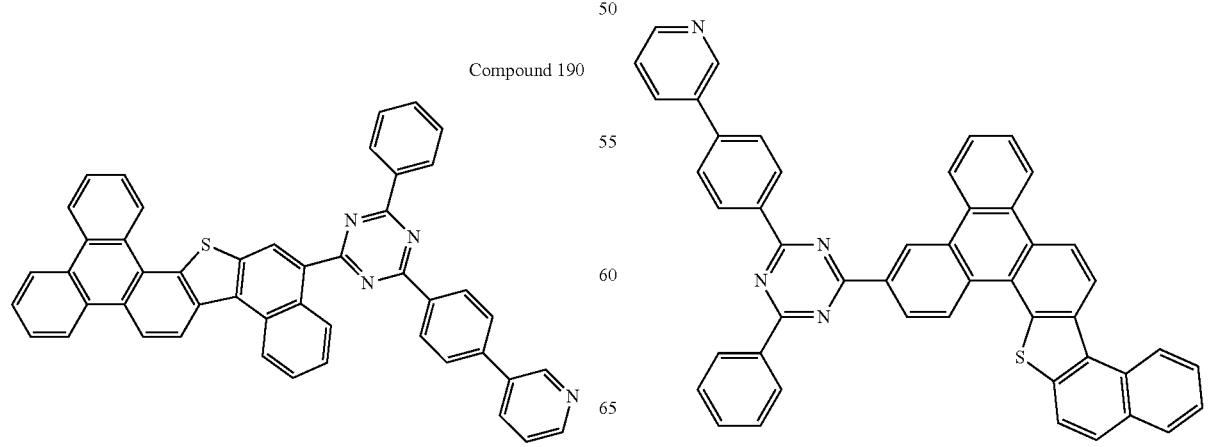

Compound 194
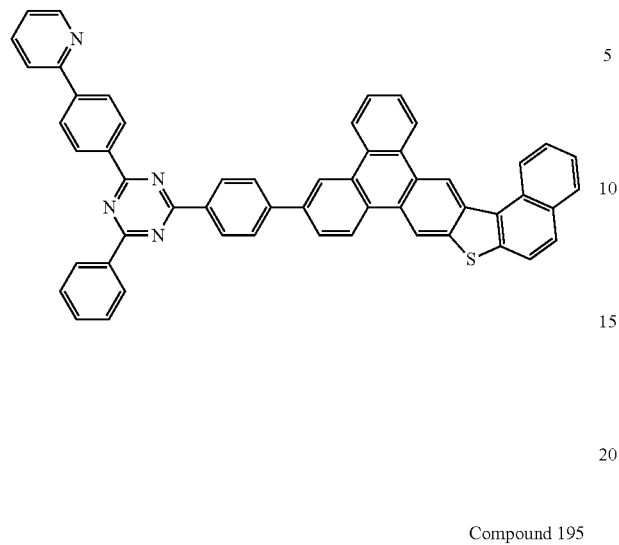
Compound 197
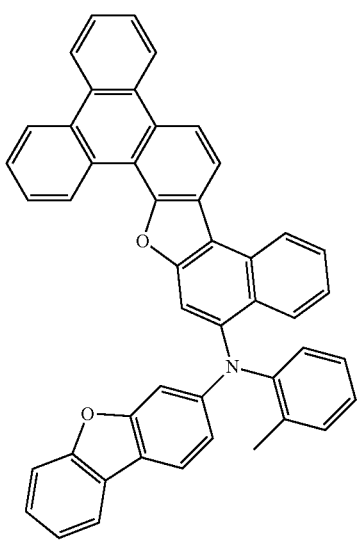
Compound 195
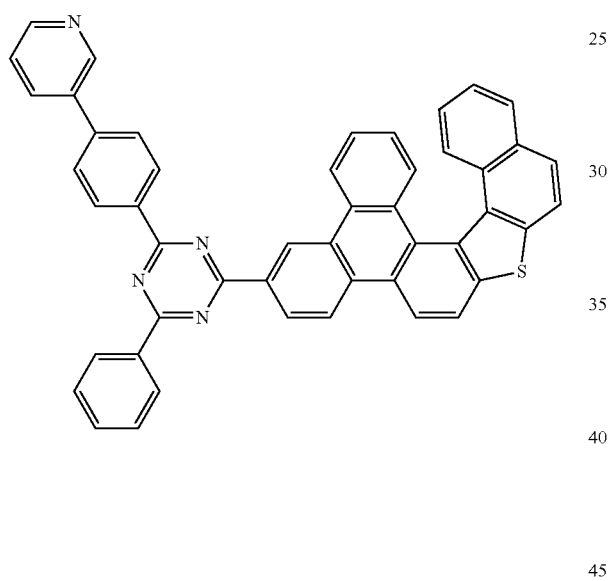
Compound 198
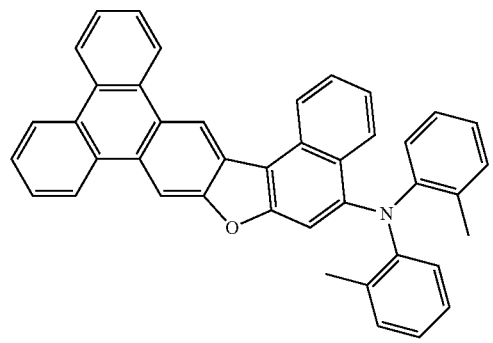
Compound 196
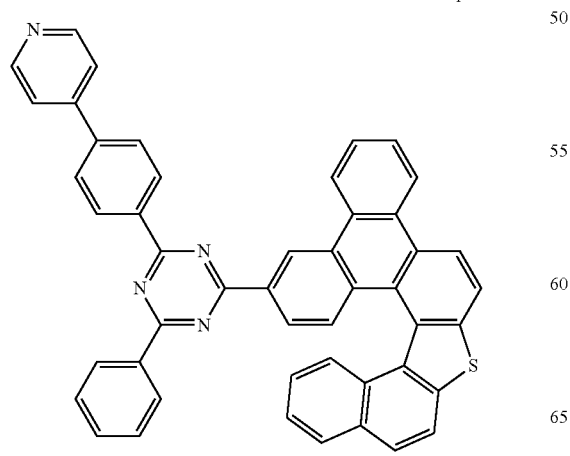
Compound 199
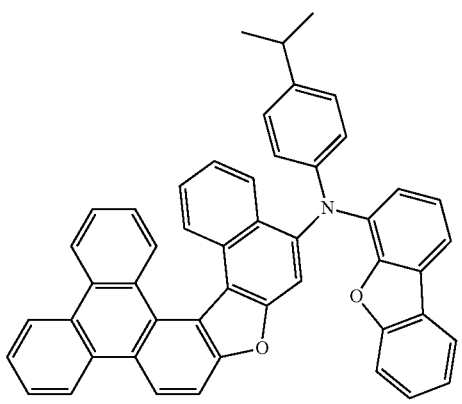

Compound 200
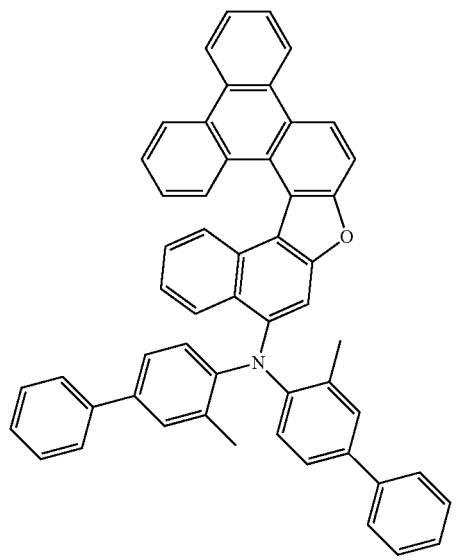
Compound 201
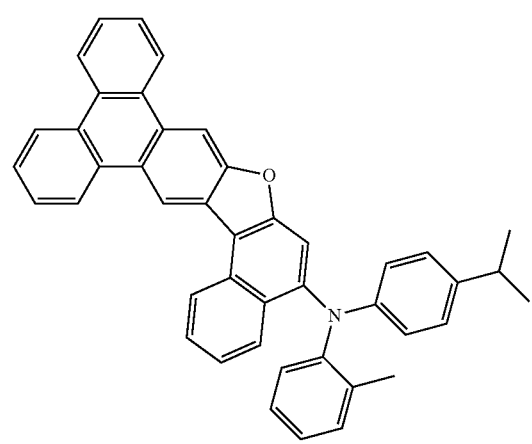
Compound 202
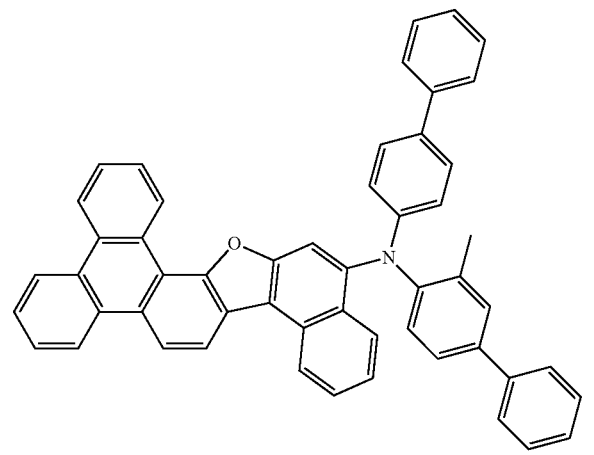
Compound 203
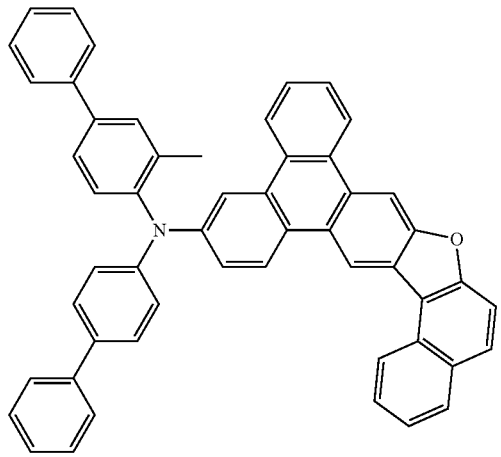
Compound 204
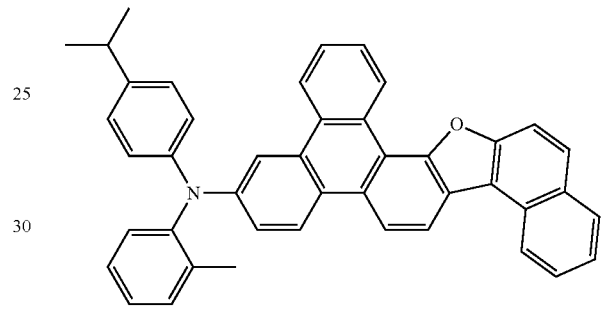
Compound 205
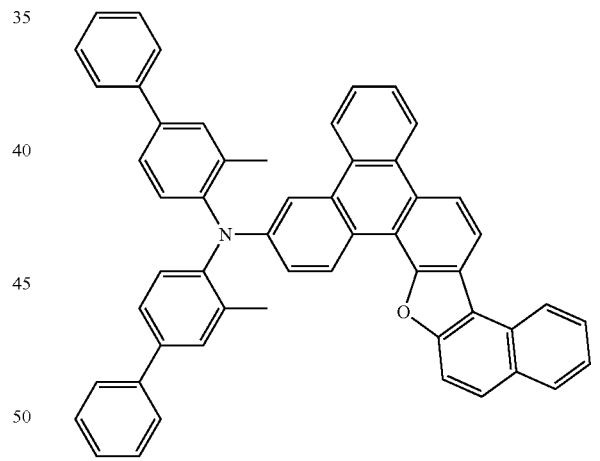
Compound 206
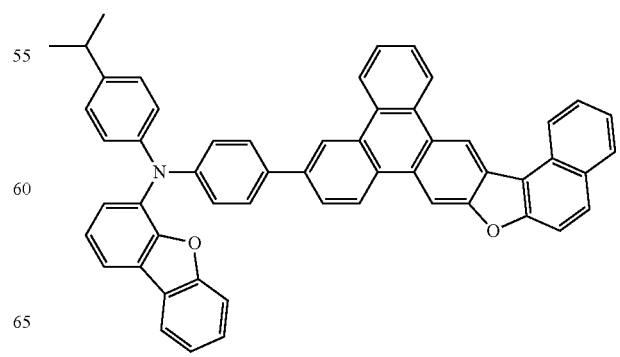

Compound 207
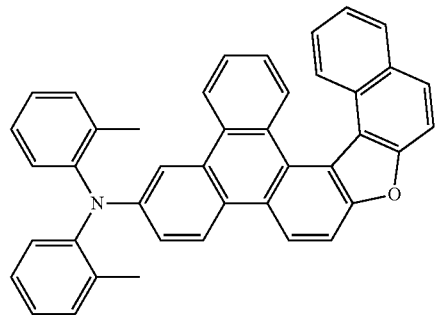
Compound 208
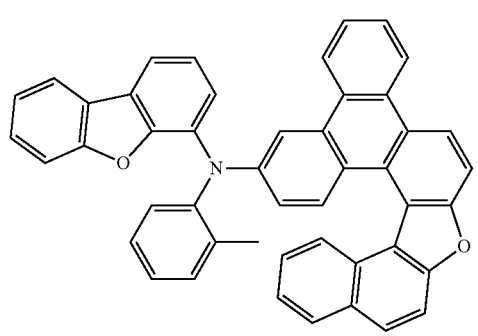
Compound 209
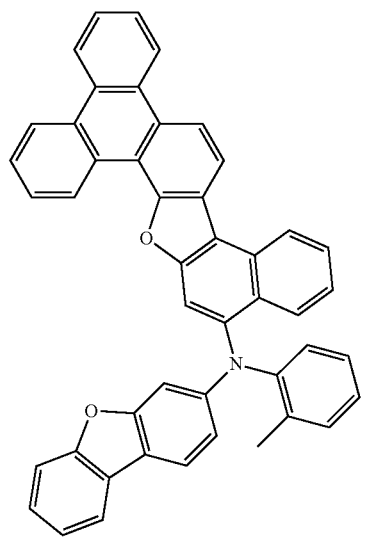
Compound 210
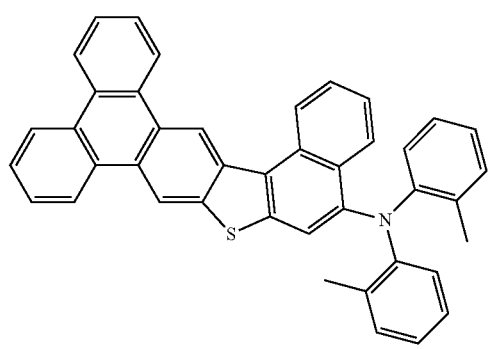
Compound 211
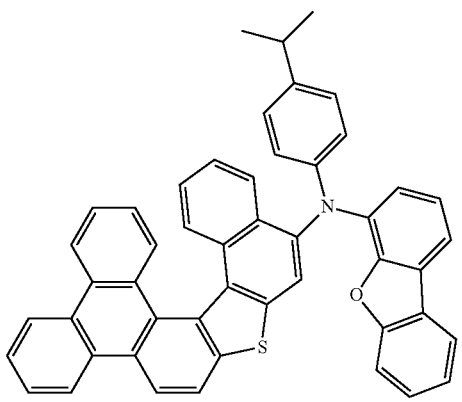
Compound 212
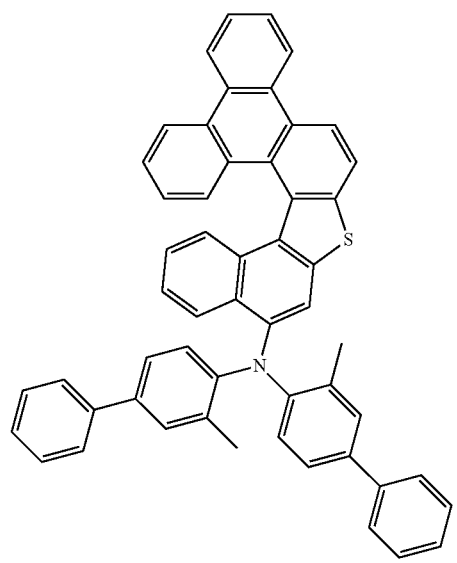
Compound 213
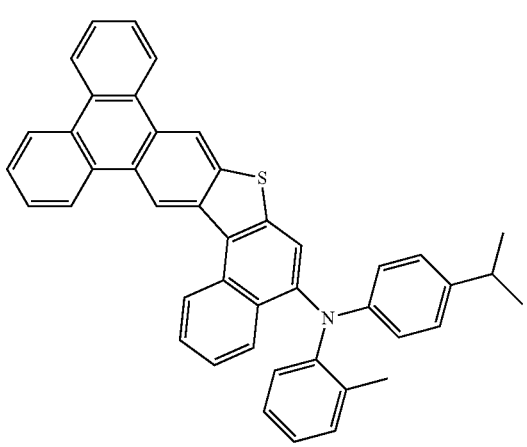

Compound 214
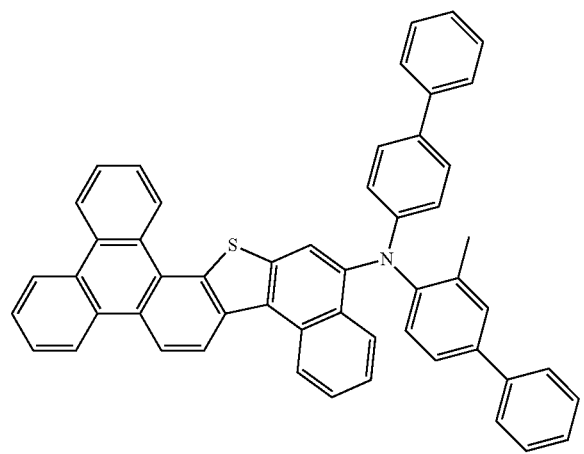
Compound 217
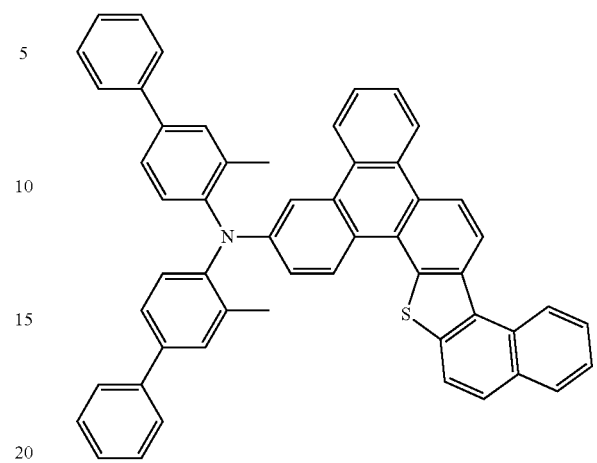
Compound 215
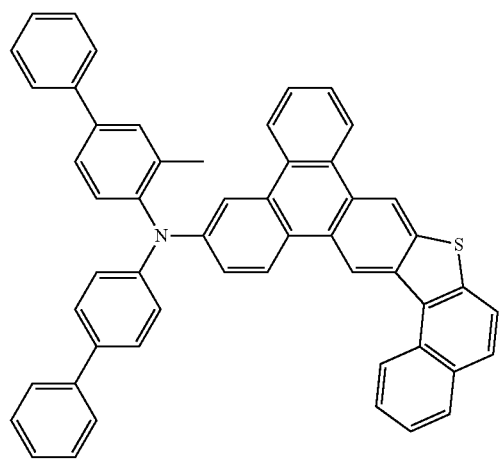
Compound 218
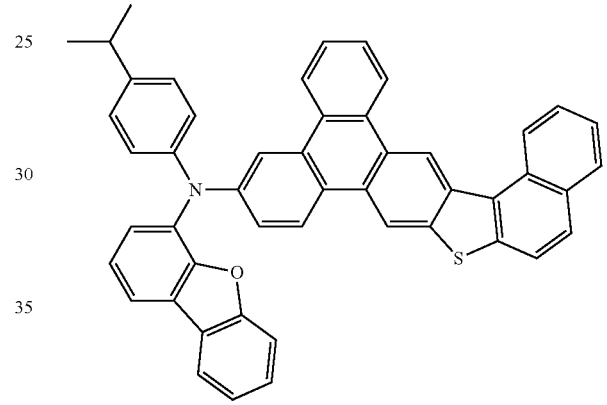
Compound 219
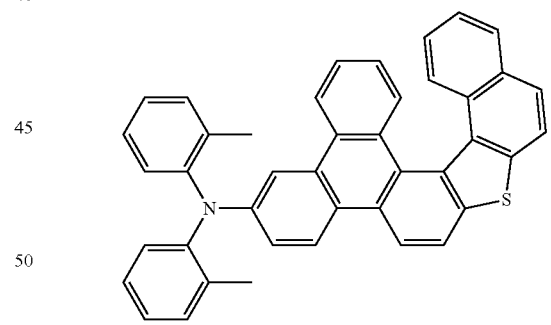
Compound 216
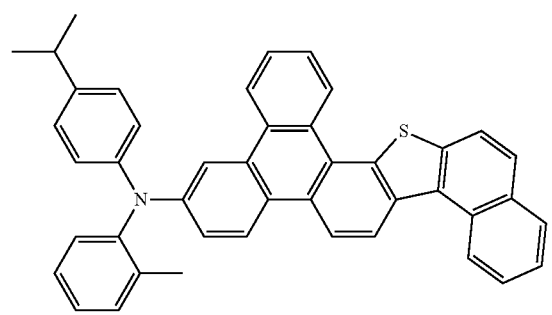
Compound 220
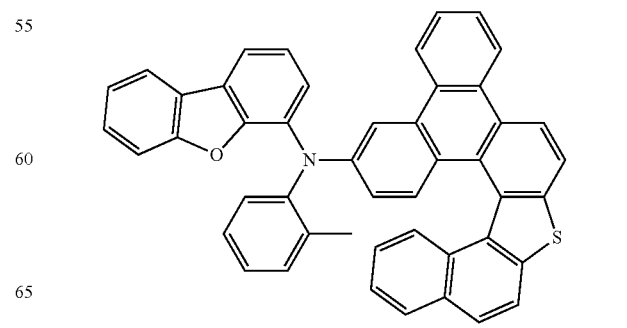

-continued
Compound 221
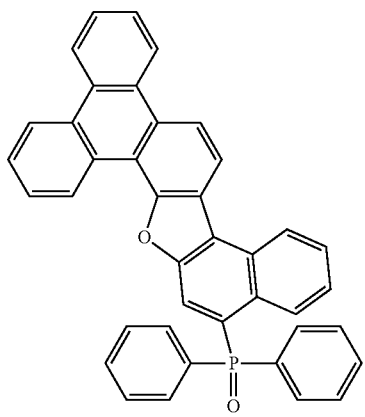
Compound 222
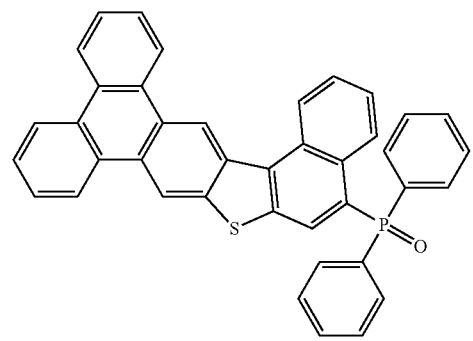
Compound 223
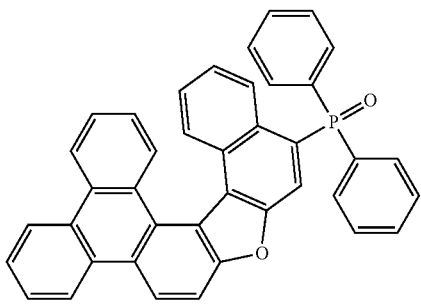
Compound 224
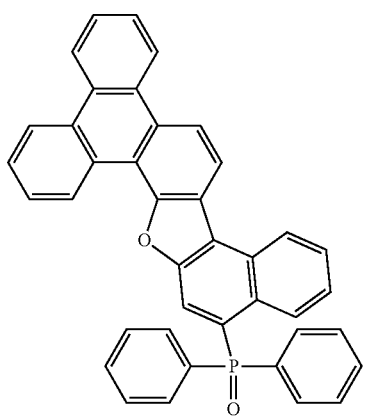
-continued
Compound 225
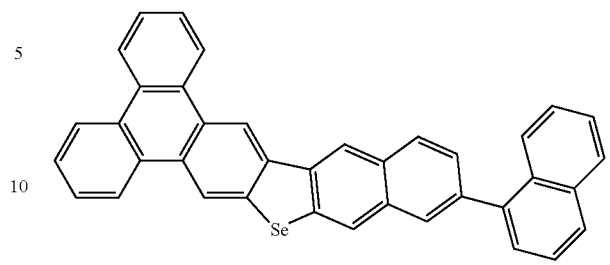
Compound 226
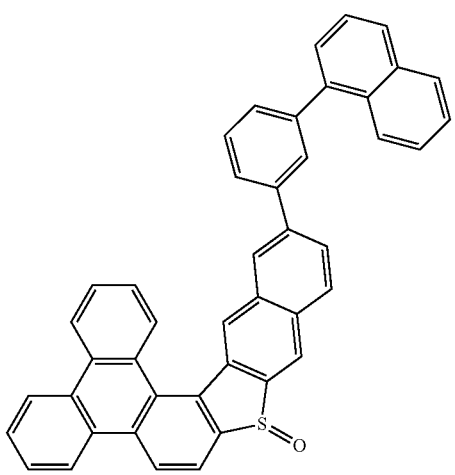
Compound 227
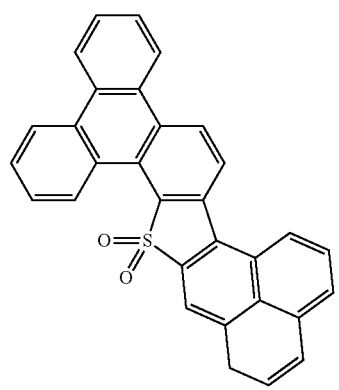
Compound 228
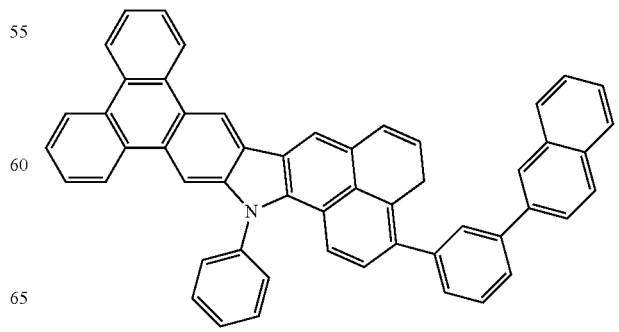

Compound 229
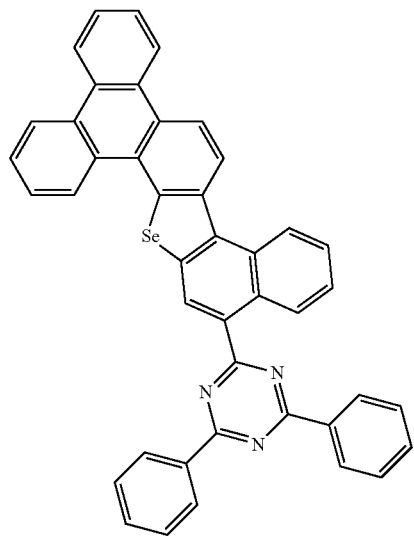
Compound 230
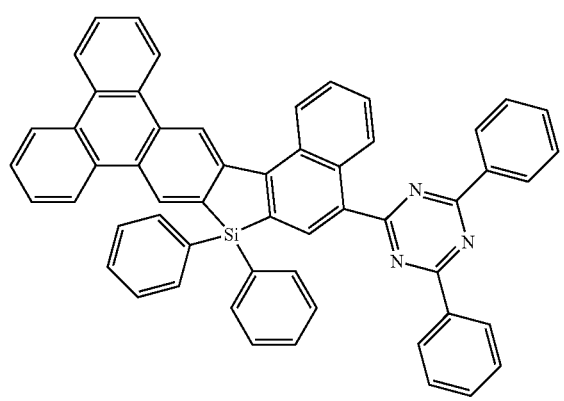
Compound 231
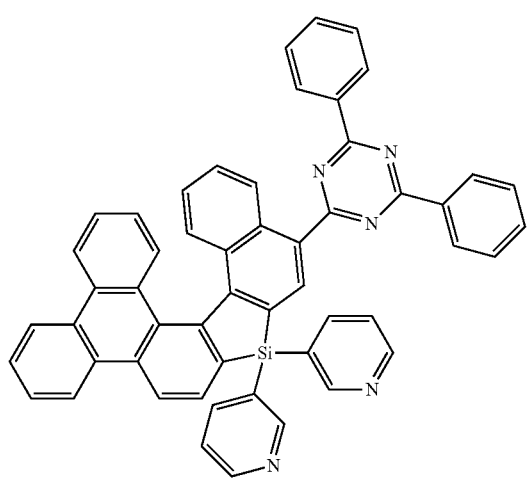
Compound 232
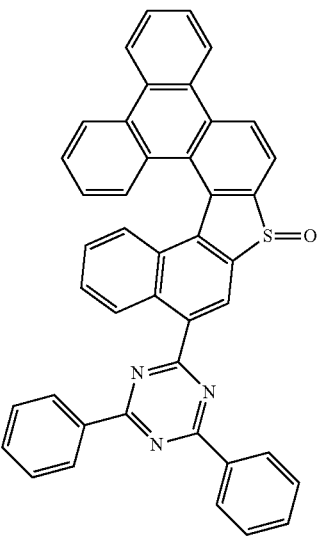
Compound 233
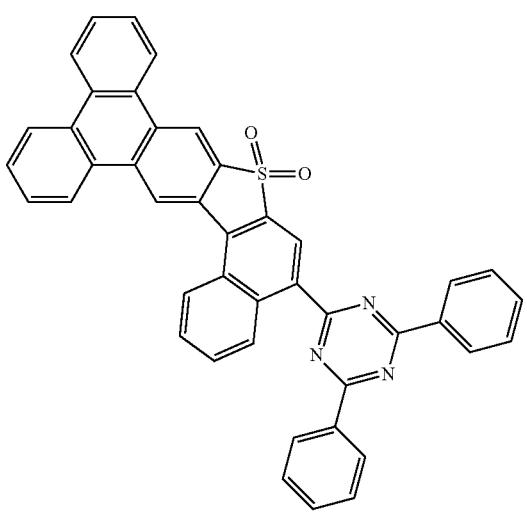
Compound 178
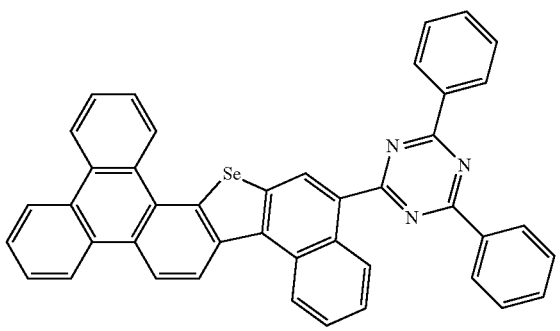

Compound 235
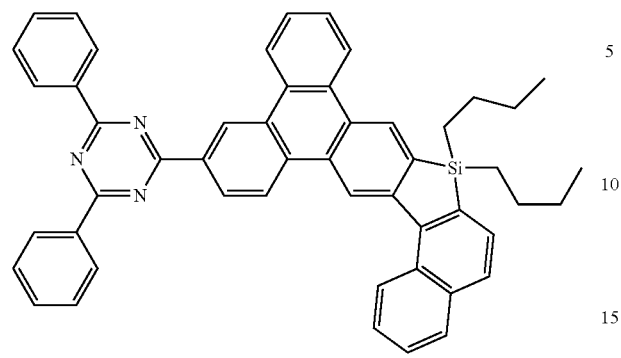
Compound 236
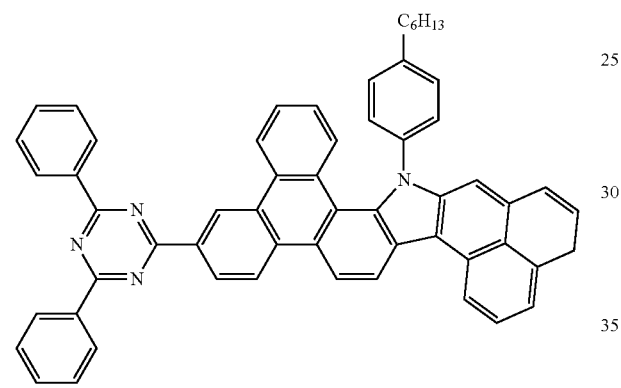
Compound 237
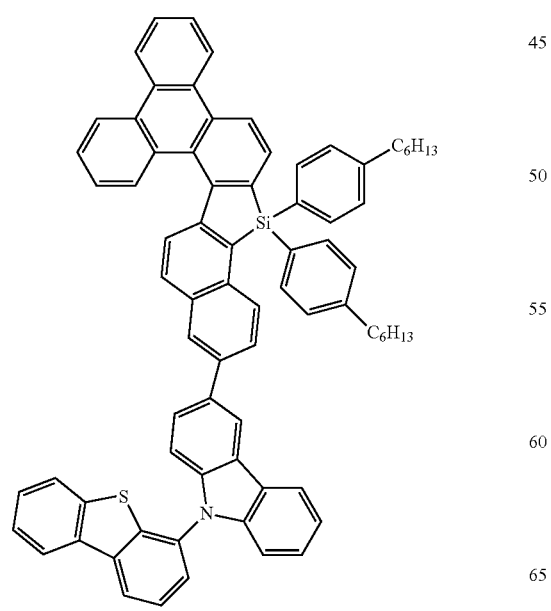
Compound 238
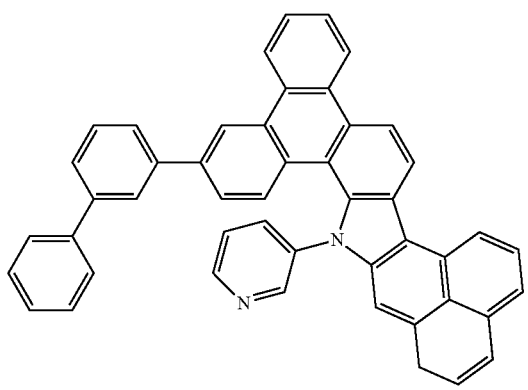
Compound 239
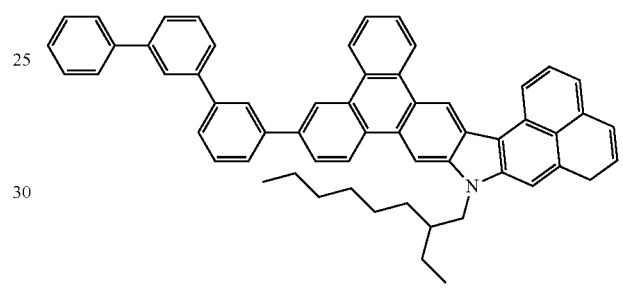
Compound 240
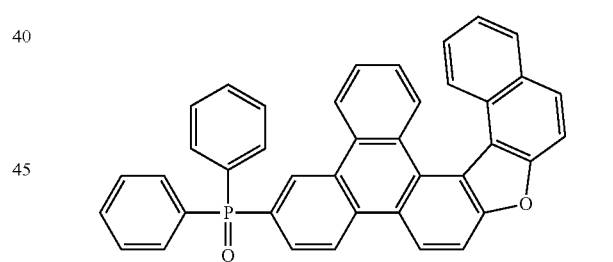
Compound 241
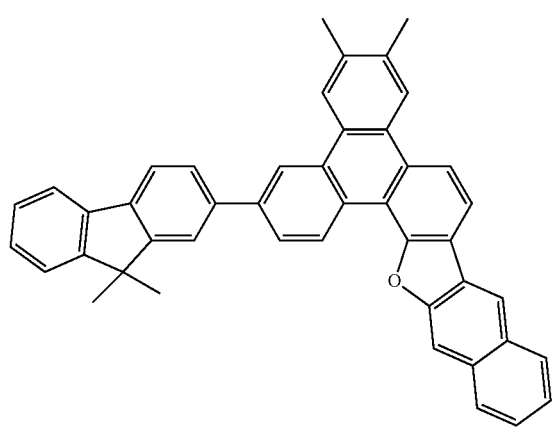

-continued

Compound 242

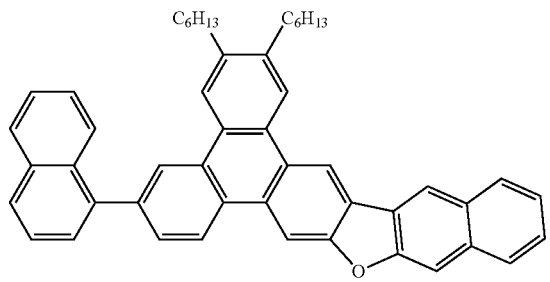

Compound 243

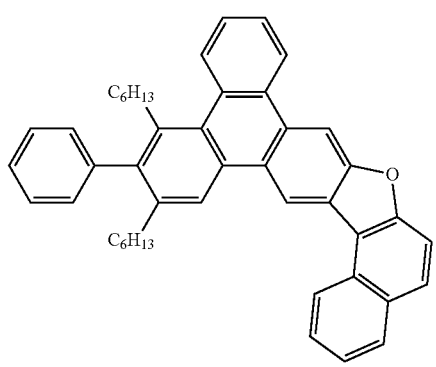

Compound 244

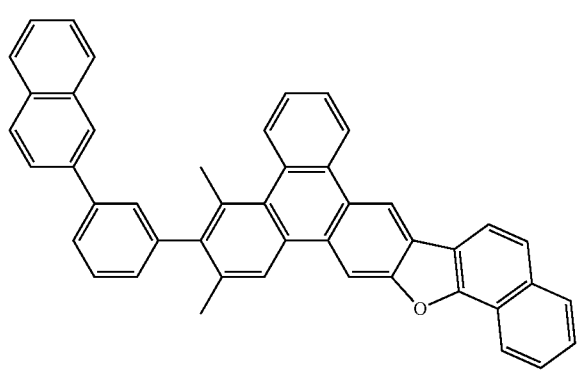

Compound 245

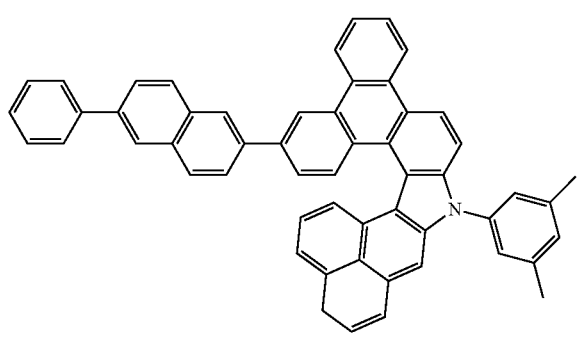

-continued

Compound 246

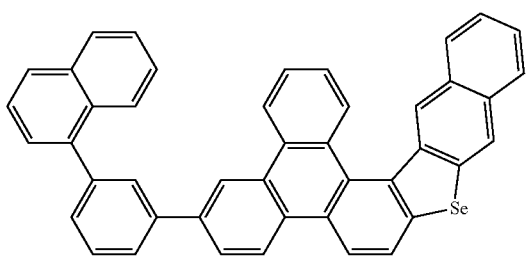

Compound 247

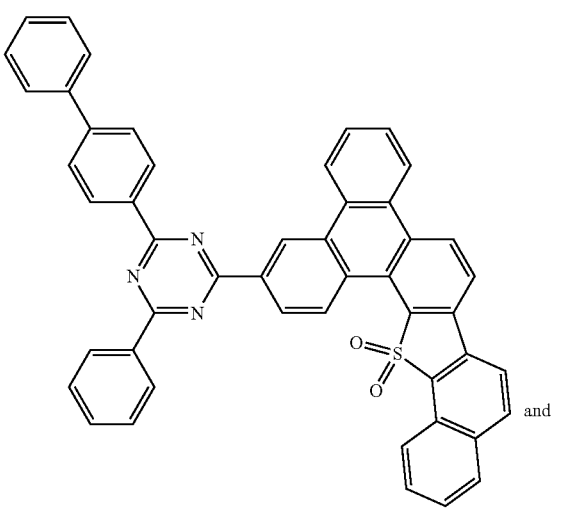

Compound 248

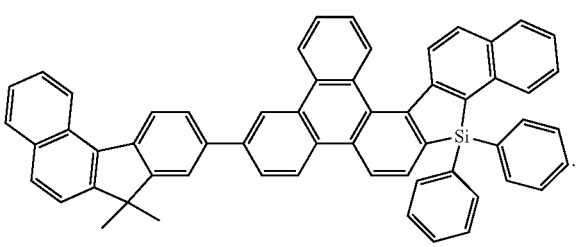

and

In another embodiment of the present invention, an organic electroluminescence device is disclosed. The organic electroluminescence device comprises a pair of electrodes composed of a cathode and an anode, and a light emitting layer between the pair of electrodes. The light emitting layer comprises the organic compound represented by formula (A).

In some embodiments, the organic compound of the light emitting layer may be a host material. The host material is capable of, for example, lowering a driving voltage, increasing a current efficiency or extending a half-life of the organic electroluminescence device.

In some embodiments, the organic compound of the light emitting layer may be a fluorescent dopant material. The dopant material is capable of, for example, lowering a driving voltage, increasing a current efficiency or extending a half-life of the organic electroluminescence device.

In some embodiments, the organic compound of the light emitting layer may be an electron transfer material.

In some embodiments, the organic compound of the light emitting layer may be a hole blocking material.

In a further embodiment of the present invention, the organic electroluminescence device is a lighting panel. In other embodiment of the present invention, the organic electroluminescence device is a backlight panel.

Detailed preparation of the organic compounds of the present invention will be clarified by exemplary embodiments below, but the present invention is not limited thereto. EXAMPLES 1 to 31 show the preparation of the organic compounds of the present invention, and EXAMPLE 32 and EXAMPLE 33 show the fabrication and test reports of the organic EL devices.

Example 1

Synthesis of 1-bromo-2-iodo-4-methoxybenzene

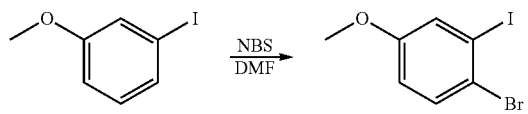

A mixture of 40 g (171 mmol) of 1-iodo-3-methoxybenzene, 32 g (179 mmol) of N-bromosuccinimide, and 600 ml of DMF was degassed and placed under nitrogen, and then heated at 80° C. for 12 hrs. After the reaction finished, the mixture was allowed to cool to room temperature. Subsequently, the solvent was removed under reduced pressure, and the crude product was purified by column chromatography, yielding 45 g of 1-bromo-2-iodo-4-methoxybenzene as yellow oil (84.1%). $^1$H NMR (CDCl$_3$, 400 MHz): chemical shift (ppm) 7.43 (dd, 1H), 7.35 (dd, 1H), 6.73 (dd, 1H), 3.74 (s, 3H).

Synthesis of 2-bromo-5-methoxy-1,1'-biphenyl

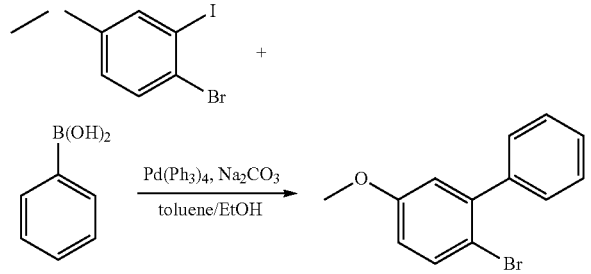

A mixture of 40 g (127.8 mmol) of 1-bromo-2-iodo-4-methoxybenzene, 15.6 g (127.8 mmol) of phenylboronic acid, 2.95 g (2.56 mmol) of Pd(Ph$_3$)$_4$, 155 ml of 2M Na$_2$CO$_3$, 100 ml of EtOH and 300 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 30 g of 2-bromo-5-methoxy-1,1'-biphenyl as colorless liquid (89.2%). $^1$H NMR (CDCl$_3$, 400 MHz): chemical shift (ppm) 7.55 (d, 1H), 7.46-7.38 (m, 5H), 6.89 (d, 1H), 6.79 (dd, 1H), 3.81 (s, 3H).

Synthesis of (5-methoxy-[1,1'-biphenyl]-2-yl)boronic Acid

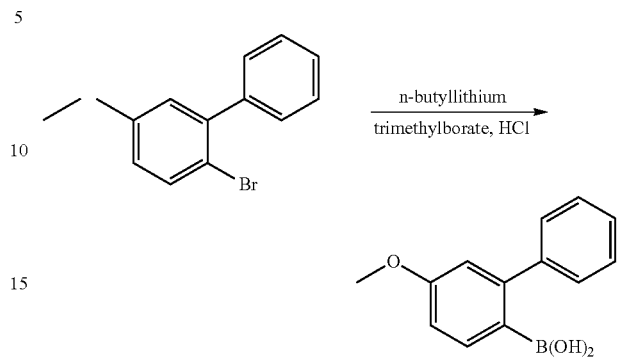

The compound 2-bromo-5-methoxy-1,1'-biphenyl (30 g, 114 mmol) was mixed with 600 ml of dry THF. To the mixture, 54.7 ml of N-butyllithium (137 mmol) was added at −60° C. and the mixture was stirred for 1 hrs. After the reaction finished, 17.8 g (171 mmol) of trimethyl borate was added and the mixture was stirred overnight. 228 ml (228 mmole) of 1M HCl was added and the mixture was stirred for 1 hrs. The mixture was extracted with ethyl acetate/H$_2$O, and the organic layer was removed under reduced pressure. The crude product was washed by hexane, yielding 19.5 g of (5-methoxy-[1,1'-biphenyl]-2-yl)boronic acid as white solid (75%).

Synthesis of 9-(5-methoxy-[1,1'-biphenyl]-2-yl) benzo[b]naphtha-[1,2-d]thiophene

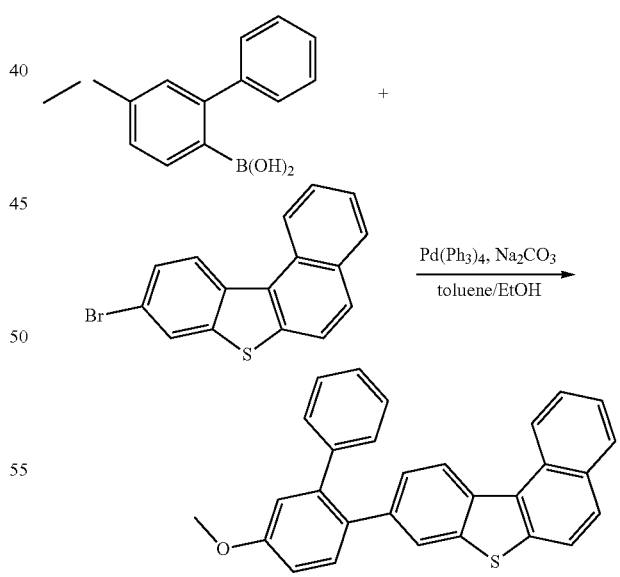

A mixture of 20 g (87.7 mmol) of (5-methoxy-[1,1'-biphenyl]-2-yl)-boronic acid, 30.2 g (96.5 mmol) of 9-bromobenzo[b]naphtho[1,2-d]thiophene, 2.03 g (1.75 mmol) of Pd(Ph$_3$)$_4$, 87.7 ml of 2M Na$_2$CO$_3$, 200 ml of EtOH and 400 ml of toluene was degassed and placed under nitrogen, and then heated to reflux for 12 hrs. After the reaction finished, the mixture was allowed to cool to room temperature.

Subsequently, the solvent was removed under reduced pressure, and the crude product was purified by column chromatography, yielding 25.2 g of 9-(5-methoxy-[1,1'-biphenyl]-2-yl)benzo[b]naphtha-[1,2-d]-thiophene as white solid (69%). $^1$H NMR (CDCl$_3$, 400 MHz): chemical shift (ppm) 8.47 (d, 1H), 8.12-8.06 (m, 3H), 8.01 (d, 1H), 7.77-7.72 (m, 4H), 7.51-7.45 (m, 5H), 7.40-7.36 (m, 2H), 7.02 (d, 1H), 3.81 (s, 3H).

Synthesis of 11-methoxynaphtho[2,1-b]triphenyleno[2,3-d]thiophene

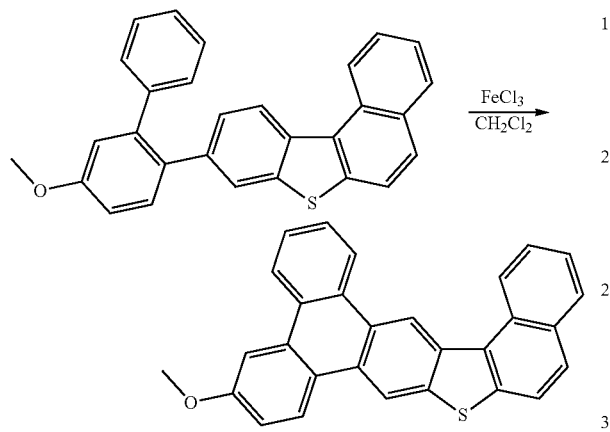

The compound 9-(5-methoxy-[1,1'-biphenyl]-2-yl)benzo[b]naphtha-[1,2-d]thiophene (20 g, 48 mmol) was mixed with 700 ml of CH$_2$Cl$_2$. To the mixture, 77.9 g of FeCl$_3$ (480 mmol) was added and the mixture was stirred for 1 hrs. After the reaction finished, the solvent was removed under reduced pressure, and the crude product was purified by column chromatography, yielding 7.6 g of 11-methoxynaphtho[2,1-b]triphenyleno-[2,3-d]thiophene as white solid (39%). $^1$H NMR (CDCl$_3$, 400 MHz): chemical shift (ppm) 8.91-8.89 (m, 2H), 8.81 (d, 1H), 8.49 (d, 1H), 8.14 (m, 2H), 7.99 (d, H), 7.88-7.82 (m, 3H), 7.62 (s, 1H), 7.57-7.52 (m, 3H), 7.36 (d, 1H), 3.82 (s, 3H).

Synthesis of naphtho[2,1-b]triphenyleno[2,3-d]thiophen-11-ol

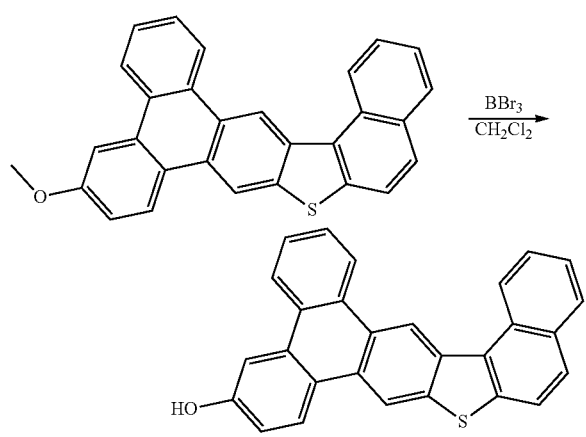

The compound 11-methoxynaphtho[2,1-b]triphenyleno[2,3-d]-thiophene (10 g, 27.4 mmol) was mixed with 400 ml of CH$_2$Cl$_2$. To the mixture, 7.24 g of BBr$_3$ (28.9 mmol) was added and the mixture was stirred overnight. After the reaction finished, the solvent was removed under reduced pressure, and the crude product was purified by column chromatography, yielding 8.4 g of naphtho[2,1-b]triphenyleno[2,3-d]thiophen-11-ol as white solid (87%). $^1$H NMR (CDCl$_3$, 400 MHz): chemical shift (ppm) 8.89-8.87 (m, 2H), 8.78 (d, 1H), 8.45 (d, 1H), 8.09 (m, 2H), 7.94 (d, H), 7.89-7.84 (m, 3H), 7.58 (s, 1H), 7.55-7.49 (m, 3H), 7.31 (d, 1H), 5.41 (s, 1H).

Synthesis of naphtho[2,1-b]triphenyleno[2,3-d]thiophen-11-yl trifluoromethanesulfonate

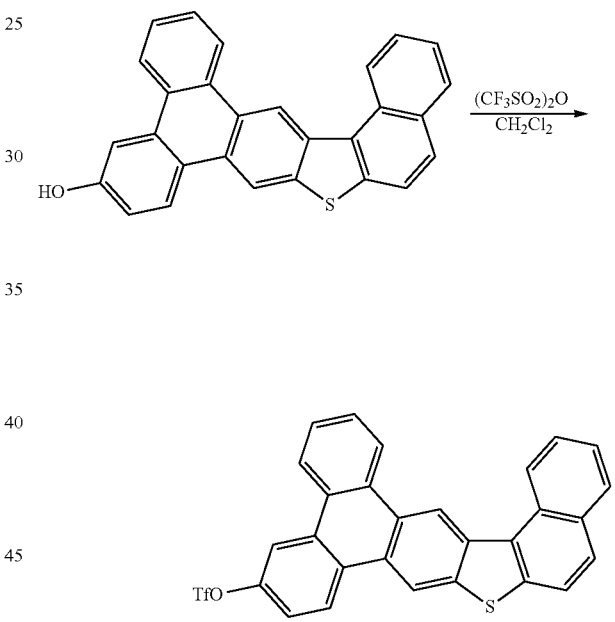

The compound naphtho[2,1-b]triphenyleno[2,3-d]thiophen-11-ol (10 g, 25 mmol) was mixed with 450 ml of CH$_2$Cl$_2$. To the mixture, 2.98 g of pyridine (37.5 mmol) was added and the mixture was stirred for 1 hrs. To the mixture, 12 g of (CF$_3$SO$_2$)$_2$O (42.5 mmol) was added and the mixture was stirred for 1 hrs. After the reaction finished, the solvent was removed under reduced pressure, and the crude product was purified by column chromatography, yielding 6.9 g of naphtho[2,1-b]triphenyleno[2,3-d]-thiophen-11-yl trifluoromethanesulfonate as yellow solid (52%). $^1$H NMR (CDCl$_3$, 400 MHz): chemical shift (ppm) 8.99-8.95 (m, 3H), 8.47 (d, 1H), 8.14-8.11 (m, 3H), 7.97 (d, H), 7.91-7.84 (m, 3H), 7.58 (s, 1H), 7.55-7.50 (m, 3H).

Synthesis of 4,4,5,5-tetramethyl-2-(naphtho[2,1-b]triphenyleno[2,3-d]-thiophen-11-yl)-1,3,2-dioxaborolane

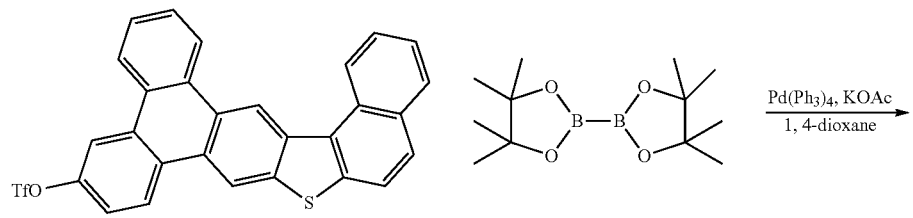

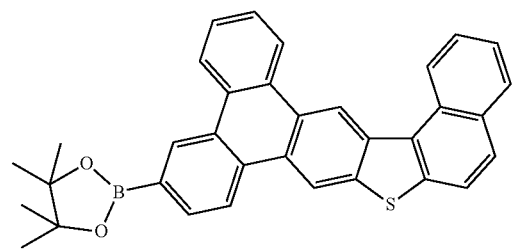

A mixture of 5 g (9.4 mmol) of naphtho[2,1-b]triphenyleno[2,3-d]-thiophen-11-yl trifluoromethanesulfonate, 2.87 g (11.3 mmol) of bis(pinacolato)diboron, 0.43 g (0.36 mmol) of Pd(Ph$_3$)$_4$, 1.84 g (18.8 mmol) of potassium acetate, and 60 ml of 1,4-dioxane was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 3.26 g of 4,4,5,5-tetramethyl-2-(naphtho[2,1-b]triphenyleno[2,3-d]-thiophen-11-yl)-1,3,2-dioxaborolane as white solid (68%). $^1$H NMR (CDCl$_3$, 400 MHz): chemical shift (ppm) 8.94-8.88 (m, 3H), 8.47 (d, 1H), 8.15-8.12 (m, 3H), 7.99 (d, 1H), 7.88-7.82 (m, 4H), 7.57-7.53 (m, 3H), 1.27 (s, 12H).

Synthesis of 11-([1,1':3',1''-terphenyl]-3-yl)naphtho[2,1-b]-triphenyleno[2,3-d]thiophene (Compound 78)

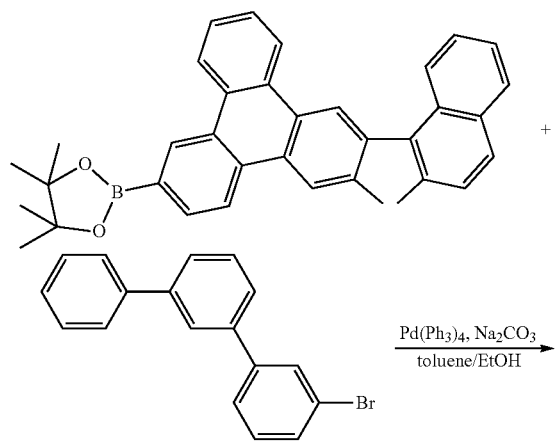

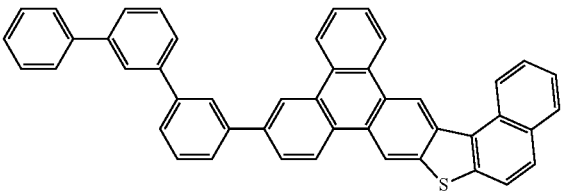

A mixture of 5 g (9.8 mmol) of 4,4,5,5-tetramethyl-2-(naphtho[2,1-b]-triphenyleno[2,3-d]thiophen-11-yl)-1,3,2-dioxaborolane, 3.33 g (10.8 mmol) of 3-bromo-1,1':3',1''-terphenyl, 0.23 g (0.2 mmol) of Pd(Ph$_3$)$_4$, 9.8 ml of 2M Na$_2$CO$_3$, 30 ml of EtOH and 60 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 3.9 g of 11-([1,1':3',1''-terphenyl]-3-yl)naphtho[2,1-b]-triphenyleno[2,3-d]thiophene as yellow solid (65%). $^1$H NMR (CDCl$_3$, 400 MHz): chemical shift (ppm) 8.99-8.93 (m, 3H), 8.46 (d, 1H), 8.33 (s, 1H), 8.29-8.23 (m, 4H), 8.14-8.09 (m, 3H), 7.97 (d, H), 7.85-7.81 (m, 2H), 7.56-7.46 (m, 7H), 7.47-7.42 (m, 3H).

Example 2-13

We have used the same synthesis methods to get a series of intermediates and the following compounds are synthesized analogously.

| Ex. | Intermediate III | Intermediate IV |
|---|---|---|
| 2 | | |
| 3 | | |
| 4 | | |
| 5 | | |
| 6 | | |
| 7 | | |

-continued
| | 103 | 104 |
|---|---|---|
| 8 | 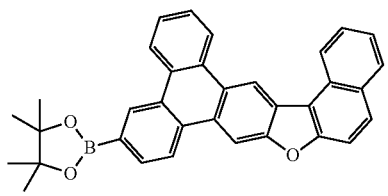 [SMILES: CC1(C)OB(c2ccc3c(c2)c2ccccc2c2cc4c(cc32)oc2ccc3ccccc3c24)OC1(C)C] | 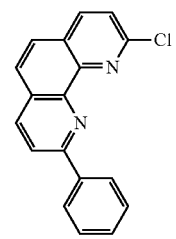 [SMILES: Clc1ccc2ccc3ccc(-c4ccccc4)nc3c2n1] |
| 9 | 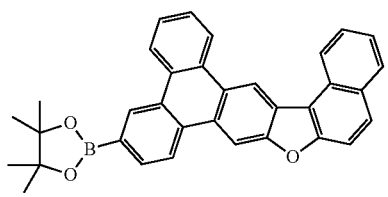 [SMILES: CC1(C)OB(c2ccc3c(c2)c2ccccc2c2cc4c(cc32)oc2ccc3ccccc3c24)OC1(C)C] | 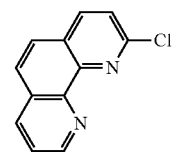 [SMILES: Clc1ccc2ccc3cccnc3c2n1] |
| 10 | 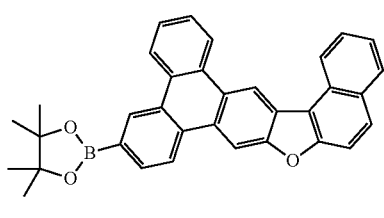 [SMILES: CC1(C)OB(c2ccc3c(c2)c2ccccc2c2cc4c(cc32)oc2ccc3ccccc3c24)OC1(C)C] | 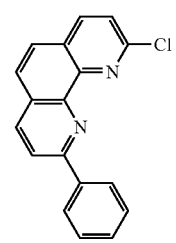 [SMILES: Clc1ccc2ccc3ccc(-c4ccccc4)nc3c2n1] |
| 11 | 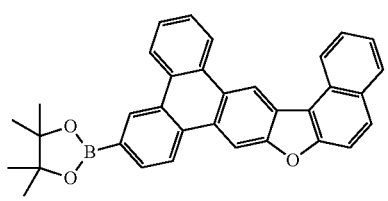 [SMILES: CC1(C)OB(c2ccc3c(c2)c2ccccc2c2cc4c(cc32)oc2ccc3ccccc3c24)OC1(C)C] | 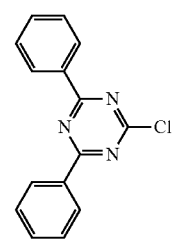 [SMILES: Clc1nc(-c2ccccc2)nc(-c2ccccc2)n1] |
| 12 | 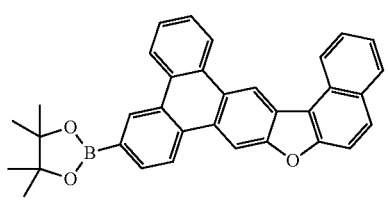 [SMILES: CC1(C)OB(c2ccc3c(c2)c2ccccc2c2cc4c(cc32)oc2ccc3ccccc3c24)OC1(C)C] | 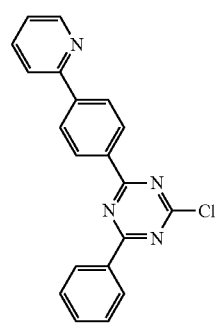 [SMILES: Clc1nc(-c2ccccc2)nc(-c2ccc(-c3ccccn3)cc2)n1] |
| 13 | 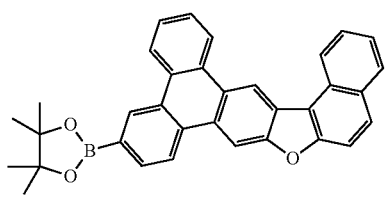 [SMILES: CC1(C)OB(c2ccc3c(c2)c2ccccc2c2cc4c(cc32)oc2ccc3ccccc3c24)OC1(C)C] | 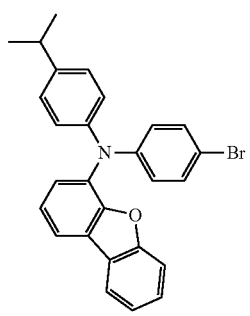 [SMILES: CC(C)c1ccc(N(c2ccc(Br)cc2)c2cccc3c2oc2ccccc23)cc1] |

-continued
| Ex. | Product | Yield |
|---|---|---|
| 2 | 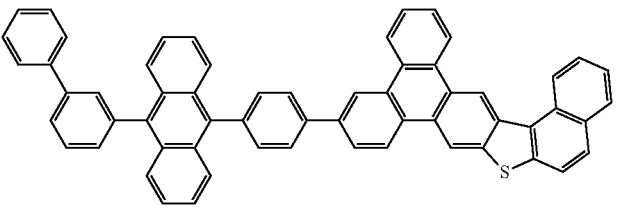<br>Compound 98 | 58% |
| 3 | 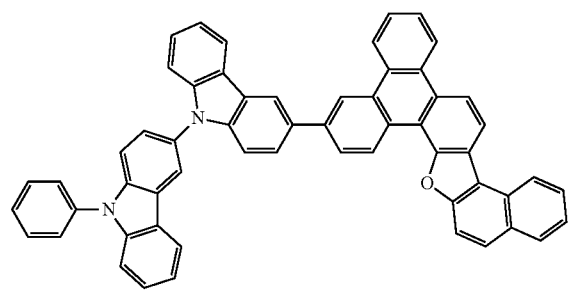<br>Compound 113 | 64% |
| 4 | 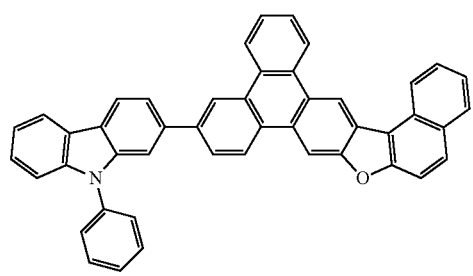<br>Compound 114 | 69% |
| 5 | 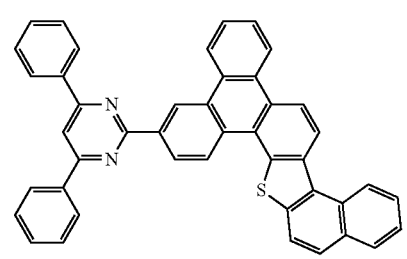<br>Compound 131 | 62% |
| 6 | 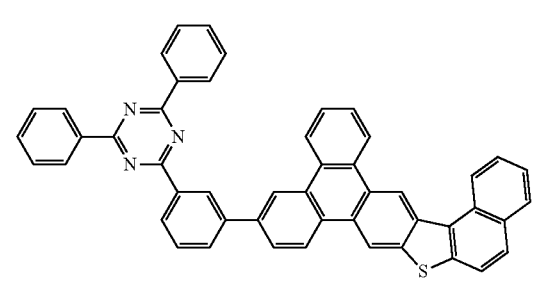<br>Compound 132 | 68% |

-continued
| | | |
|---|---|---|
| 7 | 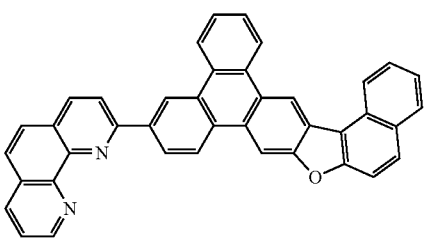<br>Compound 161 | 61% |
| 8 | 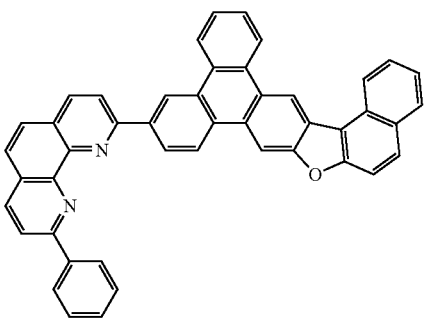<br>Compound 162 | 63% |
| 9 | 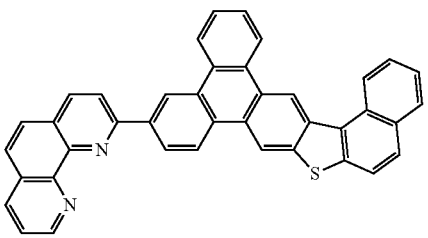<br>Compound 169 | 59% |
| 10 | 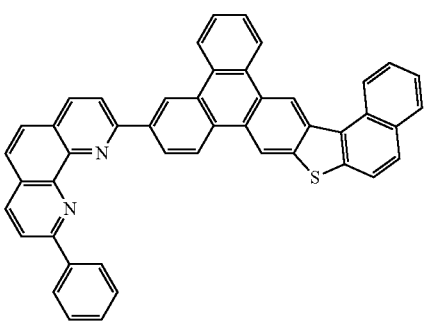<br>Compound 170 | 63% |
| 11 | 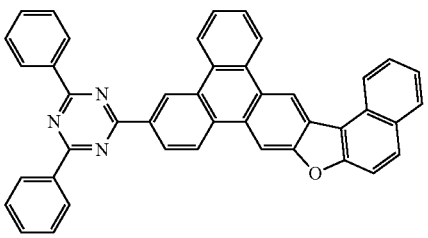<br>Compound 182 | 66% |

| | | |
|---|---|---|
| 12 | 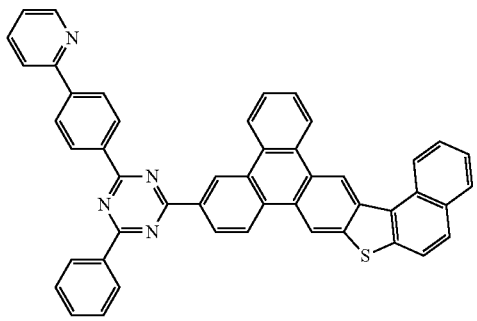

Compound 194 | 55% |
| 13 | 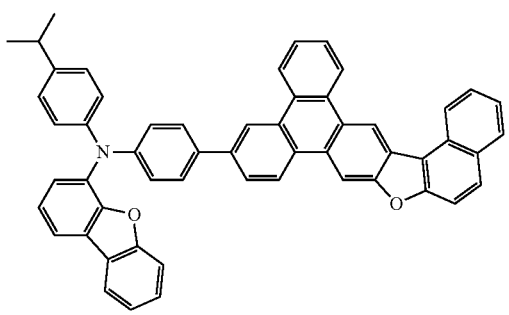

Compound 206 | 57% |

Example 14

Synthesis of 5-bromo-10-iodonaphtho[2,1-b]benzofuran

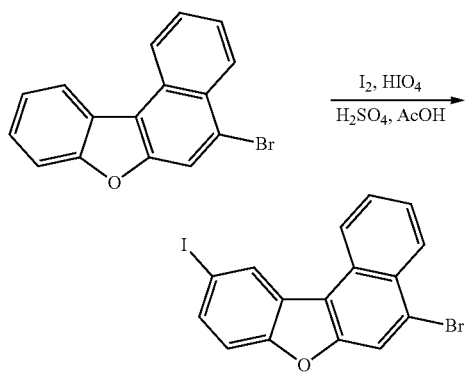

A mixture of 10 g (33.7 mmol) of 5-bromonaphtho[2,1-b]benzofuran, 60 ml of acetic acid, 6 ml of water, 6 ml of concentrated sulfuric acid, 8.55 g (33.7 mmol) of iodine, 7.67 g (33.7 mmol) of periodic acid and 60 ml of chloroform was heated at 50° C. overnight with good stirring. After cooling to room temperature, the product mixture was poured into water and extracted with dichloromethane (3×100 mL). The combined dark purple organic layer was decolorized with sodium sulfite, washed with water, dried with anhydrous $Na_2SO_4$, filtered, and evaporated to dryness. The crude product was purified by column chromatography, yielding 6.8 g of 5-bromo-10-iodonaphtho[2,1-b]benzofuran as yellow solid (47.8%). $^1$H NMR ($CDCl_3$, 400 MHz): chemical shift (ppm) 8.57 (d, 1H), 8.48 (s, 1H), 8.13 (d, 1H), 7.82 (s, 1H), 7.54-7.58 (m, 3H), 7.43 (d, 1H).

Synthesis of 10-([1,1'-biphenyl]-2-yl)-5-bromonaphtho[2,1-b]-benzofuran

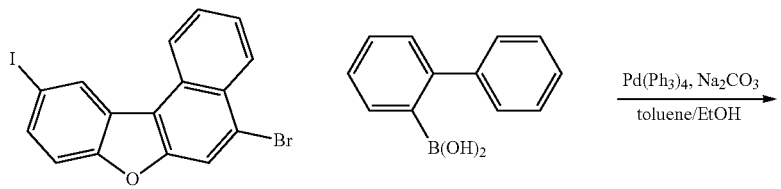

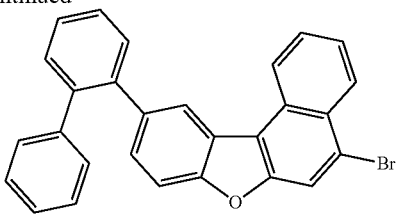

A mixture of 10 g (23.6 mmol) of 5-bromo-10-iodonaphtho[2,1-b]-benzofuran, 4.68 g (23.6 mmol) of [1,1'-biphenyl]-2-ylboronic acid, 0.23 g (0.2 mmol) of Pd(Ph$_3$)$_4$, 23.6 ml of 2M Na$_2$CO$_3$, 80 ml of EtOH and 160 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 6.9 g of 10-([1,1'-biphenyl]-2-yl)-5-bromonaphtho[2,1-b]benzofuran as white solid (64.9%). $^1$H NMR (CDCl$_3$, 400 MHz): chemical shift (ppm) 8.59 (d, 1H), 8.45 (s, 1H), 8.11 (d, 1H), 7.86-7.79 (m, 5H), 7.74-7.72 (s, 2H), 7.54-7.39 (m, 7H).

Synthesis of 5-bromonaphtho[2,1-b]triphenyleno[2,3-d]furan

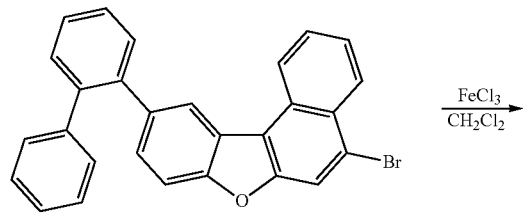

The compound 10-([1,1'-biphenyl]-2-yl)-5-bromonaphtho[2,1-b]-benzofuran (8 g, 17.8 mmol) was mixed with 100 ml of CH$_2$Cl$_2$. To the mixture, 28.9 g of FeCl$_3$ (178 mmol) was added and the mixture was stirred for 1 hrs. After the reaction finished, the solvent was removed under reduced pressure, and the crude product was purified by column chromatography, yielding 3.2 g of 5-bromonaphtho[2,1-b]triphenyleno[2,3-d]furan as white solid (40.1%). $^1$H NMR (CDCl$_3$, 400 MHz): chemical shift (ppm) 8.58 (d, 1H), 8.47 (s, 1H), 8.12 (d, 1H), 7.84-7.79 (m, 3H), 7.75-7.73 (s, 2H), 7.52-7.39 (m, 7H).

Synthesis of 5-([1,1':3',1''-terphenyl]-3-yl)naphtho[2,1-b]-triphenyleno[2,3-d]furan (Compound 2)

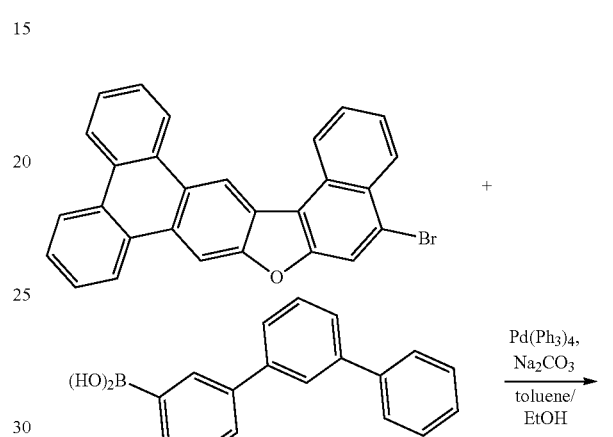

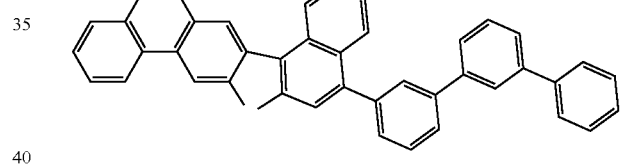

A mixture of 5 g (11.2 mmol) of 5-bromonaphtho[2,1-b]triphenyleno-[2,3-d]furan, 3.37 g (12.3 mmol) of [1,1':3',1''-terphenyl]-3-ylboronic acid, 0.26 g (0.22 mmol) of Pd(Ph$_3$)$_4$, 11.2 ml of 2M Na$_2$CO$_3$, 30 ml of EtOH and 60 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 3.5 g of 5-([1,1':3',1''-terphenyl]-3-yl)naphtho[2,1-b]triphenyleno-[2,3-d]furan as white solid (52.5%). $^1$H NMR (CDCl$_3$, 400 MHz): chemical shift (ppm) 8.94-8.89 (m, 3H), 8.57 (d, 2H), 8.14-8.10 (m, 3H), 7.89-7.84 (m, 4H), 7.72 (s, 2H), 7.65 (s, H), 7.59-7.54 (m, 4H), 7.50-7.44 (m, 8H), 7.39 (m, 1H).

Example 15-31

We have used the same synthesis methods to get a series of intermediates and the following compounds are synthesized analogously.

| Ex. | IntermediateI | IntermediateII |
|---|---|---|
| 15 | 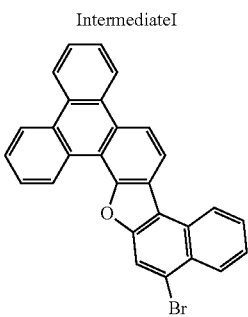 | 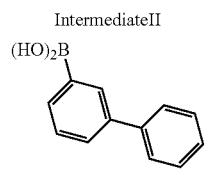 |
| 16 | 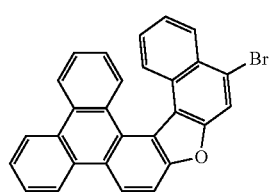 [SMILES: Brc1cc2oc3ccc4c5ccccc5c5ccccc5c4c3c2c2ccccc12] | 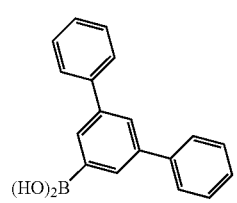 [SMILES: OB(O)c1cc(-c2ccccc2)cc(-c2ccccc2)c1] |
| 17 | 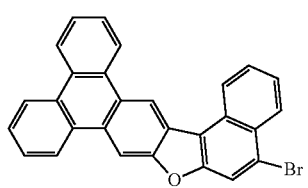 [SMILES: Brc1cc2oc3cc4c5ccccc5c5ccccc5c4cc3c2c2ccccc12] | 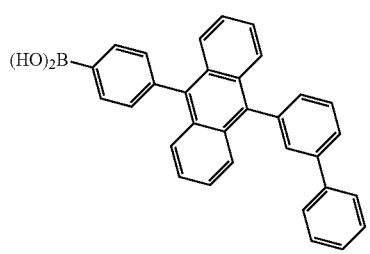 [SMILES: OB(O)c1ccc(-c2c3ccccc3c(-c3cccc(-c4ccccc4)c3)c3ccccc23)cc1] |
| 18 | 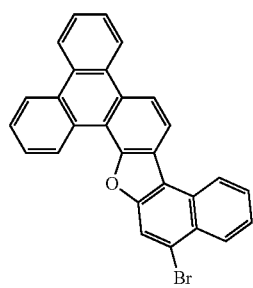 [SMILES: Brc1cc2oc3c(ccc4c5ccccc5c5ccccc5c43)c2c2ccccc12] | 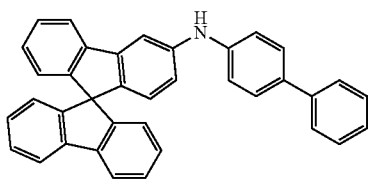 [SMILES: c1ccc(-c2ccc(Nc3ccc4c(c3)-c3ccccc3C43c4ccccc4-c4ccccc43)cc2)cc1] |
| 19 | 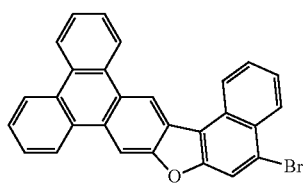 [SMILES: Brc1cc2oc3cc4c5ccccc5c5ccccc5c4cc3c2c2ccccc12] | 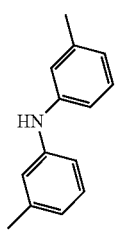 |
| 20 | 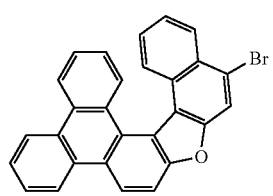 [SMILES: Brc1cc2oc3ccc4c5ccccc5c5ccccc5c4c3c2c2ccccc12] | 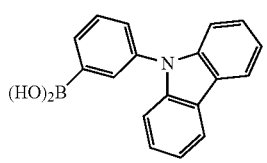 [SMILES: OB(O)c1cccc(-n2c3ccccc3c3ccccc32)c1] |

-continued
| | | |
|---|---|---|
| 21 | 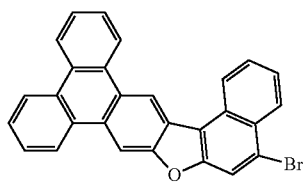 [SMILES: Brc1cc2oc3cc4c5ccccc5c5ccccc5c4cc3c2c2ccccc12] | 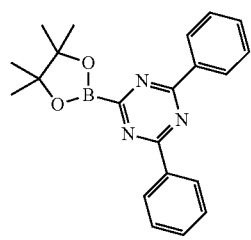 [SMILES: CC1(C)OB(c2nc(-c3ccccc3)nc(-c3ccccc3)n2)OC1(C)C] |
| 22 | 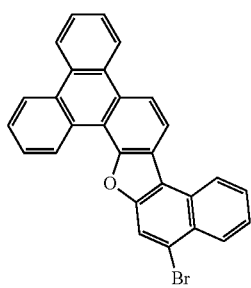 [SMILES: Brc1cc2oc3c(ccc4c5ccccc5c5ccccc5c43)c2c2ccccc12] | 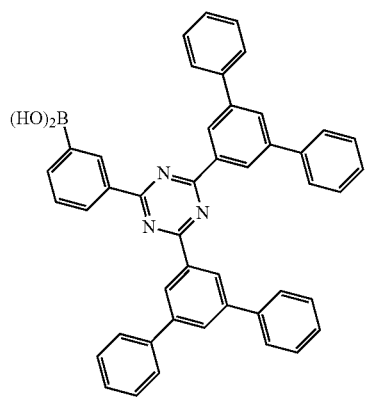 [SMILES: OB(O)c1cccc(-c2nc(-c3cc(-c4ccccc4)cc(-c4ccccc4)c3)nc(-c3cc(-c4ccccc4)cc(-c4ccccc4)c3)n2)c1] |
| 23 | 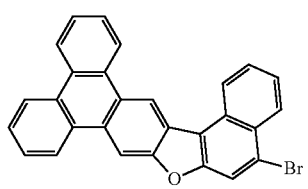 [SMILES: Brc1cc2oc3cc4c5ccccc5c5ccccc5c4cc3c2c2ccccc12] | 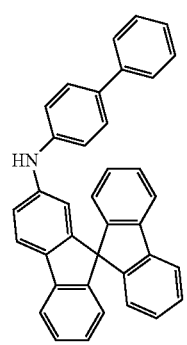 [SMILES: c1ccc(-c2ccc(Nc3ccc4c(c3)C3(c5ccccc5-c5ccccc53)c3ccccc3-4)cc2)cc1] |
| 24 | 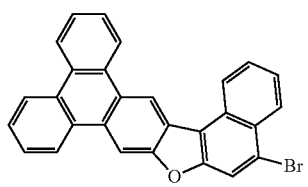 [SMILES: Brc1cc2oc3cc4c5ccccc5c5ccccc5c4cc3c2c2ccccc12] | 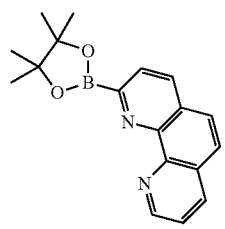 [SMILES: CC1(C)OB(c2ccc3ccc4cccnc4c3n2)OC1(C)C] |
| 25 | 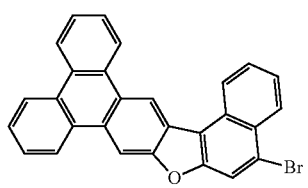 [SMILES: Brc1cc2oc3cc4c5ccccc5c5ccccc5c4cc3c2c2ccccc12] | 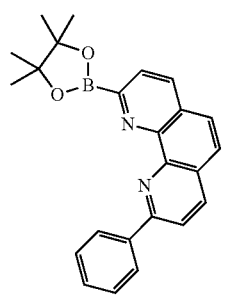 [SMILES: CC1(C)OB(c2ccc3ccc4ccc(-c5ccccc5)nc4c3n2)OC1(C)C] |

| | | |
|---|---|---|
| 26 | 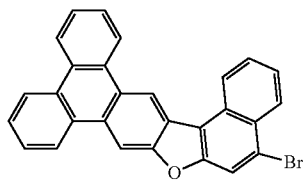 [SMILES: Brc1cc2oc3cc4c5ccccc5c5ccccc5c4cc3c2c2ccccc12] | 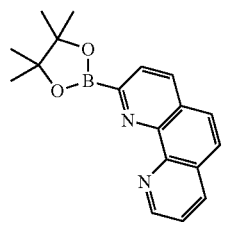 [SMILES: CC1(C)OB(c2ccc3ccc4cccnc4c3n2)OC1(C)C] |
| 27 | 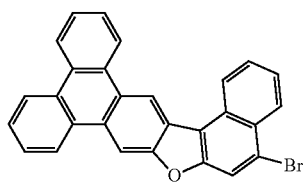 [SMILES: Brc1cc2oc3cc4c5ccccc5c5ccccc5c4cc3c2c2ccccc12] | 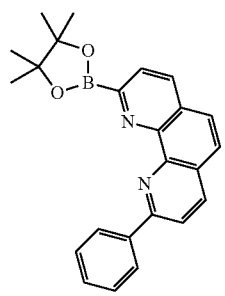 [SMILES: CC1(C)OB(c2ccc3ccc4ccc(-c5ccccc5)nc4c3n2)OC1(C)C] |
| 28 | 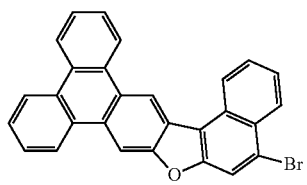 [SMILES: Brc1cc2oc3cc4c5ccccc5c5ccccc5c4cc3c2c2ccccc12] | 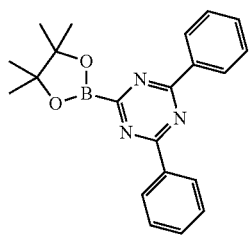 [SMILES: CC1(C)OB(c2nc(-c3ccccc3)nc(-c3ccccc3)n2)OC1(C)C] |
| 29 | 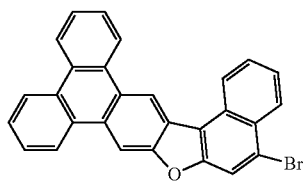 [SMILES: Brc1cc2oc3cc4c5ccccc5c5ccccc5c4cc3c2c2ccccc12] | 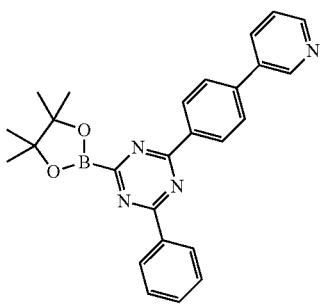 [SMILES: CC1(C)OB(c2nc(-c3ccccc3)nc(-c3ccc(-c4cccnc4)cc3)n2)OC1(C)C] |
| 30 | 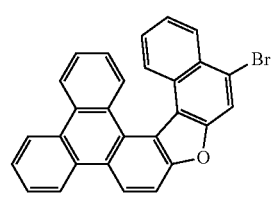 [SMILES: Brc1cc2oc3ccc4c5ccccc5c5ccccc5c4c3c2c2ccccc12] | 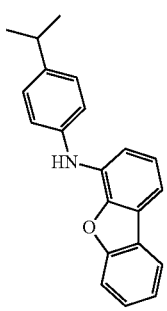 [SMILES: CC(C)c1ccc(Nc2cccc3c2oc2ccccc23)cc1] |

| 31 | 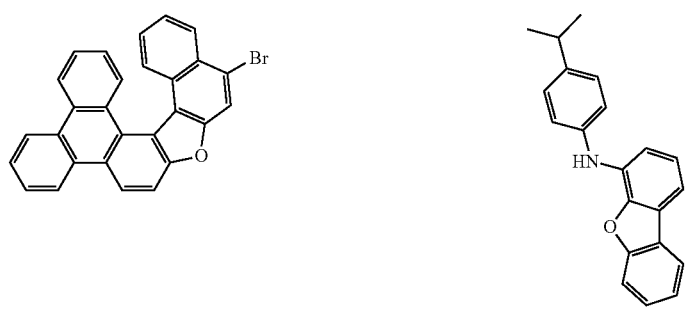 | |
| Ex. | Product | Yield |
|---|---|---|
| 15 | 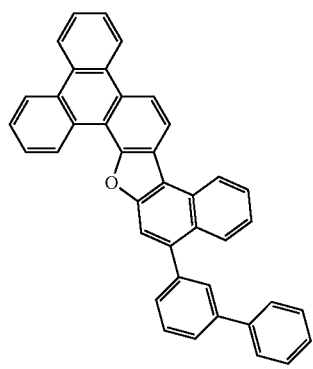
Compond 1 | 61% |
| 16 | 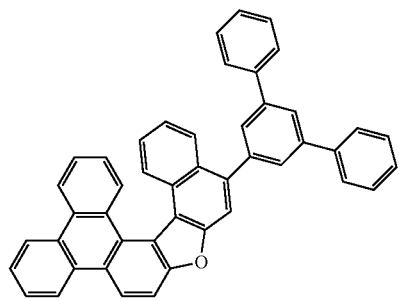
Compound 3 | 59% |
| 17 | 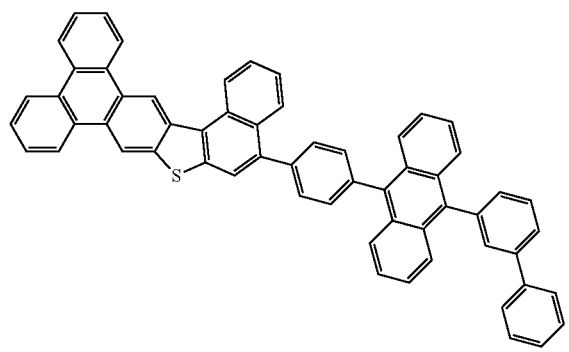
Compound 20 | 63% |

| 18 | 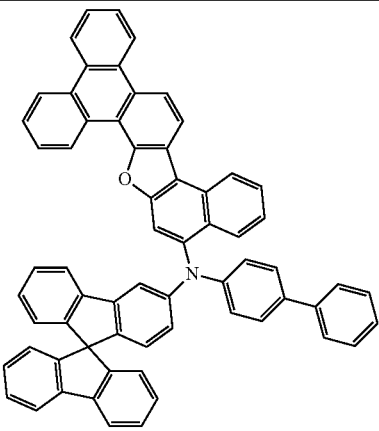
Compound 37 | 57% |
| 19 | 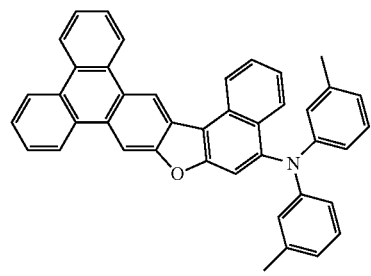
Compound 38 | 65% |
| 20 | 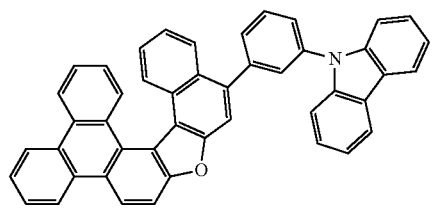
Compound 39 | 58% |
| 21 | 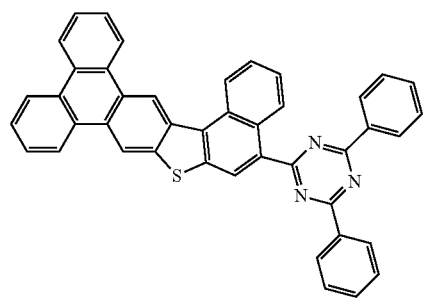
Compound 56 | 55% |

| 22 | 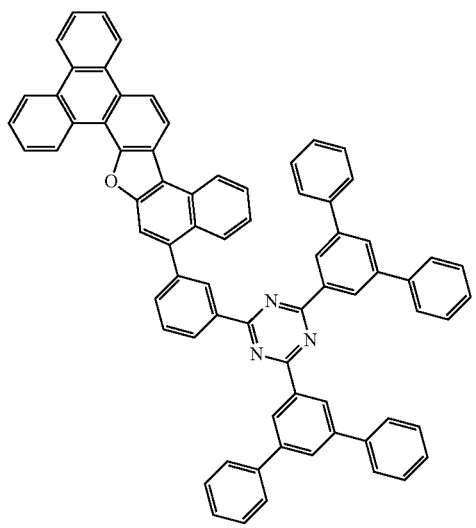
Compound 73 | 60% |
| 23 | 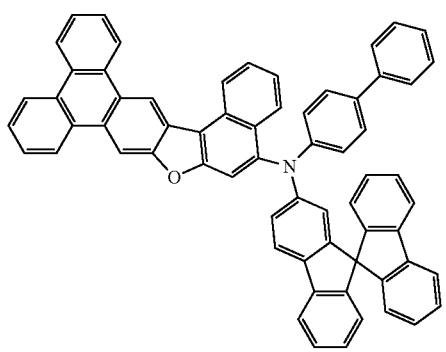
Compound 154 | 52% |
| 24 | 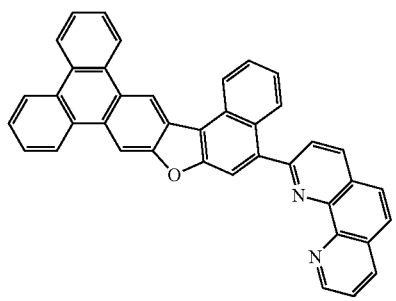
Compound 157 | 54% |

| | | |
|---|---|---|
| 25 | 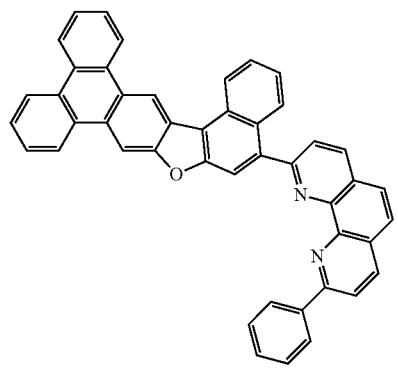
Compound 158 | 52% |
| 26 | 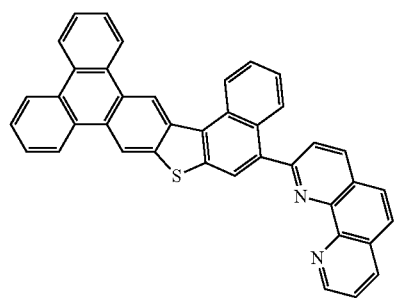
Compound 171 | 50% |
| 27 | 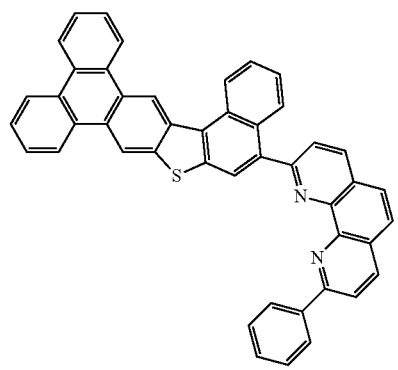
Compound 172 | 61% |
| 28 | 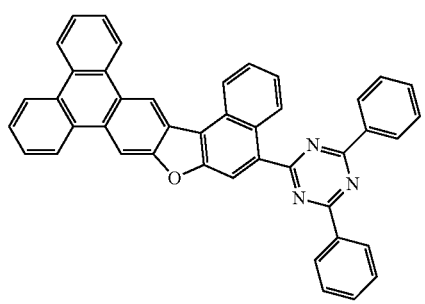
Compound 174 | 57% |

| | | |
|---|---|---|
| 29 | 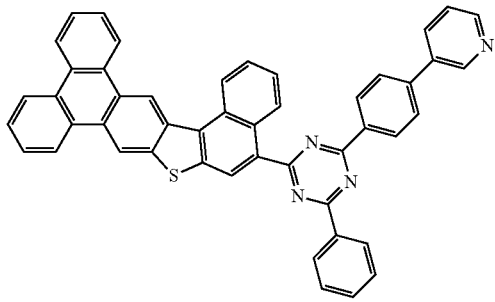<br>Compound 186 | 44% |
| 30 | 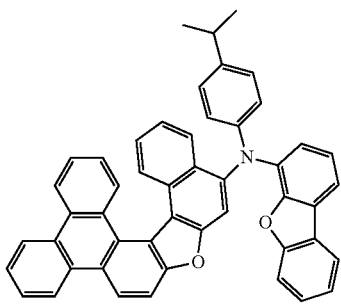<br>Compound 199 | 41% |
| 31 | 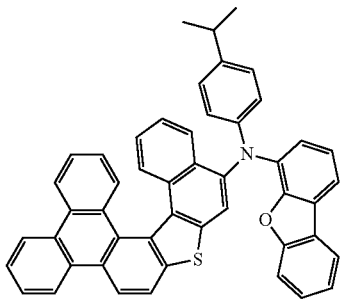<br>Compound 211 | 41% |

General Method of Producing Organic EL Device

ITO-coated glasses with 9-12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1-0.3 nm/sec) are precisely monitored or set with the aid of a quartz-crystal monitor. It is also possible, as described above, for individual layers to consist of more than one compound, i.e. in general a host material doped with a dopant material and/or co-deposited with a co-host. This is successfully achieved by co-vaporization from two or more sources, which means the naphthotriphenylenofuran and naphthotriphenylenothiophene derivatives of the present invention are thermally stable.

Dipyrazino[2,3-f:2,3-]quinoxaline-2,3,6,7,10,11-hexacarbonitrile(HAT-CN) is used as hole injection layer in this organic EL device. N,N-Bis(naphthalene-1-yl)-N,N-bis(phenyl)-benzidine(NPB) is most widely used as the hole transporting layer. 12-(4,6-diphenyl-1,3,5-triazin-2-yl)-10,10-dimethyl-10,12-dihydrophenanthro[9',10':5,6]indeno[2,1-b]carbazole (H1) and 14,14-dimethyl-11-(10-(3-(naphthalen-1-yl)phenyl) anthracen-9-yl)-14H-indeno[1,2-b]triphenylene (H2) are used as emitting hosts for comparison, and bis(2-phenylpyridinato) (2,4-diphenylpyridinato) iridium(III) (D1) and N1,N1,N6,N6-tetra-m-tolylpyrene-1,6-diamine(D2) are used as guest in the emitting layer. HB1 (see the following chemical structure) is used as hole blocking material(HBM), and 2-(naphthalen-1-yl)-9-(4-(1-(4-(10-(naphthalene-2-yl)anthracen-9-yl)-phenyl)-1H-benzo[d]imidazol-2-yl)phenyl)-1,10-phenanthroline(ET1) is used as electron transporting material to co-deposit with 8-hydroxyquinolato-lithium(LiQ) in organic EL devices. The chemical structures of conventional OLED materials and the exemplary organic compounds of the present invention for producing control and exemplary organic EL devices in this invention are shown as follows:

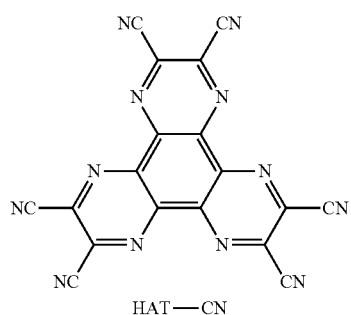
HAT—CN
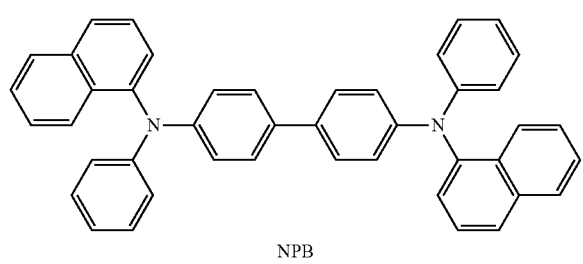
NPB
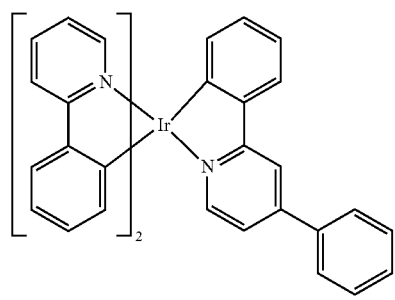
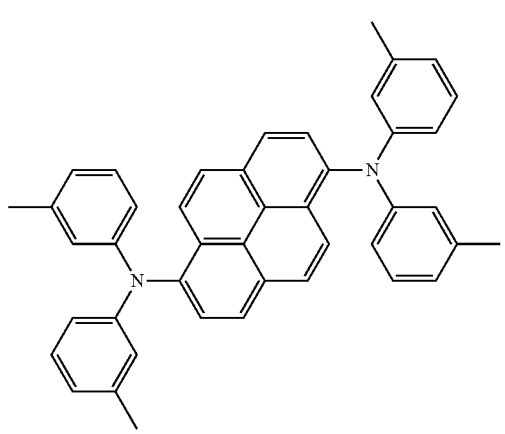
D2
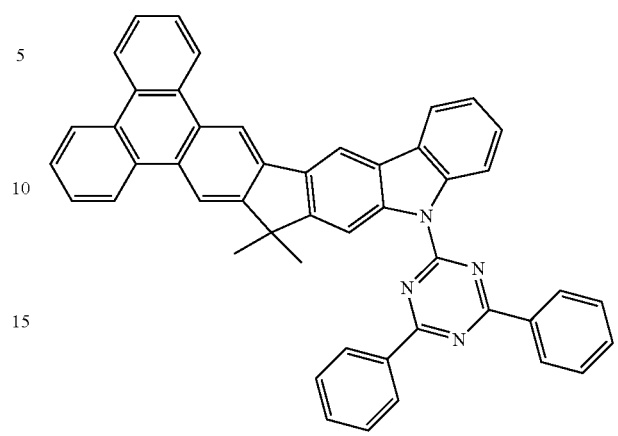
H1
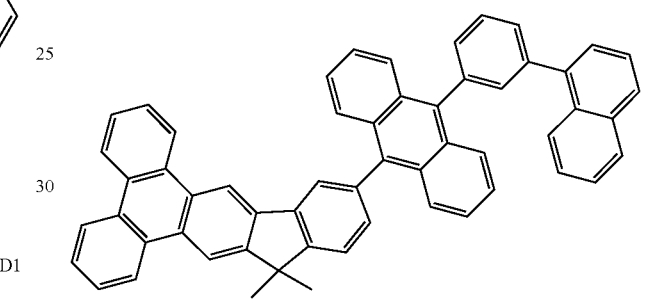
H2
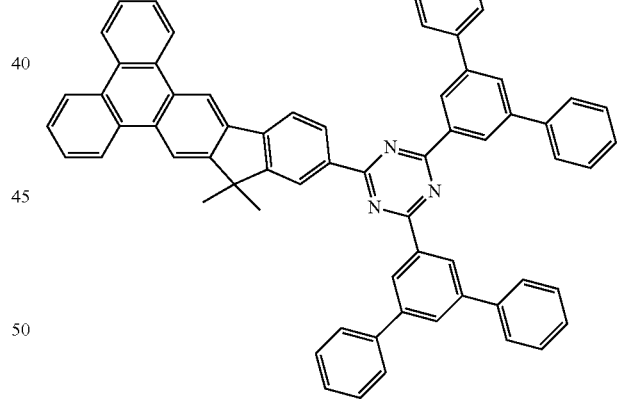
HB1
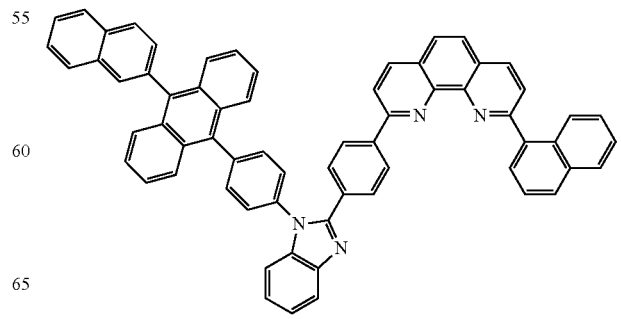
ET1

-continued
Comp. 37
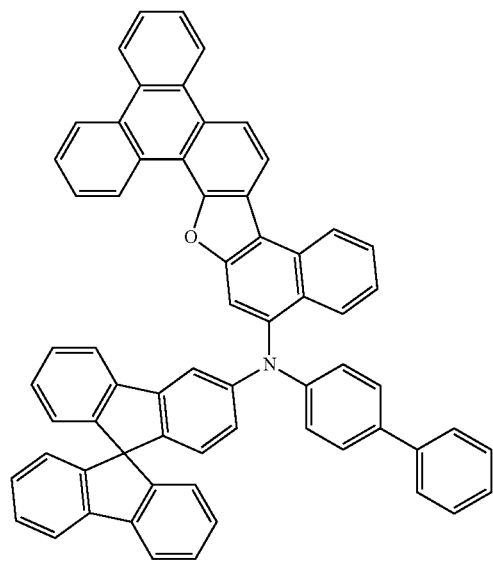
Comp. 55
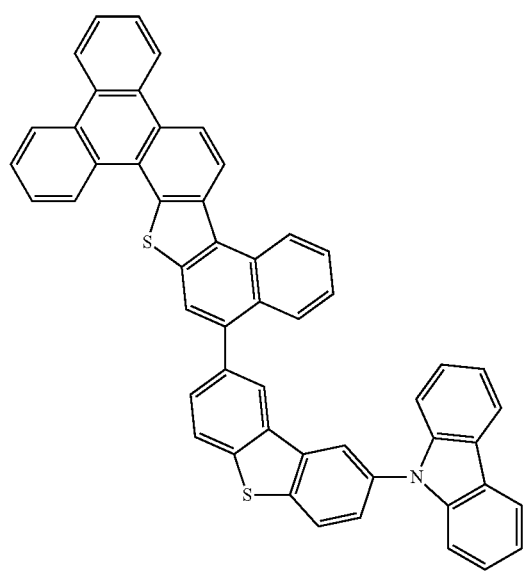
Comp. 113
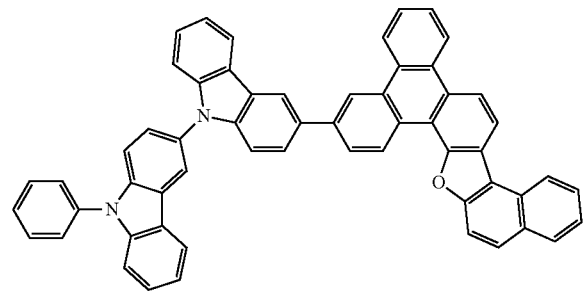
-continued
Comp. 114
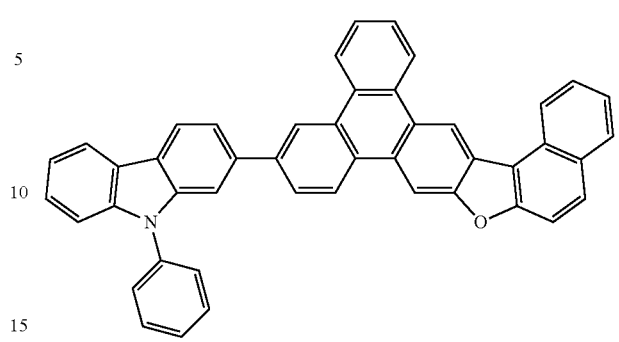
Comp. 115
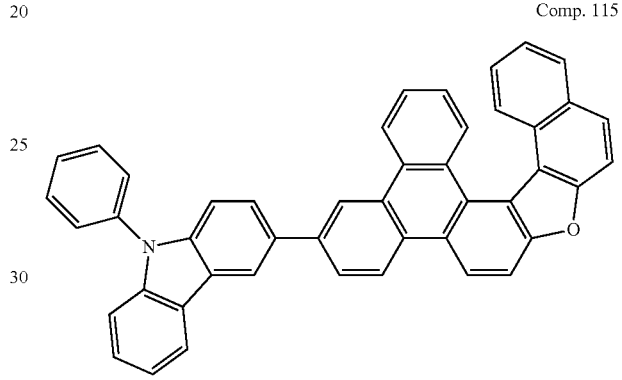
Comp. 133
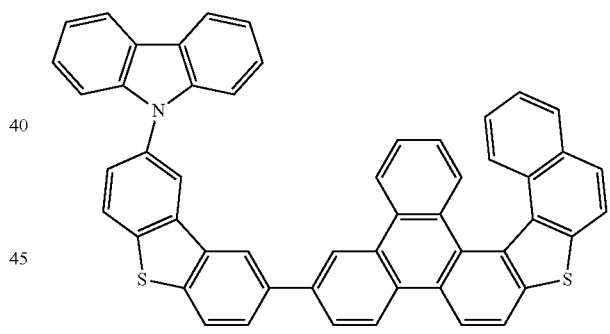
Comp. 150
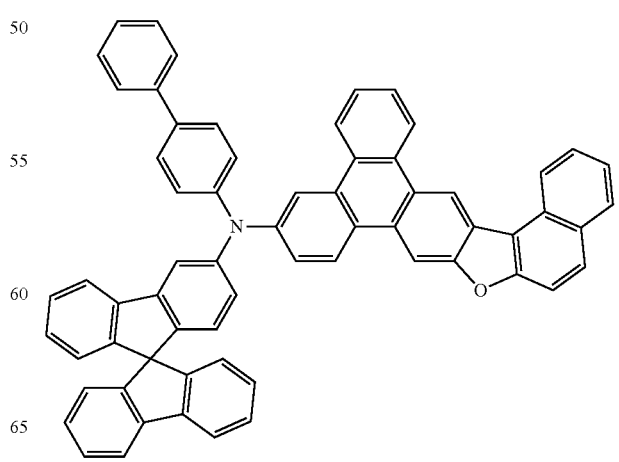

Comp. 152
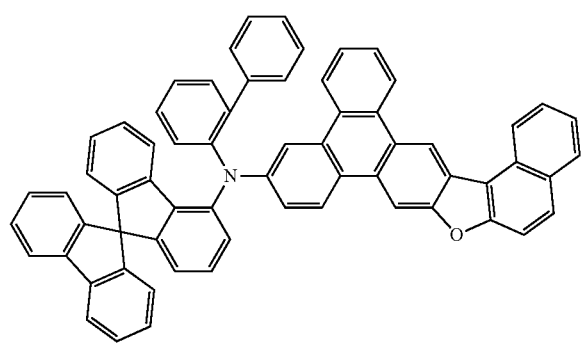
Comp. 223
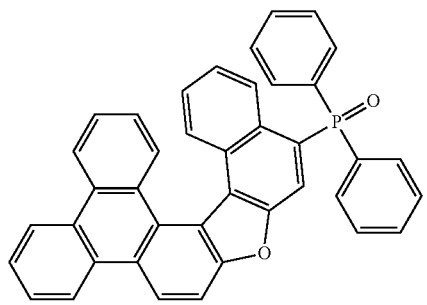
Comp. 154
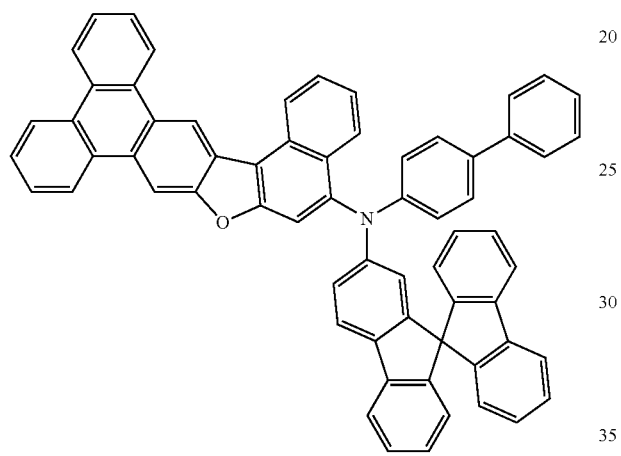
Comp. 38
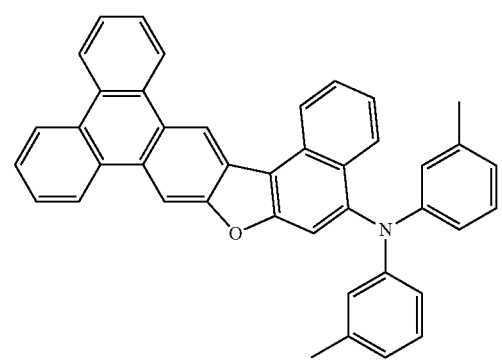
Comp. 156
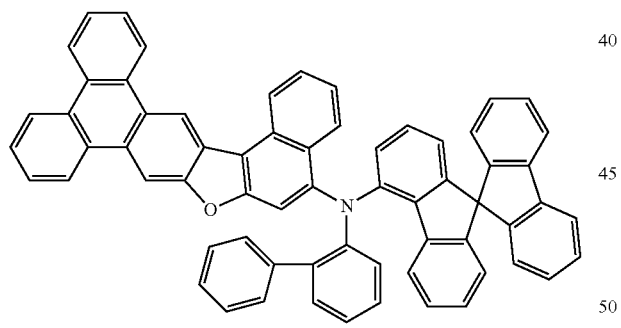
Comp. 197
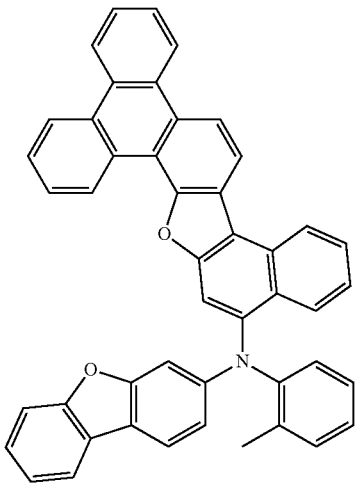
Comp. 222
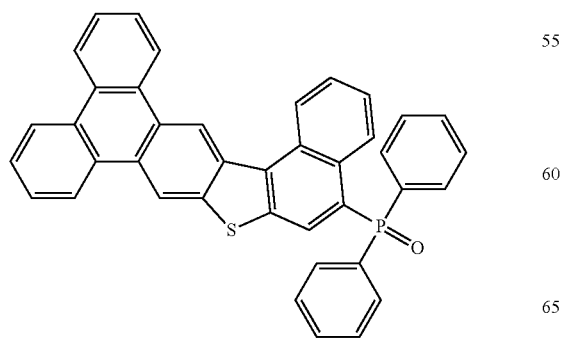
Comp. 199
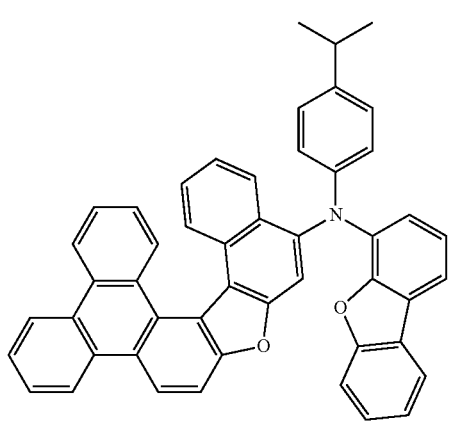

-continued
Comp. 205
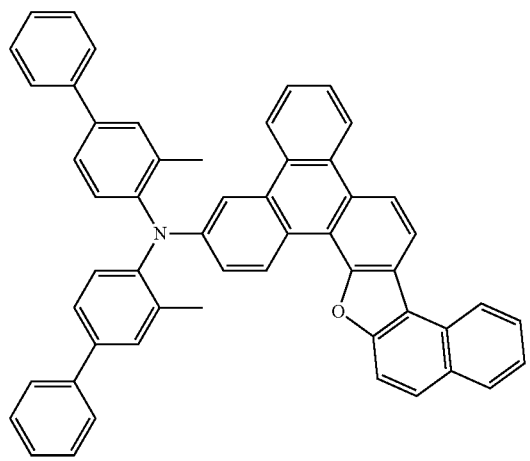
Comp. 206
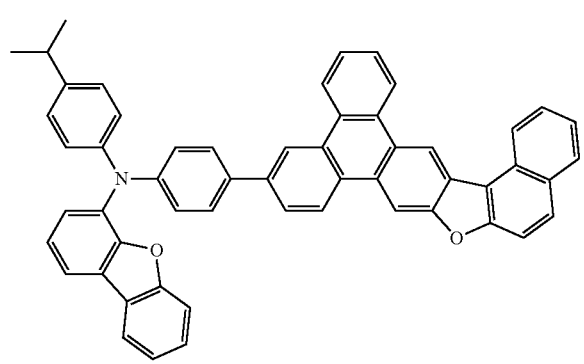
Comp. 209
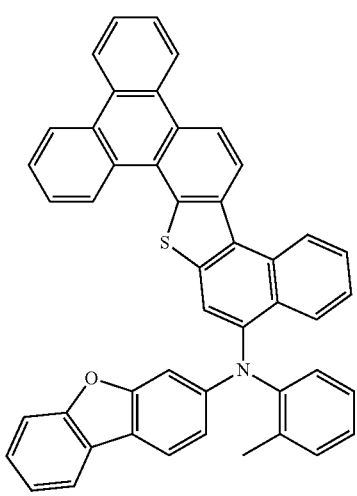
-continued
Comp. 210
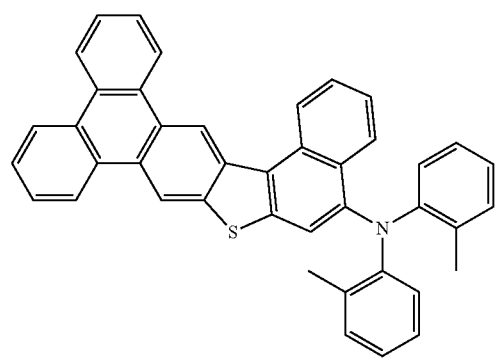
Comp. 211
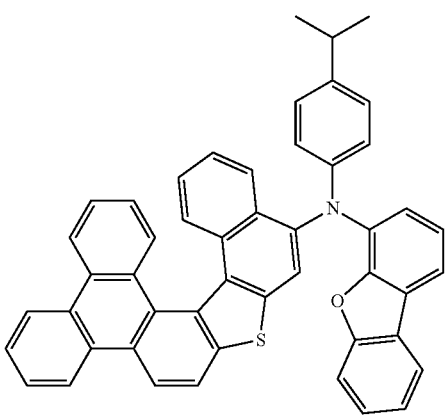
Comp. 218
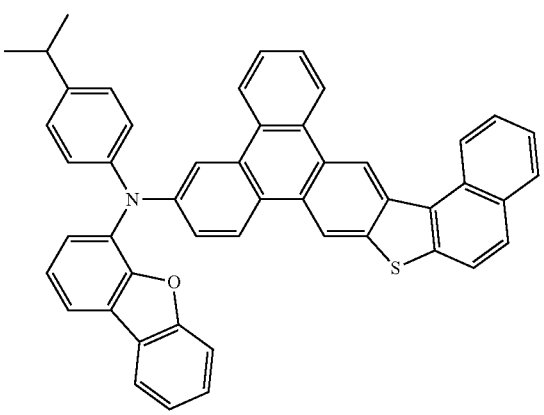

Comp. 157
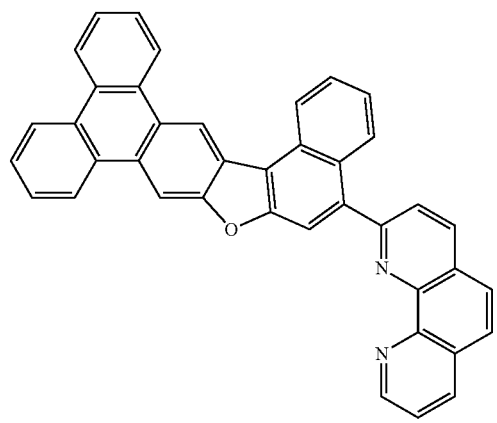
Comp. 161
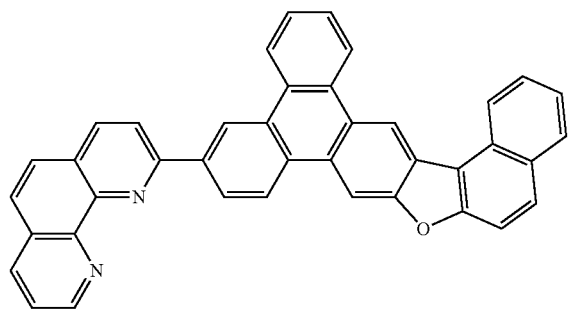
Comp. 163
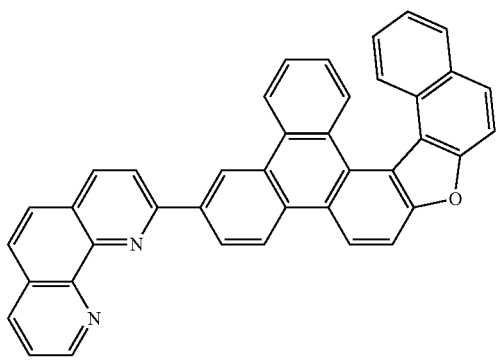
Comp. 169
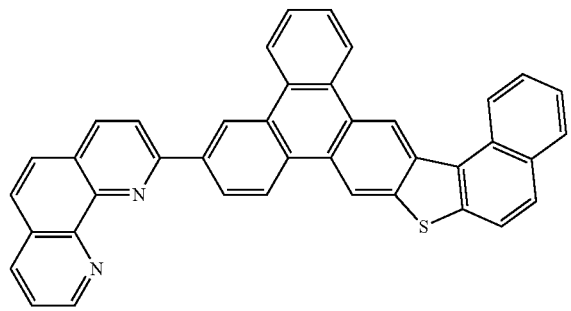
Comp. 171
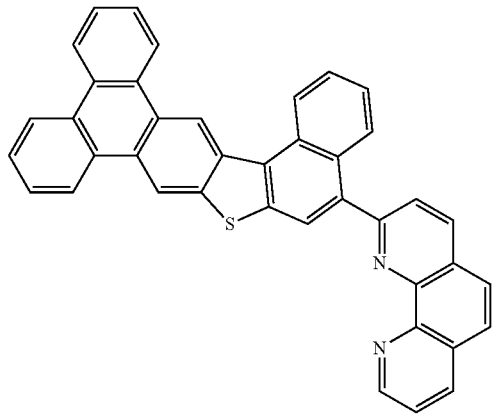
Comp. 174
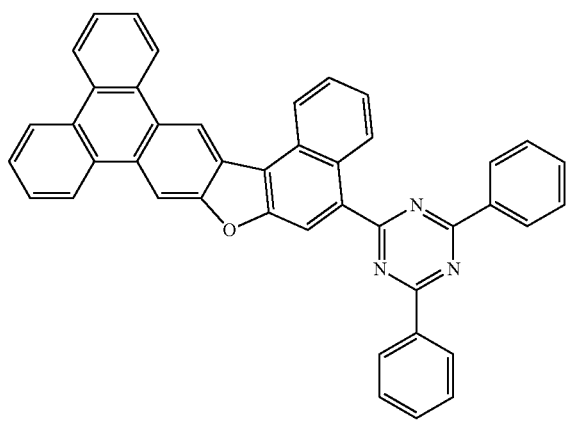
Comp. 182
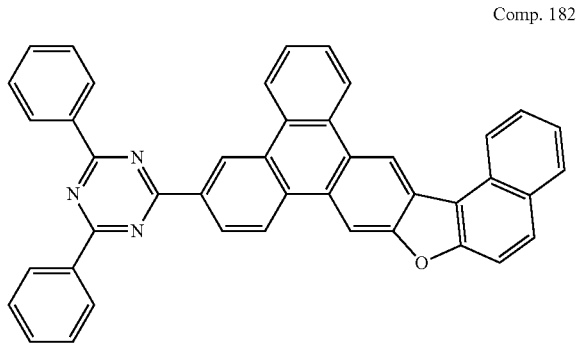
Comp. 186
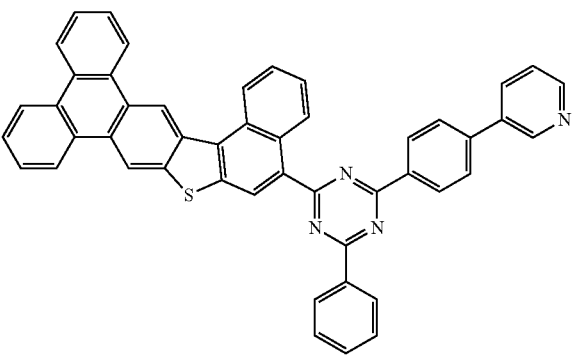

Comp. 194

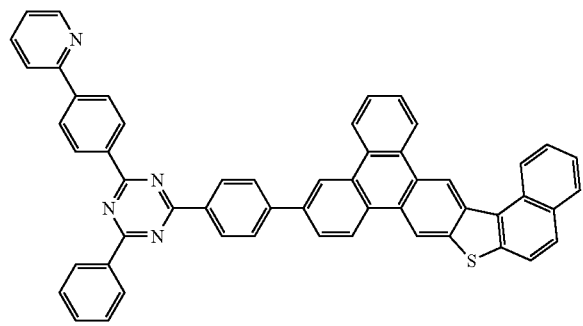

Comp. 56

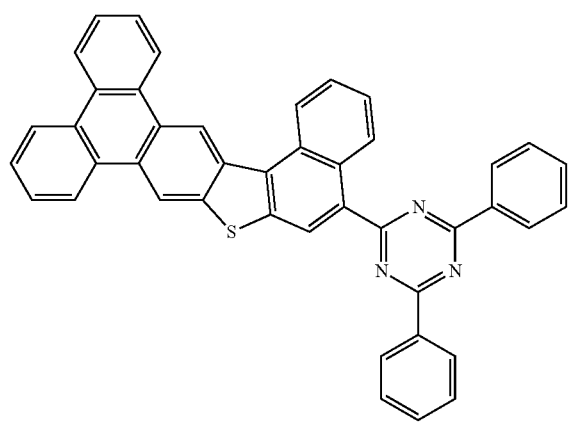

Comp. 131

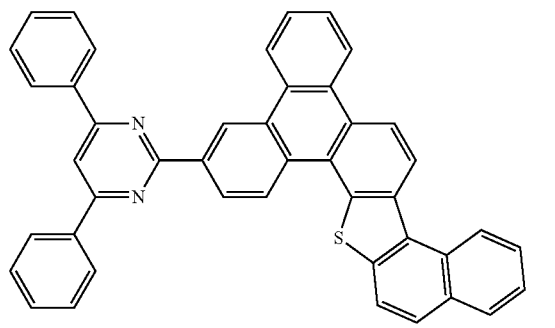

Comp. 158

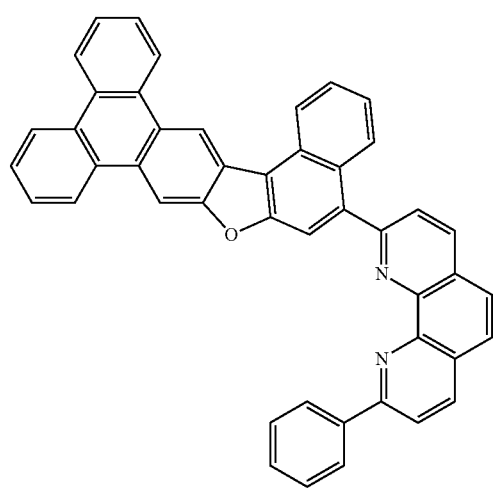

Comp. 162

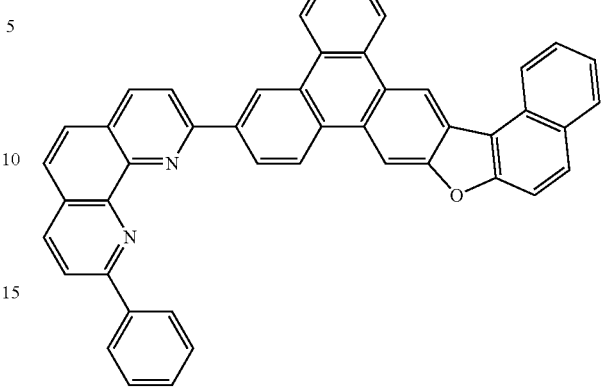

Comp. 170

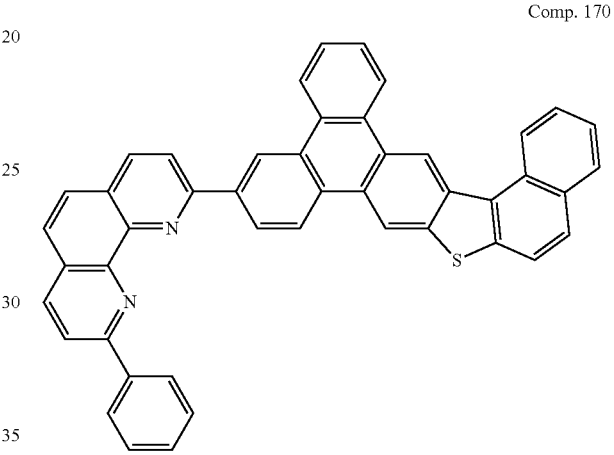

Comp. 172

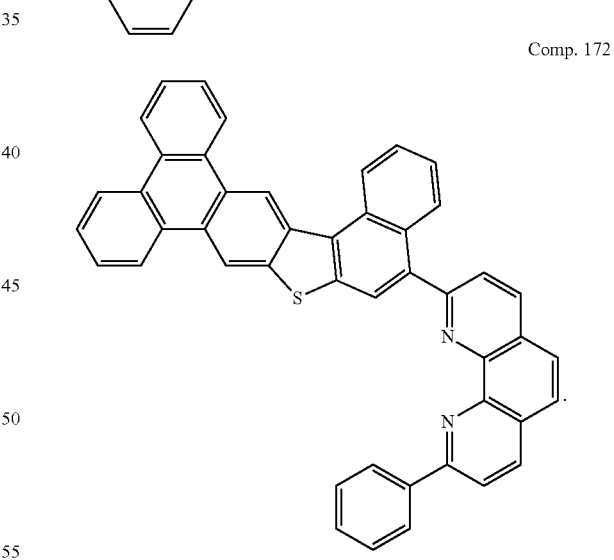

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin electron injecting layer is introduced between the cathode and the electron transporting layer. The materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

Example 32

Using a procedure analogous to the above mentioned general method, organic EL devices emitting green and blue light and having the following device structure as shown in the FIGURE. From the bottom layer 10 to the top layer 80, the following components were produced: ITO/HAT-CN(20 nm)/NPB (110 nm)/Emitting host doped with 15% dopant (30 nm)/HB1/ET1 doped 50% LiQ(35 nm)/LiQ(1 nm)/Al (160 nm). In the device illustrated in the FIGURE, the hole injection layer 20 (HAT-CN) is deposited onto the transparent electrode 10 (ITO), the hole transport layer 30 (NPB) is deposited onto the hole injection layer 20. The emitting layer 40 is deposited onto the hole transport layer 30. The emitting layer 40 may comprise an emitting host material and an emitting guest (dopant) material, as shown in, for example, Table 1. The emitting host material may be doped with about 15% emitting guest material. The emitting layer 40 may have a thickness of about 30 nm.

The hole blocking layer 50 (HB1) is deposited onto the emitting layer 40, the electron transport layer 60 (ET1 doped with 50% LiQ) is deposited onto the hole blocking layer 50, the electron injection layer 70 (LiQ) is deposited onto the electron transport layer 60. The metal electrode 80(Al) is deposited onto the electron injection layer 70. The I-V-B (at 1000 nits) test reports of these organic EL devices are summarized in Table 1 below. The half-life time is defined as the time the initial luminance of 1000 cd/m$^2$ has dropped to half.

TABLE 1

(The Comp. is short for Compound)

| Emitting Host Material | Emitting Dopant Material | Driving Voltage (V) | Current Efficiency (Yield; cd/A) | CIE(y) | Half-life time (hours) |
| --- | --- | --- | --- | --- | --- |
| H1 | D1 | 5.1 | 18 | 0.53 | 350 |
| Comp. 37 | D1 | 3.9 | 39 | 0.54 | 710 |
| Comp. 55 | D1 | 4.6 | 27 | 0.54 | 440 |
| Comp. 113 | D1 | 4.5 | 30 | 0.56 | 470 |
| Comp. 114 | D1 | 4.8 | 24 | 0.54 | 410 |
| Comp. 115 | D1 | 4.9 | 22 | 0.54 | 390 |
| Comp. 133 | D1 | 4.6 | 28 | 0.56 | 450 |
| Comp. 150 | D1 | 3.6 | 42 | 0.55 | 760 |
| Comp. 152 | D1 | 3.5 | 44 | 0.54 | 770 |
| Comp. 154 | D1 | 3.7 | 41 | 0.53 | 740 |
| Comp. 156 | D1 | 3.8 | 40 | 0.56 | 730 |
| Comp. 222 | D1 | 4.3 | 34 | 0.55 | 600 |
| Comp. 223 | D1 | 4.4 | 33 | 0.53 | 580 |
| H2 | D2 | 4.3 | 4.6 | 0.182 | 250 |
| H2 | Comp. 38 | 4.1 | 4.8 | 0.183 | 280 |
| H2 | Comp. 197 | 3.9 | 5.0 | 0.184 | 330 |
| H2 | Comp. 199 | 3.5 | 5.7 | 0.182 | 400 |
| H2 | Comp. 205 | 3.6 | 5.4 | 0.181 | 380 |
| H2 | Comp. 206 | 3.7 | 5.2 | 0.180 | 350 |
| H2 | Comp. 209 | 4.0 | 4.9 | 0.182 | 300 |
| H2 | Comp. 210 | 4.2 | 4.7 | 0.181 | 270 |
| H2 | Comp. 211 | 4.0 | 5.0 | 0.183 | 310 |
| H2 | Comp. 218 | 3.4 | 6.0 | 0.182 | 450 |

Example 33

Using a procedure analogous to the above mentioned general method, organic EL devices emitting green and blue light and having the following device structure as shown in the FIGURE. From the bottom layer 10 to the top layer 80, the following components were produced: ITO/HAT-CN(20 nm)/NPB (110 nm)/Emitting host doped with 15% dopant (30 nm)/HB1/ET1 doped 50% LiQ(35 nm)/LiQ(1 nm)/Al (160 nm). In the device illustrated in the FIGURE, the hole injection layer 20 (HAT-CN) is deposited onto the transparent electrode 10 (ITO), the hole transport layer 30(NPB) is deposited onto the hole injection layer 20. The emitting layer 40 is deposited onto the hole transport layer 30. The emitting layer 40 may comprise an emitting host material and an emitting guest (dopant) material, as shown in, for example, Table 1. The emitting host material may be doped with about 15% emitting guest material. The emitting layer 40 may have a thickness of about 30 nm.

The hole blocking layer (HBL) 50 (e.g., HB1) is deposited onto the emitting layer 40, the electron transport layer (ETL) 60 (e.g., ET1 doped with 50% LiQ) is deposited onto the hole blocking layer 50, the electron injection layer 70 (LiQ) is deposited onto the electron transport layer 60. The metal electrode 80(Al) is deposited onto the electron injection layer 70. The I-V-B (at 1000 nits) test reports of these organic EL devices are summarized in Table 1 below. The half-life time is defined as the time the initial luminance of 1000 cd/m$^2$ has dropped to half.

TABLE 2

(The Comp. is short for Compound)

| HBL | ETL | Driving Voltage (V) | Current Efficiency (Yield; cd/A) | CIE(y) | Half-life time (hours) |
| --- | --- | --- | --- | --- | --- |
| HB1 | ET1 | 5.1 | 18 | 0.53 | 350 |
| HB1 | Comp. 157 | 3.9 | 33 | 0.55 | 540 |
| HB1 | Comp. 161 | 3.6 | 37 | 0.55 | 600 |
| HB1 | Comp. 163 | 3.7 | 35 | 0.54 | 580 |
| HB1 | Comp. 169 | 3.8 | 34 | 0.55 | 550 |
| HB1 | Comp. 171 | 4.1 | 30 | 0.54 | 510 |
| HB1 | Comp. 174 | 4.8 | 21 | 0.55 | 410 |
| HB1 | Comp. 182 | 4.6 | 23 | 0.54 | 440 |
| HB1 | Comp. 186 | 4.5 | 25 | 0.55 | 450 |
| HB1 | Comp. 194 | 4.4 | 27 | 0.53 | 480 |
| Comp. 56 | ET1 | 4.8 | 24 | 0.56 | 420 |
| Comp. 131 | ET1 | 4.9 | 21 | 0.53 | 400 |
| Comp. 158 | ET1 | 4.5 | 28 | 0.53 | 450 |
| Comp. 162 | ET1 | 4.1 | 33 | 0.56 | 530 |
| Comp. 170 | ET1 | 4.3 | 31 | 0.54 | 480 |
| Comp. 172 | ET1 | 4.6 | 26 | 0.56 | 430 |

In the above test reports of an organic EL device (see Table 1 and Table 2), the organic compound represented by formula (A) used as an emitting host material, a fluorescent dopant material, an electron transfer or a hole blocking material for the organic EL device in the present invention displays better performance than a prior art organic EL material. More specifically, an organic compound represented by formula (A) for an organic EL device of the present invention is used as an emitting host material, an electron transfer or a hole blocking material to collocate with an emitting guest material, such as D1, and used as an fluorescent emitting dopant material to collocate with an emitting host material, such as H2, thereby lowering a driving voltage, increasing a current efficiency or extending a half-life of the organic EL device.

Obviously, many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. An organic compound represented by the following formula (A):

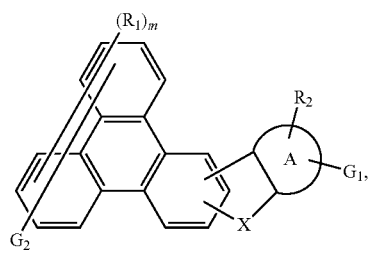

formula (A)

wherein X is a divalent bridge selected from the group consisting of O, S, SO, $SO_2$, Se, $NR_3$ and $SiR_4R_5$; m represents an integer of 0, 1, 2, 3, 4, 5, 6, 7 or 8; A represents a substituted or unsubstituted fused ring hydrocarbons unit with three rings if X is $NR_3$; A represents a substituted or unsubstituted fused ring hydrocarbons unit with two to three rings if X is O, S, SO, $SO_2$, Se or $SiR_4R_5$; $R_1$ to $R_5$ are independently selected from the group consisting of a hydrogen atom, a halogen, a substituted or unsubstituted alkyl group having 1 to 30 carbon atoms, a substituted or unsubstituted aralkyl group having 7 to 30 ring carbon atoms, a substituted or unsubstituted aryl group having 6 to 30 ring carbon atoms, and a substituted or unsubstituted heteroaryl group having 3 to 30 ring carbon atoms; and $G_1$ and $G_2$ independently represent a substituted or unsubstituted phenyl group, a substituted or unsubstituted biphenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group , a substituted or unsubstituted chrysenyl group, a substituted or unsubstituted triphenylenyl group, a substituted or unsubstituted benzimidazole group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted diphenylphosphine oxide group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group, a substituted or unsubstituted dihydrophenazine group, a substituted or unsubstituted diphenylamine group, a substituted or unsubstituted triphenylamine group, a substituted or unsubstituted phenyldibenzofuranylamine group, or a substituted or unsubstituted phenyldibenzothiophenylamine group.

2. The organic compound according to claim 1, wherein $G_1$ and $G_2$ independently represent one of the following substituents:

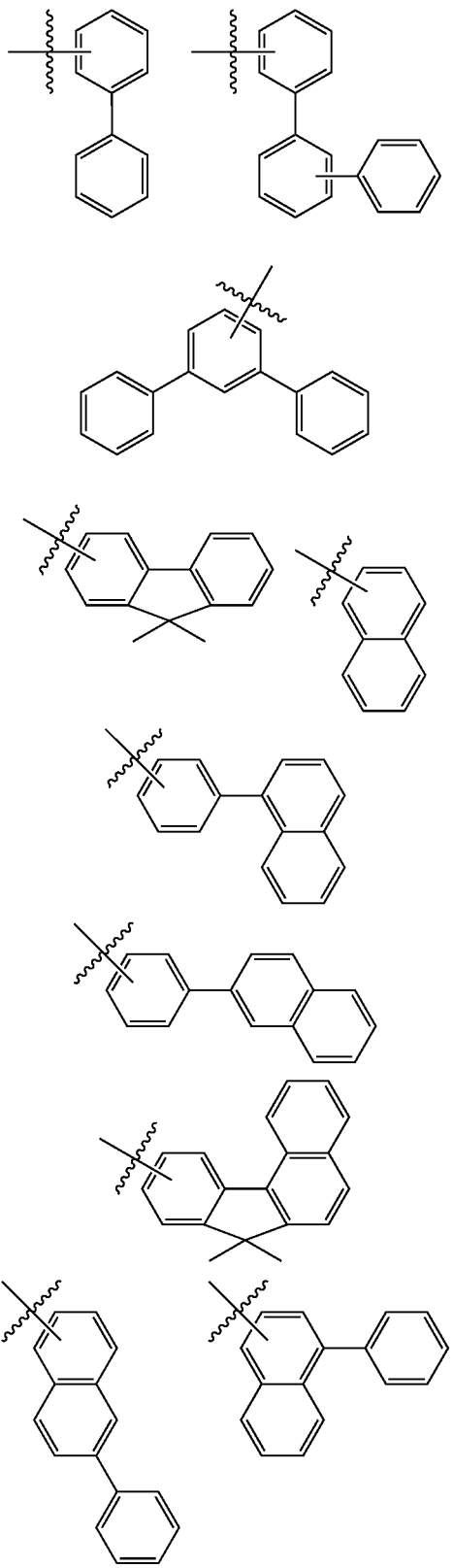

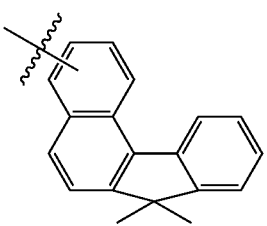
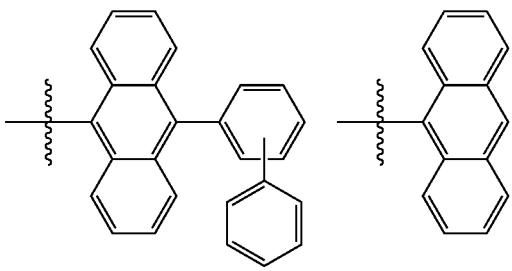
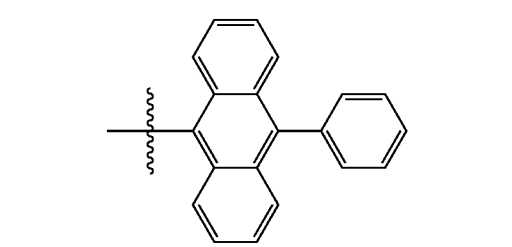
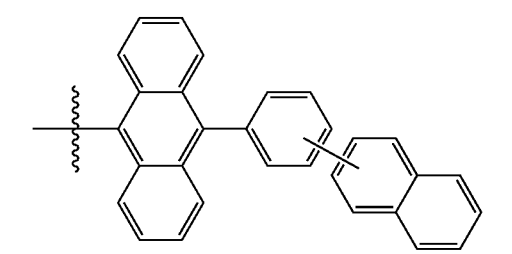
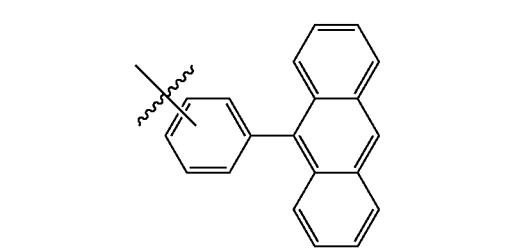
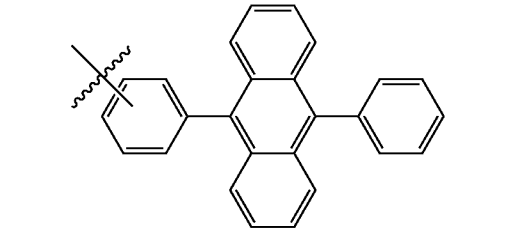
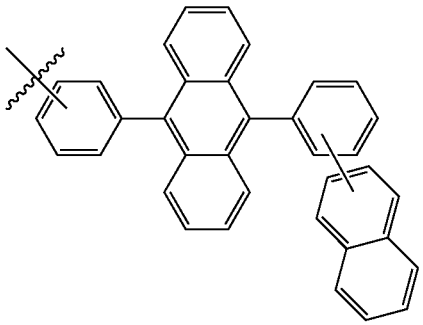
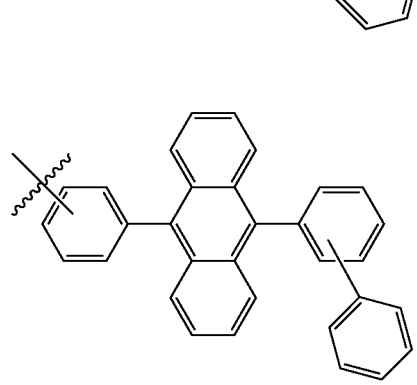
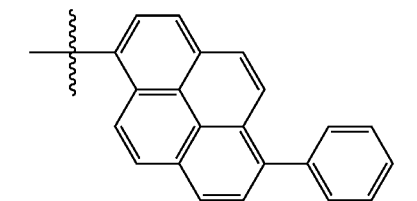
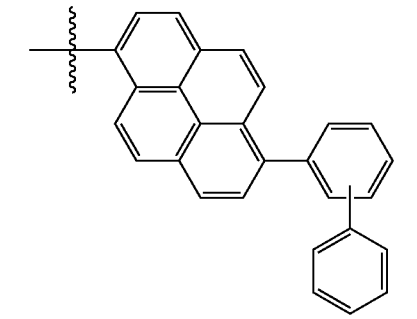
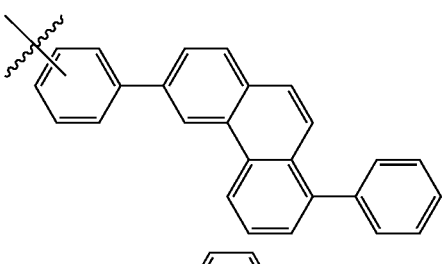
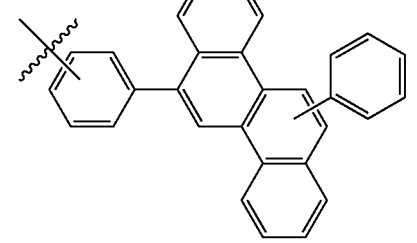

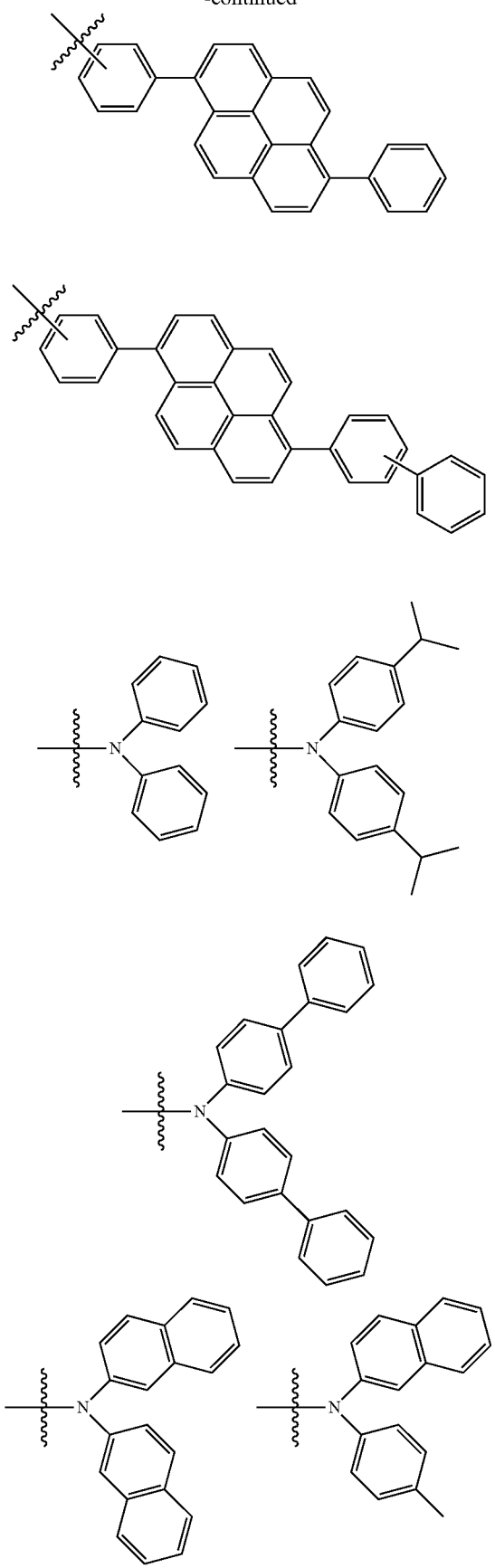
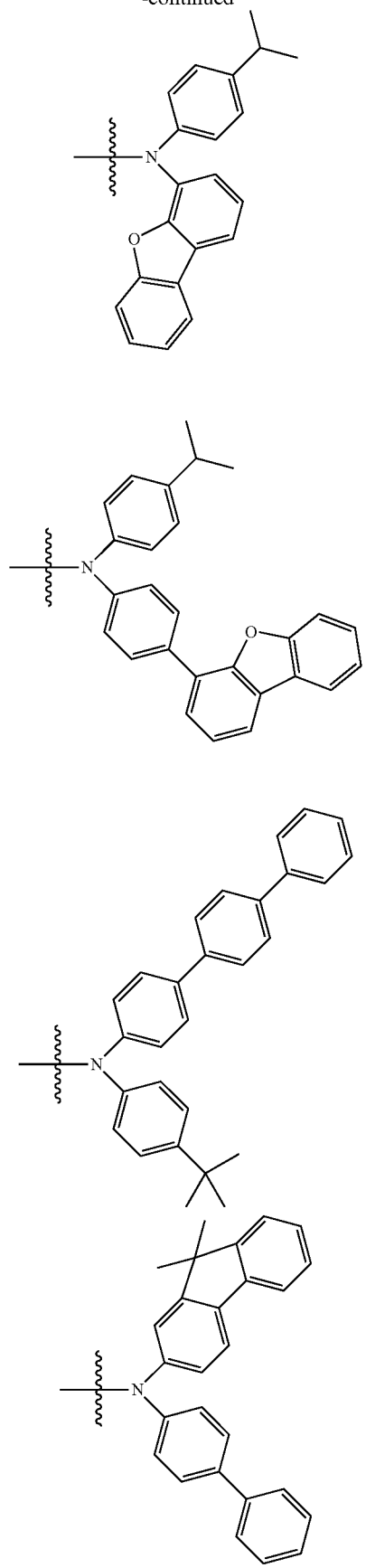

149
-continued
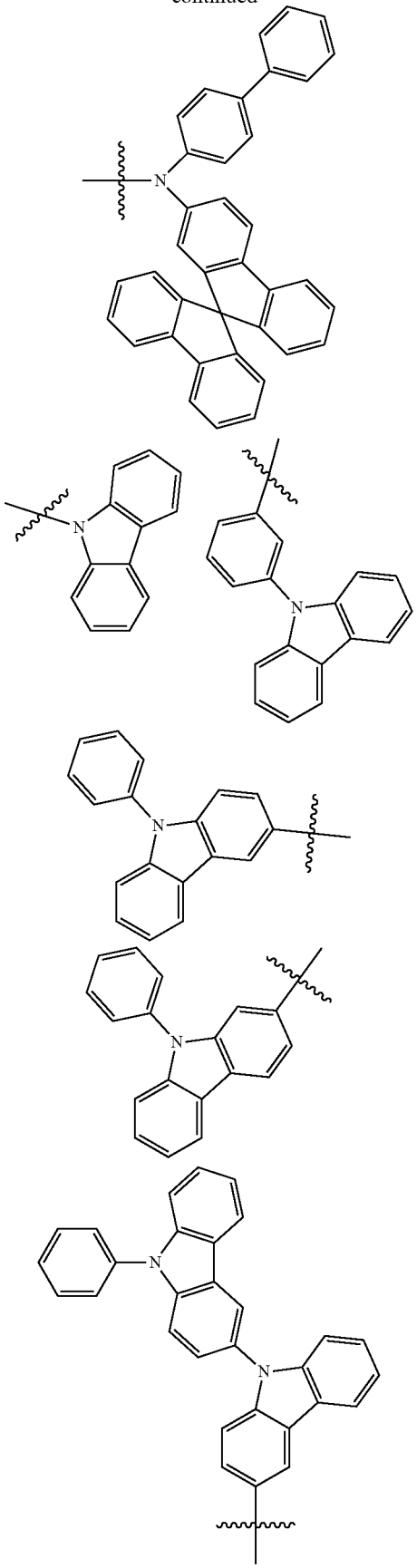
150
-continued
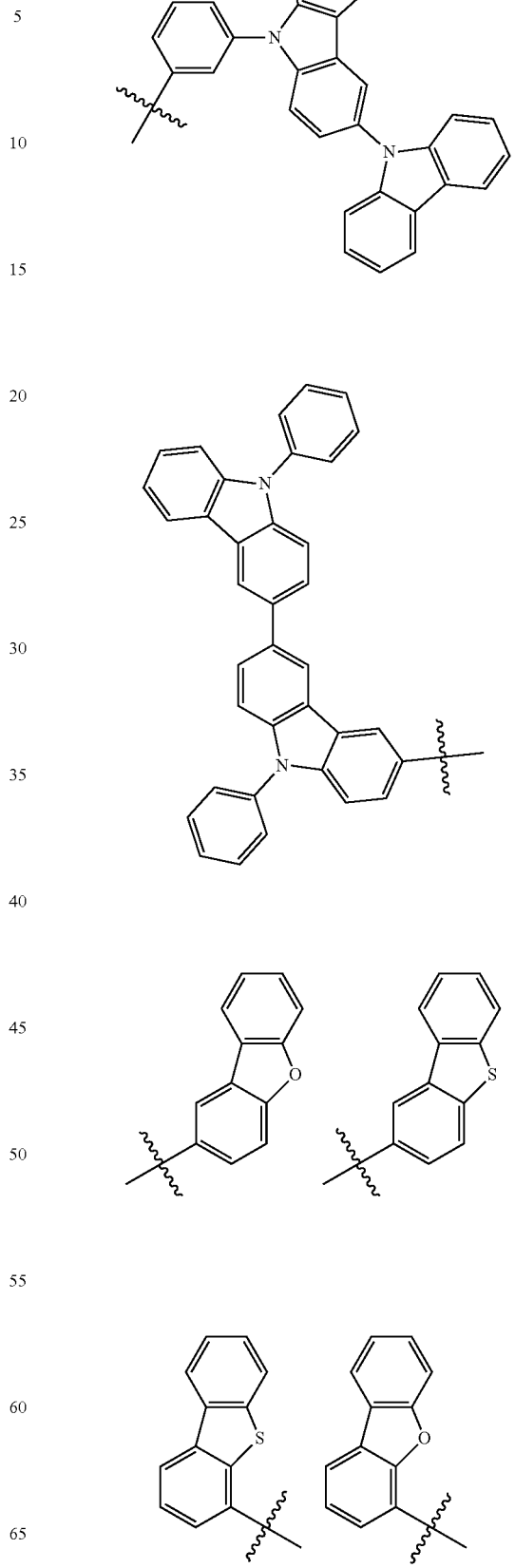

151
-continued
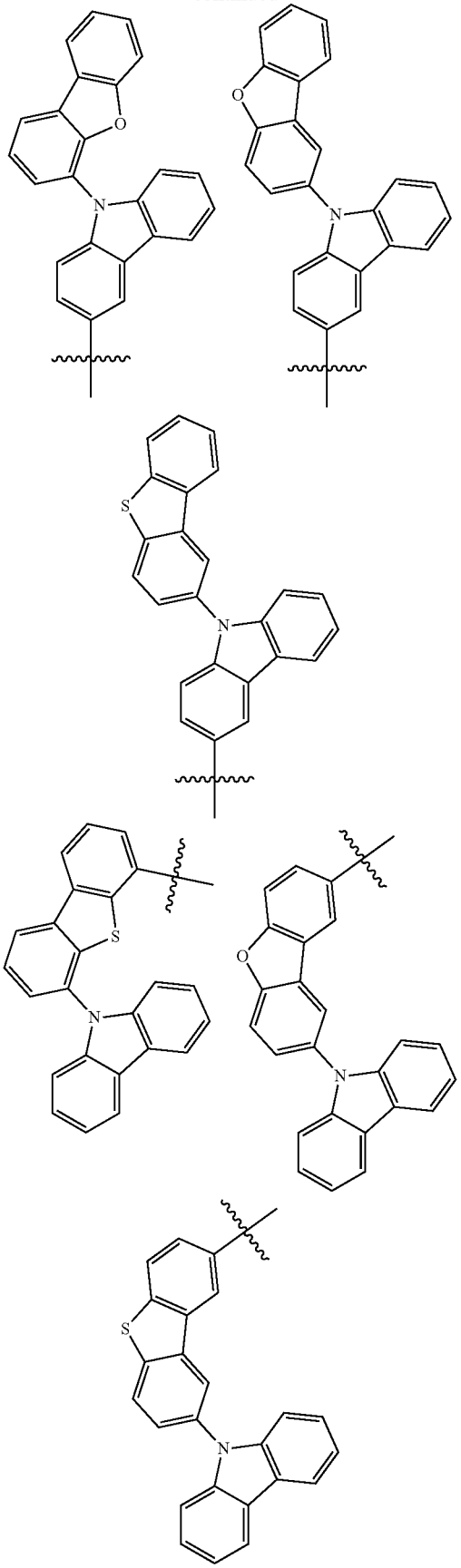
152
-continued
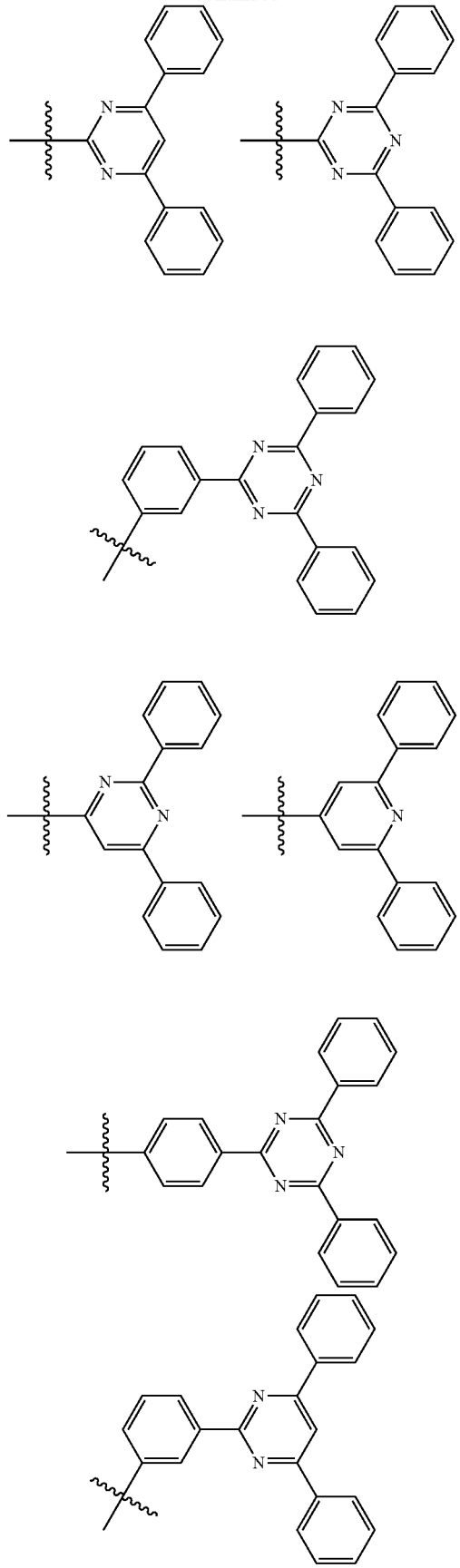

153
-continued
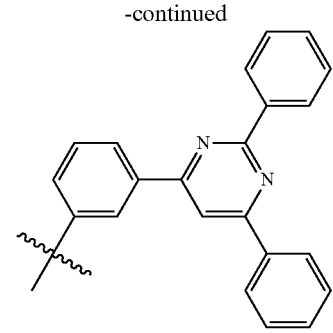
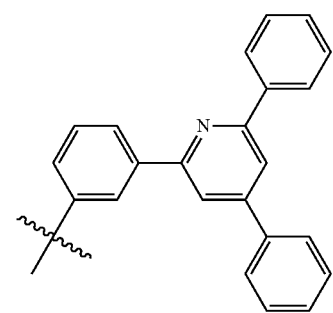
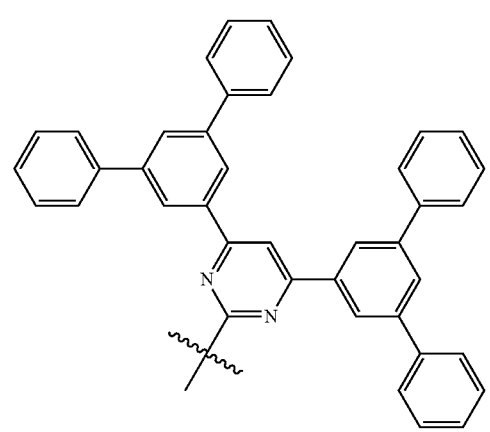
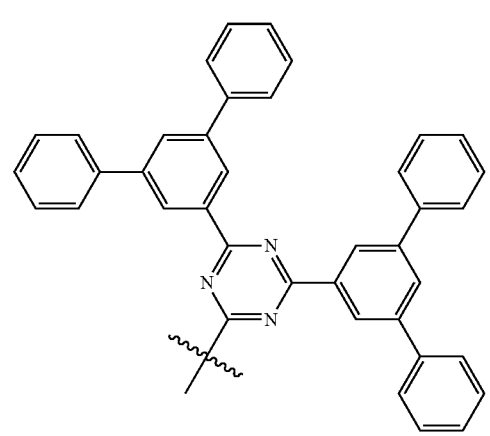
154
-continued
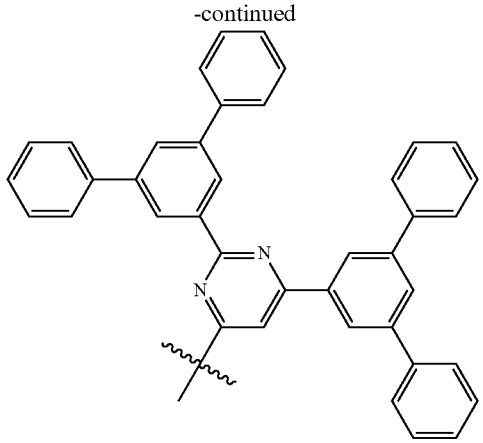
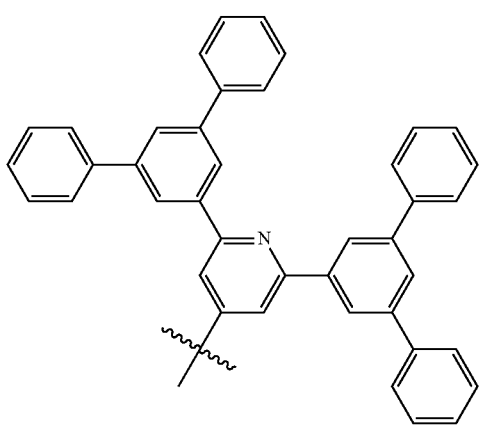
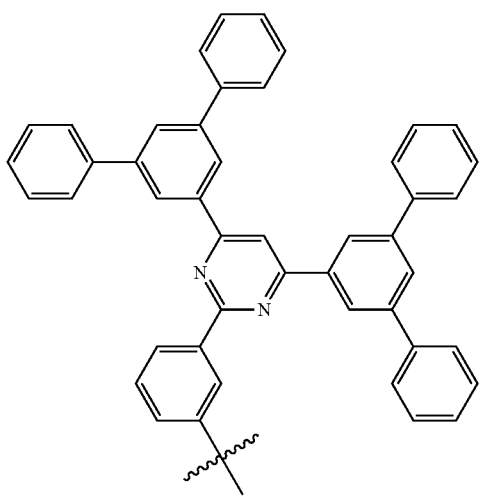

155
-continued
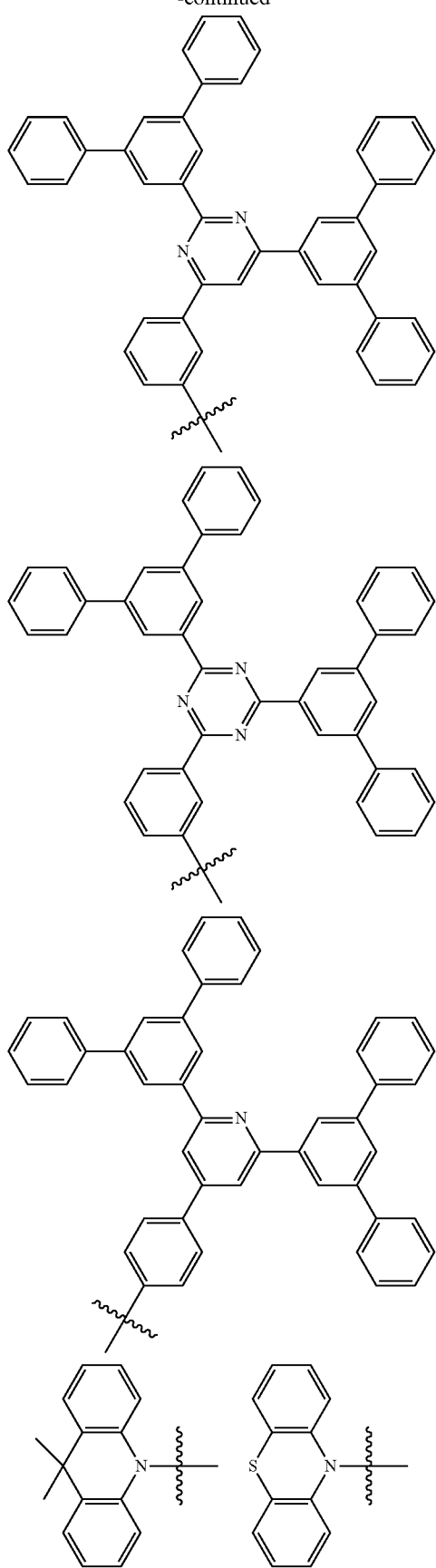
156
-continued
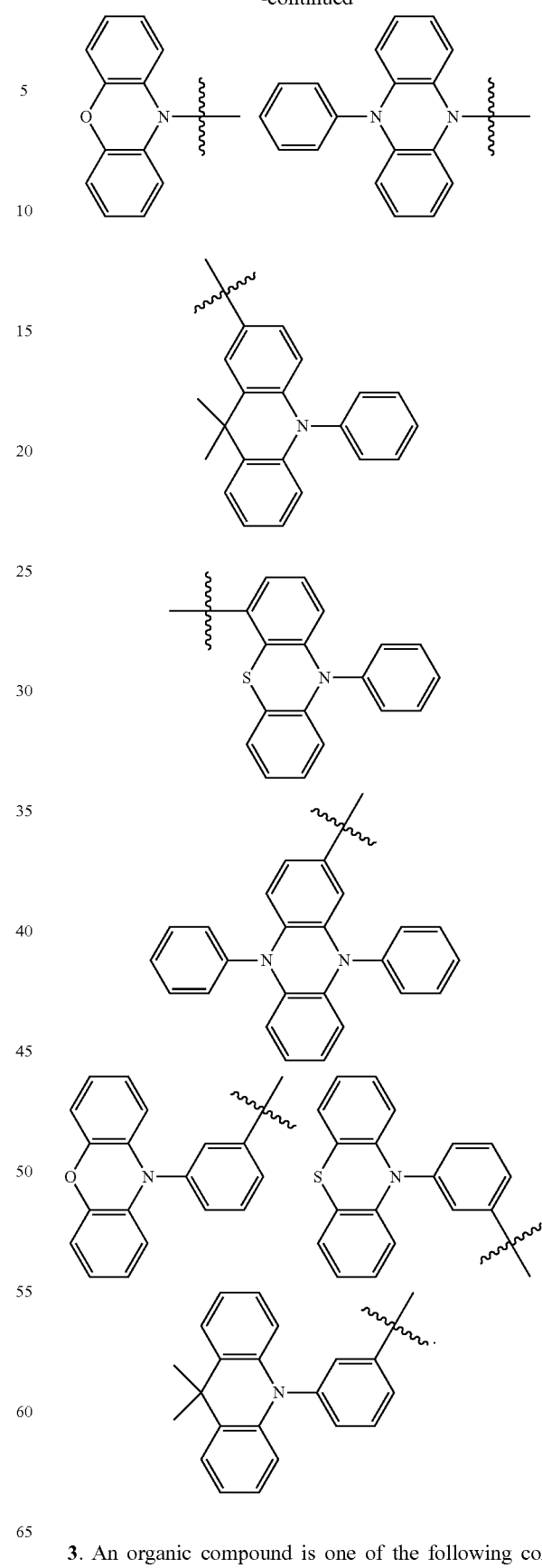
3. An organic compound is one of the following compounds:

Compound 1
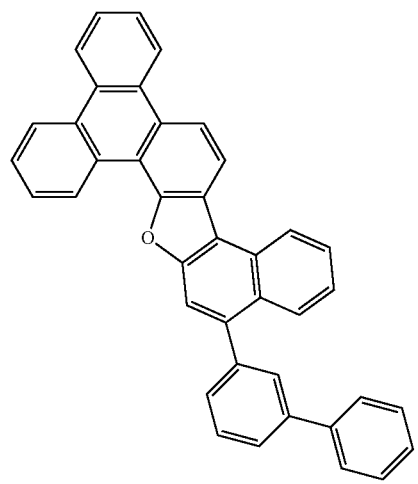
Compound 2
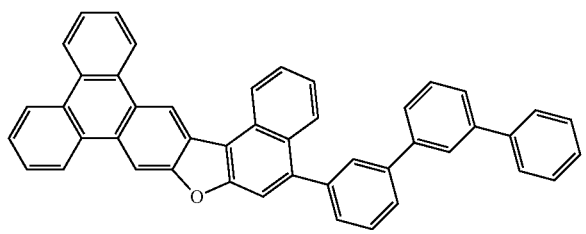
Compound 3
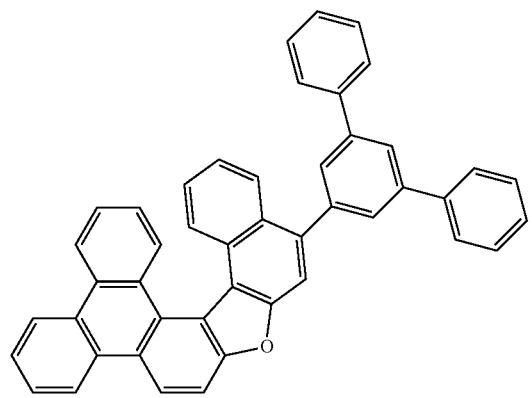
Compound 4
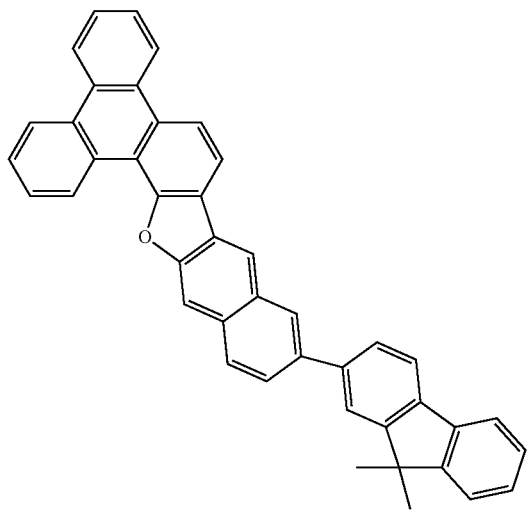
Compound 5
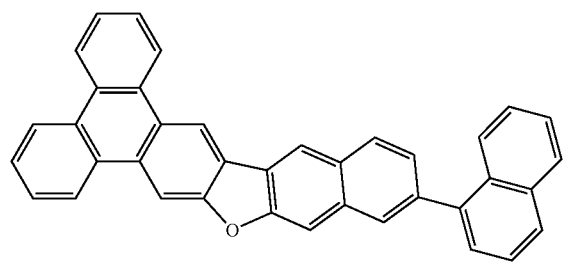
Compound 6
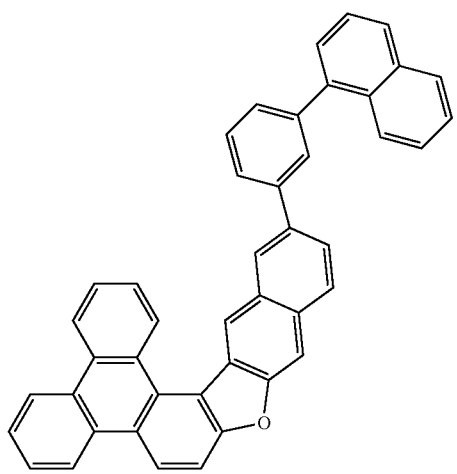

-continued
Compound 7
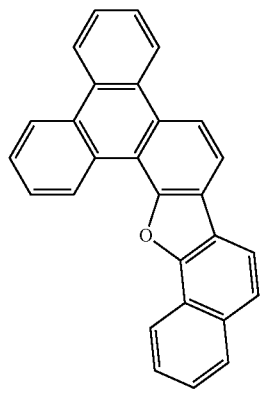
Compound 8
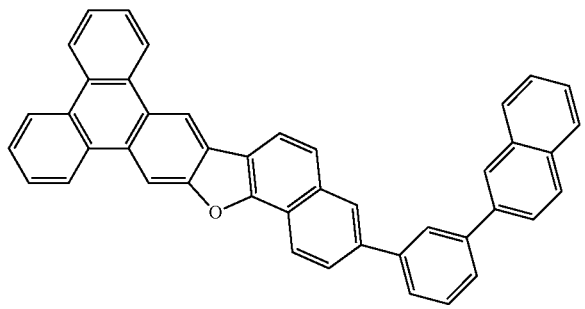
Compound 9
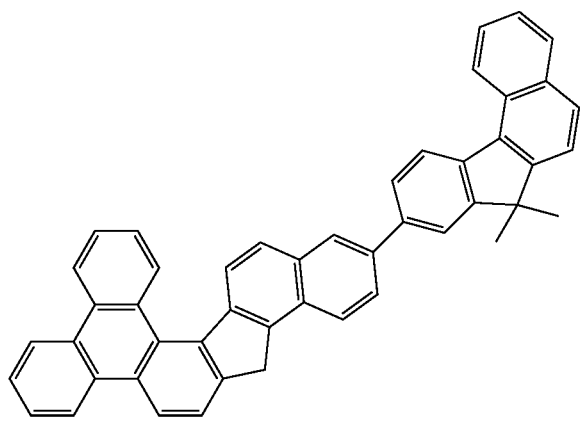
Compound 10
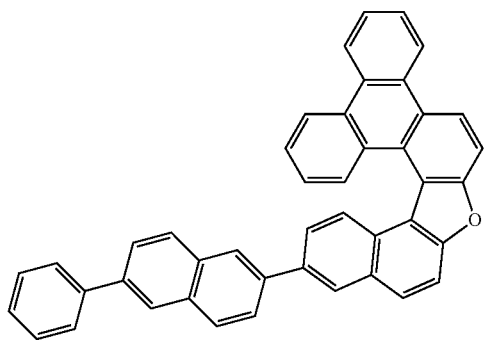
Compound 11
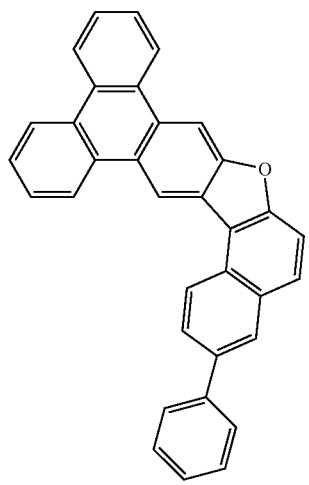
Compound 12
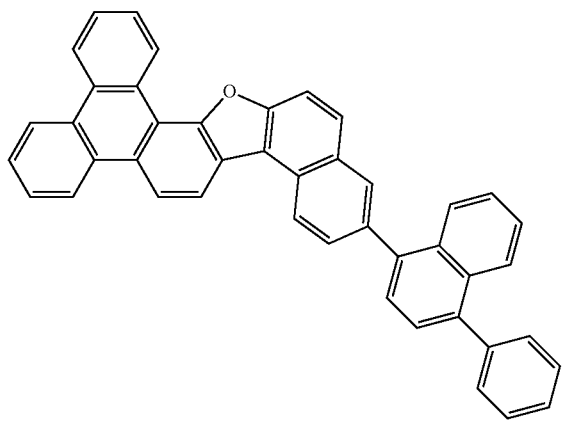

-continued
Compound 13
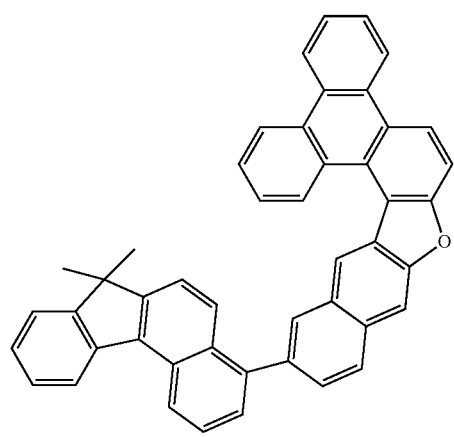
Compound 14
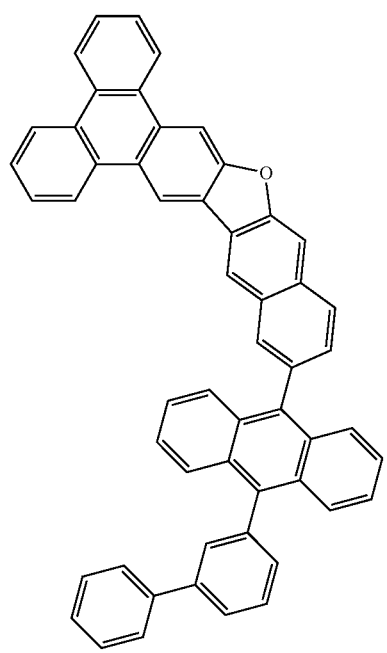
Compound 15
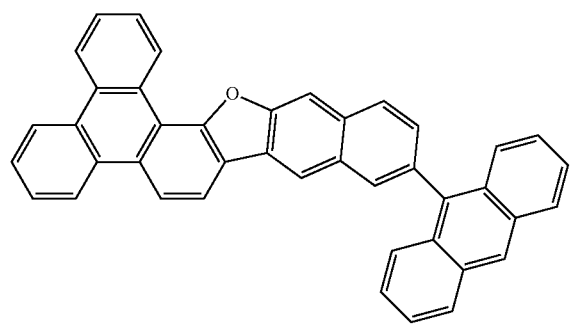
Compound 16
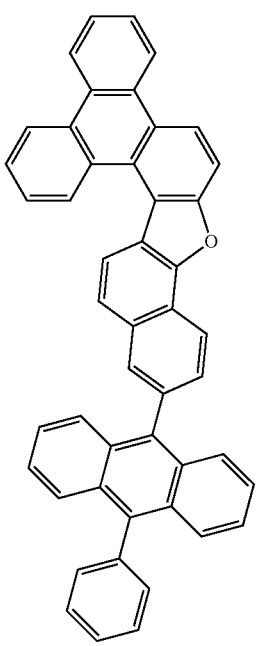

Compound 17
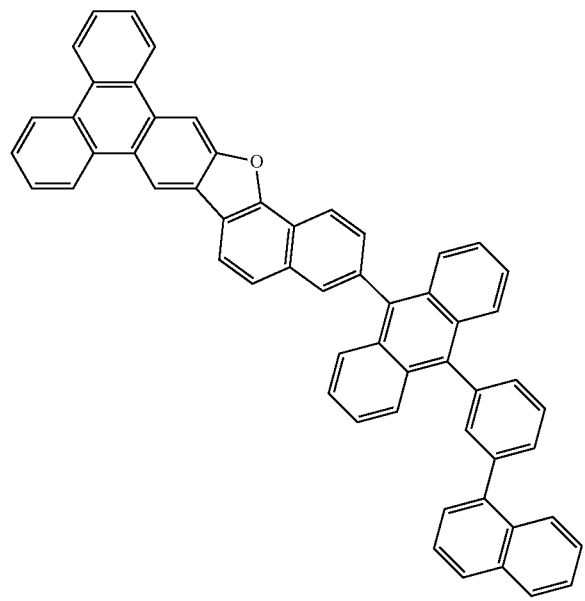
Compound 18
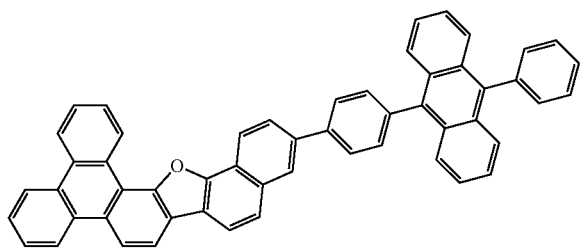
Compound 19
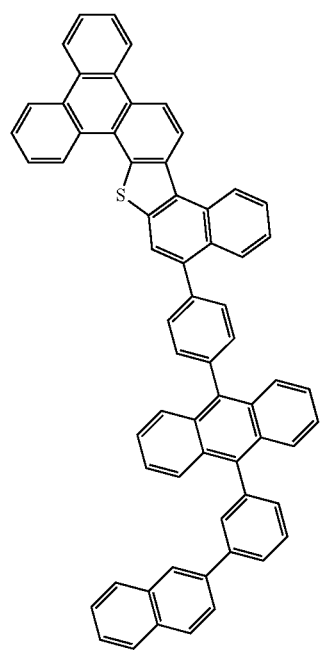
Compound 20
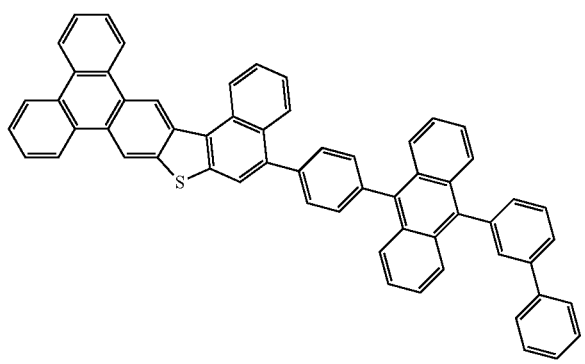

-continued
Compound 21
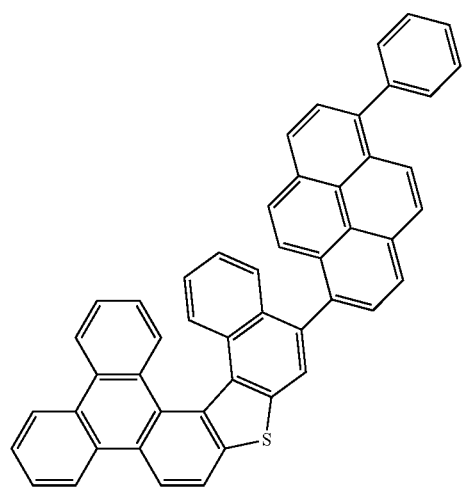
Compound 22
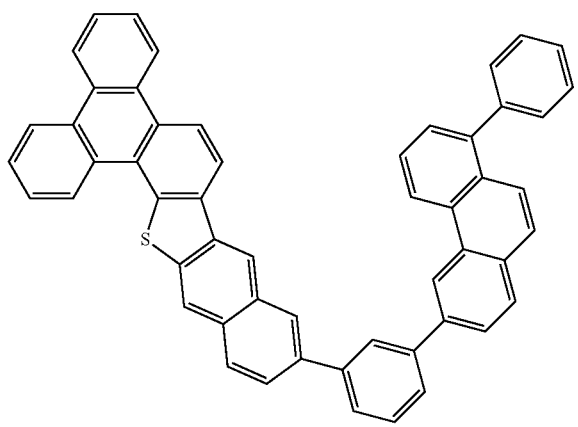
Compound 23
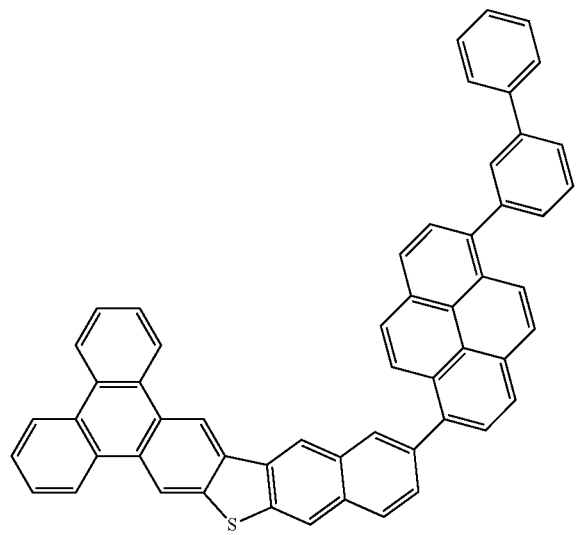
Compound 24
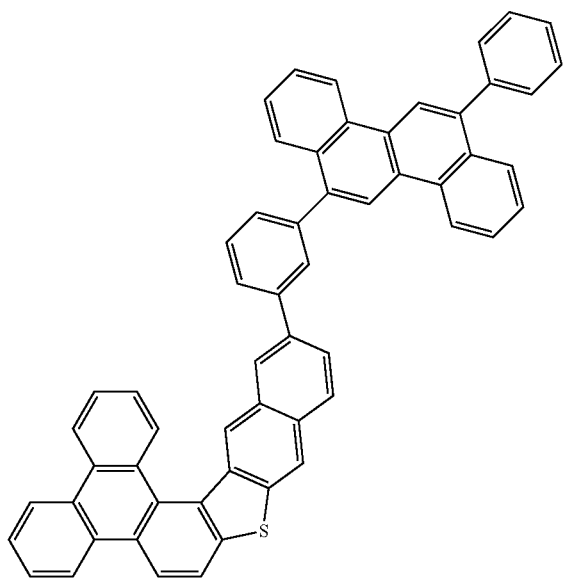
Compound 25
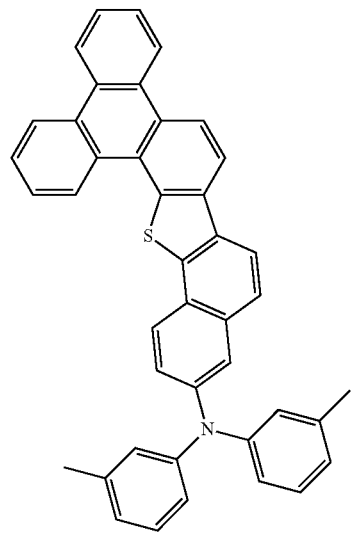

-continued
Compound 26
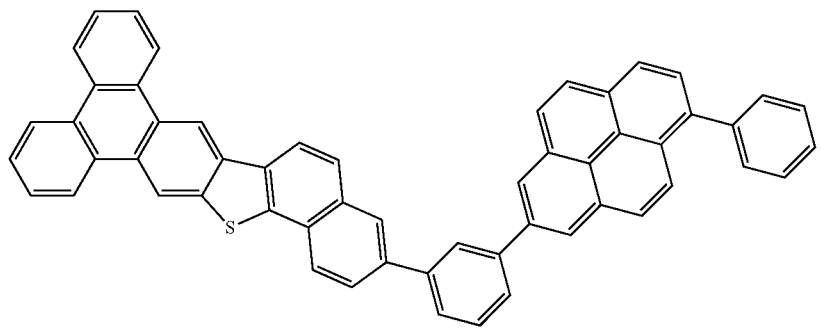
Compound 27
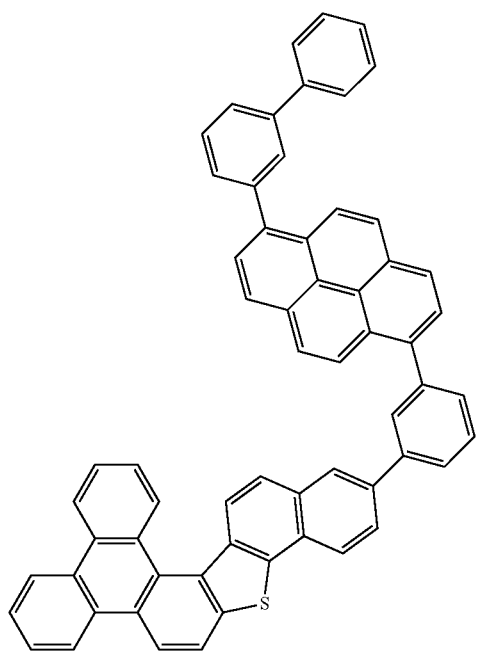
Compound 28
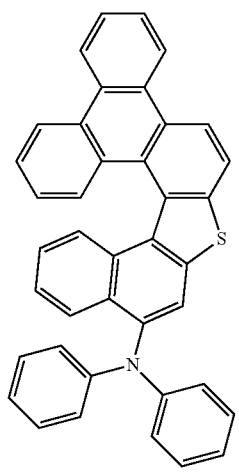
Compound 29
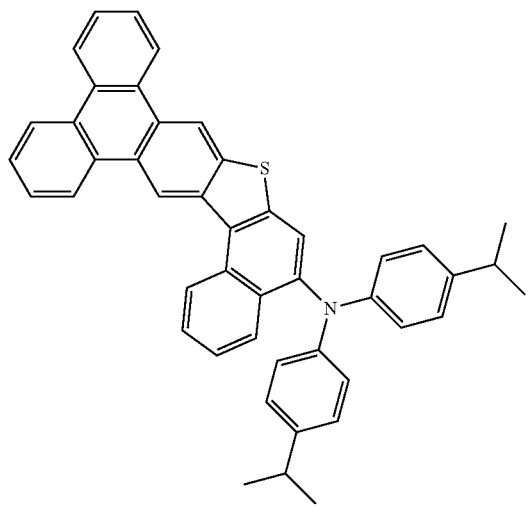
Compound 30
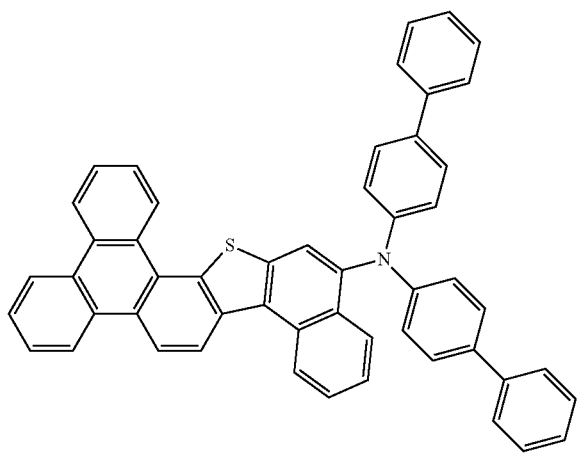

-continued
Compound 31
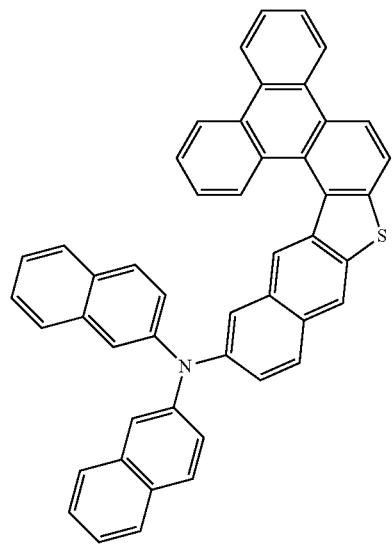
Compound 32
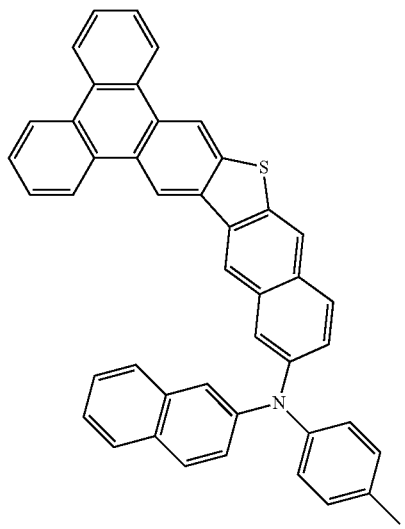
Compound 33
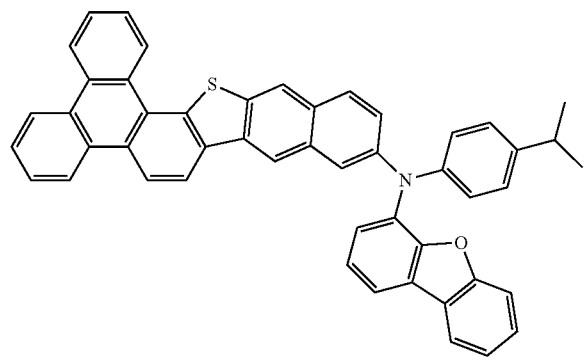
Compound 34
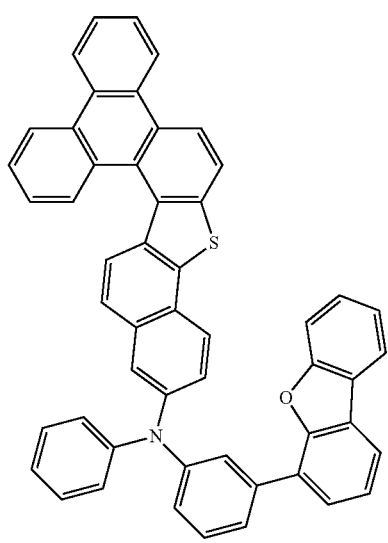

Compound 35
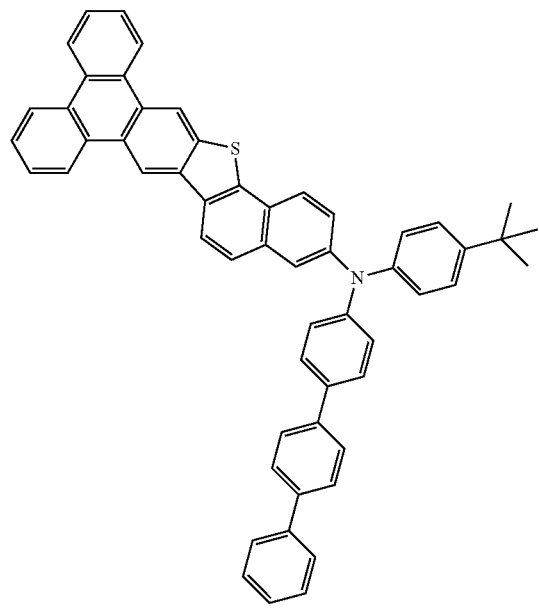
Compound 36
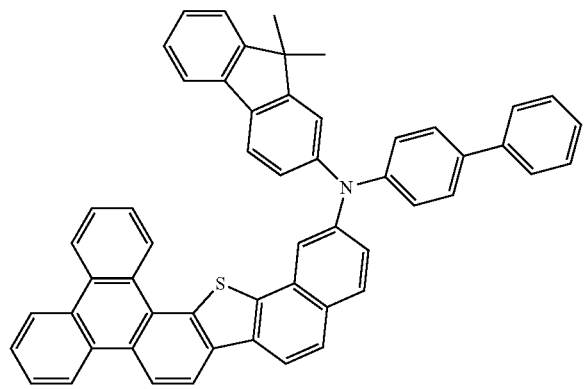
Compound 37
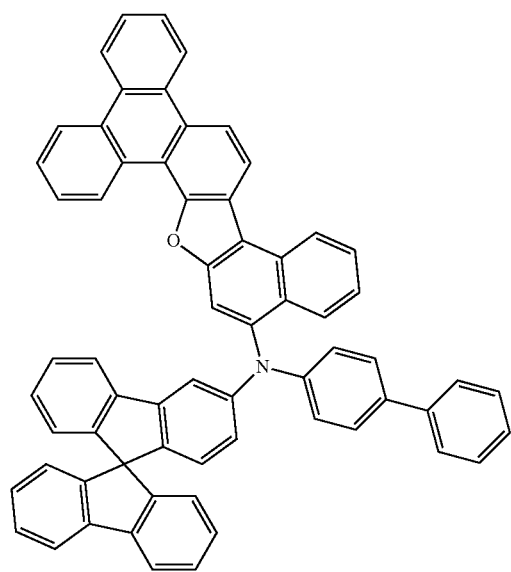
Compound 38
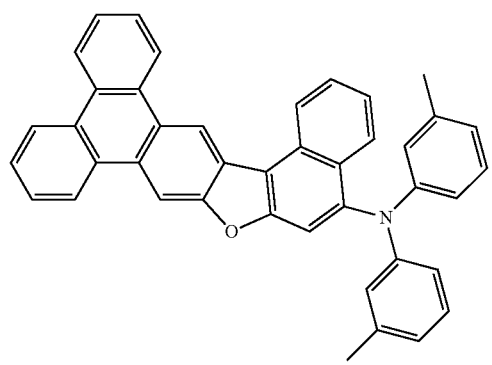

-continued
Compound 39
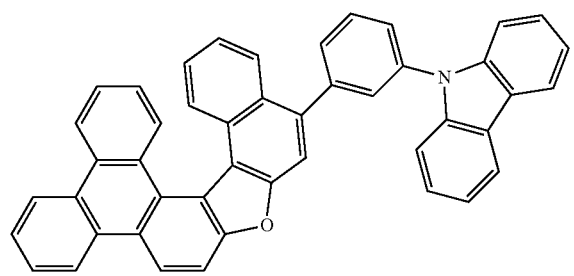
Compound 40
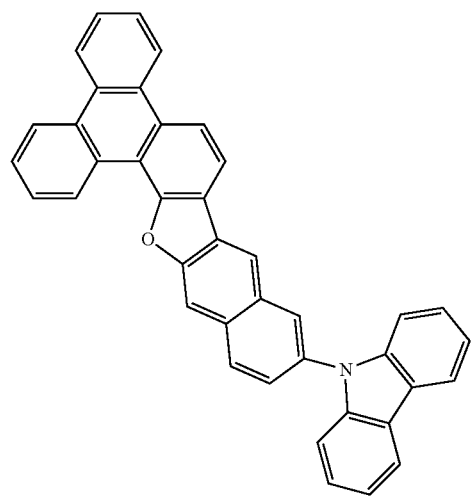
Compound 41
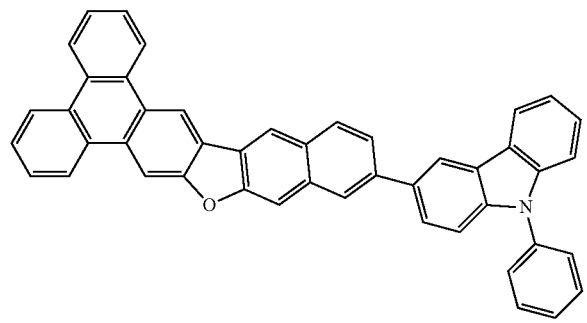
Compound 42
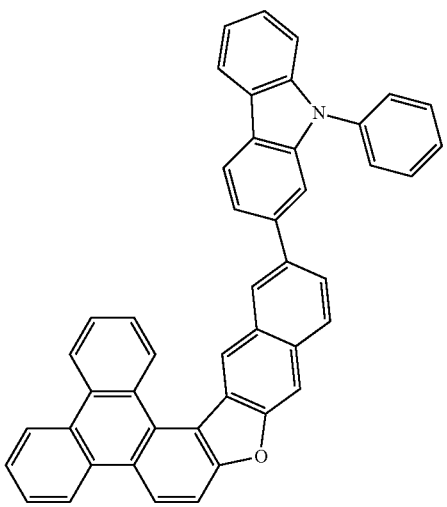
Compound 43
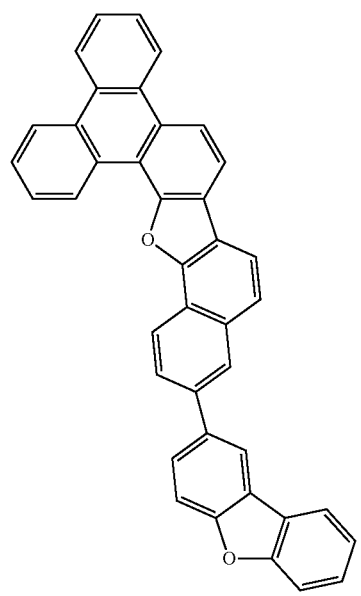
Compound 44
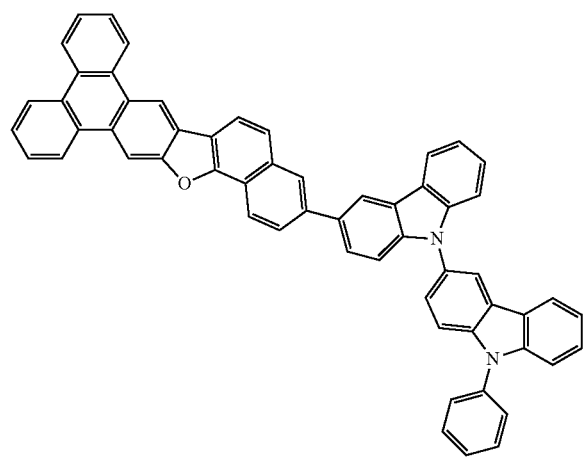

-continued
Compound 45
Compound 46
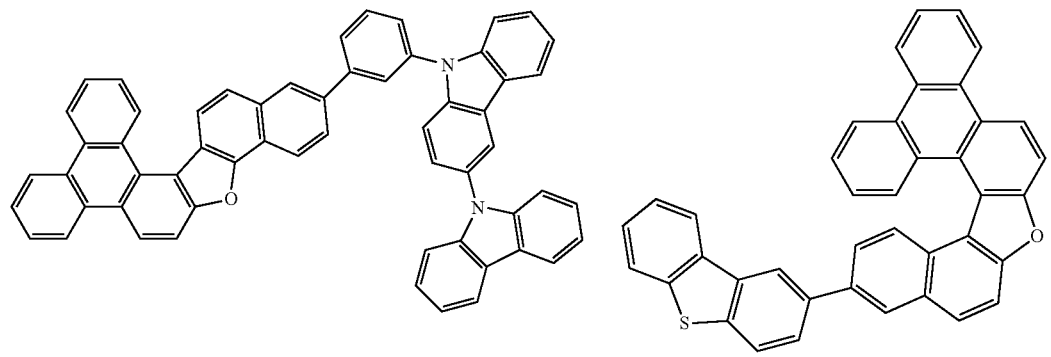
Compound 47
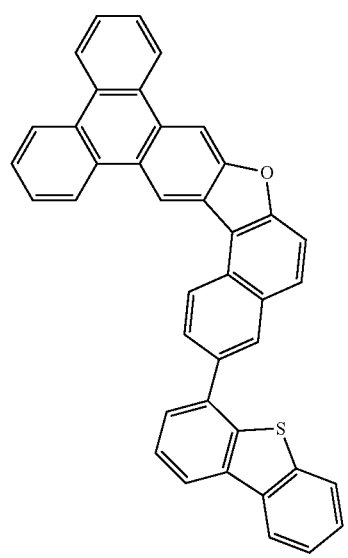
Compound 48
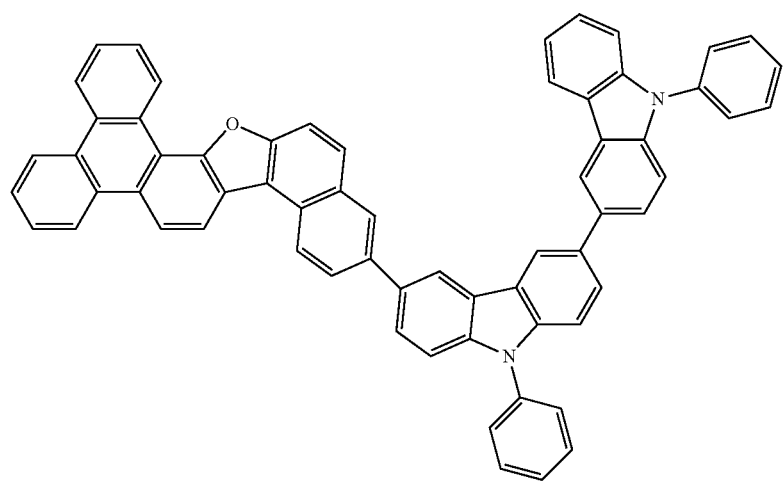

-continued
Compound 49
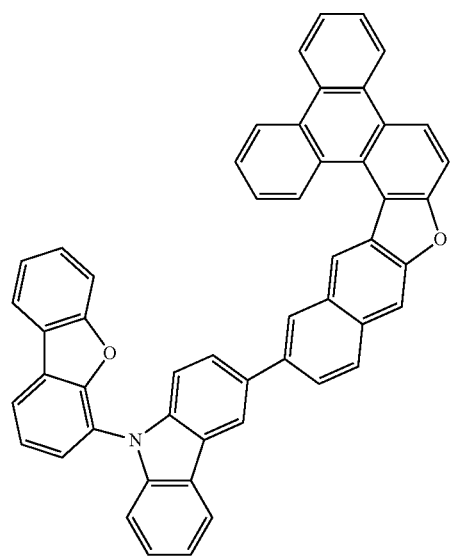
Compound 50
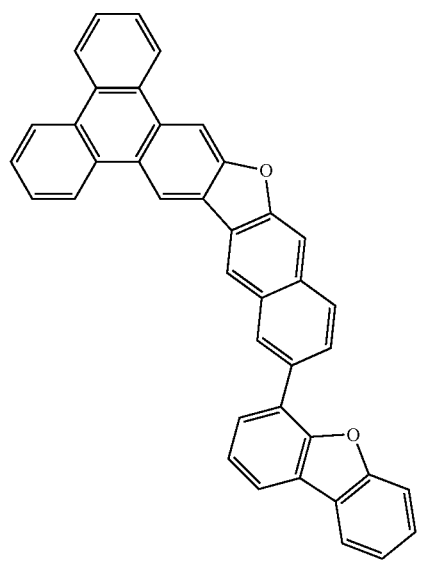
Compound 51
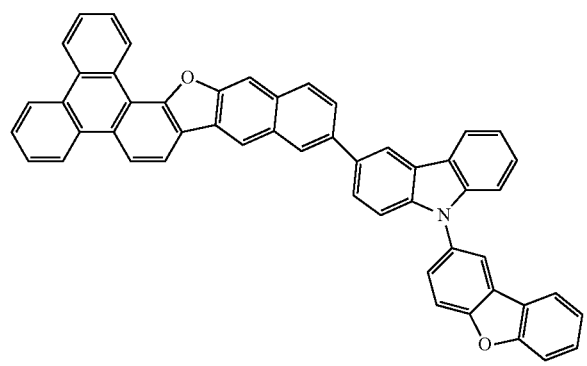
Compound 52
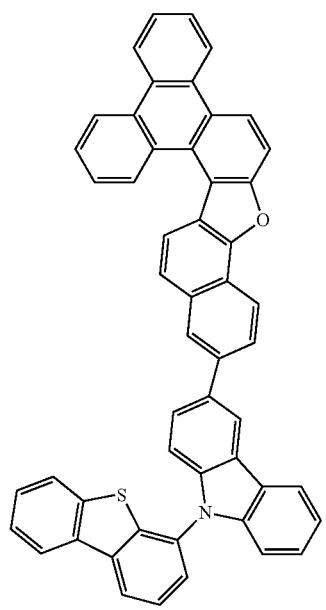

-continued
Compound 53
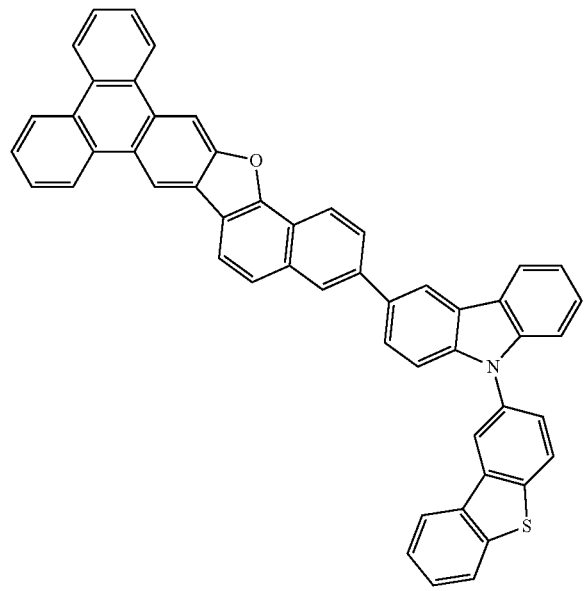
Compound 54
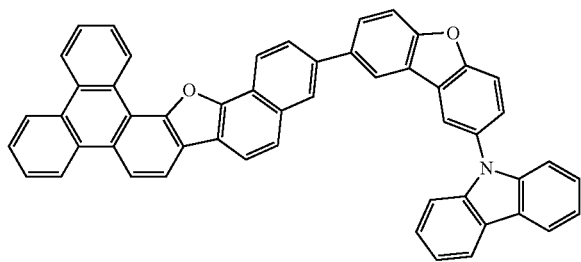
Compound 55
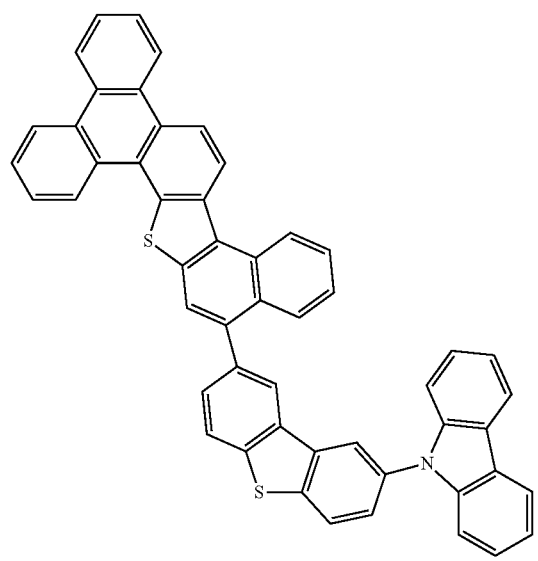
Compound 56
Compound 57
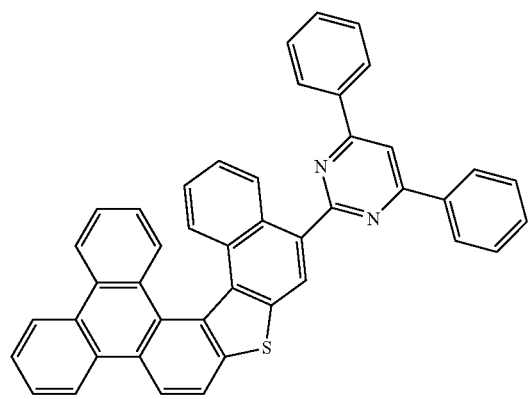
Compound 58
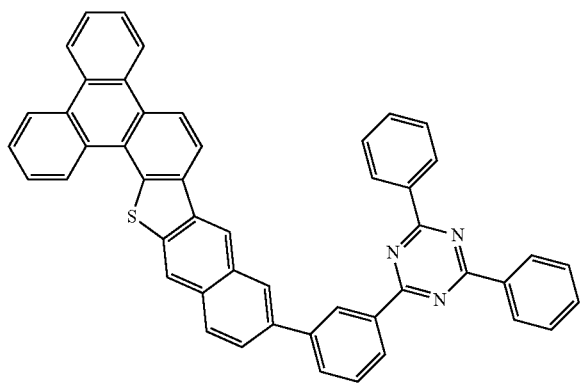

-continued
Compound 59
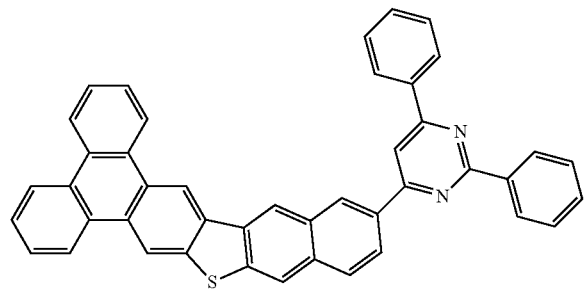
Compound 60
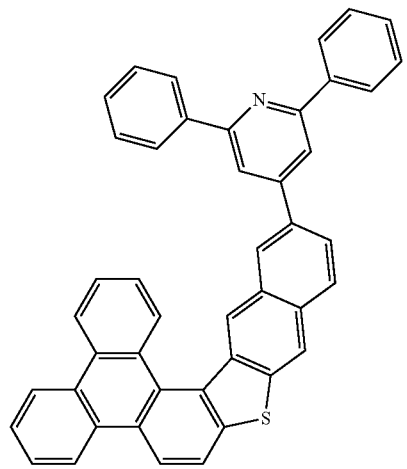
Compound 61
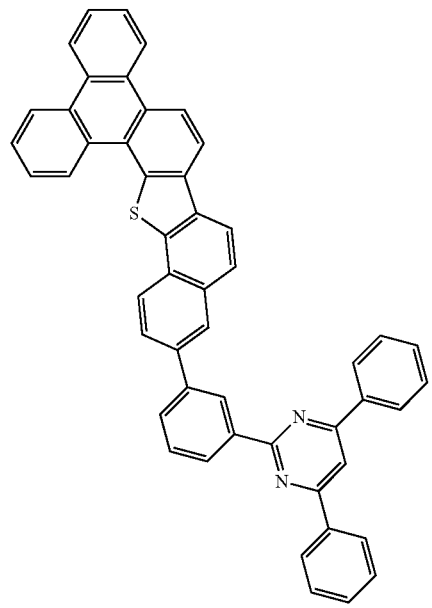
Compound 62
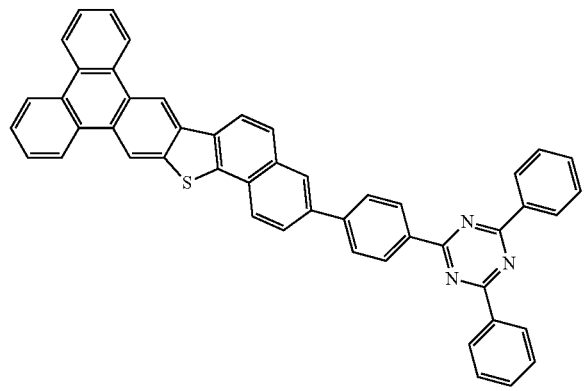
Compound 63
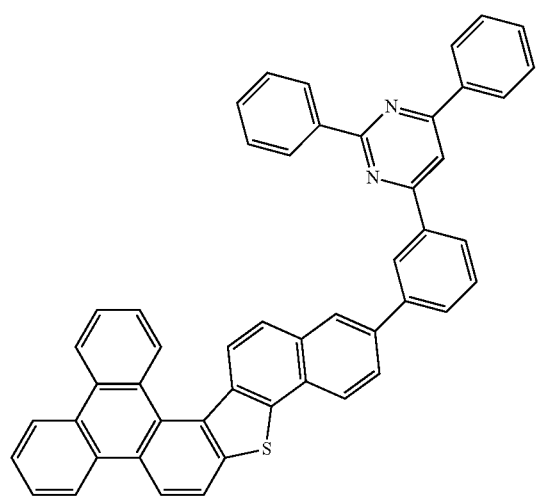
Compound 64
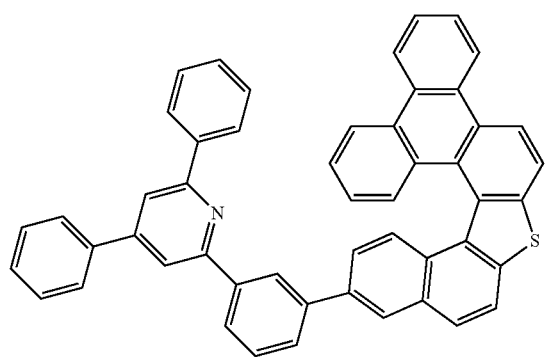

Compound 65
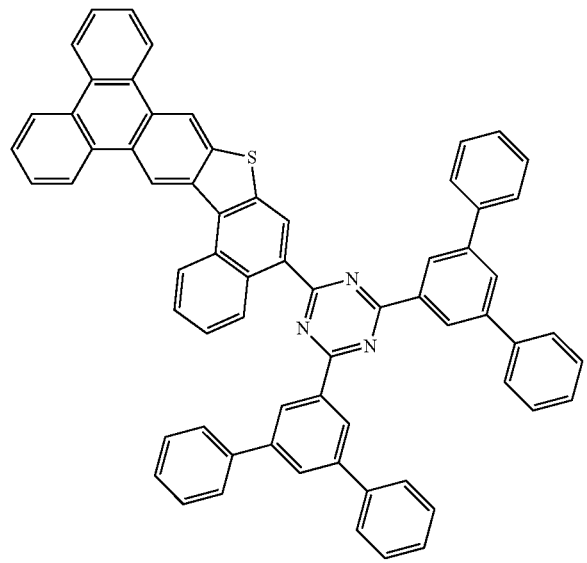
Compound 66
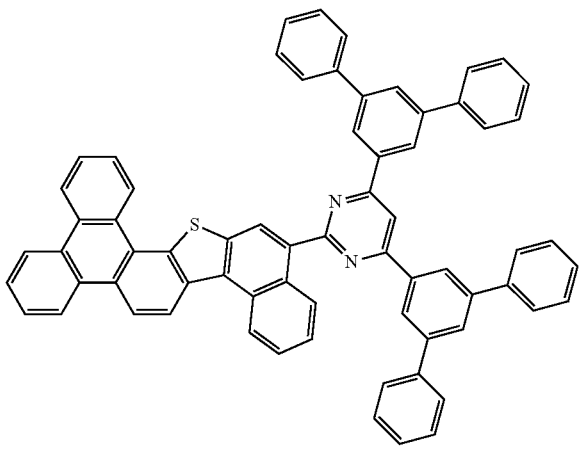
Compound 67
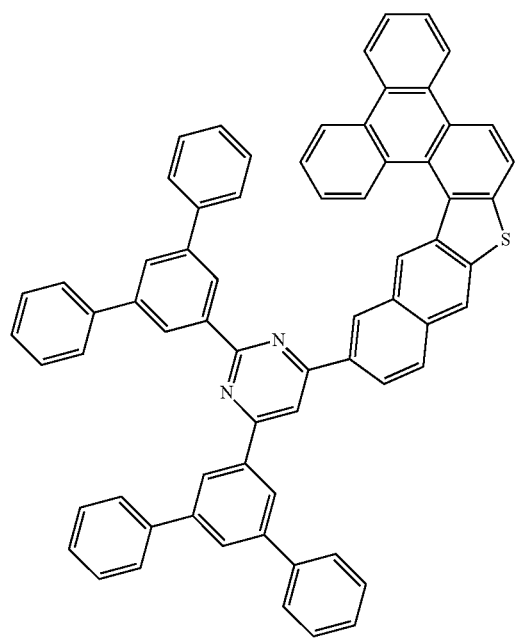
Compound 68
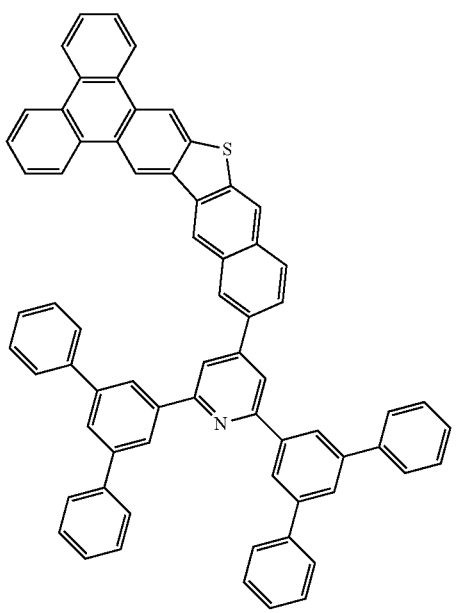

-continued
Compound 69
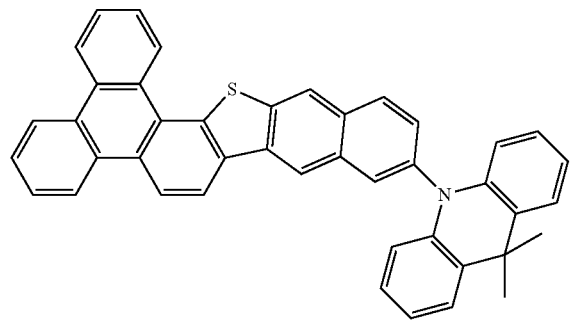
Compound 70
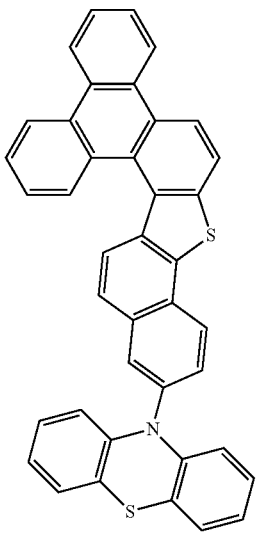
Compound 71
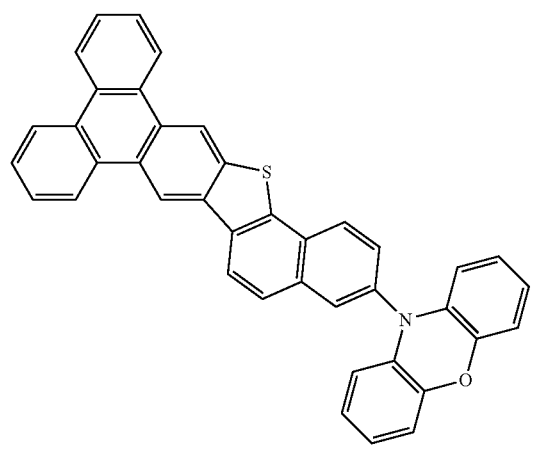
Compound 72
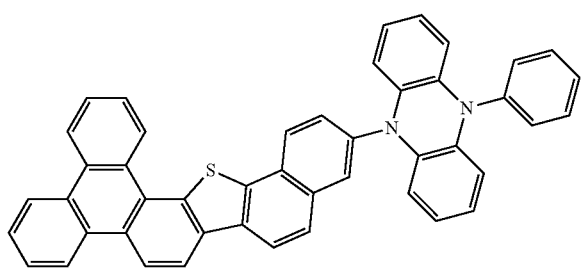
Compound 73
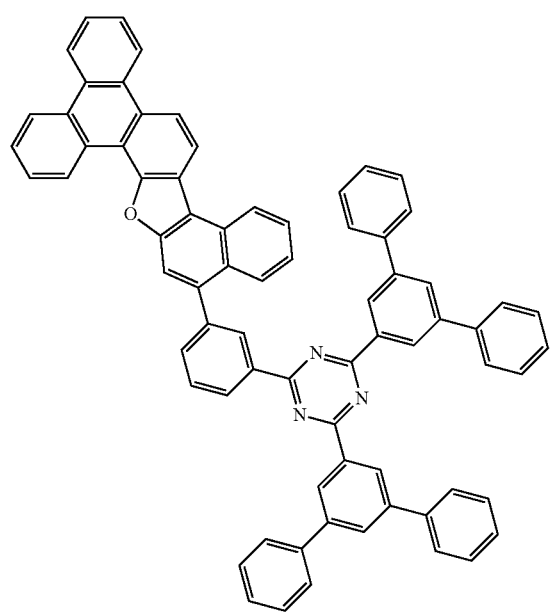
Compound 74
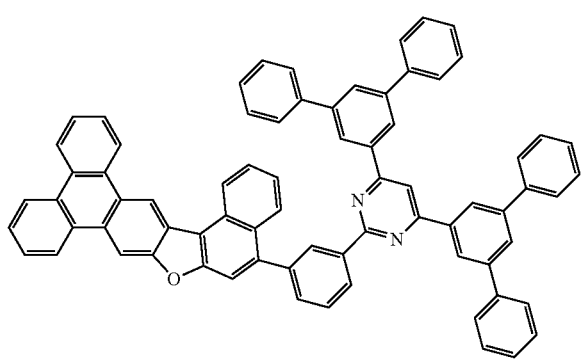

-continued
Compound 75
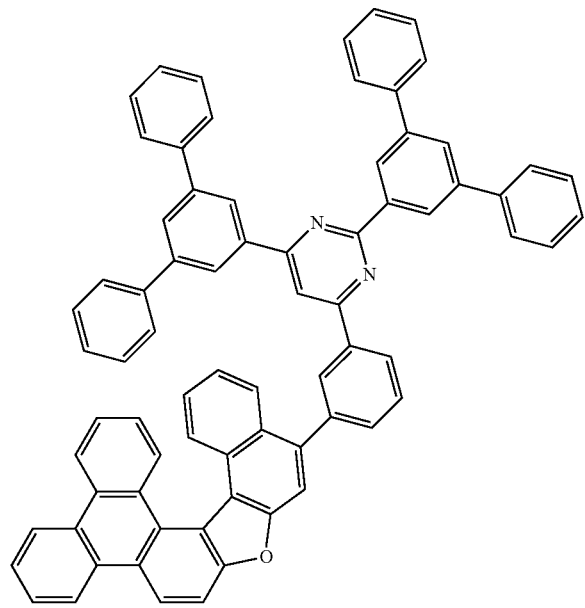
Compound 76
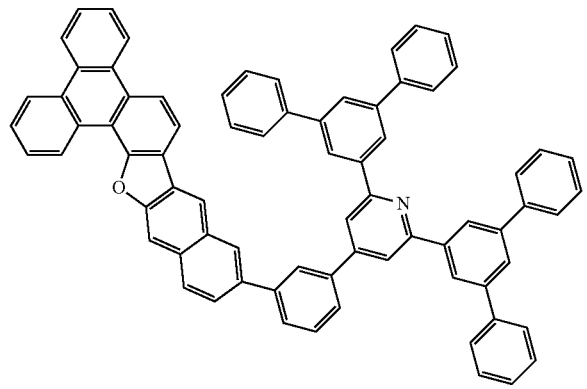
Compound 77
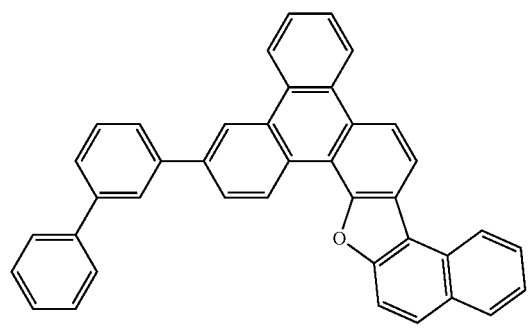
Compound 78
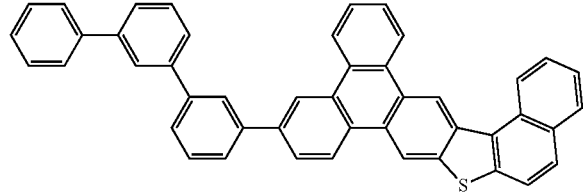
Compound 79
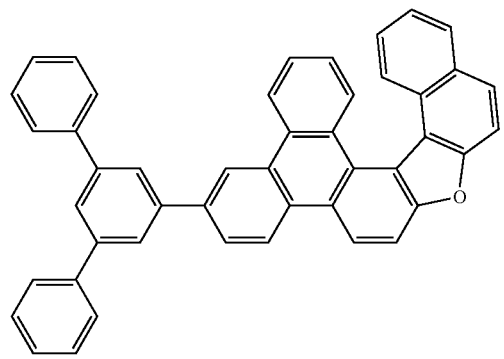
Compound 80
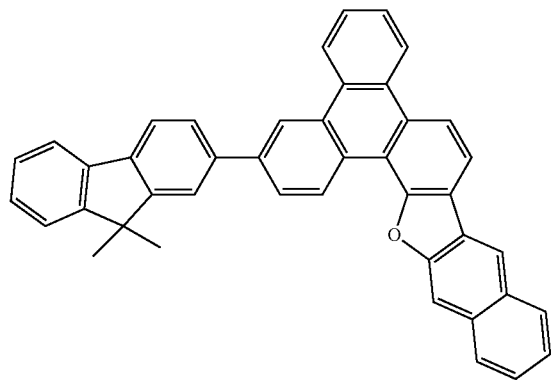

-continued
Compound 81
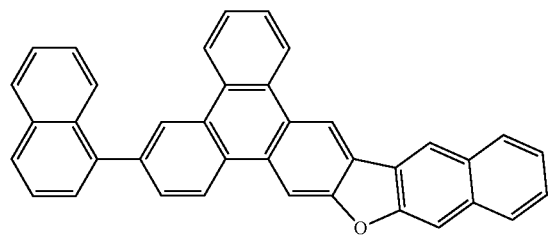
Compound 82
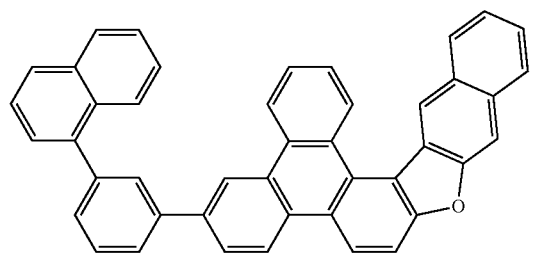
Compound 83
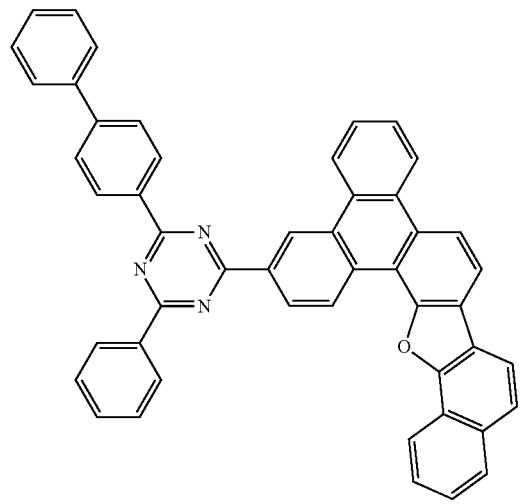
Compound 84
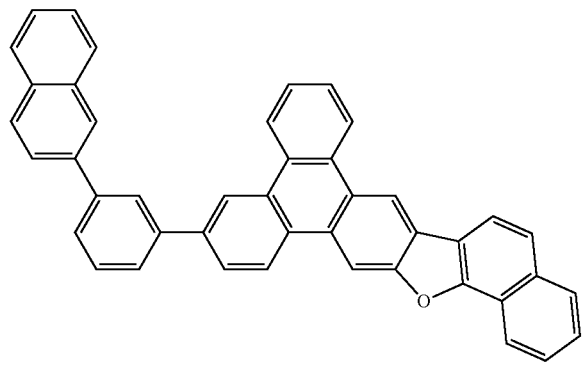
Compound 85
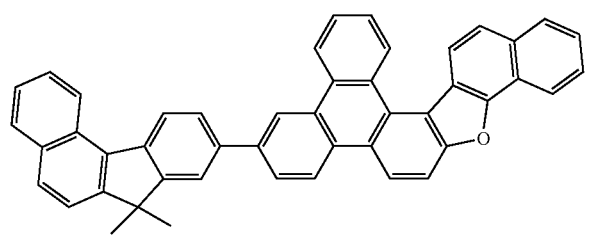
Compound 86
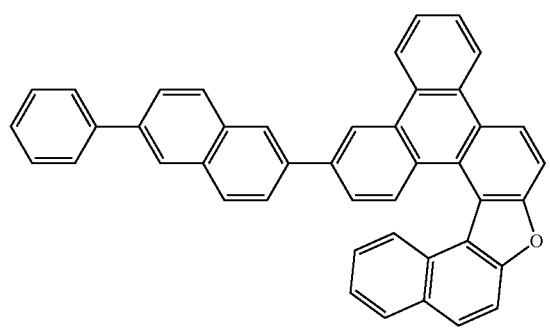
Compound 87
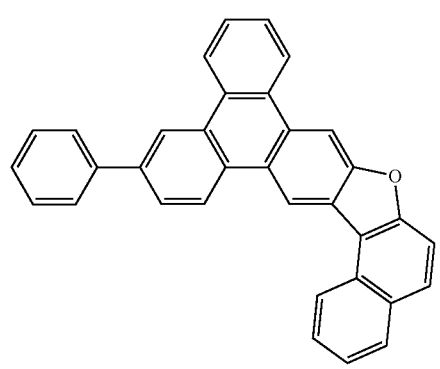
Compound 88
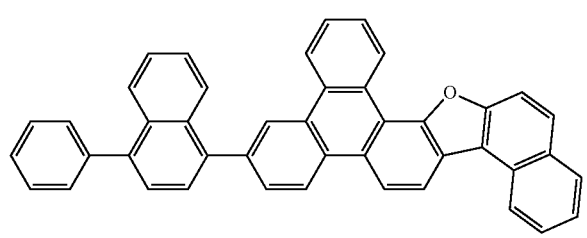

-continued
Compound 89
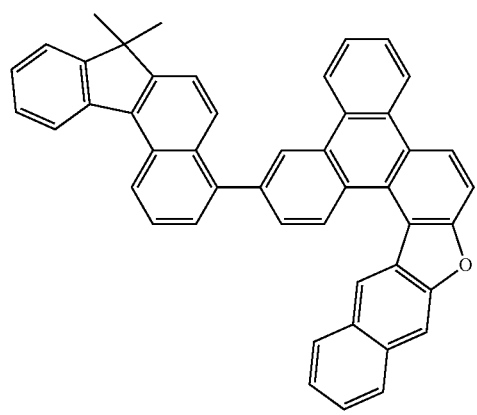
Compound 90
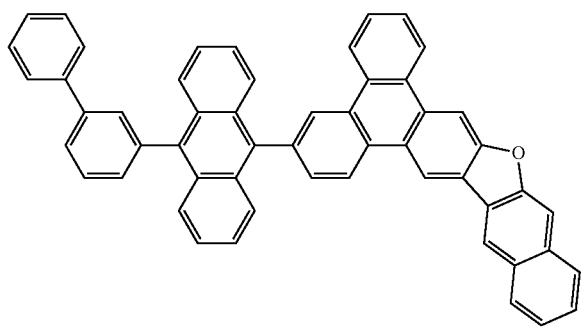
Compound 91
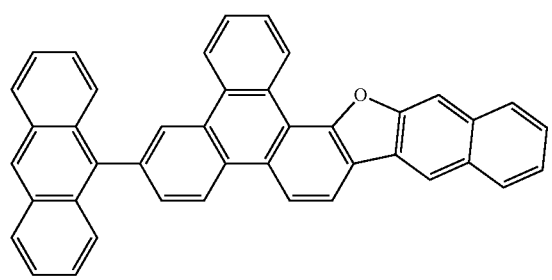
Compound 92
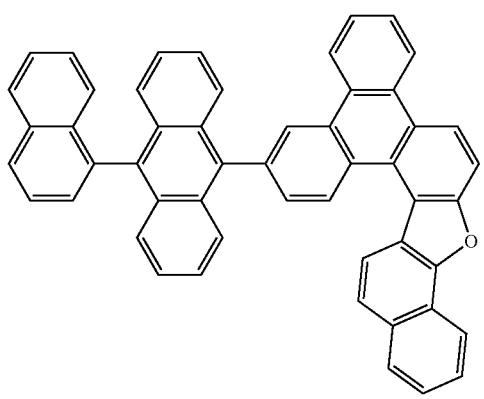
Compound 93
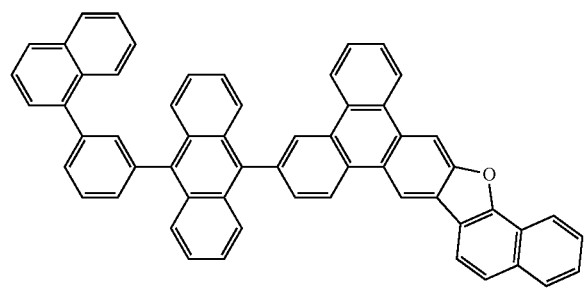
Compound 94
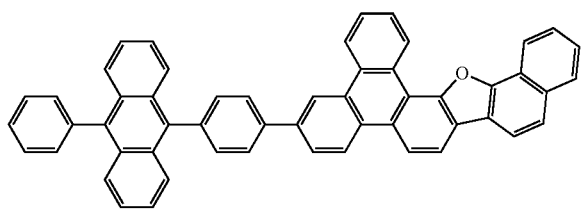

-continued
Compound 95
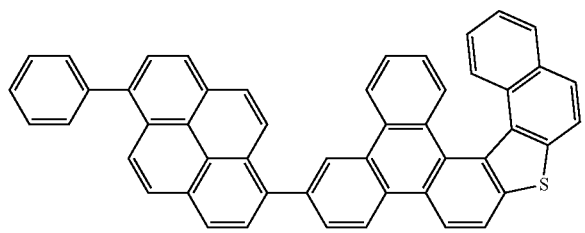
Compound 96
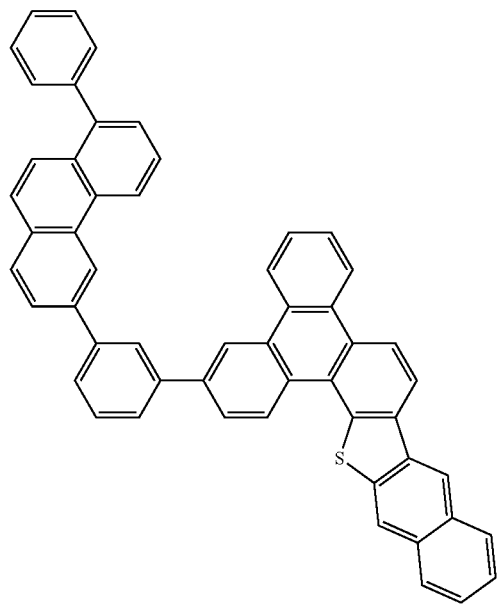
Compound 97
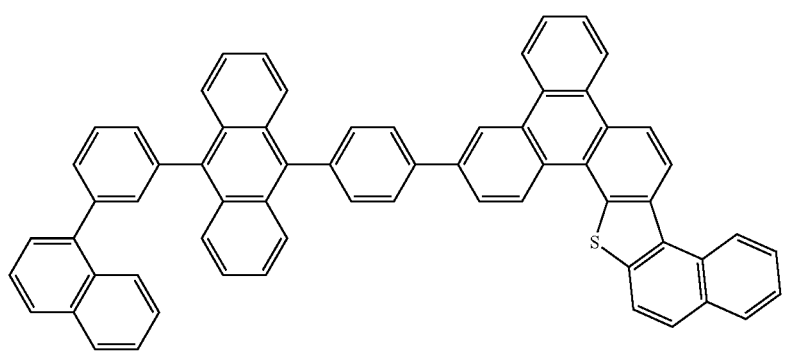
Compound 98
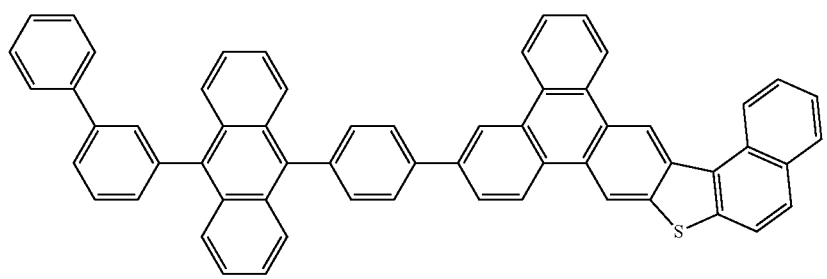
Compound 99
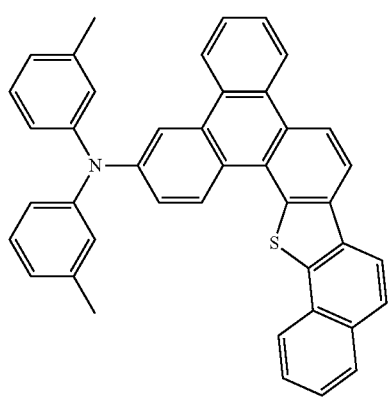
Compound 100
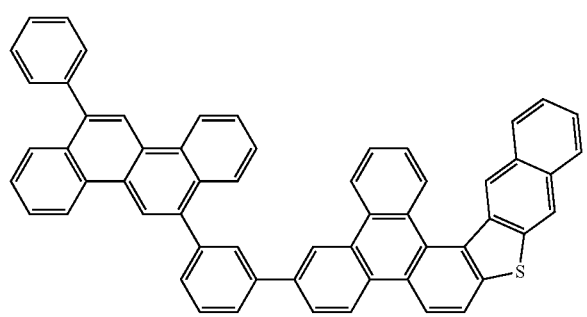

Compound 101
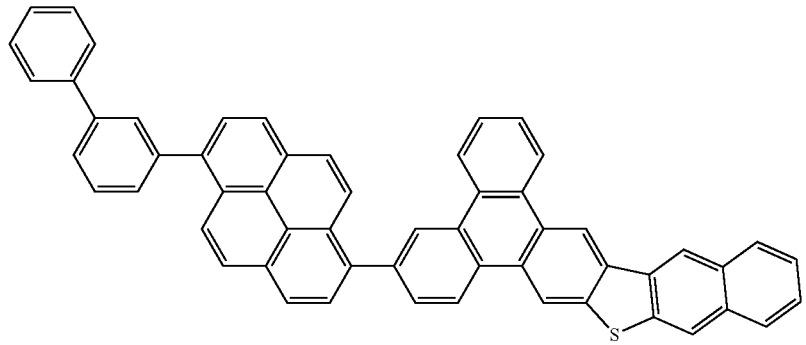
Compound 102
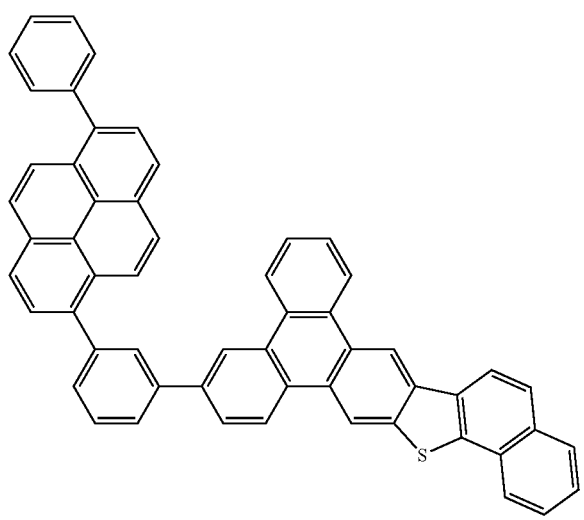
Compound 103
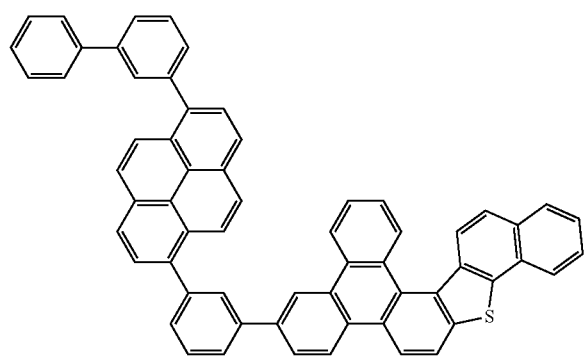
Compound 104
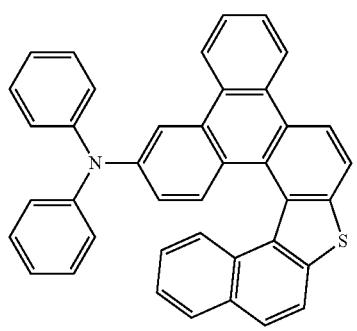
Compound 105
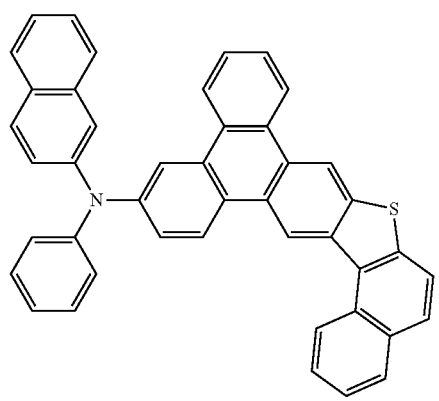

-continued
Compound 106
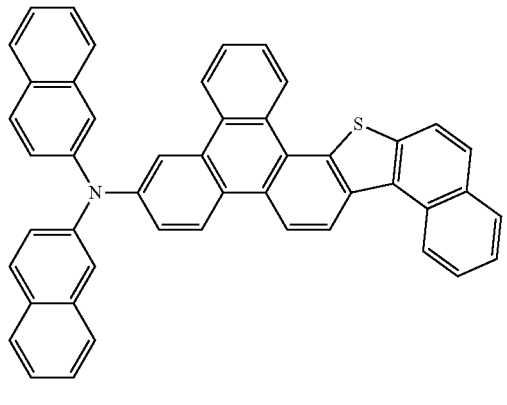
Compound 107
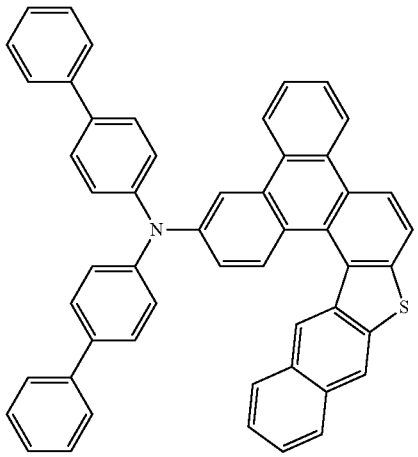
Compound 108
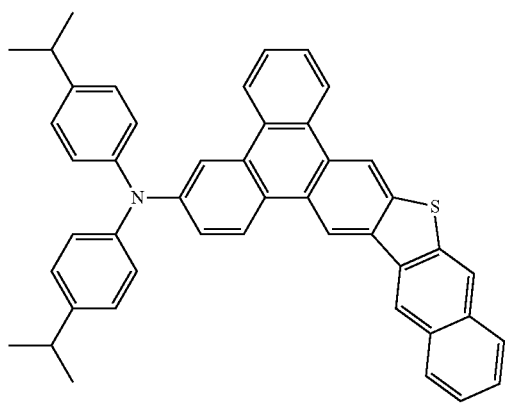
Compound 109
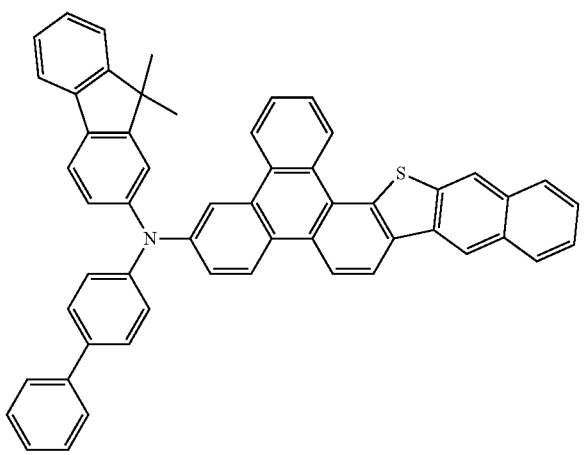
Compound 110
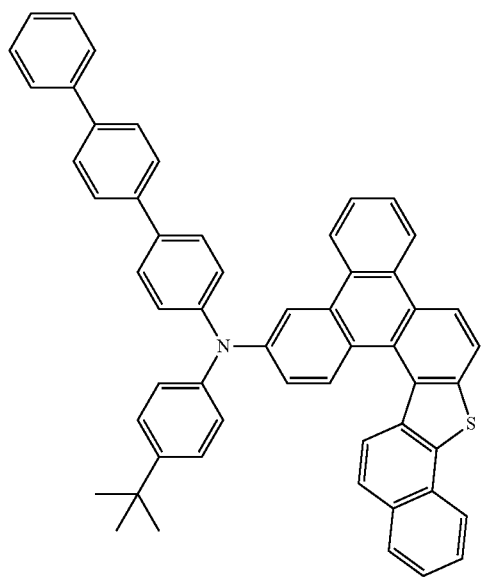
Compound 111
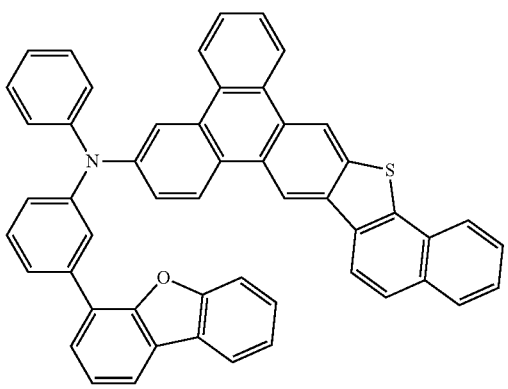

-continued
Compound 112
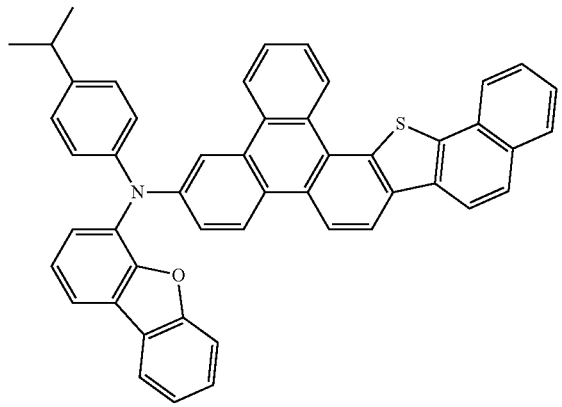
Compound 113
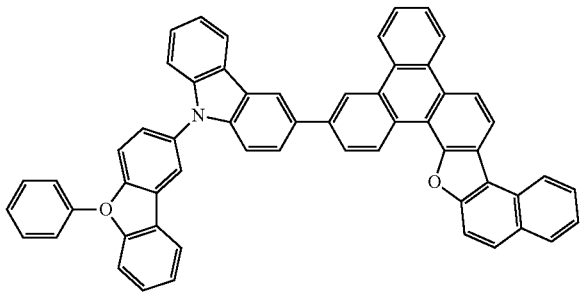
Compound 114
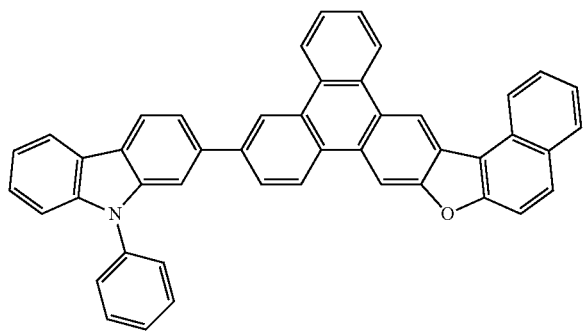
Compound 115
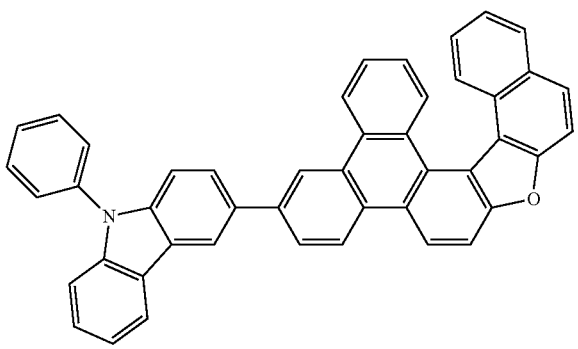
Compound 116
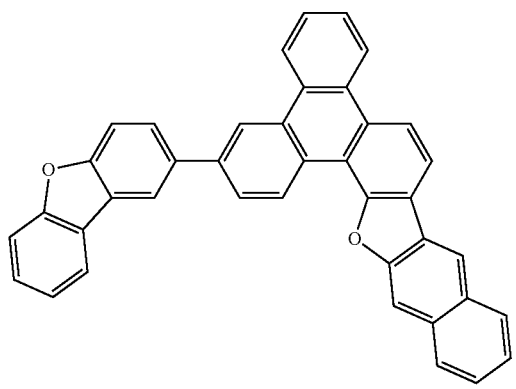
Compound 117
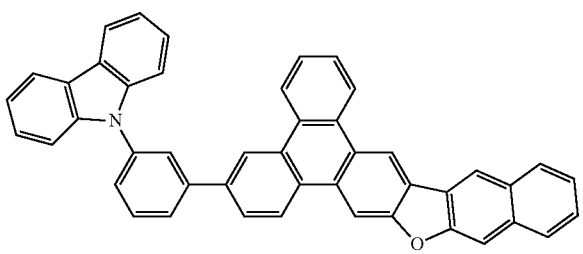
Compound 118
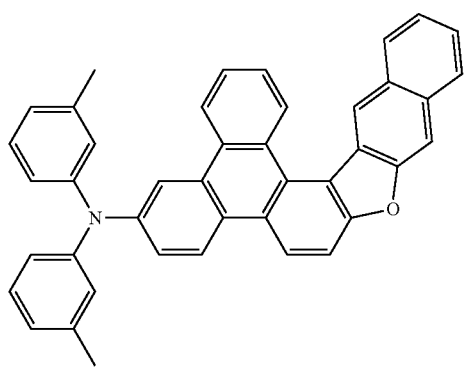
Compound 119
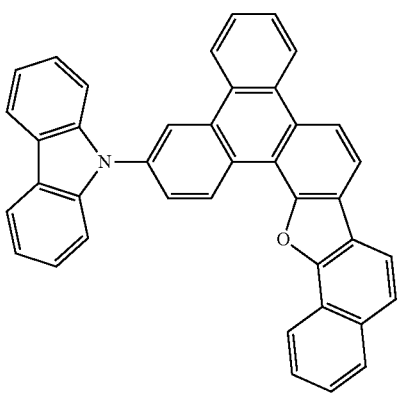

-continued
Compound 120
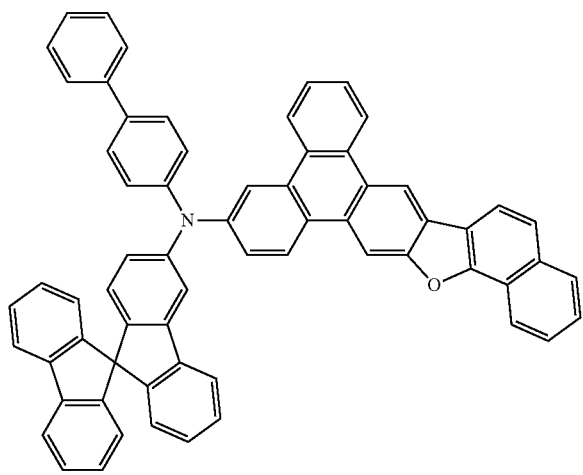
Compound 121
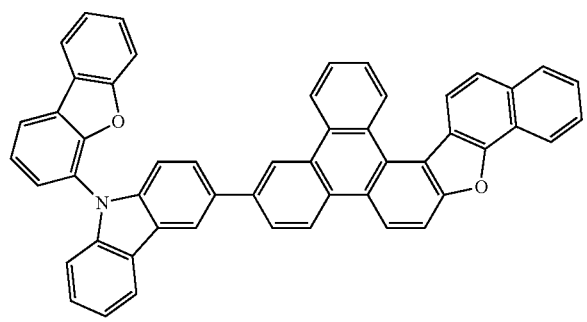
Compound 122
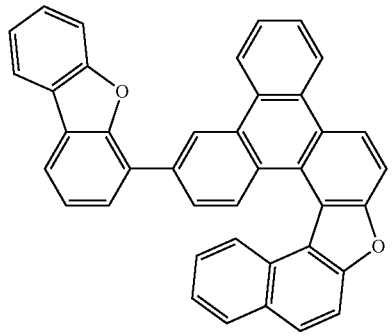
Compound 123
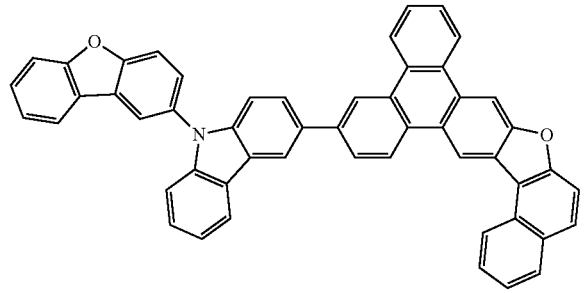
Compound 124
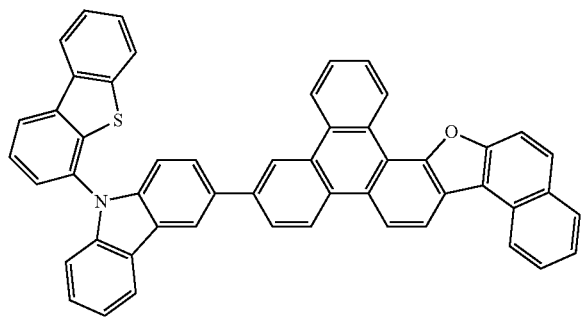
Compound 125
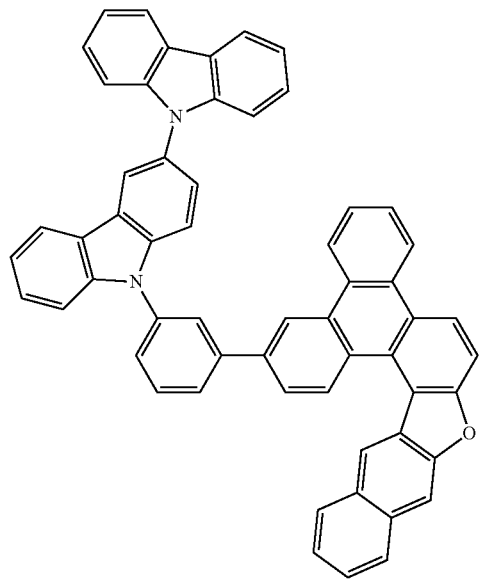

-continued
Compound 126
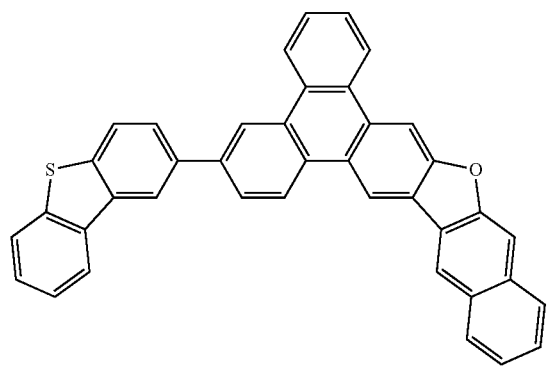
Compound 127
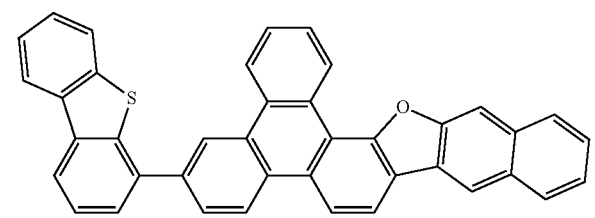
Compound 128
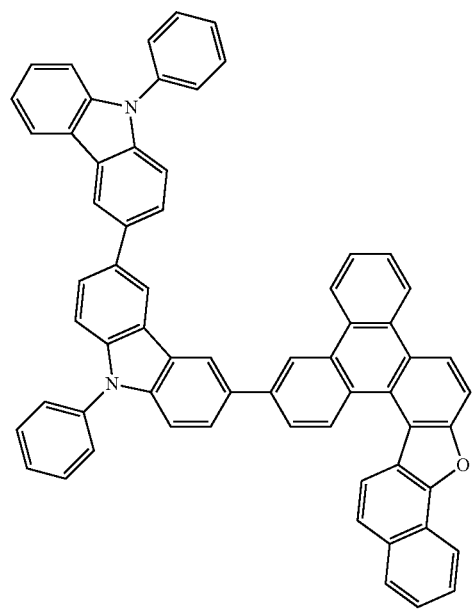
Compound 129
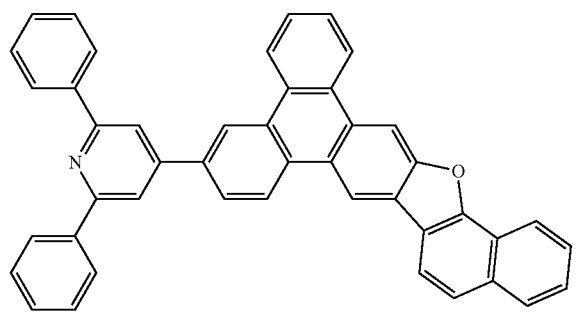
Compound 130
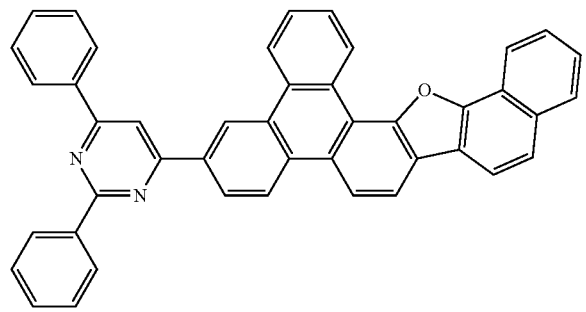
Compound 131
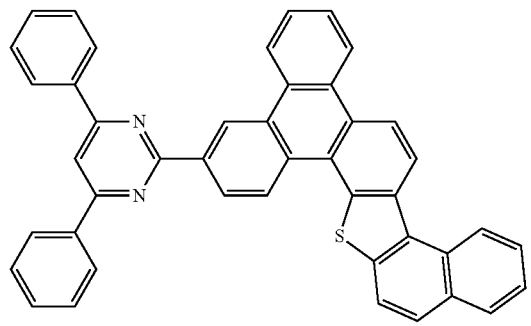

Compound 132
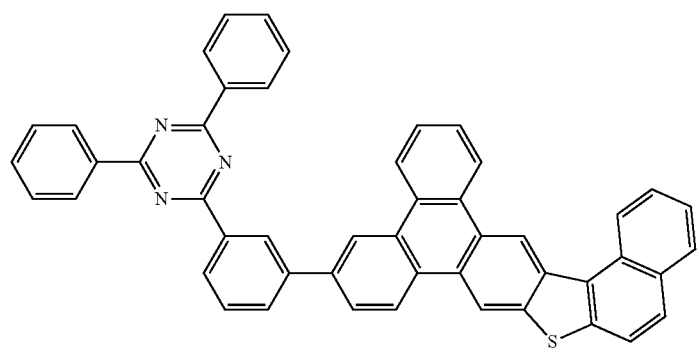
-continued
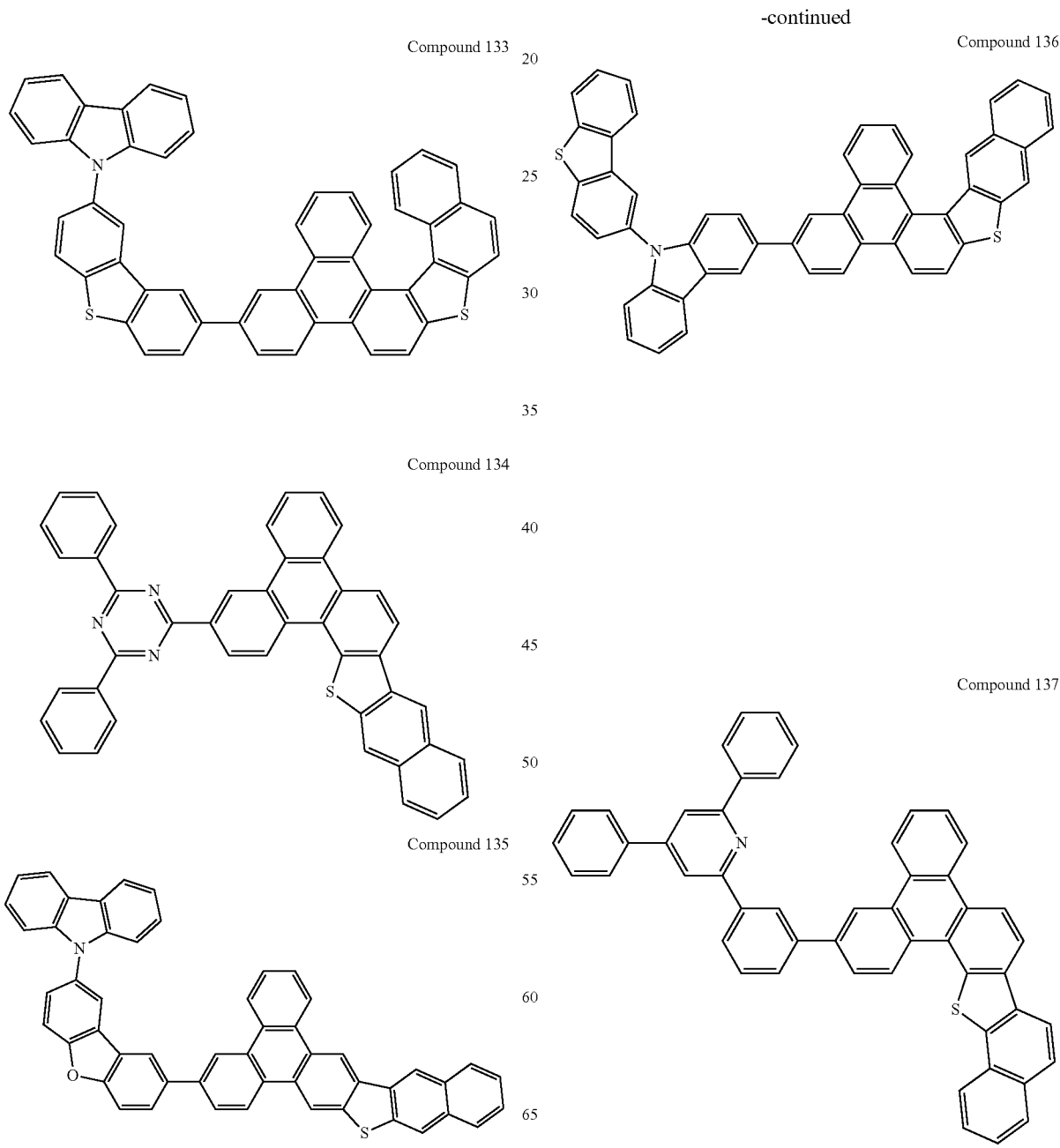

Compound 138
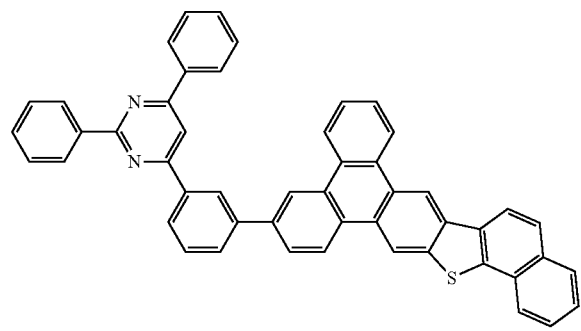
Compound 139
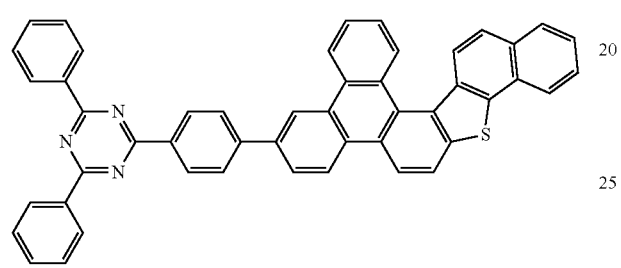
Compound 140
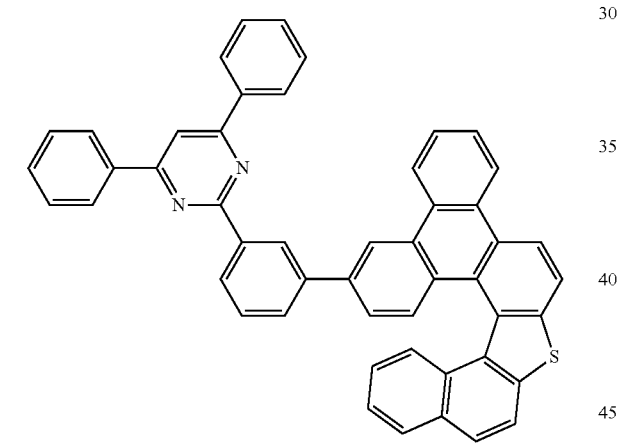
Compound 141
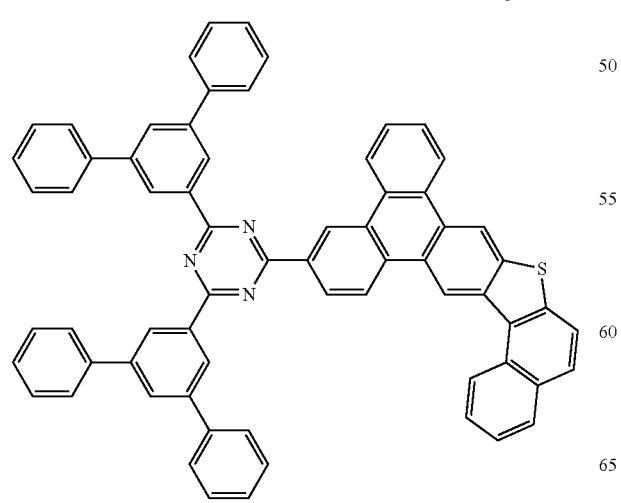
Compound 142
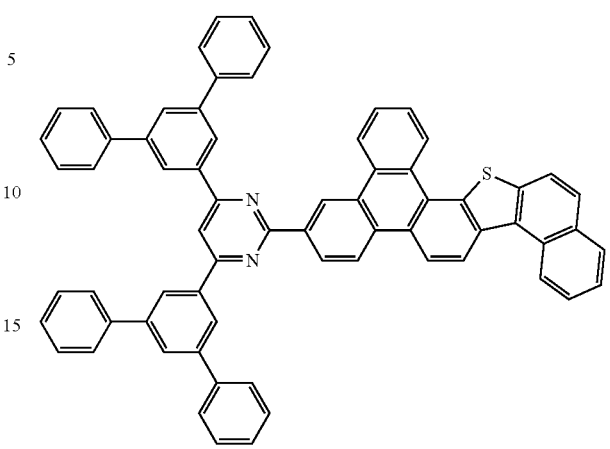
Compound 143
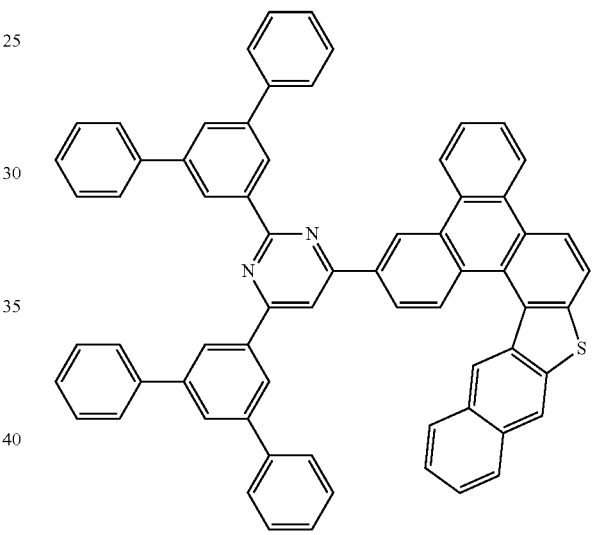
Compound 144
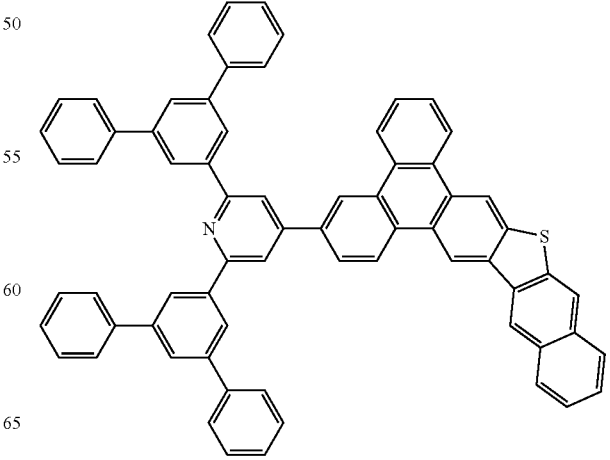

Compound 145
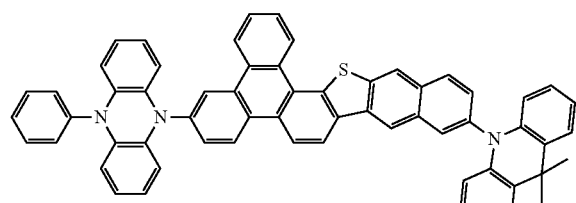
Compound 146
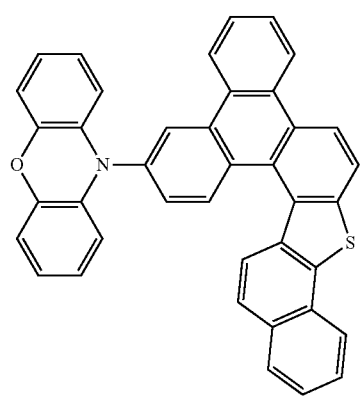
Compound 147
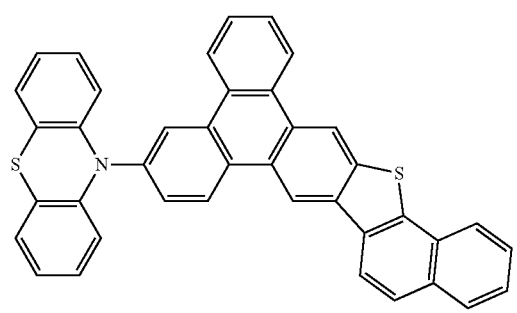
Compound 148
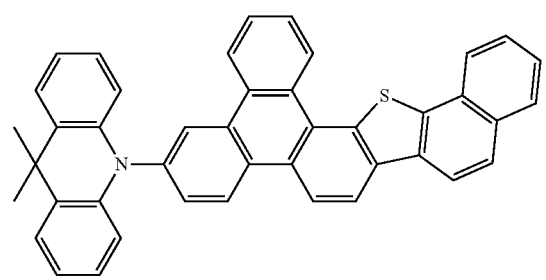
Compound 149
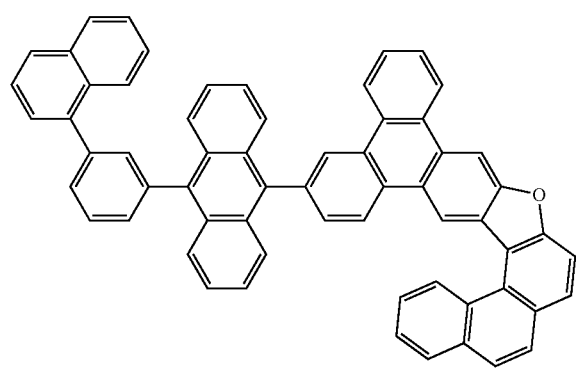
Compound 150
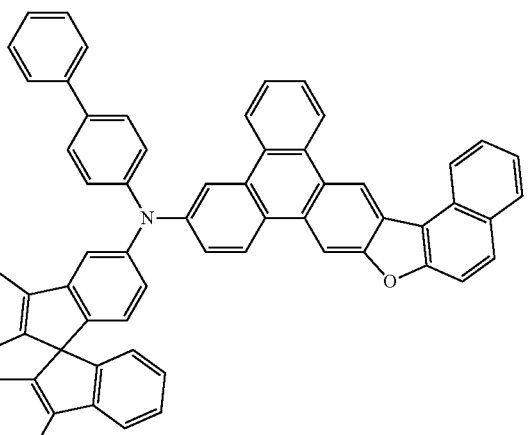
Compound 151
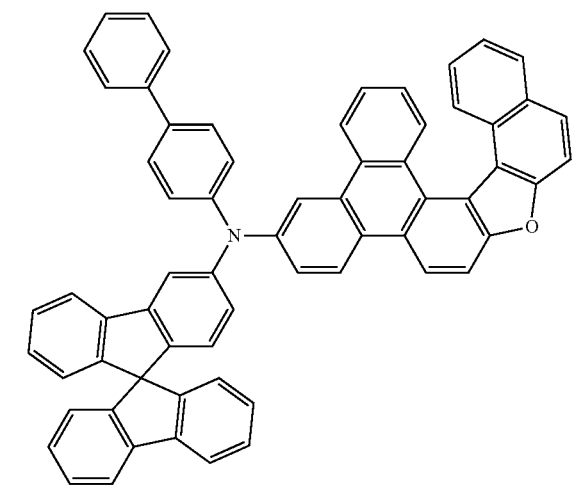
Compound 152
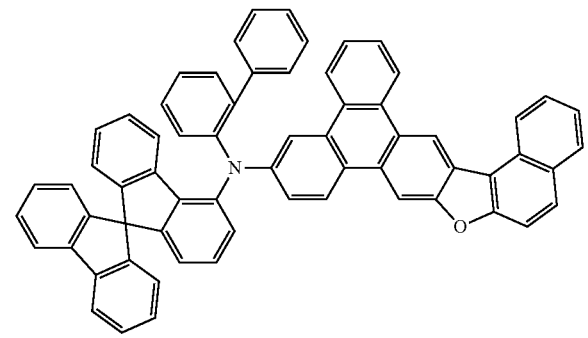

Compound 153
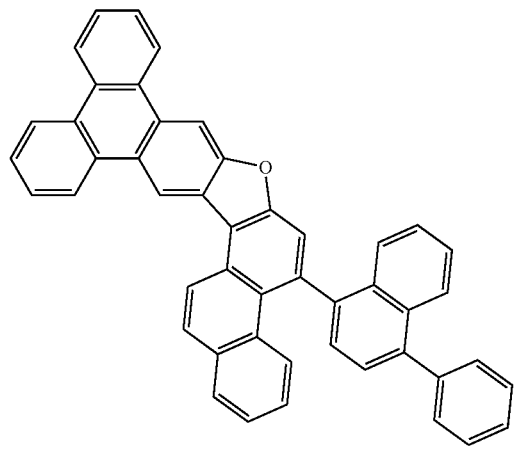
Compound 154
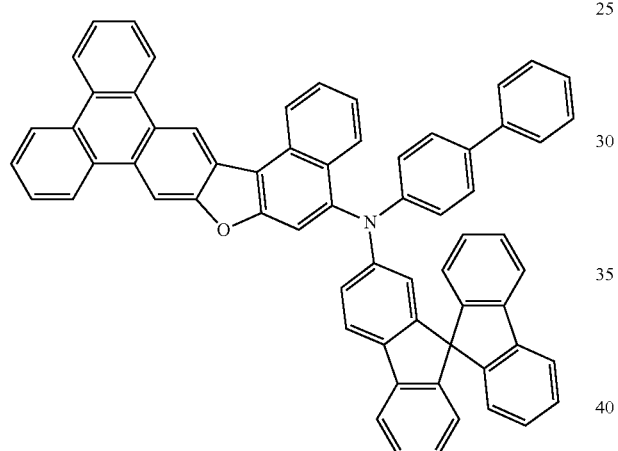
Compound 155
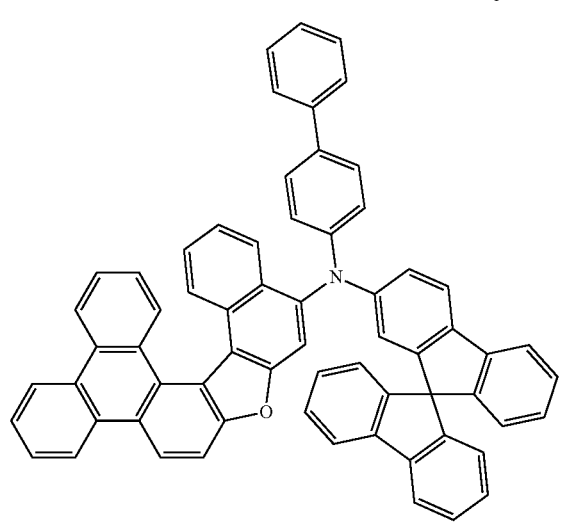
Compound 156
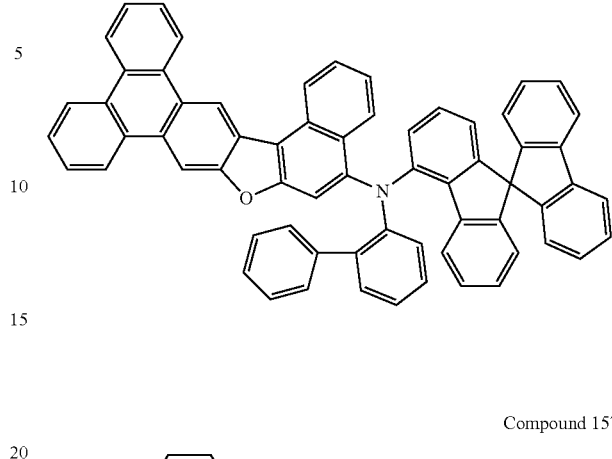
Compound 157
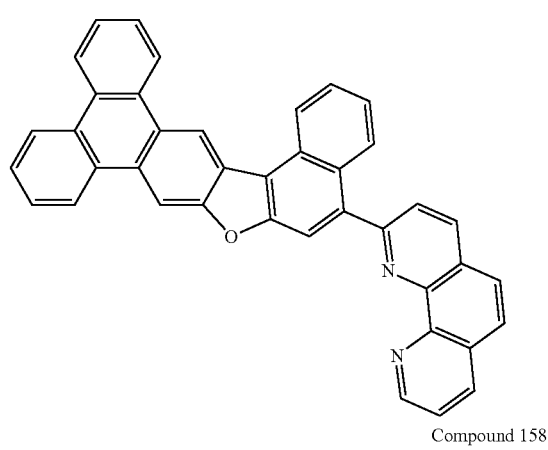
Compound 158
Compound 159
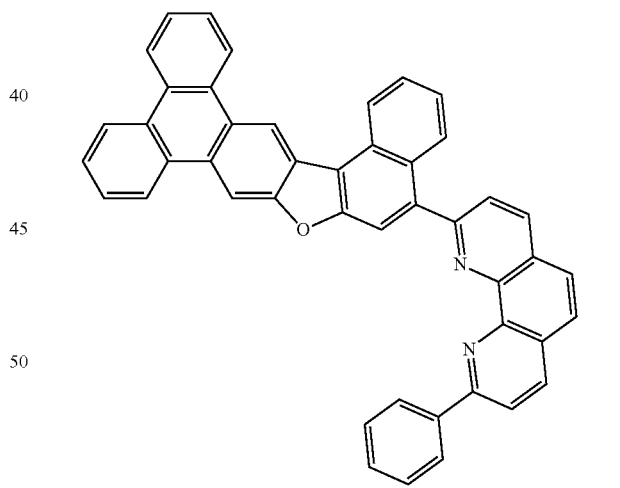

Compound 160
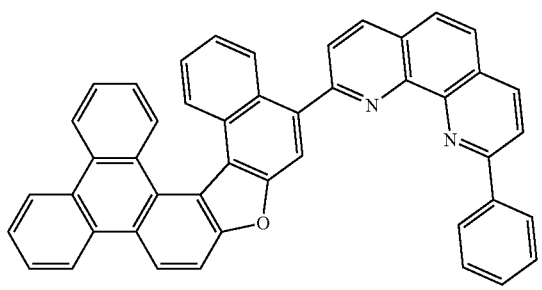
Compound 161
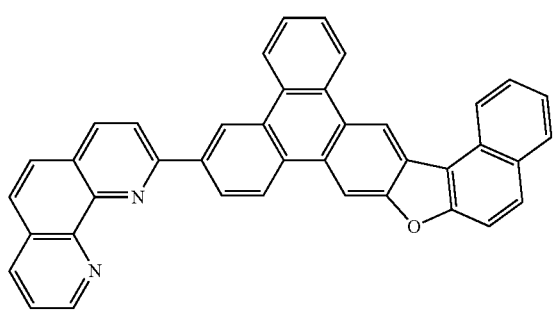
Compound 162
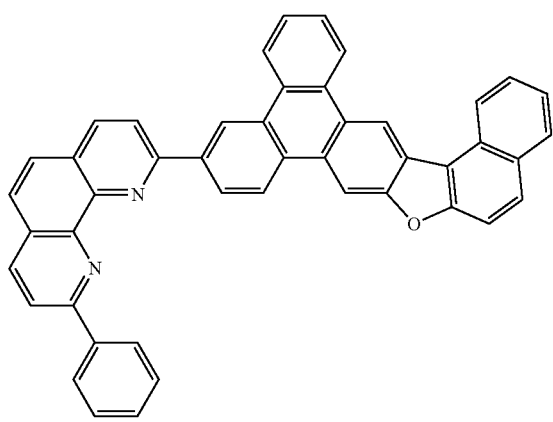
Compound 163
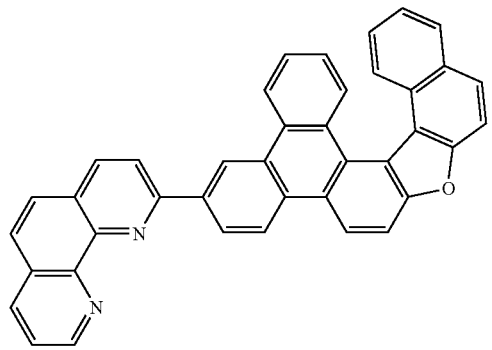
Compound 164
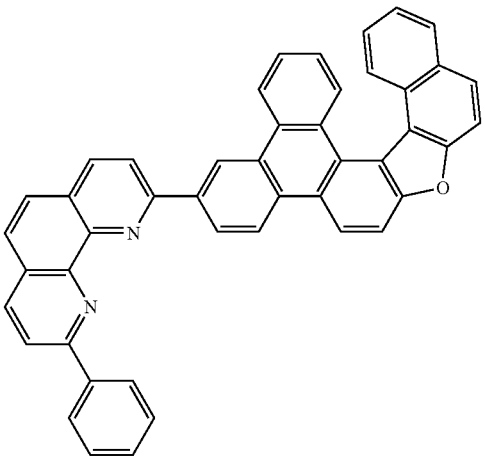
Compound 165
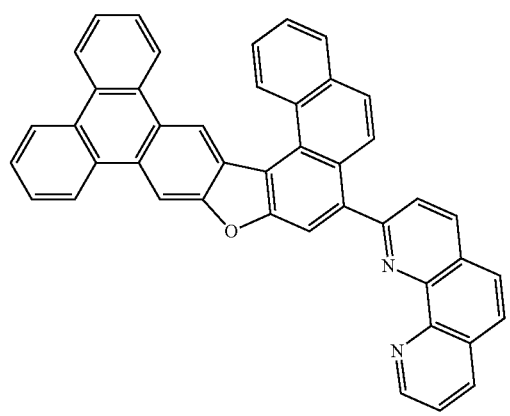
Compound 166
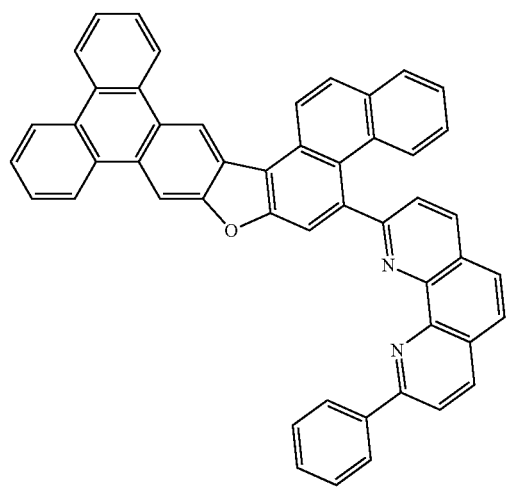

Compound 167
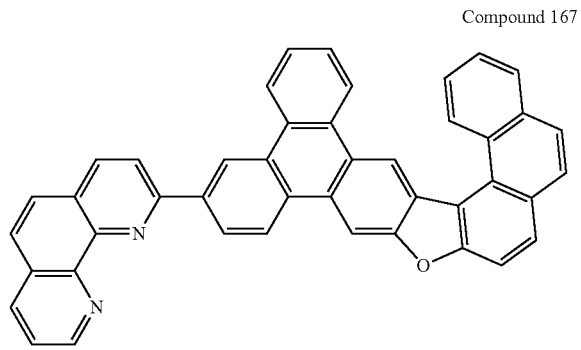
Compound 168
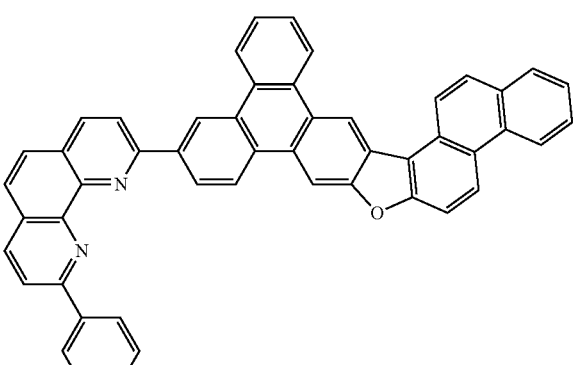
Compound 169
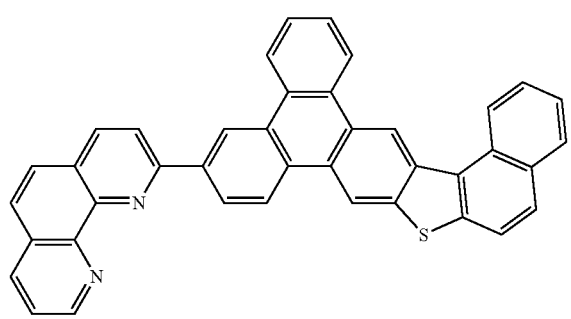
Compound 170
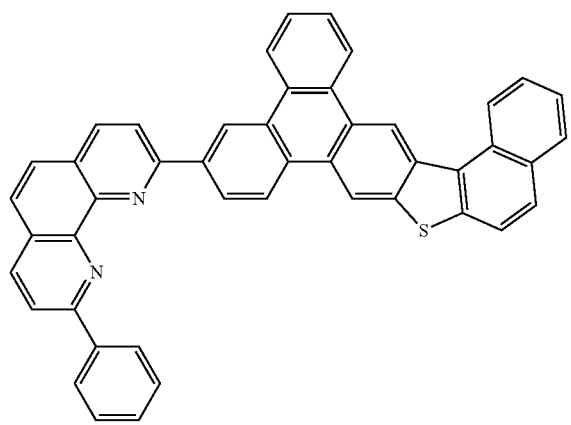
Compound 171
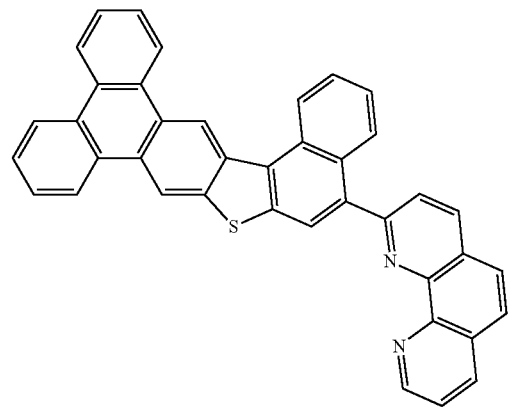
Compound 172
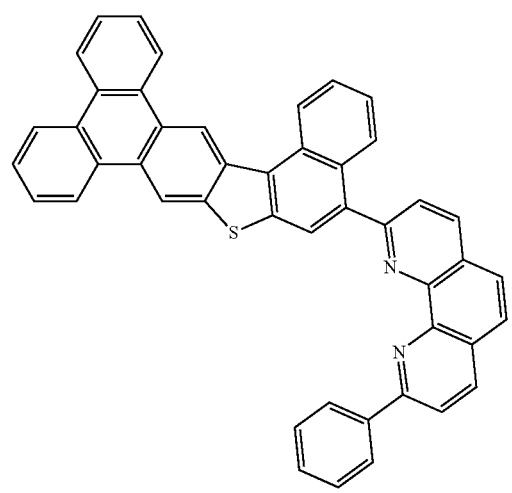
Compound 173
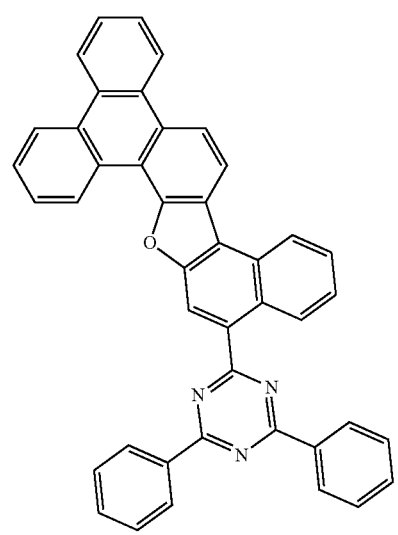

Compound 174
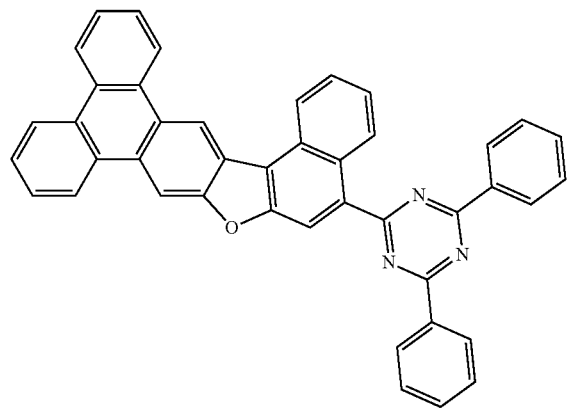
Compound 175
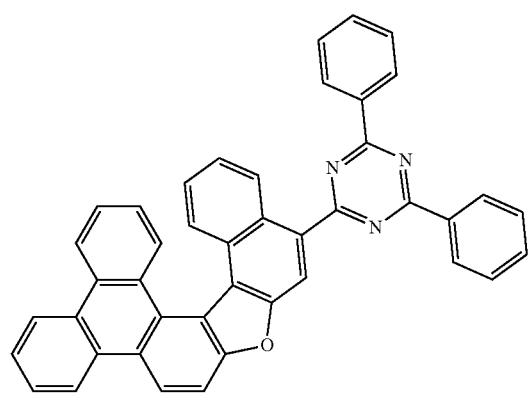
Compound 176
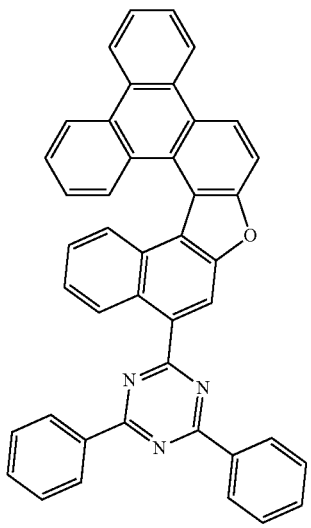
Compound 177
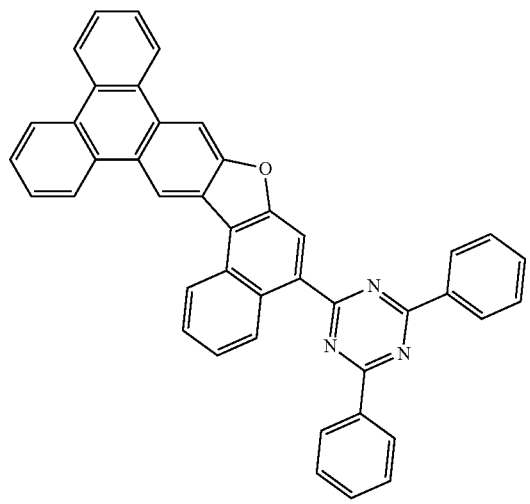
Compound 178
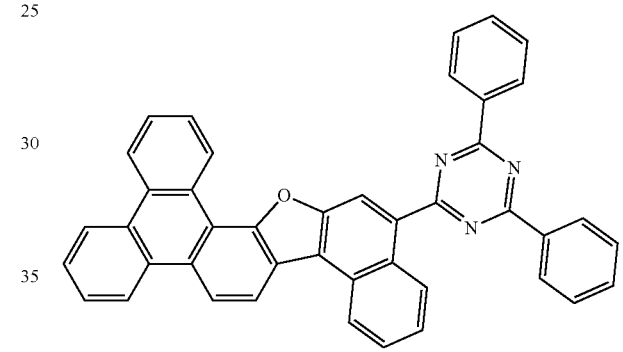
Compound 179
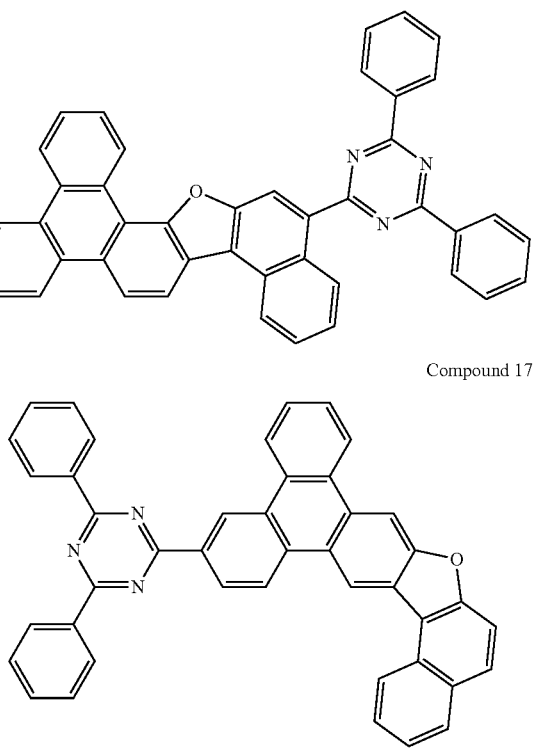
Compound 180
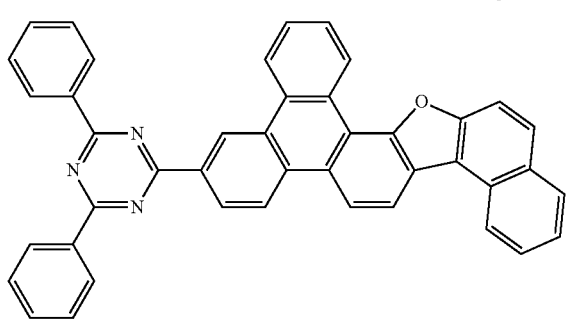

Compound 181
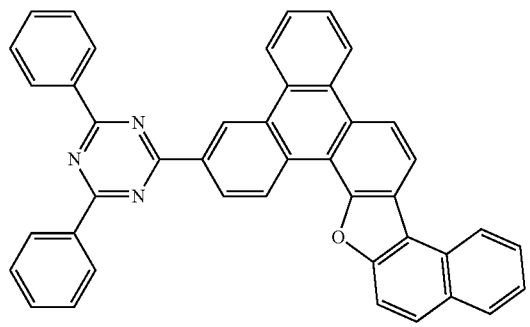
Compound 182
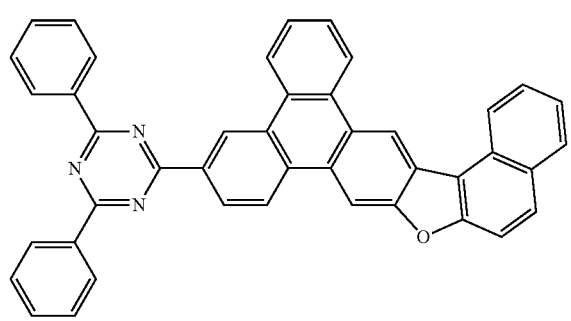
Compound 183
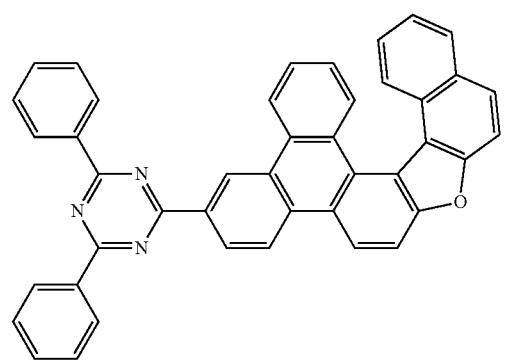
Compound 184
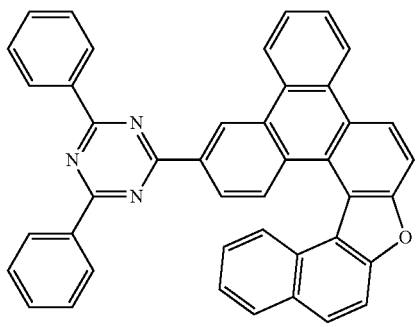
Compound 185
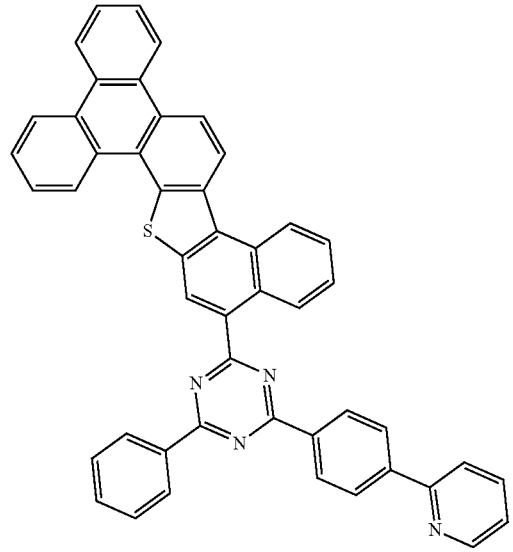
Compound 186
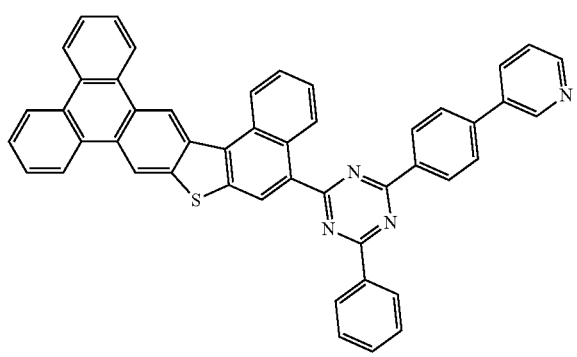
Compound 187
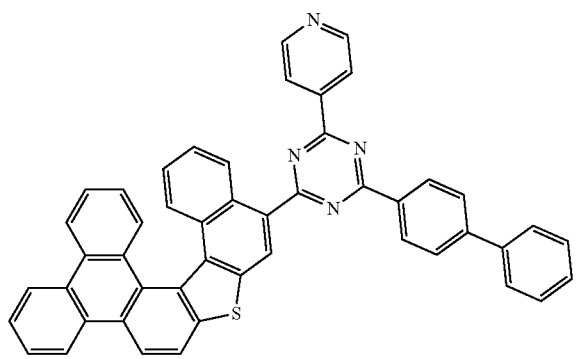

Compound 188
Compound 191
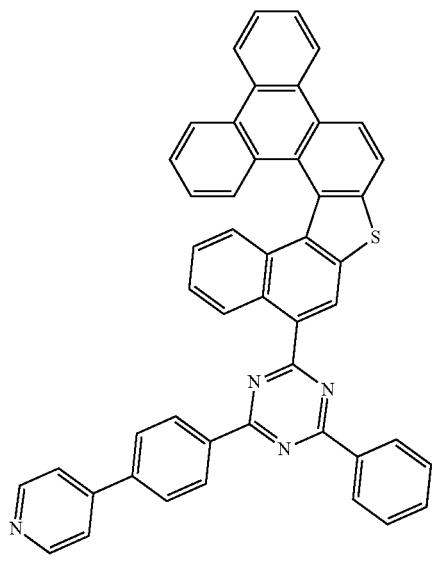
Compound 189
Compound 192
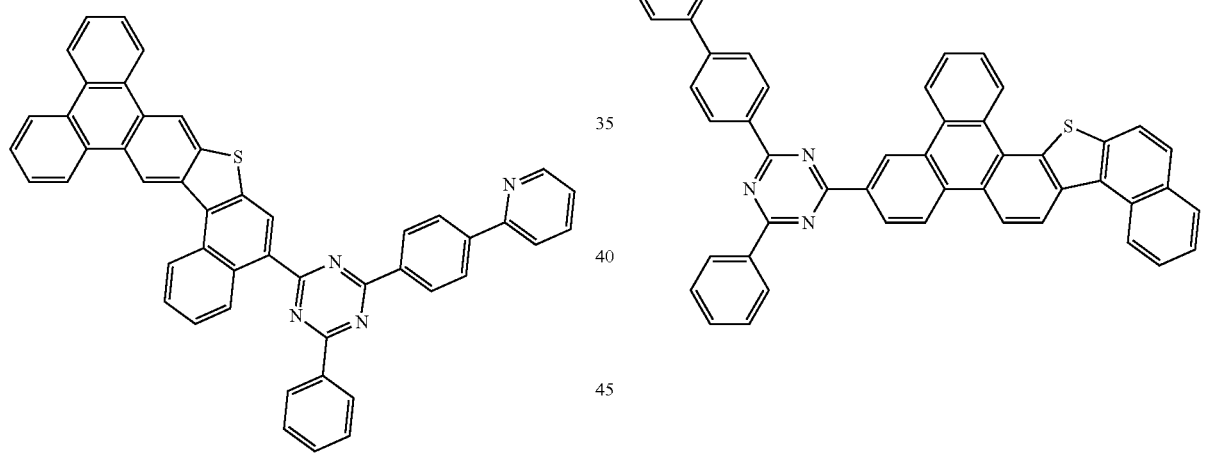
Compound 190
Compound 193
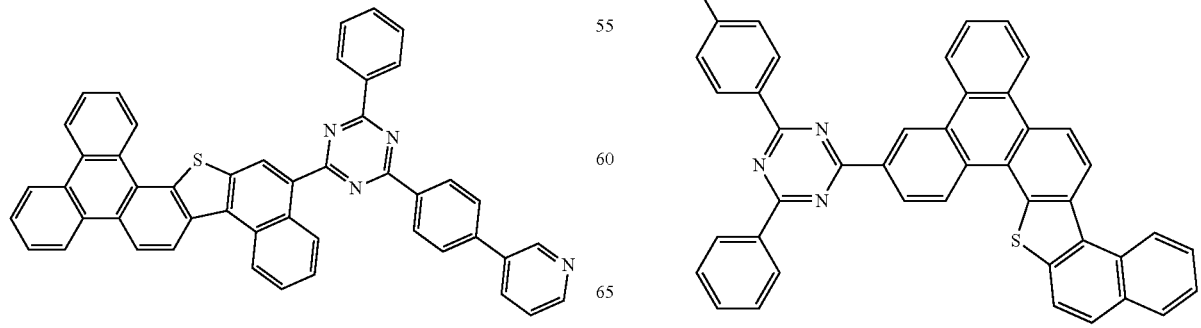

Compound 194
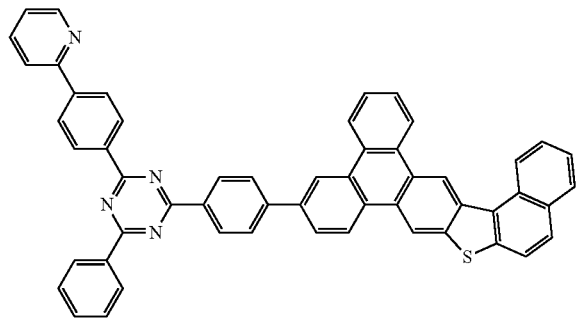
Compound 195
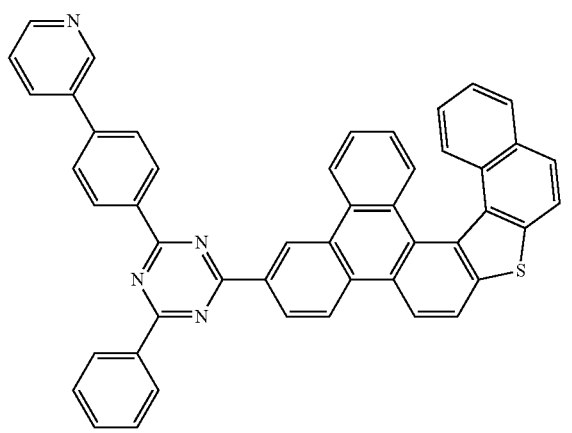
Compound 196
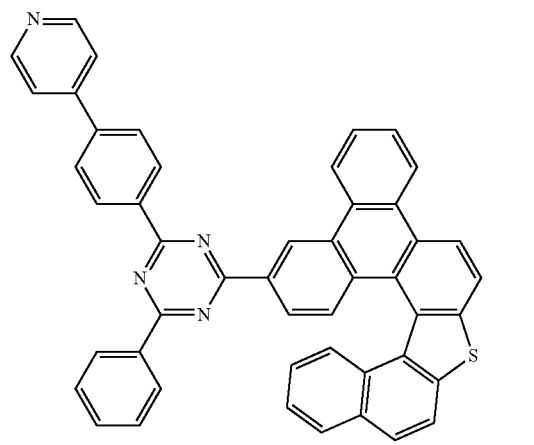
Compound 197
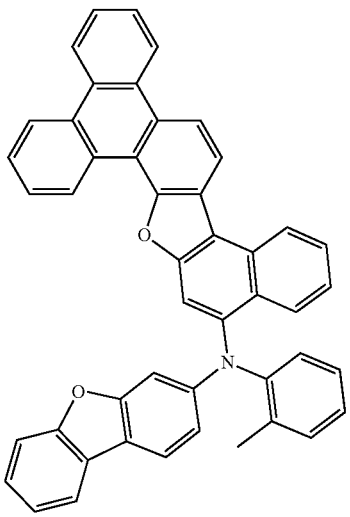
Compound 198
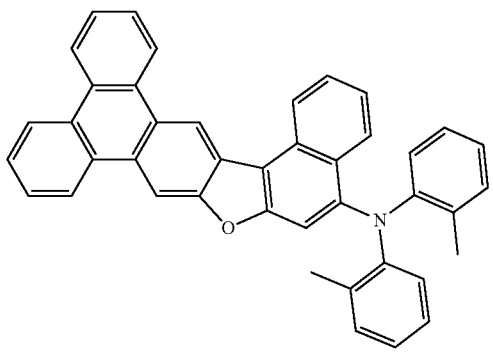
Compound 199
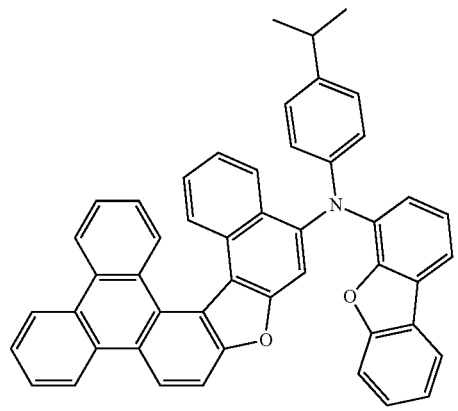

Compound 200
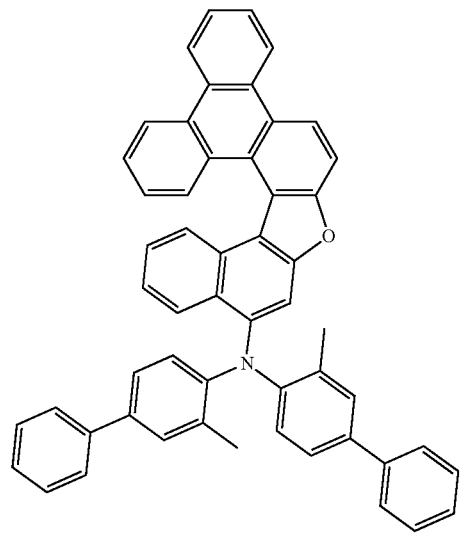
Compound 201
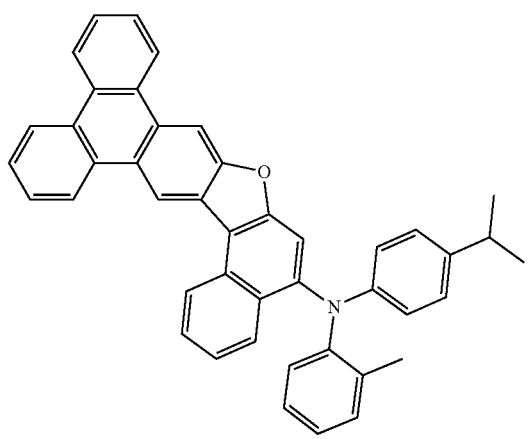
Compound 202
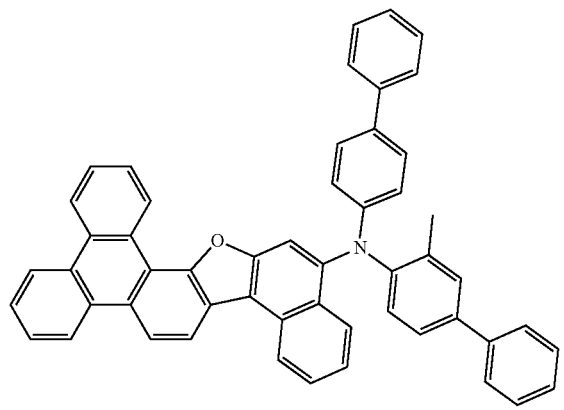
Compound 203
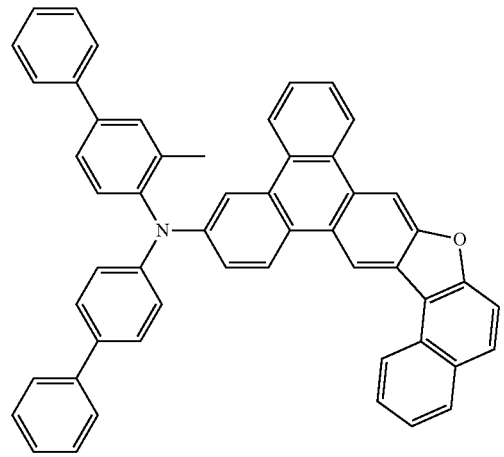
Compound 204
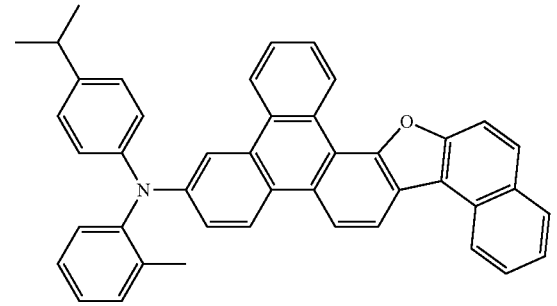
Compound 205
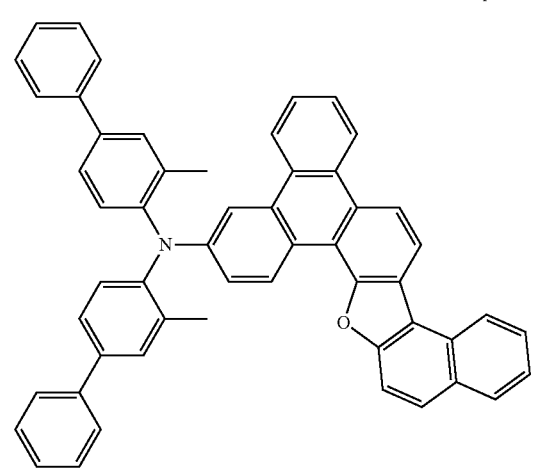
Compound 206
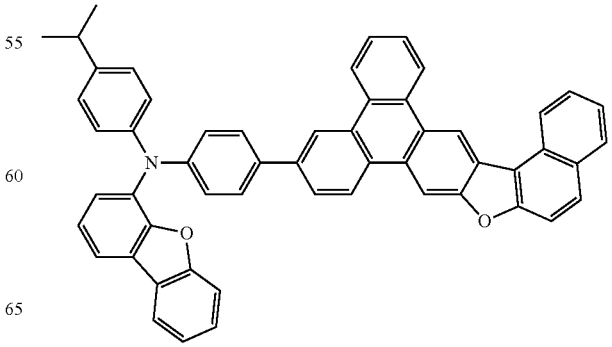

Compound 207
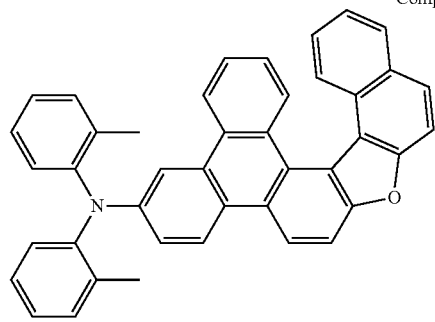
Compound 208
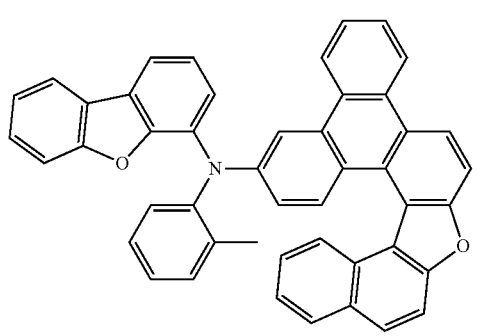
Compound 209
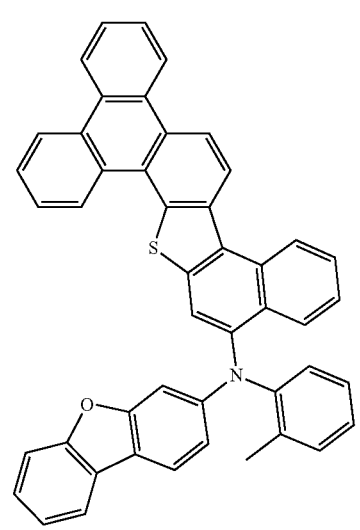
Compound 210
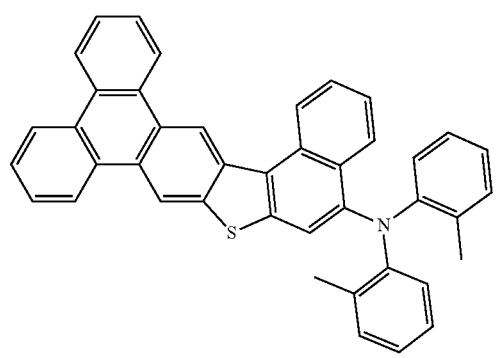
Compound 211
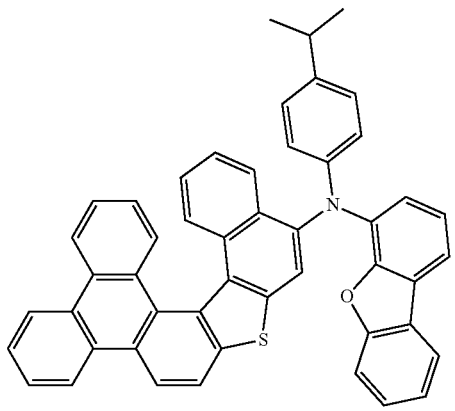
Compound 212
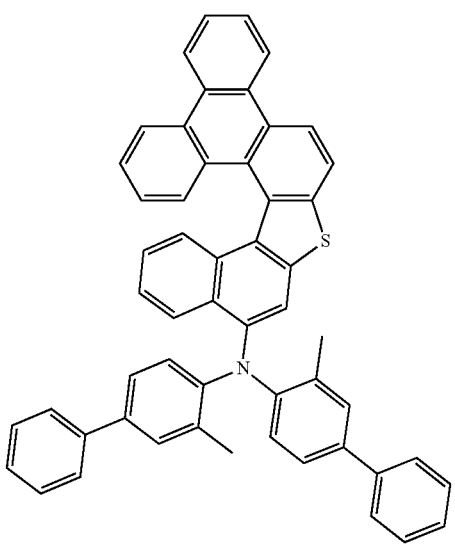
Compound 213
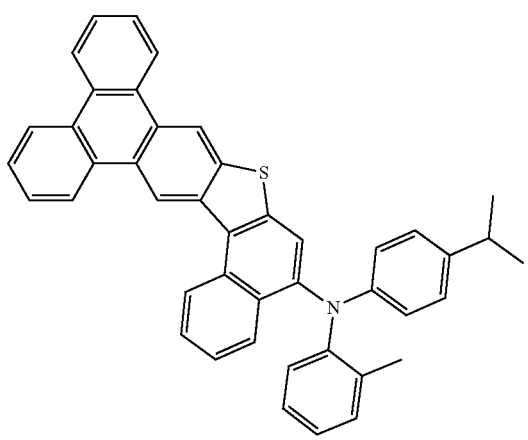

Compound 214
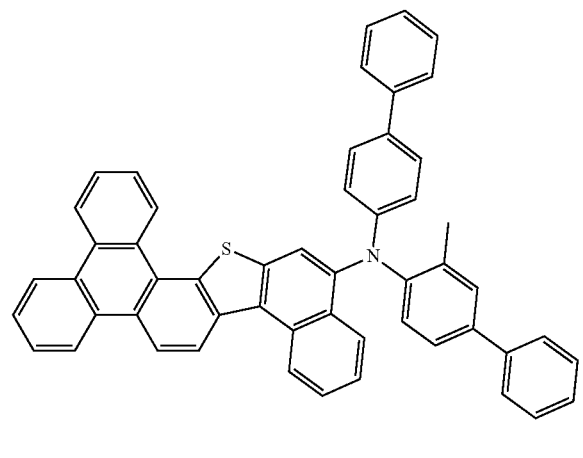
Compound 215
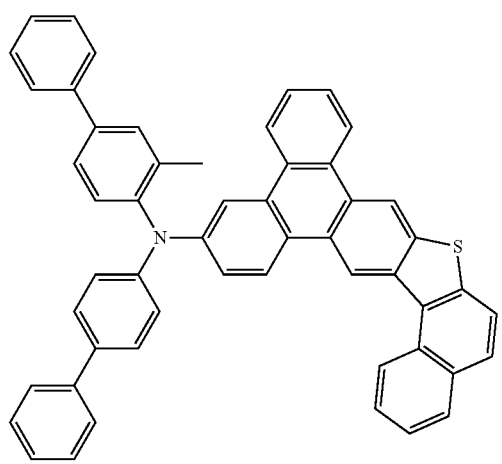
Compound 216
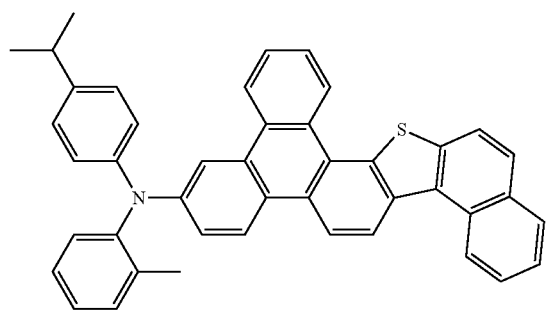
Compound 217
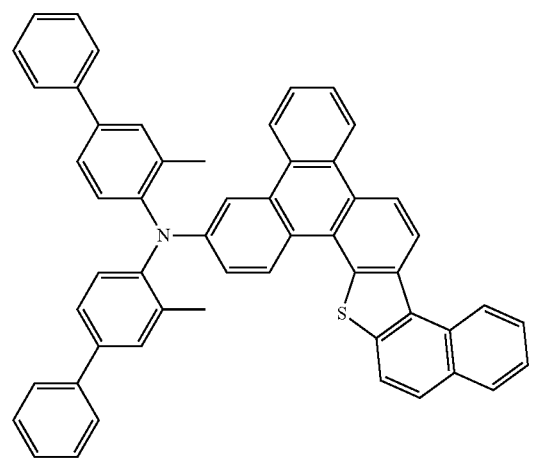
Compound 218
Compound 219
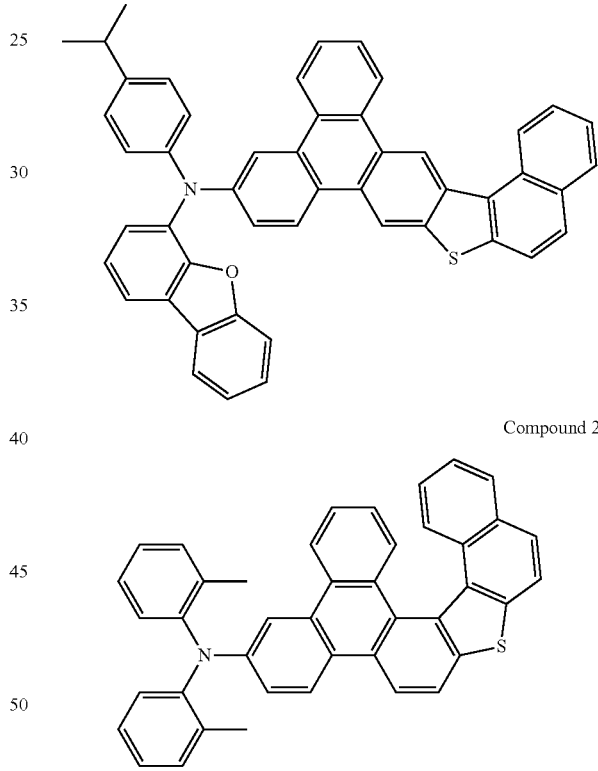
Compound 220
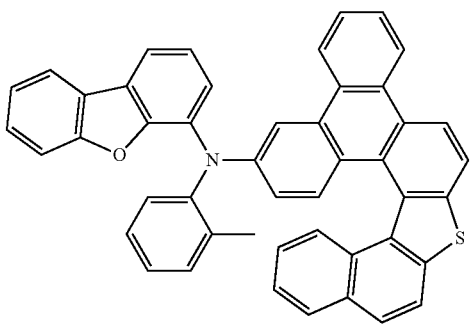

Compound 221
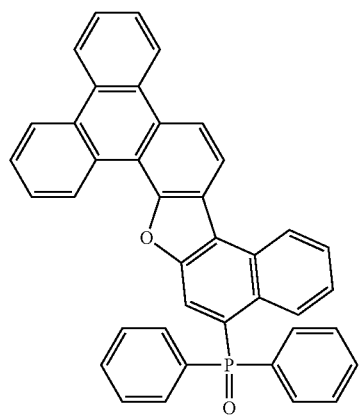
Compound 222
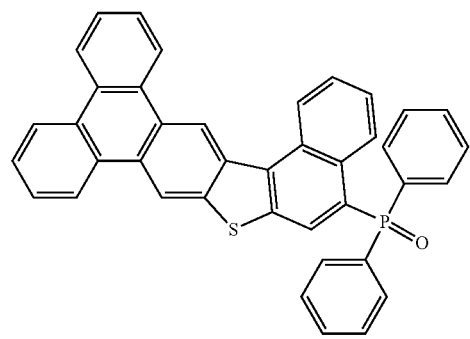
Compound 223
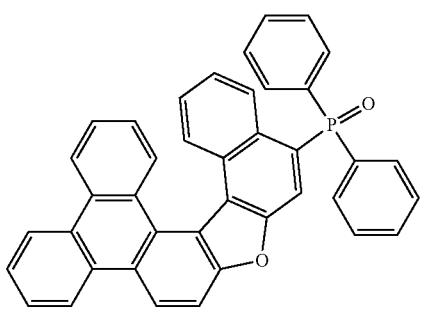
Compound 224
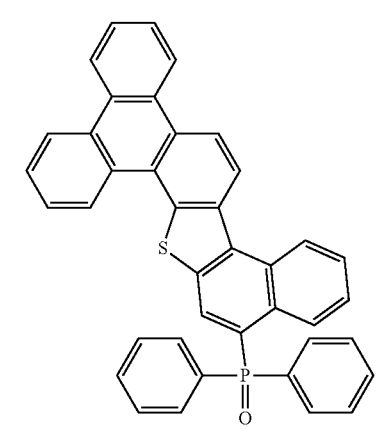
Compound 225
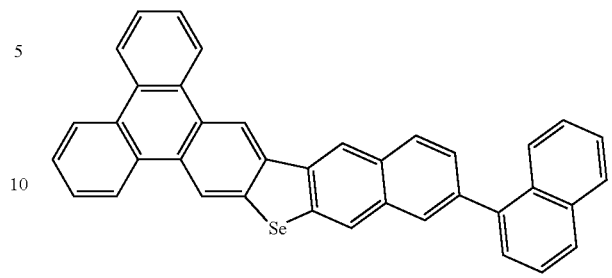
Compound 226
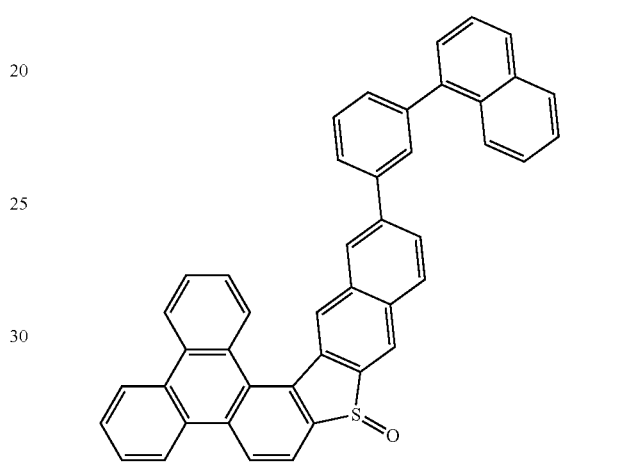
Compound 227
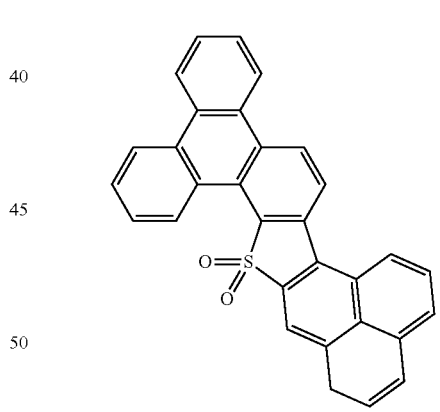
Compound 228
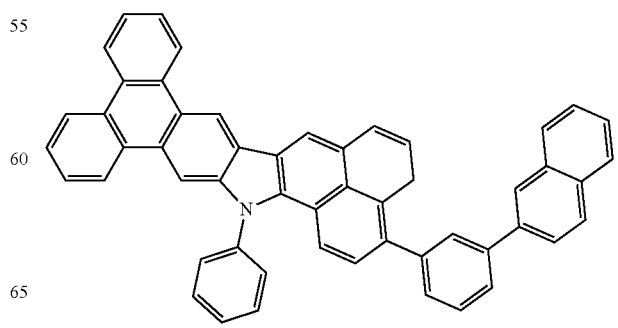

-continued
Compound 229
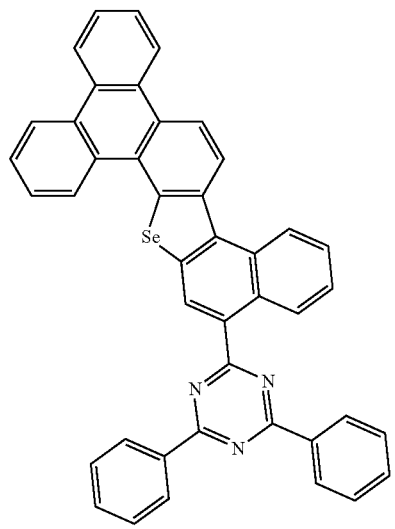
Compound 230
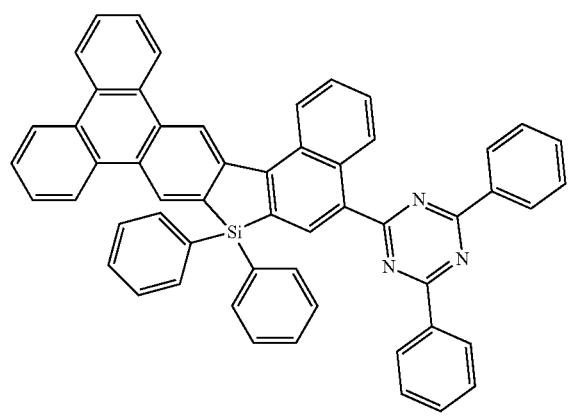
Compound 231
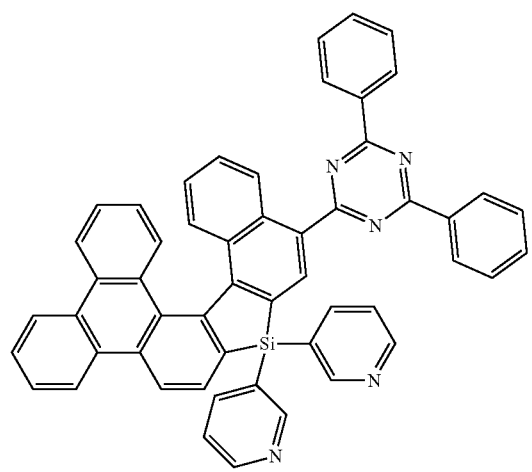
-continued
Compound 232
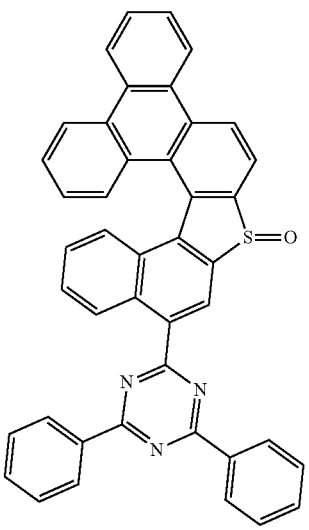
Compound 233
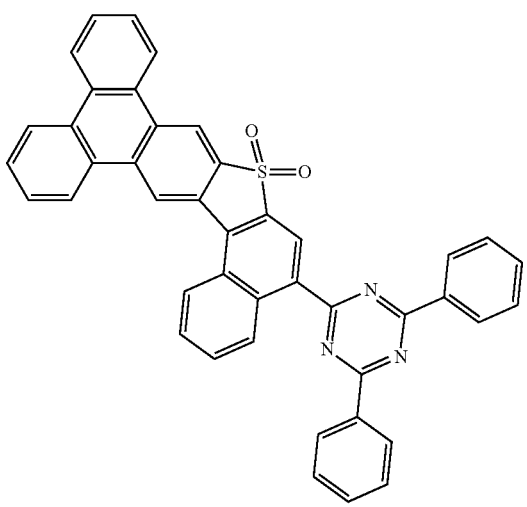
Compound 178
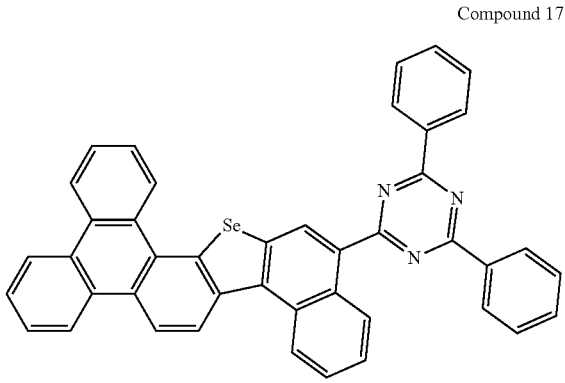

Compound 235
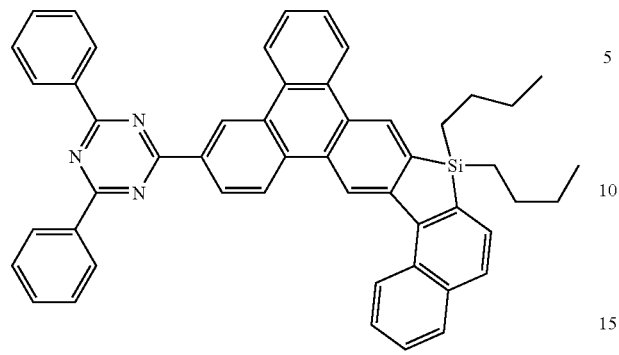
Compound 236
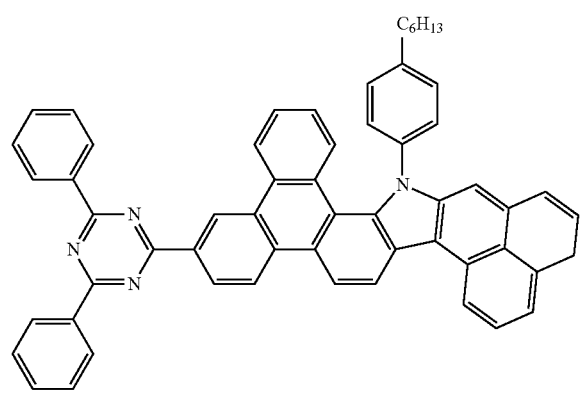
Compound 237
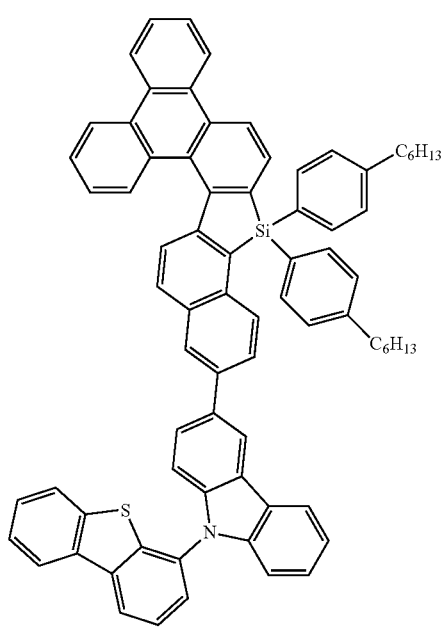
Compound 238
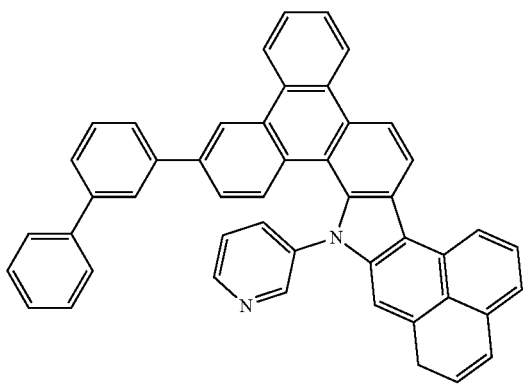
Compound 239
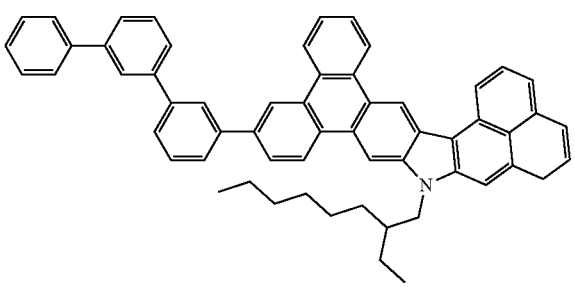
Compound 240
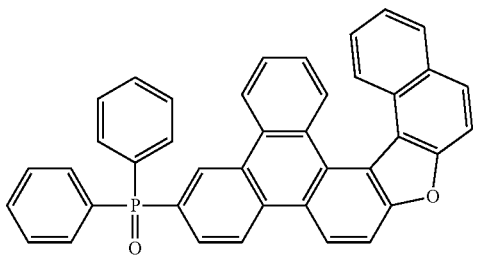
Compound 241
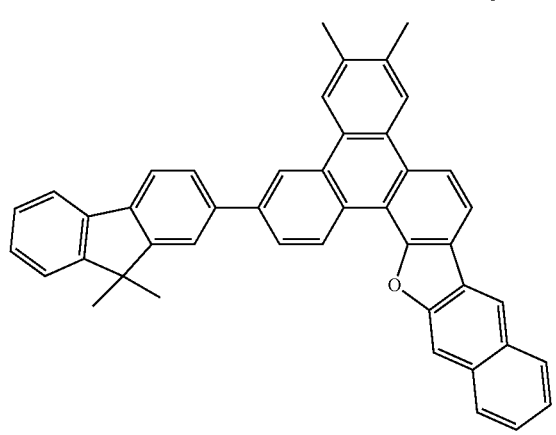

Compound 242

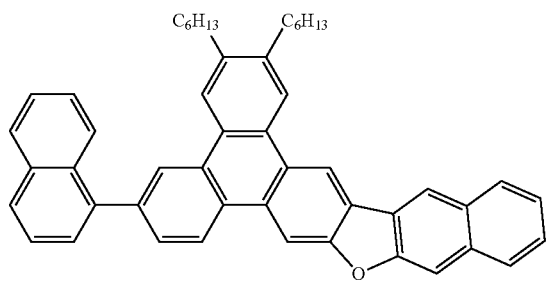

Compound 243

Compound 244

Compound 245

Compound 246

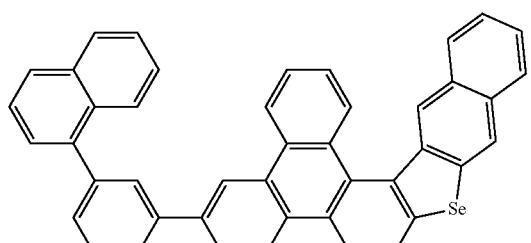

Compound 247

Compound 248

4. An organic electroluminescence device comprising a pair of electrodes having a cathode and an anode, and between the pairs of electrodes comprising at least a light emitting layer and one or more layers of organic thin film layers, wherein the light emitting layer and/or the one or more thin film layers comprise the organic compound according to claim 3.

5. The organic electroluminescence device according to claim 4, wherein the light emitting layer comprising the organic compound of formula (A) as a host material.

6. The organic electroluminescence device according to claim 4, wherein the light emitting layer comprising the organic compound of formula (A) as a fluorescent dopant material.

7. The organic electroluminescence device according to claim 4, wherein the organic thin film layer comprising the organic compound of formula (A) as a hole blocking material.

8. The organic electroluminescence device according to claim 4, wherein the organic thin film layer comprising the organic compound of formula (A) is an electron transporting layer.

9. The organic electroluminescence device according to claim 4, wherein the organic electroluminescence device is a lighting panel.

10. The organic electroluminescence device according to claim 4, wherein the organic electroluminescence device is a backlight panel.

* * * * *